(12) United States Patent
Floersheimer et al.

(10) Patent No.: US 7,652,022 B2
(45) Date of Patent: Jan. 26, 2010

(54) DIARYL UREA DERIVATIVES USEFUL FOR THE TREATMENT OF PROTEIN KINASE DEPENDENT DISEASES

(75) Inventors: Andreas Floersheimer, Dornach (CH); Pascal Furet, Thann (FR); Paul William Manley, Arlesheim (CH); Guido Bold, Gipf-Oberfrick (CH); Eugen Boss, Birsfelden (CH); Vito Guagnano, Basel (CH); Andrea Vaupel, Riehen (CH)

(73) Assignee: Novartis AG, Basel (CH)

( * ) Notice: Subject to any disclaimer, the term of this patent is extended or adjusted under 35 U.S.C. 154(b) by 608 days.

(21) Appl. No.: 10/515,113

(22) PCT Filed: May 28, 2003

(86) PCT No.: PCT/EP03/05634

§ 371 (c)(1),
(2), (4) Date: Dec. 8, 2005

(87) PCT Pub. No.: WO03/099771

PCT Pub. Date: Dec. 4, 2003

(65) Prior Publication Data

US 2006/0128734 A1 Jun. 15, 2006

(30) Foreign Application Priority Data

May 29, 2002 (GB) .................................. 0212413.9
Mar. 12, 2003 (GB) .................................. 0305684.3
Apr. 23, 2003 (GB) .................................. 0309219.4

(51) Int. Cl.
*A01N 43/54* (2006.01)
*A01N 43/40* (2006.01)
*A61K 31/505* (2006.01)
*A61K 31/44* (2006.01)
*C07D 239/02* (2006.01)

(52) U.S. Cl. ..................... 514/275; 514/349; 544/314

(58) Field of Classification Search .................. None
See application file for complete search history.

(56) References Cited

FOREIGN PATENT DOCUMENTS

| WO | 98 50346 | 11/1998 |
|---|---|---|
| WO | 99 32436 | 7/1999 |
| WO | 99 32463 | 7/1999 |
| WO | 00 41698 | 7/2000 |
| WO | 01 87846 | 11/2001 |
| WO | 02 32872 | 4/2002 |
| WO | WO 0232872 | * 4/2002 |
| WO | 02 50041 | 6/2002 |
| WO | 02 062763 | 8/2002 |
| WO | 2004 037789 | 5/2004 |
| WO | 2004 043379 | 5/2004 |

OTHER PUBLICATIONS

Ohyama, et. al., Yakubutsu Dotai (1994), 9(4), 437-57.*
Dorwald F. A. Side Reactions in Organic Synthesis, 2005, Wiley: VCH, Weinheim p. IX of Preface.*
Hotte et al., "BAY 43-9006: Early Clinical Data in Patients with Advanced Solid Malignancies," Current Pharmaceutical Design, vol. 8, No. 25, pp. 2249-2253 (2002).
Heidel et al., "Clinical resistance to the kinase inhibitor PKC412 in acute myeloid leukemia by mutation of Asn-676 in the FLT3 tyrosine kinase domain", Blood, 2006 vol. 107 No. 1 pp. 293-300.

* cited by examiner

*Primary Examiner*—James O Wilson
*Assistant Examiner*—Jeffrey H Murray

(57) ABSTRACT

The invention relates to the use of diaryl urea derivatives in the treatment of protein kinase dependent diseases or for the manufacture of pharmaceutical compositions for use in the treatment of said diseases, methods of use of diaryl urea derivatives in the treatment of said diseases, pharmaceutical preparations comprising diaryl urea derivatives for the treatment of said diseases, diaryl urea derivatives for use in the treatment of said diseases, novel diaryl urea derivatives, pharmaceutical preparations comprising these novel diaryl urea derivatives, processes for the manufacture of the novel diaryl urea derivatives, the use or methods of use of the novel diaryl urea derivatives as mentioned above, and/or these novel diaryl urea derivatives for use in the treatment of the animal or human body.

9 Claims, No Drawings

DIARYL UREA DERIVATIVES USEFUL FOR THE TREATMENT OF PROTEIN KINASE DEPENDENT DISEASES

SUMMARY OF THE INVENTION

The invention relates to the use of diaryl urea derivatives in the treatment of protein kinase dependent diseases or for the manufacture of pharmaceutical compositions for use in the treatment of said diseases, methods of use of diaryl urea derivatives in the treatment of said diseases, pharmaceutical preparations comprising diaryl urea derivatives for the treatment of said diseases, diaryl urea derivatives for use in the treatment of said diseases, novel diaryl urea derivatives, pharmaceutical preparations comprising these novel diaryl urea derivatives, processes for the manufacture of the novel diaryl urea derivatives, the use or methods of use of the novel diaryl urea derivatives as mentioned above, and/or these novel diaryl urea derivatives for use in the treatment of the animal or human body.

BACKGROUND OF THE INVENTION

Protein kinases (PKs) are enzymes which catalyze the phosphorylation of specific serine, threonine or tyrosine residues in cellular proteins. These post-translational modifications of substrate proteins act as molecular switch regulating cell proliferation, activation and/or differentiation. Aberrant or excessive PK activity has been observed in many disease states including benign and malignant proliferative disorders. In many cases, it has been possible to treat diseases in vitro and in many cases in vivo, such as proliferative disorders, by making use of PK inhibitors.

In view of the large number of protein kinase inhibitors and the multitude of proliferative and other PK-related diseases, there is an ever-existing need to provide novel classes of compounds that are useful as PK inhibitors and thus in the treatment of these PTK related diseases. What is required are new classes of pharmaceutically advantageous PK inhibiting compounds.

GENERAL DESCRIPTION OF THE INVENTION

It has now been found that various compounds of the diaryl urea derivative class show inhibition of a number of protein tyrosine kinases. Among the advantages, a good bioavailability and, especially where substituents at the ring with A and A' in formula I or I* given below are present, lower accessibility to metabolism are to be mentioned. The compounds of formula I or I*, described below in more detail, especially show inhibition of one or more of the following protein tyrosine kinases: c-Abl, Bcr-Abl, the receptor tyrosine kinases Flt3, VEGF-R or c-Kit, as well as combinations of tow or more of these; in the case of novel diaryl urea derivatives according to the invention, the compounds are appropriate for the inhibition of these and/or other protein tyrosine kinases, especially those mentioned above and/or, in addition, the non-receptor tyrosine kinase Raf, and/or for the inhibition of mutants of these enzymes, especially of Bcr-Abl, for example the Glu255->Lysine mutant. In view of these activities, the compounds can be used for the treatment of diseases related to especially aberrant or excessive activity of such types of kinases, especially those mentioned.

DETAILED DESCRIPTION OF THE INVENTION

The invention especially relates to the use of diaryl urea derivatives that are compounds of the formula I

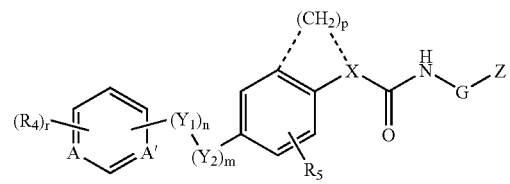

wherein G is either not present, lower alkylene or $C_3$-$C_5$cycloalkylene and Z is a radical of the formula Ia

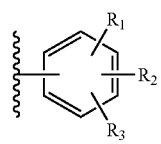

or G is not present and Z is a radical of the formula Ib

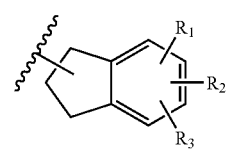

A is CH, N or N→O and A' is N or N→O, with the proviso that not more than one of A and A' can be N→O;

n is 1 or 2;

m is 0, 1 or 2;

p is 0, 2 or 3;

r is 0 to 5;

X is NR if p is 0, wherein R is hydrogen or an organic moiety, or if p is 2 or 3, X is nitrogen which together with $(CH_2)_p$ and the bonds represented in dotted (interrupted) lines (including the atoms to which they are bound) forms a ring, or X is CHK wherein K is lower alkyl or hydrogen and p is zero, with the proviso that the bonds represented in dotted lines, if p is zero, are absent;

$Y_1$ is O, S or $CH_2$;

$Y_2$ is O, S or NH;

with the proviso that $(Y_1)_n$—$(Y_2)_m$ does not include O—O, S—S, NH—O, NH—S or S—O groups;

each of $R_1$, $R_2$, $R_3$ and $R_5$, independently of the others, is hydrogen or an inorganic or organic moiety or any two of them together form a lower alkylene-dioxy bridge bound via the oxygen atoms, and the remaining one of these moieties is hydrogen or an inorganic or organic moiety;

and $R_4$ (if present, that is, if r is not zero) is an inorganic or organic moiety;

or a tautomer thereof;

or a pharmaceutically acceptable salt thereof;

in the treatment of protein kinase (especially tyrosine protein kinase) dependent diseases or for the manufacture of pharmaceutical compositions for use in the treatment of said diseases, methods of use of diaryl urea derivatives in the treatment of said diseases, pharmaceutical preparations comprising diaryl urea derivatives for the treatment of said diseases, diaryl urea derivatives for use in the treatment of said diseases.

The invention further also relates to the use or diaryl urea derivatives as described above, wherein the diaryl urea derivative is a compound of the formula I*

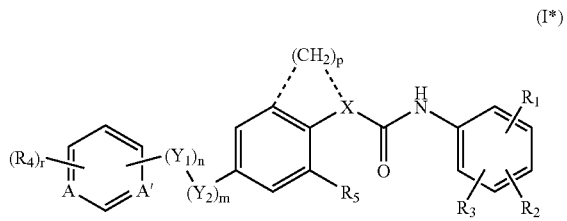

(I*)

wherein A, A', n, m, p, r, X, $Y_1$, $Y_2$ and $R_1$—$R_5$ have the meanings as defined above for a compound of formula I;

or a tautomer thereof;

or pharmaceutically acceptable salts thereof.

The invention especially relates to novel diaryl urea derivatives, especially a compound selected from the compounds of the formula I or I* in the Examples, or a salt thereof, especially (i) the novel compounds of the formula I wherein A is CH, N or N→O and A' is N or N→O, with the proviso that not more than one of A and A' can be N→O;

n is 1 or 2;

m is 0, 1 or 2;

p is 0, 2 or 3;

r is 1 to 5;

X is NR if p is 0, wherein R is hydrogen or an organic moiety, or if p is 2 or 3, X is nitrogen which together with $(CH_2)_p$ and the bonds represented in dotted (interrupted) lines (including the atoms to which they are bound) forms a ring, with the proviso that if X is NH, each of $R_4$, independently of the others if r>1, is a moiety as defined above under formula I but not bound to the rest of formula I via a —C(=O)—, —C(NR)— or —S(O$_2$)— bridge, or X is CHK wherein K is lower alkyl or hydrogen and p is zero, with the proviso that the bonds represented in dotted lines, if p is zero, are absent;

$Y_1$ is O, S or $CH_2$;

$Y_2$ is O, S or NH;

with the proviso that $(Y_1)_n$—$(Y_2)_m$ does not include O—O, S—S, NH—O, NH—S or S—O groups;

each of $R_1$, $R_2$, $R_3$ and $R_5$, independently of the others, is hydrogen or an inorganic or organic moiety or any two of $R_1$, $R_2$ and $R_3$ together form a lower alkylene-dioxy bridge bound via the oxygen atoms, and the remaining one of these moieties is hydrogen or an inorganic or organic moiety, with the proviso that if G is not present and Z is a radical of the formula Ia, $R_1$, $R_2$ and $R_3$ cannot all be hydrogen and with the further proviso that if one of $R_1$, $R_2$ and $R_3$ is halo or lower alkyl-sulfonyl, the other two cannot both be hydrogen;

$R_4$ is an inorganic or organic moiety, with the proviso that if n is 1, m is 0, p is 0, r is 1, X is NH, $Y_1$ is O, G is not present and Z is a radical of the formula Ia, $R_4$, together with the benzene ring containing A and A', does not form methylpyridinyl, 2-hydroxy-pyridin-4-yl or 1-H-2-oxo-1,2-dihydropyridin-4-yl; and G and Z have the meanings given above under formula I;

or a tautomer thereof;

or pharmaceutically acceptable salts thereof; and (ii) the novel compounds of the formula I* wherein A is CH, N or N→O and A' is N or N→O, with the proviso that not more than one of A and A' can be N→O;

n is 1;

m is 0;

p is 0, 2 or 3;

r is 1;

X is NR if p is 0, wherein R is hydrogen or lower alkyl, or if p is 2 or 3, X is nitrogen which together with $(CH_2)_p$ and the bonds represented in dotted (interrupted) lines (including the atoms to which they are bound) forms a ring, or X is $CH_2$ and p is zero, with the proviso that the bonds represented in dotted lines, if p is zero, are absent;

$Y_1$ is O or $CH_2$;

each of $R_1$, $R_2$ and $R_3$ independently of the others, is hydrogen, lower alkyl, halo, especially bromo or chloro, halo-lower alkyl, especially trifluoromethyl, lower alkoxy, especially methoxy, halo-lower alkoxy, especially 2,2,2-trifluoroethoxy, phenyl, piperidyl, especially piperidin-1-yl, piperazinyl, especially piperazin-1-yl, morpholinyl, especially morpholine, thiomorpholinyl, especially thiomorpholino, or any two of them together form a lower alkylene-dioxy bridge bound via the oxygen atoms, and the remaining one of these moieties is hydrogen or one of the moieties mentioned, with the proviso that $R_1$, $R_2$ and $R_3$ cannot all be hydrogen and with the further proviso that if one of $R_1$, $R_2$ and $R_3$ is halo, the other two cannot both be hydrogen;

$R_4$ is lower alkoxy, especially methoxy, lower alkanoylamino, especially acetylamino, hydroxyphenylamino, especially p-hydroxyphenylamino, amino-lower alkyl-oxyphenyl-amino, especially 4-[(2-aminoethyl)-oxyphenyl]-amino, sulfamoylphenylamino, especially 4-sulfamoylphenylamino, carbamoylphenylamino, especially 4-carbamoylphenylamino, [N-(hydroxy-lower alkyl)-carbamoyl]-phenylamino, especially [N-(2-hydroxyethyl)-carbamoyl]-phenylamino, or halo, especially chloro; and $R_5$ is hydrogen, lower alkyl or halo, especially hydrogen;

or a tautomer thereof;

or pharmaceutically acceptable salts thereof;

to pharmaceutical preparations comprising these novel diaryl urea derivatives or pharmaceutically acceptable salts thereof, processes for the manufacture of the novel diaryl urea derivatives or pharmaceutically acceptable salts thereof, the use or methods of use of the novel diaryl urea derivatives or pharmaceutically acceptable salts thereof as mentioned above, and/or these novel diaryl urea derivatives or pharmaceutically acceptable salts thereof for use in the treatment of the animal or human body.

The general terms used hereinbefore and hereinafter preferably have, within this disclosure, the following meanings, unless otherwise indicated:

The prefix "lower" denotes a radical having 1 up to and including a maximum of 7, especially 1 up to and including a maximum of 4 carbon atoms, the radicals in question being either linear or branched with single or multiple branching.

Lower alkyl, for example, is methyl, ethyl, n-propyl, sec-propyl, n-butyl, isobutyl, sec-butyl, tert-butyl, n-pentyl, n-hexyl or n-heptyl.

Where the plural form is used for compounds, salts, pharmaceutical preparations, diseases and the like, this is intended to mean also a single compound, salt, or the like.

Halo(geno) is preferably iodo, bromo, chloro or fluoro, especially fluoro, chloro or bromo.

In view of the close relationship between the diaryl urea derivatives in free form and in the form of their salts, including those salts that can be used as intermediates, for example in the purification or identification of the novel compounds, tautomers or tautomeric mixtures and their salts, any reference hereinbefore and hereinafter to these compounds, especially the compounds of the formula I or I*, is to be understood as referring also to the corresponding tautomers of these compounds, especially of compounds of the formula I or I*, tautomeric mixtures of these compounds, especially of compounds of the formula I or I*, or salts of any of these, as appropriate and expedient and if not mentioned otherwise. Tautomers can, e.g., be present in cases where amino or hydroxy, each with a least one bound hydrogen, are bound to carbon atoms that are bound to adjacent atoms by double bonds (e.g. keto-enol or imine-enamine tautoemerism). Preferred tautomers are the pyridin-on-yl or pyrimidin-on-yl forms of compounds wherein $R_4$ is hydroxy and the other moieties are defined as for compounds of the formula I or I*, respectively.

Where "a compound . . . , a tautomer thereof; or a salt thereof" or the like is mentioned, this means "a compound . . . , a tautomer thereof, or a salt of the compound or the tautomer".

Any asymmetric carbon atom may be present in the (R)—, (S)— or (R,S)-configuration, preferably in the (R)— or (S)-configuration. Substituents at a ring at atoms with saturated bonds may, if possible, be present in cis-(=Z-) or trans (=E-) form. The compounds may thus be present as mixtures of isomers or preferably as pure isomers, preferably as enantiomer-pure diastereomers or pure enantiomers.

Salts are preferably the pharmaceutically acceptable salts of the diaryl urea derivatives, especially of compounds of the formula I or I* if they are carrying salt-forming groups.

Salt-forming groups are groups or radicals having basic or acidic properties. Compounds having at least one basic group or at least one basic radical, for example amino, a secondary amino group not forming a peptide bond or a pyridyl radical, may form acid addition salts, for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxy-benzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethanesulfonic acid, or aromatic sulfonic acids, for example benzene-, p-toluene- or naphthalene-2-sulfonic acid. When several basic groups are present mono- or poly-acid addition salts may be formed.

Compounds having acidic groups, a carboxy group or a phenolic hydroxy group, may form metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri-(2-hydroxy-ethyl)-amine, or heterocyclic bases, for example N-ethyl-piperidine or N,N'-dimethylpiperazine. Mixtures of salts are possible.

Compounds having both acidic and basic groups can form internal salts.

For the purposes of isolation or purification, as well as in the case of compounds that are used further as intermediates, it is also possible to use pharmaceutically unacceptable salts, e.g. the picrates. Only pharmaceutically acceptable, non-toxic salts may be used for therapeutic purposes, however, and those salts are therefore preferred.

An organic moiety R is preferably unsubstituted or substituted alkyl, unsubstituted or substituted alkenyl, unsubstituted or substituted alkynyl, unsubstituted or substituted aryl, unsubstituted or substituted heterocyclyl, unsubstituted or substituted cycloalkyl or unsubstituted or substituted cycloalkenyl; preferred is unsubstituted alkyl.

"Substituted", whereever used for a moiety, means that one or more hydrogen atoms in the respective moiety, especially up to 5, more especially up to three, of the hydrogen atoms are replaced independently of each other by the corresponding number of substituents which preferably are independently selected from the group consisting of lower alkyl, for example methyl, ethyl or propyl, halo-lower alkyl, for example trifluoromethyl, $C_6$-$C_{16}$-aryl, especially phenyl or naphthyl (where $C_6$-$C_{16}$-aryl, especially phenyl or napthyl, is unsubstituted or substituted by one or more, especially up to three moieties selected from halogen, carboxy, lower alkoxycarbonyl, hydroxy, lower alkoxy, phenyl-lower alkoxy, lower alkanoyloxy, lower alkanoyl, amino, N-lower alkylamino, N,N-di-lower alkylamino, N-phenyl-lower alkylamino, N,N-bis(phenyl-lower alkyl)amino, lower alkanoylamino, halo, halo-lower alkyl, e.g. trifluoro-methyl, sulfo, sulfamoyl, carbamoyl, N-lower alkyl-carbamoyl, N-(hydroxy-lower alkyl)-carbamoyl, such as N-(2-hydroxyethyl)-carbamoyl, cyano, cyano-lower alkyl and nitro), $C_3$-$C_{10}$-cycloalkyl, especially cyclopropyl or cyclohexyl, hydroxy-$C_3$-$C_8$-cycloalkyl, such as hydroxy-cyclohexyl, heterocyclyl with 5 or 6 ring atoms and 1 to 3 ring heteroatoms selected from O, N and S, especially piperidinyl, especially piperidin-1-yl, piperazinyl, especially piperazin-1-yl, morpholinyl, especially morpholin-1-yl, hydroxy, lower alkoxy, for example methoxy, halo-lower alkoxy, especially 2,2,2-trifluoroethoxy, phenyl-lower alkoxy, amino-lower alkoxy, such as 2-eminoethoxy; lower alkanoyloxy, hydroxy-lower alkyl, such as hydroxymethyl or 2-hydroxyethyl, amino, N-lower alkylamino, N,N-di-lower alkylamino, N-phenyl-lower alkylamino, N,N-bis(phenyl-lower alkyl)amino, lower alkanoylamino, especially acetylamino, benzoylamino, carbamoyl-lower alkoxy, N-lower alkylcarbamoyl-lower alkoxy or N,N-di-lower alkyl-carbamoyl-lower alkoxy, amidino, N-hydroxy-amidino, guanidino, amino-lower alkyl, such as aminomethyl or 2-aminoethyl, amidino-lower alkyl, such as 2-amidinoethyl, N-hydroxyamidino-lower alkyl, such as N-hydroxy-amidino-methyl or -2-ethyl, halogen, for example fluoro, chloro, bromo or iodo, carboxy, lower alkoxycarbonyl, phenyl-, naphthyl- or fluorenyl-lower alkoxycarbonyl, such as benzyloxycarbonyl, lower alkanoyl, sulfo, lower alkanesulfonyl, for example methanesulfonyl ($CH_3$—$S(O)_2$—), phosphono (—$P(=O)(OH)_2$), hydroxy-lower alkoxy phosphoryl or di-lower alkoxyphosphoryl, carbamoyl, mono- or di-lower alkylcarbamoyl, mono- or di-(hydroxy-lower alkyl)-carbamoyl, sulfamoyl, mono- or di-lower alkylaminosulfonyl, nitro, cyano-lower alkyl, such as cyanomethyl, and cyano. It goes without saying that substitutents are only at positions where they are chemically possible, the person skilled in the art being able to decide (either experimentally or theoretically) without inappropriate effort which substitutions are possible and which are not. For example, amino or hydroxy groups with free hydrogen may be unstable if bound to carbon atoms with unsaturated (e.g. olefinic) bonds.

Alkyl preferably has up to 20, more preferably up to 12 carbon atoms and is linear or branched one or more times; preferred is lower alkyl, especially $C_1$-$C_4$-alkyl, in particular methyl, ethyl or n-propyl. Alkyl is unsubstituted or substituted, preferably by one or more substituents independently selected from those mentioned above under "Substituted". Unsubstituted alkyl, preferably lower alkyl, is especially preferred as an organic moiety R.

Among the moieties corresponding to substituted alkyl, hydroxy-lower alkyl, especially 2-hydroxyethyl, and/or halo-lower alkyl, especially trifluoromethyl or 2,2,2-trifluoroethyl, are especially preferred.

Alkenyl is preferably a moiety with one or more double bonds and preferably has 2 to 20, more preferably up to 12, carbon atoms; it is linear or branched one or more times (as far as possible in view of the number of carbon atoms). Preferred is $C_2$-$C_7$-alkenyl, especially $C_3$-$C_4$-alkenyl, such as allyl or crotyl. Alkenyl can be unsubstituted or substituted, especially by one or more, more especially up to three, of the substituents mentioned above under "substituted". Substituents such as amino or hydroxy (with free dissociable hydrogen) preferably are not bound to carbon atoms that participate at a double bond, and also other subtituents that are not sufficiently stable are preferably excluded. Unsubstituted alkenyl, in particular $C_2$-$C_7$-alkenyl, is preferred.

Alkynyl is preferably a moiety with one or more triple bonds and preferably has 2 to 20, more preferably up to 12, carbon atoms; it is linear of branched one or more times (as far as possible in view of the number of carbon atoms). Preferred is $C_2$-$C_7$-alkynyl, especially $C_3$-$C_4$-alkynyl, such as ethinyl or propin-2-yl. Alkynyl can be unsubstituted or substituted, especially by one or more, more especially up to three, of the substituents mentioned above under "substituted". Substituents such as amino or hydroxy (with free dissociable hydrogen) preferably are not bound to carbon atoms that participate at a triple bond, and also other subtituents that are not sufficiently stable are preferably excluded. Unsubstituted alkynyl, in particular $C_2$-$C_7$-alkynyl, is preferred.

Aryl preferably has a ring system of not more than 16 carbon atoms, is preferably mono-, bi- or tric-cyclic, and is unsubstituted or substituted preferably as defined above under "Substituted". Preferably, aryl is selected from phenyl, naphthyl, indenyl, azulenyl and anthryl, and is preferably in each case unsubstituted or lower alkyl, especially methyl, ethyl or n-propyl, halo (especially fluoro, chloro, bromo or iodo), halo-lower alkyl (especially trifluoromethyl), hydroxy, lower alkoxy (especially methoxy), halo-lower alkoxy (especially 2,2,2-trifluoroethoxy), amino-lower alkoxy (especially 2-amino-ethoxy), lower alkyl (especially methyl or ethyl) carbamoyl, N-(hydroxy-lower alkyl)-carbamoyl (especially N-(2-hydroxyethyl)-carbamoyl) and/or sulfamoyl-substituted aryl, especially a corresponding substituted or unsubstituted phenyl.

Heterocyclyl is preferably a heterocyclic radical that is unsaturated, saturated or partially saturated in the bonding ring and is preferably a monocyclic or in a broader aspect of the invention bicyclic or tricyclic ring; has 3 to 24, more preferably 4 to 16 ring atoms; wherein at least in the ring bonding to the radical of the molecule of formula I or I* one or more, preferably one to four, especially one or two carbon ring atoms are replaced by a heteroatom selected from the group consisting of nitrogen, oxygen and sulfur, the bonding ring preferably having 4 to 12, especially 5 to 7 ring atoms; heteroaryl being unsubstituted or substituted by one or more, especially 1 to 3, substitutents independently selected from the group consisting of the substituents defined above under "Substituted"; especially being a heteroaryl radical selected from the group consisting of oxiranyl, azirinyl, 1,2-oxathiolanyl, imidazolyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, pyranyol, thiazolyl, isothiazolyl, dithiazolyl, oxazolyl, isoxazolyl, pyridyl, pyrazinyl, pyrimidinyl, piperidyl, especially piperidin-1-yl, piperazinyl, especially piperazin-1-yl, pyridazinyl, morpholinyl, especially morpholino, thiomorpholinyl, especially thiomorpholino, indolizinyl, isoindolyl, 3H-indolyl, indolyl, benzimidazolyl, cumaryl, indazolyl, triazolyl, tetrazolyl, purinyl, 4H-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, β-carbolinyl, phenanthridinyl, acridinyl, perimidinyl, phenanthrolinyl, furazanyl, phenazinyl, phenothiazinyl, phenoxazinyl, chromenyl, isochromanyl and chromanyl, each of these radicals being unsubstituted or substituted by one to two radicals selected from the group consisting of lower alkyl, especially methyl or tert-butyl, lower alkoxy, especially methoxy, and halo, especially bromo or chloro. Unsubstituted heterocyclyl, especially piperidyl, piperazinyl, thiomorpholino or morpholino, is preferred.

Cycloalkyl is preferably $C_3$-$C_{10}$-cycloalkyl, especially cyclopropyl, dimethylcyclopropyl, cyclobutyl, cyclopentyl, cyclohexyl or cycloheptyl, cycloalkyl being unsubstituted or substituted by one or more, especially 1 to 3, substitutents independently selected from the group consisting of the substituents defined above under "Substituted".

Cycloalkenyl is preferably $C_5$-$C_{10}$-cycloalkenyl, especially cyclopentenyl, cyclohexenyl or cycloheptenyl, cycloalkenyl being unsubstituted or substituted by one or more, especially 1 to 3, substitutents independently selected from the group consisting of the substituents defined above under "Substituted".

An inorganic moiety is preferably halogen, hydroxy, amino, or nitro.

The bonds represented by dotted (interrupted) lines and binding $(CH_2)_p$, are present if p is 2 or 3, or absent if p is zero.

An organic moiety is preferably unsubstituted or substituted alkyl, unsubstituted or substituted alkenyl, unsubstituted or substituted alkynyl, unsubstituted or substituted unsubstituted or substituted aryl, unsubstituted or substituted heterocyclyl, unsubstituted or substituted cycloalkyl or unsubstituted or substituted cycloalkenyl, unsubstituted or substituted alkoxy, unsubstituted or substituted alkenyloxy, unsubstituted or substituted alkynyloxy, unsubstituted or substituted aryloxy, unsubstituted or substituted heterocycly-loxy, unsubstituted or substituted cycloalkoxy or unsubstituted or substituted cycloalkenyloxy, or unsubstituted or substituted alkylamino, unsubstituted or substituted alkenylamino, unsubstituted or substituted alkynylamino, unsubstituted or substituted arylamino, unsubstituted or substituted heterocyclylamino, unsubstituted or substituted cycloalkylamino or unsubstituted or substituted cycloalkenylamino.

An organic moiety is preferably alkyl, especially lower alkyl, such as methyl, ethyl or propyl, halo-lower alkyl, such as trifluoromethyl, lower alkoxy, such as methoxy, halo-lower alkoxy, such as 2,2,2-trifluoroethoxy, halo, such as chloro or bromo, phenyl, phenylamino, hydroxy-phenyl-amino, such as 4-hydroxyphenylamino, amino-lower alkyl-oxyphenylamino, such as [4-(2-aminoethyl)oxy]-phenyl-amino, carbamoylphenyl-amino, such as 4-sulfamoyl-phenyl-amino, [N-(hydroxy-lower alkyl)-carbamoyl]-phenyl-amino, such as {N-[4-(2-hydroxyethyl)-carbamoyl]-phenyl}-amino, 5- or 6-membered saturated heterocyclyl with 1 or 2 heteroatoms selected from the group consisting of N, O and S, especially piperidyl, such as piperidin-1-yl, piperazinyl, such as piperazin-1-yl, morpholinyl, such as morpholino, or further thiomorpholinyl, such as thiomorpholino.

A basic organic moiety is a moiety selected from the definition of an organic moiety as given herein and having basic (alkaline) properties. Preferably a basic organic moiety is piperidyl, especially piperidin-1-yl, piperidyl-lower alkyl, especially piperidin-1-ylmethyl, lower alkyl-piperazinyl, especially 4-methyl-piperazin-1-yl or 4-ethyl-piperazin-1-yl, or lower alkyl-piperazinyl-lower alkyl, especially 4-methyl-piperazin-1-ylmethyl or 4-ethyl-piperazin-1-ylmethyl.

If any two of $R_1$, $R_2$ and $R_3$ together form a lower alkylenedioxy bridge bound via the oxygen atoms said bridge is preferably methylendioxy (O—$CH_2$—O) or ethylendioxy (O—$CH_2$—$CH_2$—O) bound via the oxygen atoms to vicinal carbon atoms, and the remaining one of these moieties is hydrogen or an inorganic or organic moiety as described above.

The term "treatment of tyrosine protein kinase dependent diseases" refers to the prophylactic or preferably therapeutic (including palliative and/or curing) treatment of said diseases, especially of the diseases mentioned below.

Where subsequently the term "USE" is mentioned, this includes any one or more of the following embodiments of the invention, respectively: the use in the treatment of (especially tyrosine) protein kinase dependent diseases, the use for the manufacture of pharmaceutical compositions for use in the treatment of said diseases, methods of use of diaryl urea derivatives in the treatment of said diseases, pharmaceutical preparations comprising diaryl urea derivatives for the treatment of said diseases, and diaryl urea derivatives for use in the treatment of said diseases, as appropriate and expedient, if not stated otherwise. In particular, diseases to be treated and are thus preferred for USE of a compound of formula I or I* are selected from (especially tyrosine) protein kinase dependent ("dependent" meaning also "supported", not only "solely dependent") diseases mentioned below, especially corresponding proliferative diseases, more especially diseases that depend on ras, Abl, VEGF-receptor tyrosine kinase, Flt3, and/or Bcr-Abl activity, especially the diseases mentioned below under these specific tyrosine protein kinases. Other kinases of interest include PDGF receptor, c-KIT or EphB4 receptor.

In the novel diaryl urea derivatives of the formula I or I* in the examples, or salts thereof, or the novel compounds of the formula I or I*, the proviso that if X is NH, each of $R_4$ independently of the others, is a substituent not bound to the rest of formula I or I*, respectively, via a —C(=O)—, —C(NR)— or —$S(O_2)$— bridge means that the substituents are such that they do not comprise any of these bridges. Preferred are the substituents given above and below as "organic moieties".

The diaryl urea derivatives, especially the compounds of formula I or I*, have valuable pharmacological properties and are useful in the treatment of protein kinase dependent diseases, especially of tyrosine protein kinase dependent for example, as drugs to treat proliferative diseases.

The efficacy of the compounds of the invention as inhibitors of c-Abl protein-tyrosine kinase activity can be demonstrated as follows:

An in vitro enzyme assay is performed in 96-well plates as a filter binding assay as described by Geissler et al. in Cancer Res. 1992; 52:4492-4498, with the following modifications. The His-tagged kinase domain of c-Abl is cloned and expressed in the baculovirus/Sf9 system as described by Bhat et al. in J. Biol. Chem. 1997; 272:16170-16175. A protein of 37 kD (c-Abl kinase) is purified by a two-step procedure over a Cobalt metal chelate column followed by an anion exchange column with a yield of 1-2 mg/L of Sf9 cells (Bhat et al., reference cited). The purity of the c-Abl kinase is >90% as judged by SDS-PAGE after Coomassie blue staining. The assay contains (total volume of 30 μL): c-Abl kinase (50 ng), 20 mM Tris·HCl, pH 7.5, 10 mM $MgCl_2$, 10 μM $Na_3VO_4$, 1 mM DTT and 0.06 μCi/assay [$\gamma^{33}$ P]-ATP (5 μM ATP) using 30 μg/mL poly-Ala,Glu,Lys,Tyr-6:2:5:1 (Poly-AEKY, Sigma P1152) in the presence of 1% DMSO. Reactions are terminated by adding 10 μL of 250 mM EDTA and 30 μL of the reaction mixture is transferred onto Immobilon-PVDF membrane (Millipore, Bedford, Mass., USA) previously soaked for 5 min with methanol, rinsed with water, then soaked for 5 min with 0.5% $H_3PO_4$ and mounted on vacuum manifold with disconnected vacuum source. After spotting all samples, vacuum is connected and each well rinsed with 200 μL 0.5% $H_3PO_4$. Membranes are removed and washed on a shaker with 0.5% $H_3PO_4$ (4 times) and once with ethanol. Membranes are counted after drying at ambient temperature, mounting in Packard TopCount 96-well frame, and addition of 10 μL/well of Microscint™ (Packard). Using this test system, compounds of the formula I or I* show $IC_{50}$ values of inhibition in the range of 0.001 to 100 μM, usually between 0.05 and 5 μM.

The inhibition of VEGF-induced receptor autophosphorylation can be confirmed with a further in vitro experiments in cells such as transfected CHO cells, which permanently express human VEGF-R2 receptor (KDR), are seeded in complete culture medium (with 10% fetal calf serum=FCS) in 6-well cell-culture plates and incubated at 37° C. under 5% $CO_2$ until they show about 80% confluency. The compounds to be tested are then diluted in culture medium (without FCS, with 0.1% bovine serum albumin) and added to the cells. (Controls comprise medium without test compounds). After two hours of incubation at 37° C., recombinant VEGF is added; the final VEGF concentration is 20 ng/ml. After a further five minutes incubation at 37° C., the cells are washed twice with ice-cold PBS (phosphate-buffered saline) and immediately lysed in 100 μl lysis buffer per well. The lysates are then centrifuged to remove the cell nuclei, and the protein concentrations of the supernatants are determined using a commercial protein assay (BIORAD). The lysates can then either be immediately used or, if necessary, stored at −20° C.

A sandwich ELISA is carried out to measure the VEGF-R2 phosphorylation: a monoclonal antibody to VEGF-R2 (for example Mab 1495.12.14; prepared by H. Towbin, Novartis or comparable monoclonal antibody) is immobilized on black ELISA plates (OptiPlate™ HTRF-96 from Packard). The plates are then washed and the remaining free protein-binding sites are saturated with 3% TopBlock® (Juro, Cat. # TB232010) in phosphate buffered saline with Tween 20® (polyoxyethylen(20)sorbitane monolaurate, ICI/Uniquema) (PBST). The cell lysates (20 μg protein per well) are then incubated in these plates overnight at 4° C. together with an antiphosphotyrosine antibody coupled with alkaline phosphatase (PY20:AP from Zymed). The (plates are washed again and the) binding of the antiphosphotyrosine antibody to the captured phosphorylated receptor is then demonstrated using a luminescent AP substrate (CDP-Star, ready to use, with Emerald II; Applied Biosystems). The luminescence is measured in a Packard Top Count Microplate Scintillation Counter. The difference between the signal of the positive control (stimulated with VEGF) and that of the negative control (not stimulated with VEGF) corresponds to VEGF-induced VEGF-R2 phosphorylation (=100%). The activity of the tested substances is calculated as percent inhibition of VEGF-induced VEGF-R2 phosphorylation, wherein the concentration of substance that induces half the maximum inhibition is defined as the $IC_{50}$ (inhibitory dose for 50% inhibition). Compounds of the formula I or I* here show an $IC_{50}$ in the range of 0.0003 to 20 µM, preferably between 0.001 and 10 µM.

In analogy, VEGF-R1 inhibition can be shown as follows: The test is conducted using Flt-1 VEGF receptor tyrosine kinase. The detailed procedure is as follows: 30 µl kinase solution (10 ng of the kinase domain of Flt-1, Shibuya et al., Oncogene 5, 519-24 (1990)) in 20 mM Tris-HCl pH 7.5, 3 mM manganese dichloride ($MnCl_2$), 3 mM magnesium chloride ($MgCl_2$), 10 mM sodium vanadate, 0.25 mg/ml polyethylenglycol (PEG) 20 000, 1 mM dithiothreitol and 3 µg/ml poly(Glu, Tyr) 4:1 (Sigma, Buchs, Switzerland), 8 µM [$^{33}$P]-ATP (0.2 µCi), 1% dimethyl sulfoxide, and 0 to 100 µM of the compound of formula I or I* to be tested are incubated together for 10 min at room temperature. The reaction is then terminated by the addition of 10 µl 0.25 M ethylenediamine tetraacetate (EDTA) pH 7. Using a multichannel dispenser (LAB SYSTEMS, USA), an aliquot of 20 µl is applied to a PVDF (=polyvinyl difluoride) Immobilon P membrane (Millipore, USA), through a Millipore microtiter filter manifold and connected to a vacuum. Following complete elimination of the liquid, the membrane is washed 4 times successively in a bath containing 0.5% phosphoric acid ($H_3PO_4$) and once with ethanol, incubated for 10 min each while shaking, then mounted in a Hewlett Packard TopCount Manifold and the radioactivity measured after the addition of 10 µl Microscint® (β-scinitillation counter liquid). $IC_{50}$ values are determined by linear regression analysis of the percentages of inhibition of each compound in three conditions (as a rule 0.01, 0.1 and 1 µmol). The $IC_{50}$ values that can be found with compounds of the formula I or I* are in the range of 0.01 to 100 µM, preferably in the range from 0.01 to 50 µM.

Flt3 kinase inhibition is determined as follows: The baculovirus donor vector pFbacG01 (GIBCO) is used to generate a recombinant baculovirus expressing the amino acid region amino acids 563-993 of the cytoplasmic kinase domain of human Flt-3. The coding sequence for the cytoplasmic domain of Flt-3 is amplified by PCR from human c-DNA libraries (Clontech). The amplified DNA fragments and the pFbacG01 vector are made compatible for ligation by digestion with BamH1 and HindIII. Ligation of these DNA fragments results in the baculovirus donor plasmid Flt-3(1.1). The production of the viruses, the expression of proteins in Sf9 cells and the purification of the GST-fused proteins are performed as follows:

Production of virus: Transfer vector (pFbacG01-Flt-3) containing the Flt-3 kinase domain is transfected into the DH10Bac cell line (GIBCO) and the transfected cells are plated on selective agar plates. Colonies without insertion of the fusion sequence into the viral genome (carried by the bacteria) are blue. Single white colonies are picked and viral DNA (bacmid) is isolated from the bacteria by standard plasmid purification procedures. Sf9 or Sf21 cells (American Type Culture Collection) are then transfected in flasks with the viral DNA using Cellfectin reagent.

Determination of small scale protein expression in Sf9 cells: Virus containing media is collected from the transfected cell culture and used for infection to increase its titre. Virus containing media obtained after two rounds of infection is used for large-scale protein expression. For large-scale protein expression 100 $cm^2$ round tissue culture plates are seeded with $5\times10^7$ cells/plate and infected with 1 mL of virus-containing media (approx. 5 MOIs). After 3 days the cells are scraped off the plate and centrifuged at 500 rpm for 5 min. Cell pellets from 10-20, 100 $cm^2$ plates, are resuspended in 50 mL of ice-cold lysis buffer (25 mM Tris-HCl, pH 7.5, 2 mM EDTA, 1% NP-40, 1 mM DTT, 1 mM PMSF). The cells are stirred on ice for 15 min and then centrifuged at 5000 rpms for 20 min.

Purification of GST-tagged proteins: The centrifuged cell lysate is loaded onto a 2 mL glutathione-sepharose column (Pharmacia) and washed three times with 10 mL of 25 mM Tris-HCl, pH 7.5, 2 mM EDTA, 1 mM DTT, 200 mM NaCl. The GST-tagged protein is then eluted by 10 applications (1 mL each) of 25 mM Tris-HCl, pH 7.5, 10 mM reduced-glutathione, 100 mM NaCl, 1 mM DTT, 10% Glycerol and stored at −70° C.

Measurement of enzyme activity: Tyrosine protein kinase assays with purified GST-Flt-3 are carried out in a final volume of 30 µL containing 200-1800 ng of enzyme protein (depending on the specific activity), 20 mM Tris-HCl, pH 7.6, 3 mM $MnCl_2$, 3 mM $MgCl_2$, 1 mM DTT, 10 µM $Na_3VO_4$, 3 µg/mL poly(Glu,Tyr) 4:1, 1% DMSO, 8.0 µM ATP and 0.1 µCi [$\gamma^{33}$P] ATP). The activity is assayed in the presence or absence of inhibitors, by measuring the incorporation of $^{33}$P from [$\gamma^{33}$P] ATP into the poly(Glu,Tyr) substrate. The assay (30 µL) is carried out in 96-well plates at ambient temperature for 20 min under conditions described below and terminated by the addition of 20 µL of 125 mM EDTA. Subsequently, 40 µL of the reaction mixture is transferred onto Immobilon-PVDF membrane (Millipore, Bedford, Mass., USA) previously soaked for 5 min with methanol, rinsed with water, then soaked for 5 min with 0.5% $H_3PO_4$ and mounted on vacuum manifold with disconnected vacuum source. After spotting all samples, vacuum is connected and each well rinsed with 200 µL 0.5% $H_3PO_4$. Membranes are removed and washed 4× on a shaker with 1.0% $H_3PO_4$, once with ethanol. Membranes are counted after drying at ambient temperature, mounting in Packard TopCount 96-well frame, and addition of 10 µL/well of Microscint™ (Packard). $IC_{50}$ values are calculated by linear regression analysis of the percentage inhibition of each compound in duplicate, at four concentrations (usually 0.01, 0.1, 1 and 10 µM). One unit of protein kinase activity is defined as 1 mmole of $^{33}$P ATP transferred from [$\gamma^{33}$P] ATP to the substrate protein per minute per mg of protein at 37° C. The compounds of the formula I or I* here show $IC_{50}$ values in the range between 0.005 and 20 µM, preferably between 0.01 and 10 µM.

Bcr-Abl inhibition can be determined by a capture ELISA as follows: The murine myeloid progenitor cell line 32Dcl3 transfected with the p210 Bcr-Abl expression vector pGDp210Bcr/Abl (32D-bcr/abl) is obtained from J Griffin (Bazzoni et al., J. Clin Invest. 98, 521-8 (1996); Zhao et al., Blood 90, 4687-9 (1997)). The cells express the fusion bcr-abl protein with a constitutively active abl kinase and proliferate growth factor-independent. The cells are expanded in RPMI 1640 (AMIMED; cat# 1-41F01), 10% fetal calf serum, 2 mM glutamine (Gibco) ("complete medium"), and a working stock is prepared by freezing aliquots of 2×10$^6$ cells per vial in freezing medium (95% fetal calf serum, 5% dimethylsulfoxide (SIGMA, D-2650). After thawing, the cells are used during maximally 10-12 passages for the experiments. The antibody anti-abl SH3 domain cat. # 06-466 from Upstate Biotechnology is used for the ELISA. For detection of bcr-abl phosphorylation, the anti-phosphotyrosine antibody Ab PY20, labelled with alkaline phosphatase (PY10(AP)) from ZYMED (cat. # 03-7722) is used. As comparison and reference compound, (N-{5-[4-(4-methyl-piperazino-methyl)-benzoylamido]-2-methylphenyl}-4-(3-pyridyl)-2-pyrimidine-amine, in the form of the methane sulfonate (monomesylate) salt (ST1571) (marketed as Gleevec® or Glivec®, Novartis), is used. A stock solution of 10 mM is prepared in DMSO and stored at −20° C. For the cellular assays, the stock solution is diluted in complete medium in two steps (1:100 and 1:10) to yield a starting concentration of 10 μM followed by preparation of serial three-fold dilutions in complete medium. No solubility problems are encountered using this procedure. The test compounds of formula I or I* are treated analogously. For the assay, 200'000 32D-bcr/abl cells in 50 μl are seeded per well in 96 well round bottom tissue culture plates. 50 μl per well of serial threefold dilutions of the test compound are added to the cells in triplicates. The final concentration of the test compound range e.g. from 5 μM down to 0.01 μM. Untreated cells are used as control. The compound is incubated together with the cells for 90 min at 37° C., 5% CO$_2$, followed by centrifugation of the tissue culture plates at 1300 rpm (Beckman GPR centrifuge) and removal of the supernatants by careful aspiration taking care not to remove any of the pelleted cells. The cell pellets are lysed by addition of 150 μl lysis buffer (50 mM Tris/HCl, pH 7.4, 150 mM sodium chloride, 5 mM EDTA, 1 mM EGTA, 1% NP-40 (non-ionic detergent, Roche Diagnostics GmbH, Mannheim, Germany), 2 mM sodium ortho-vanadate, 1 mM phenylmethyl sulfonylfluoride, 50 μg/ml aprotinin and 80 μg/ml leupeptin) and either used Immediately for the ELISA or stored frozen at −20° C. until usage.

The anti-abl SH3 domain antibody is coated at 200 ng in 50 μl PBS per well to black ELISA plates (Packard HTRF-96 black plates; 6005207) overnight at 4° C. After washing 3× with 200 μl/well PBS containing 0.05% Tween 20 (PBST) and 0.5% TopBlock (Juro, Cat. # TB 232010), residual protein binding sites are blocked with 200 μl/well PBST, 3% TopBlock for 4 h at room temperature, followed by incubation with 50 μl lysates of untreated or test compound-treated cells (20 μg total protein per well) for 3-4 h at 4° C. After 3 x washing, 50 μl/well PY20(AP) (Zymed) diluted to 0.5 μg/ml in blocking buffer is added and incubated over-night (4 IC). For all incubation steps, the plates are covered with plate sealers (Costar, cat. # 3095). Finally, the plates are washed another three times with washing buffer and once with deionized water before addition of 90 μl/well of the AP substrate CPDStar RTU with Emerald II. The plates now sealed with Packard Top Seal™-A plate sealers (cat. # 6005185) are incubated for 45 min at room temperature in the dark and luminescence is quantified by measuring counts per second (CPS) with a Packard Top Count Microplate Scintillation Counter (Top Count). For the final optimized version of the ELISA, 50 μl of the lysates of the cells grown, treated and lysed in 96 well tissue culture plates, are transferred directyl from these plates to the ELISA plates that are precoated with 50 ng/well of the rabbit poylclonal ant-abl-SH3 domain AB 06-466 from Upstate. The concentration of the anti-phosphotyrosine AB PY20 (AP) can be reduced to 0.2 μg/ml. Washing, blocking and incubation with the luminescent substrate are as above. The quantification is achieved as follows: The difference between the ELISA readout (CPS) obtained for with the lysates of the untreated 32D-bcr/abl cells and the readout for the assay background (all components, but without cell lysate) is calculated and taken as 100% reflecting the constitutively phosphorylated bcr-abl protein present in these cells. The activity of the compound in the bcr-abl kinase activity is expressed as percent reduction of the bcr-abl phosphorylation. The values for the IC$_{50}$ are determined from the dose response curves by graphical inter- or extrapolation. The compounds of the formula I or I* here preferably show IC$_{50}$ values in the range from 20 nM to 200 μM.

In addition to or instead of inhibiting the above-mentioned protein kinases, the compounds of formula I or I* also inhibit other tyrosine protein kinases that are involved in the signal transmission mediated by trophic factors, for example kinases of the src kinase family, such as especially the c-Src kinase, members of the PDGF receptor tyrosine protein kinase family, for example the PDGF receptor (PDGF-R), c-Kit, VEGF-R and/or FGF-R; all of which play a part in growth regulation and transformation in animal, especially mammal cells, including human cells. An appropriate assay is described in Andrejauskas-Buchdunger et al., Cancer Res. 52, 5353-8 (1992).

The diaryl urea derivatives useful according to the invention, especially compounds of formula I or I*, that inhibit the protein kinase activities mentioned, especially tyrosine protein kinases mentioned above and below, can therefore be used in the treatment of protein kinase dependent diseases. Protein kinase dependent diseases are especially proliferative diseases, preferably benign or especially malignant tumours (for example carcinoma of the kidneys, liver, adrenal glands, bladder, breast, stomach, ovaries, colon, rectum, prostate, pancreas, lungs, vagina or thyroid, sarcoma, glioblastomas and numerous tumours of the neck and head, as well as leukemias). They are able to bring about the regression of tumours and to prevent the formation of tumour metastases and the growth of (also micro) metastases. In addition they can be used in epidermal hyperproliferation (e.g. psoriasis), in prostate hyperplasia, and in the treatment of neoplasias, especially of epithelial character, for example mammary carcinoma. It is also possible to use the compounds of formula I or I* in the treatment of diseases of the immune system insofar as several or, especially, individual tyrosine protein kinases are involved; furthermore, the compounds of formula I or I* can be used also in the treatment of diseases of the central or peripheral nervous system where signal transmission by at least one tyrosine protein kinase, especially selected from those mentioned specifically, is involved.

The p21ras oncogene is a major contributor to the development and progression of human solid cancers and is mutated in 30% of all human cancers. The endogenous GTPase activity, if alleviated in ras mutated cancer cells, mediates constitutive growth signals to down-stream effectors such as raf kinase. Inhibiting the raf kinase signalling pathway can therefore be used for inhibiting the effect of active ras. The diaryl urea derivatives useful according to the present invention, especially the compounds of formula I or I*, as ras inhibitors are thus especially appropriate for the therapy of diseases related to ras overexpression or overactivity.

Vascular endothelial growth factor receptor-2 (VEGF-R2; KDR) is selectively expressed on the primary vascular endothelium and is essential for normal vascular development. In order to grow beyond minimal size, tumors must generate new vascular supply. Anglogenesis, or the sprouting of new blood vessels, is a central process in the growth of solid tumors. For many cancers, the extent of vascularization of a tumor is a negative prognostic indicator signifying aggressive disease and increased potential for metastasis. Recent efforts to understand the molecular basis of tumor-associated angiogenesis have identified several potential therapeutic targets, including the receptor tyrosine kinases for the angiogenic factor vascular endothelial growth factor (VEGF) (see Zeng et al., J. Biol. Chem. 276(35), 32714-32719 (2001)). The diaryl urea derivatives useful according to the present invention, especially the compounds of formula I or I*, as KDR inhibitors are thus especially appropriate for the therapy of diseases related to VEGF receptor tyrosine kinase overexpression. Among these diseases, especially retinopathies, age-related macula degeneration, psoriasis, haemangioblastoma, haemangloma, arteriosclerosis, inflammatory diseases, such as rheumatoid or rheumatic inflammatory diseases, especially arthritis, such as rheumatoid arthritis, or other chronic inflammatory disorders, such as chronic asthma, arterial or post-transplantational atherosclerosis, endometriosis, and especially neoplastic diseases, for example so-called solid tumors (especially cancers of the gastrointestinal tract, the pancreas, breast, stomach, cervix, bladder, kidney, prostate, ovaries, endometrium, lung, brain, melanoma, Kaposi's sarcoma, squamous cell carcinoma of heand and neck, malignant pleural mesotherioma, lymphoma or multiple myeloma) and liquid tumors (e.g. leukemias) are especially important.

Flt3 (FMD-like tyrosine kinase) is especially expressed in hematopoietic progenitor cells and in progenitors of the lymphoid and myeloid series. Aberrant expression of the Flt3 gene has been documented in both adult and childhood leukemias including AML (acute myelogenous leukemia), AML with trilineage myelodysplasia (AML/TMDS), ALL (acute lymphoblastic leukemia), CML (chronic myelogenous leukemia) and myelodysplastic syndrome (MDS), which are therefore the preferred diseases to be treated with compounds of the formula I or I*. Activating mutations in Flt3 have been found in approximately 25 to 30% of patients with AML. Thus there is accumulating evidence for the role of Flt3 in human leukemias, and the diaryl urea derivatives useful according to the invention, especially the compounds of the formula I or I*, as Flt3 inhibitors are especially of use in the therapy of this type of diseases (see Tse et al., Leukemia 15(7), 1001-1010 (2001); Tomoki et al., Cancer Chemother. Pharmacol. 48 (Suppl. 1), S27-S30 (2001); Birkenkamp et al., Leukemia 15(12), 1923-1921 (2001); Kelly et al., Neoplasia 99(1), 310-318 (2002)).

In chronic myelogeous leukemia (CML), a reciprocally balanced chromosomal translocation in hematopoietic stem cells (HSCs) produces the BCR-ABL hybrid gene. The latter encodes the oncogenic Bcr-Abl fusion protein. Whereas ABL encodes a tightly regulated protein tyrosine kinase, which plays a fundamental role in regulating cell proliferation, adherence and apoptosis, the BCR-ABL fusion gene encodes as constitutively activated kinase, which transforms HSCs to produce a phenotype exhibiting deregulated clonal proliferation, reduced capacity to adhere to the bone marrow stroma and a reduces apoptotic response to mutagenic stimuli, which enable it to accumulate progressively more malignant transformations. The resulting granulocytes fail to develop into mature lymphocytes and are released into the circulation, leading to a deficiency in the mature cells and increased susceptibility to infection. ATP-competitive inhibitors of Bcr-Abl have been described which prevent the kinase from activating mitogenic and anti-apoptotic pathways (e.g. P-3 kinase and STAT5), leading to the death of the BCR-ABL phenotype cells and thereby providing an effective therapy against CML. The diaryl urea derivatives useful according to the present invention, especially the compounds of the formula I or I*, as Bcr-Abl inhibitors are thus especially appropriate for the therapy of diseases related to its overexpression, especially leukemias, such as leukemias, e.g. CML or ALL.

Compounds of the formula I or I*, in view of their activity as PDGF receptor inhibitors, are also especially appropriate in the treatment of prolifeative diseases, especially small lung cancer, atherosclerosis, thrombosis, psoriasis, scleroderma or fibrosis.

There are also experiments to demonstrate the antitumor activity of compounds of the formula I or I* in vivo: The in vivo antitumor activity is tested, for example, using breast carcinoma cell lines, such as the human estrogen dependent breast carcinoma MCF-7 (ATCC: HTB22) or ZR-75-1 (ATCC: CRL1500), or the estrogen-independen breast carcinomas MDA-MB468 (ATCC: HTB132) or MDA-MB231 (ATCC: HTB26); colon carcinoma cell lines, such as the colon-carcinoma Colo 205 (ATCC: CCL222); glioblastoma cell lines, such as the glioblastomas U-87MG (ATCC: HTB14) or U-373MG (ATCC: HTB17); lung carcinoma cell lines, such as the "small cell lung carcinomas" NCI—H69 (ATCC: HTB119) or NCI—H209 (ATCC: HTB172), or the lung carcinoma NCI—H596 (ATCC: HTB178); skin tumor cell lines, such as the melanomas Hs294T (ATCC: HTB140) or A375 (ATCC: CRL1619); tumor cell lines from the genitourinry systems, such as the ovarial carcinoma NIH-Ovcar3 (ATCC: HTB161), as well as the prostate carcinomas DU145 (ATCC: HTB81) or PC-3 (ATCC: CRL1435), or the bladder carcinoma T24 (ATCC: HTB4); epithelial carcinomas, such as the epithelial carcinoma KB31; or (especially with regard to leukemias) K562 cells (American Type Culture Collection, Mannassas, Va.) or human CFU-G cells (CFU-G stands for granulocyte colony forming unit, and it represents an early but commited granulocyte forming precursor cell that circulates in the blood stream or bone marrow) each of which is transplanted into female or male Balb/c nude mice. Other cell lines include leukemic cell lines such as K-562, SUPB15, MEG01, Ku812F, MOLM-13, BaF3, CEM/0, JURKAT/0 or U87MG.

Tumors are obtained after subcutaneous injection of the respective cells (minimum $2 \times 10^6$ cells in 100 ml phosphate buffered physiological saline) into the carrier mice (e.g. 48 mice per cell line). The resulting tumors are passed serially through at least three subsequent transplantations before treatment is started. Tumor fragments (about 25 mg each) are injected s.c. into the left flank of the animals using a 13-gauge Trocar needle under Forene narcosis (Abbott, Switzerland) for implantation. Mice transplanted with estrogen-dependent tumor are, in addition, supplied with an estrogen pellet (1.0 cm of a tube with a quality appropriate for medical purposes, Dow Chemicals, with 5 mg estradiole, Sigma). The treatment is started routinely (that is at low or intermediate tumor burden), as soon as the tumor has reached an average size of 100 $mm^3$. Tumor growth is determined once, twice or thrice weekly (depending on tumor growth of the cell line) and 24 h after the last treatment by measurement of the perpendicular diameter. In case of tumors, tumor volumes are determined according to the formula $L \times D \times p/6$ (see Evans, B. D., Smith, I. E., Shorthouse, A. J. and Millar, J. J., Brit. J. Cancer, 45: 466-468, 1982). The antitumor activity is expressed as T/C% (average increase of the tumor volume of treated animals divided by the average increase of tumor volume in control animals multiplied by 100). Tumor regression (%) represents the smallest mean tumor volume compared to the mean tumor volume at the beginning of the treatment. Each animal in which the tumor reaches a diameter of more than 1,5 to 2 $cm^3$ is sacrificed. Leukemia burden is assessed by examining both peripheral white blood count and weight of spleen and thymus in animals tumored with leukemia cell lines.

An exemplary (though not limiting) schedule for administration of a diaryl urea derivative, especially of formula I or I*, or a salt thereof, is daily administration, with preferably 1 to 3 daily dosages for a longer time, possibly until the disease is cured or, if only palliative treatment is achieved, for as long as required; alternatively, treatment e.g. for 5 days, and/or administration at days 1, 4 and 9, with eventual repetition after a certain time without treatment is possible. Alternatively, treatment several times a day (e.g. 2 to 5 times) or treatment by continuous administration (e.g. infusion), e.g. at the time points indicated in the last sentence, are possible. Generally, administration is orally or parenterally, preferably orally. The test compounds are preferably diluted in water or in sterile 0.9% saline.

All human tumor cell lines are obtained from the American Type Culture Collection (ATCC, Rockville, Md., USA) if not indicated otherwise and are cultivated in the suggested media with the corresponding additives (ATCC culture conditions), if not mentioned otherwise. The c-sis- and v-sis- transformed BALB/c 3T3 cells are obtained from Dr. C. Stiles (Dana Farber Cancer Institute, Boston, Mass., USA). They are cultured in "Dulbecco's modified Eagle's medium" (DMEM), that is supplemented with 10% calf serum and Hygromycin B in a concentration of 0.2 mg/ml or G418 in a concentration of 0.5 mg/mi. BALB/c AMuLV A.6R.1 cells (ATCC) are kept in DMEM, supplemented with 10% fetal calf serum.

The pharmacological activity of a diaryl urea derivative of the formula I or I* may, for example, be demonstrated in a clinical study or in a test procedure as essentially described hereinafter.

Suitable clinical studies are, for example, open label non-randomized, dose escalation studies in patients with one of the tumor diseases mentioned above. The beneficial effects on proliferative diseases can be determined directly through the results of these studies or by changes in the study design which are known as such to a person skilled in the art. The efficacy of the treatment can be determined in such studies, e.g., in case of tumors after 18 or 24 weeks by radiologic evaluation of the tumors every 6 weeks, in case of a leukaemia e.g. by determination of the count of aberrant white blood cells, and by staining mononuclear cells and/or by means of determining minimum residual disease (MRD) e.g. by FACS-LPC MRD or PCR.

Alternatively, a placebo-controlled, double blind study can be used in order to prove the benefits of the diaryl urea derivatives useful according to the invention, especially the compounds of the formula I or I*, mentioned herein.

The diaryl urea derivatives useful according to the invention, especially the compounds of the formula I, preferably the novel compounds of the formula I, can be prepared according to methods that are known in the art, especially whereby (a) for the synthesis of a compound of the formula I wherein X NR if p is 0, or if p is 2 or 3, X is nitrogen which together with $(CH_2)_p$ and the bonds represented in dotted (interrupted) lines (including the atoms to which they are bound) forms a ring, and G, Z, A, A', $Y_1$, $Y_2$, R, $R_1$, $R_2$, $R_3$, $R_4$, $R_5$, m, n, p and r have the meanings given under formula I, an amino compound of the formula II

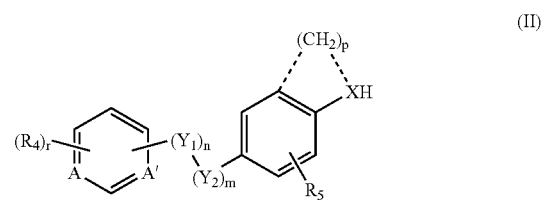

wherein X is as just defined and $R_4$, $R_5$, A, A', $Y_1$, $Y_2$, m, n, p, r and the bonds represented in dotted (interrupted) lines have the meanings given under formula I, is reacted with an isocyanate of the formula III

O=C=N-G-Z (III)

wherein G, Z, $R_1$, $R_2$ and $R_3$ are as defined for compounds of the formula I, or (b) for the synthesis of a compound of the formula I wherein m is 0 (and thus $Y_2$ is missing), n is 1, $Y_1$ is O and G, Z, X, $R_1$, $R_2$, $R_3$, $R_4$, $R_5$, A, A', p and r are as defined for compounds of the formula I, a hydroxy compound of the formula IV

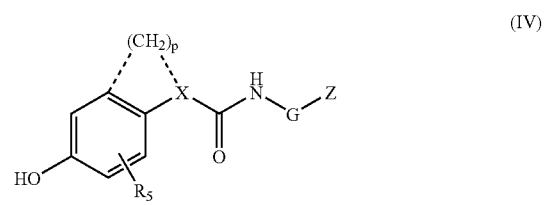

wherein G, Z, X, $R_1$, $R_2$, $R_3$, $R_5$, p and the bonds represented in dotted (interrupted) lines have the meanings given under formula I, is etherified with a halo compound of the formula V

wherein $R_4$ and r have the meanings as defined for a compound of formula I and Hal is halo, especially chloro, or (c) for the synthesis of a compound of the formula I wherein p is zero, X is CHK, especially $CH_2$, and G, Z, K, $Y_1$, $Y_2$, $R_1$, $R_2$, $R_3$, $R_4$, $R_5$, A', m, n and r have the meanings given for a compound of the formula I, a carboxyl compound of the formula VI

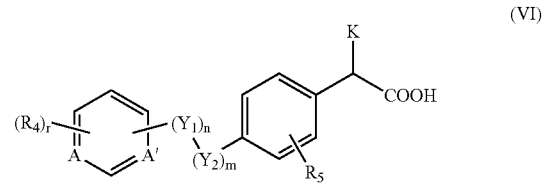

wherein K is lower alkyl or preferably hydrogen and A, A', $Y_1$, $Y_2$, $R_4$, $R_5$, m, n and r have the meanings given for compounds of the formula I, or a reactive derivative thereof, is condensed with an amino compound of the formula VII $$H_2N-G-Z \quad (VII)$$

wherein G, Z, $R_1$, $R_2$ and $R_3$ are as defined for compounds of the formula I, or (d) for the synthesis of a compound of the formula I wherein X is NH, p is zero and G, Z, A, A', $Y_1$, $Y_2$, $R_1$, $R_2$, $R_3$, $R_4$, $R_5$, m, n and r have the meanings given under formula I, an isocyanate of the formula VIII

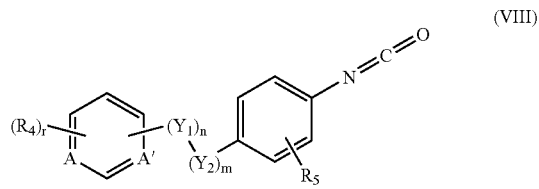

(VIII)

wherein $R_4$, A, A', $Y_1$, $Y_2$, m, n, r and $R_5$ are as defined for compounds of the formula I, is reacted with an amino compound of the formula IX $$H_2N-G-Z \quad (IX)$$

wherein G, Z, $R_1$, $R_2$ and $R_3$ are as defined for compounds of the formula I, and, if desired, after reaction (a), (b), (c) or (d) an obtainable compound of formula I is transformed into a different compound of formula I, a salt of an obtainable compound of formula I is transformed into the free compound or a different salt, or an obtainable free compound of formula I is transformed into a salt; and/or an obtainable mixture of isomers of compounds of formula I is separated into the individual isomers;

where for all reactions mentioned functional groups in the starting materials that shall not take part in the reaction are, if required, present in protected form by readily removable protecting groups, and any protecting groups are subsequently removed.

The following reaction conditions are preferred, respectively:

Within the scope of this text, only a readily removable group that is not a constituent of the particular desired end product of formula I is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/I, Georg Thieme Verlag, Stuttgart 1974, in H.-D. Jakubke and H. Jeschkeit, "Aminosäuren, Peptide, Proteine" (*Amino acids, Peptides, Proteins*), Verlag Chemie, Weinheim, Deerfield Beach, and Basel 1982, and in Jochen Lehmann, "Chemie der Kohlenhydrate: Monosaccharide und Derivate" (*Chemistry of Carbohydrates: Monosaccharides and Derivatives*), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

A protecting group for an OH group, namely a tri-lower alkylsilyl group, such as tert-butyl-di-methylsilyl, can, for example, be removed in the presence of fluoride anions, e.g. by reaction with an appropriate ammonium fluoride, such as tert-butylammonium fluoride, or preferably with HF in the presence of a nitrogen base, especially pyridine, in an aprotic solvent, especially an ether, such as tetrahydrofurane, a nitrile, such as acetonitrile, or a mixture thereof, at temperatures between 0 and 50° C., e.g. at room temperature.

Reactions (a) and (d) preferably take place in an appropriate solvent, e.g. an ether, such as tetrahydrofurane (other solvents, such as toluene, may also be present, especially in low amounts), preferably at temperatures in the range from 0 to 50° C., e.g. at room temperature.

Reaction (b), that is, the formation of ethers, preferably takes place in the presence of a metal alcoholate, especially an alkali metal alcoholate, such as potassium tert-butylate, in an appropriate solvent, such as N,N'-dimethypropyleneura or a di-lower alkyl-lower alkanoyl-amide, such as dimethylformamide, or mixtures thereof, at preferred temperatures between 50° C. and the reflux temperature of the reaction mixture, for example at 100° C.

The ether formation can also take place under the conditions of the Hartwig-Buchwald type etherification reactions (see e.g. Mann et al., J. Am. Chem. Soc. 121(13), 3224-5 (1999), or Aranyos et al., J. Am. Chem. Soc. 121, 4369-78 (1999)).

Reaction (c), that is, the formation of amide bonds, preferably takes place under standard conditions for the formation of peptide bonds (condensation reaction). In a reactive derivative of a compound of the formula I, the carboxyl group is either functionalized as activated ester (reactive form). The reactive carboxyl groups are, however, preferably synthesized in situ (for example making use of reagents customary in peptide chemistry, e.g. for the preparation of 1-hydroxybenzotriazole, succinimide- or N-hydroxysuccinimide esters, or in situ derivatisation with condensing agents, e.g. with carbodiimides, such as dicyclohexylcarbodiimide, with carbonylimidazole, with N-[(dimethylamino)-1H-1,2,3-triazolo[4,5-b]pyridin-1-ylmethylene]-N-methylmethanaminium-hexafluorophosphate-N-oxide (HATU); with 2-(1H-benzotriazol-1-yl)-1,1,3,3-tetramethyluroniumtetrafluoroborat (HBTU), with 2-(pyridon-1-yl)-1,1,3,3-tetramethyluroniumtetrafluoroborate (TPTU); or benzotriazol-1-yl-oxy-tris (dimethylamino)-phosphoniumhexafluorophosphate (BOP), or similar reagents). The condensation reaction preferably takes place in the presence of a condensing agent, especially HBTU, in an aprotic polar solvent, preferably a N,N-di-(lower alkyl)-lower alkanoylamide, such as dimethylformamide, at preferred temperatures in the range from 0 to 50° C., e.g. at room temperature.

Compounds of formula I can be transformed into different compounds of formula I.

Especially, the following transformations are of interest:

In compounds of the formula I wherein A and/or A' is N, a N may be oxidised to an N→O by oxidation in the presence of a peroxide, especially a peroxybenzoic acid derivative, such as 3-chloroperoxybenzoic acid, in the presence of a base, e.g. an alkali metal carbonate, such as sodium carbonate, and in an appropriate solvent, e.g. a halogenated hydrocarbon, such as chloroform or methylene chloride.

In compounds of the formula I where a lower alkoxy, especially methoxy, substituent $R_4$ is present, this substituent may be transformed into the corresponding hydroxy substituent $R_4$, for example in an alcohol, such as ethanol, in the presence of an acid, such as HCl, preferably at elevated temperatures, e.g. under reflux, or in the presence of a tri-lower alkylsilaneiodide, especially $Me_3Si$—I, in an appropriate solvent, e.g. a chlorinated hydrocarbon, such as chloroform or methylene chloride, at elevated temperatures, for example at 40 to 60° C. The corresponding hydroxy group may then, by way of tautomerism transferring the hydrogen to an adjacent carbon atom with a double bond, form an oxo group, thus leading, if only one of A and A' is N, to a pyridin-on-yl moeity, if both are N, to a pyrimidin-on-yl moiety.

Salts of compounds of formula I having at least one salt-forming group may be prepared in a manner known per se. For example, salts of compounds of formula I having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of formula I are obtained in customary manner, e.g. by treating the compounds with an acid or a suitable anion exchange reagent. Internal salts of compounds of formula I containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-)crystallization, and the like.

Starting Materials

Within the following description of the synthesis of starting materials G, Z, X, $Y_1$, $Y_2$, $R_1$, $R_2$, $R_3$, $R_4$, $R_5$, A, A', m, n, p and r have the meanings indicated for compounds of the formula I, if not indicated otherwise. The starting materials of the formulae II-IX are known, commercially avaiable and/or can be prepared according to methods known in the art; in particular, they can be prepared using processes as described in the Examples.

In the subsequent description of some preferred synthesis methods for preferred starting materials, functional groups that shall not take part in the respective reactions can be present in protected form and the protective groups can be removed at appropriate stages; for protecting groups, there introduction and removal, reference is made to the standard text-books and methods already mentioned above.

A compound of the formula II, for example, wherein $Y_1$ is O and $Y_2$ is absent or $CH_2$, n is 1 and m is 0 or 1, X is NH and p is zero is preferably prepared by reacting a hydroxy compound of the formula X

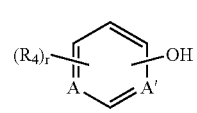

(X)

wherein A, A', $R_4$ and r have the meanings indicated for formula I, preferably only one of A and A' is N, the other CH, and the OH is in para-position to the N, is reacted with a compound of the formula XI

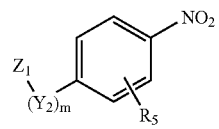

(XI)

wherein $R_5$ is as defined for formula I, $Z_1$ is halo, especially bromo or iodo, and $Y_2$ is absent (m=0) or $CH_2$ (m=1), in the presence of a base, especially an alkali metal carbonate, such as potassium carbonate, and of CuBr or CuI, if required in a solvent, resulting in a compound of the formula XII,

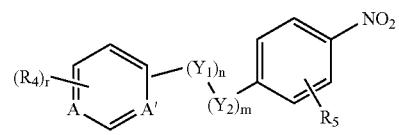

(XII)

wherein A, A', $R_4$, $R_5$, $Y_1$, $Y_2$, n, m and r have the meaning given under formulae X and XI, which is then reduced with hydogen in the presence of an appropriate catalyst, especially Raney-Co or more preferably Raney-Ni, in an appropriate solvent, e.g. an alcohol, such as methanol, to yield the corresponding amino compound (X is NH, p is zero) of the formula II.

Alternatively, for the synthesis of a compound of the formula II wherein all moieties have the meanings given under formulae X, XI and XII, except that in addition X is NR wherein R has the meanings given for compounds of the formula I, a compound of the formula XIII

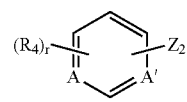

(XIII)

wherein $R_4$ and r have the meanings indicated for formula I, $Z_2$ is halo, especially chloro, A is N or CH, A' is N and $Z_2$ is preferably in p-position to N as A or A', is reacted with a compound of the formula XIV

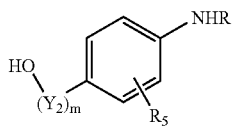

(XIV)

wherein R has the meanings indicated for formula I, $Y_2$ and m as well as $R_5$ are as defined under formula XI (preferably, $Y_2$ is absent, m=0), in the presence of an alkali metal alcoholate, such as potassium tert-butylate, in an appropriate solvent, e.g. a N,N-di-lower alkyl-lower alkanoylamide, such as dimethylformamide, and/or N,N'-dimethylpropyleneurea, to yield the corresponding compound of the formula II. Still alternatively, a compound of the formula II wherein each of A and A' is nitrogen, X is NH and the remaining moieties are as defined for compounds of the formula II resulting from a compound of the formula XII, can be obtained by reacting a compound of the formula XIII wherein A and A' are N and $R_4$, r and $Z_2$ are as defined under formula XIII, is reacted with a compound of the formula XV

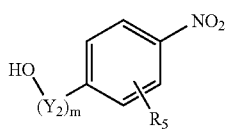

(XV)

wherein $Y_2$, m and $R_5$ have the meanings given for compounds of the formula XIV, in the presence of a base, especially an alkali metal hydroxide, such as sodium hydroxide, in an aqueous solvent, e.g. water in mixture with a ketone, such as acetone, resulting in a compound of the formula XII wherein A is N, A' is N, Y, is O, n is 1, $Y_2$ is $CH_2$ (m=1) or absent (m=0), which is then reduced as described for a compound of the formula XII to the corresponding amino compound of the formula II.

Compounds of the formula II wherein X is nitrogen and p is 2 or 3, $Y_1$ is O (n=1) and $Y_2$ is absent (m=0) or $CH_2$ (m=1), while A, A', $R_4$, $R_5$ and r have the meanings given under formula I, is preferably prepared by reacting a compound of the formula XVI

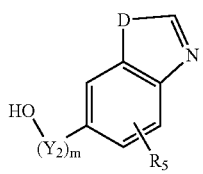

(XVI)

wherein D is $CH_2$ or CH=CH and $Y_2$, m and $R_5$ are as just defined, with a compound of the formula XIII as defined above in the presence of an alkali metal alcoholate, such as potassium tert-butylate, in an appropriate solvent, e.g. a N,N-di-lower alkyl-lower alkanoylamide, such as dimethylformamide, and/or N,N'-dimethylpropyleneurea, to yield the corresponding compound of the formula XVII

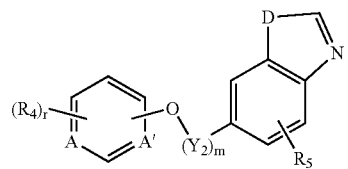

(XVII)

wherein A, A', $R_4$, $R_5$, r, $Y_2$, m and D are as just defined. The double bond(s) in the ring with D are then reduced, preferably with an appropriate complex hydride, especially with sodium cyanoborhhydride ($NaBH_3CN$) in an organic acid, especially acetic acid, to the corresponding compound of the formula II. Alternatively, first reduction of the double bond(s) in the ring with D and then the reaction with a compound of the formula XIII can lead to the compound of formula II.

A compound of the formula III or VIII can, for example, be synthesized from the corresponding amine compound (with —$NH_2$ instead of the —N=C=O), e.g. by reaction with phosgene or triphosgene in an appropriate tertiary nitrogen base, such as pyridine.

Compounds of the formula IV are known in the art or can be prepared according to methods that are known in the art; for example, compounds of the formula IV in which X is CHK, wherein K is lower alkyl or hydrogen, and p is zero can be obtained by condensation of a compound of the formula XVIII

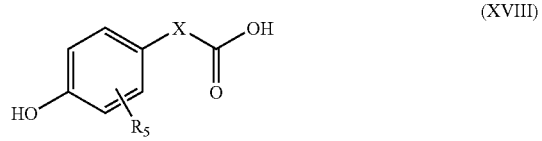

(XVIII)

wherein p and X are as just defined, or a reactive derivative thereof, with a compound of the formula VII as defined above; the reactive derivatives and the reaction conditions correspond to those mentioned above for the reaction of a compound of the formula VI with a compound of the formula VII. The result is the corresponding compound of the formula IV.

Compounds of the formula V, VI and VII are known, can be prepared according to methods that are known in the art or analogous to those described above and/or are commercially available.

Other starting materials are either known in the art, can be prepared according to methods that are known in the art, e.g. analogously to the methods described hereinabove or in the examples, and/or are commercially available. Starting materials are also available according to or analogously to methods described in WO 00/42012, WO 00/41698, WO 99/32436 and WO 99/32463.

The present invention relates also to novel starting materials and/or intermediates and to processes for their preparation. The starting materials used and the reaction conditions selected are preferably those that result in the compounds described as being preferred.

General Process Conditions

The following applies in general to all processes mentioned hereinbefore and hereinafter, while reaction conditions specifically mentioned above or below are preferred:

All the above-mentioned process steps can be carried out under reaction conditions that are known per se, preferably those mentioned specifically, in the absence or, customarily, in the presence of solvents or diluents, preferably solvents or diluents that are inert towards the re-agents used and dissolve them, in the absence or presence of catalysts, condensation or neutralising agents, for example ion exchangers, such as cation exchangers, e.g. in the H⁺ form, depending on the nature of the reaction and/or of the reactants at reduced, normal or elevated temperature, for example in a temperature range of from about −100° C. to about 190° C., preferably from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofurane or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as intermediate at any stage of the process is used as starting material and the remaining process steps are carried out, or in which a starting material is formed under the reaction conditions or is used in the form of a derivative, for example in protected form or in the form of a salt, or a compound obtainable by the process according to the invention is produced under the process conditions and processed further in situ. In the process of the present invention those starting materials are preferably used which result in new compounds of formula I described at the beginning as being especially valuable. Special preference is given to reaction conditions that are identical or analogous to those mentioned in the Examples.

Preferred Embodiments According to the Invention

In the following preferred embodiments, general expression can be replaced by the corresponding more specific definitions provided above and below, thus yielding stronger preferred embodiments of the invention.

Preferred is the USE of compounds of the formula I or I*, tautomers thereof or pharmaceutically acceptable salts thereof, where the tyrosine protein kinase dependent disease to be treated is a proliferative disease depending on any one or more of the following tyrosine protein kinases: ras, Abl, VEGF receptor tyrosine kinase, Flt3, and/or Bcr-Abl activity.

Preferred is further the USE of a compound of the formula I or a tautomer thereof, or pharmaceutically acceptable salts thereof, where, in the compound of the formula I G is either not present, lower alkylene, especially methylene or ethylene, or $C_3$-$C_5$cycloalkylene, especially cyclopropylene, and Z is a radical of the formula Ia, or G is not present and Z is a radical of the formula Ib;

A is CH or N and A' is N or N→O;

n is 1;

m is 0 or 1;

p is 0, 2 or 3;

r is 0 or 1;

X is NR if p is 0, wherein R is hydrogen or lower alkyl, or if p is 2 or 3, X is nitrogen which together with $(CH_2)_p$ and the bonds represented in dotted (interrupted) lines (including the atoms to which they are bound) forms a ring, or X is CHK wherein K is hydrogen and p is zero, with the proviso that the bonds represented in dotted lines, if p is zero, are absent;

$Y_1$ is O, S or $CH_2$;

$Y_2$ is O;

with the proviso that $(Y_1)_n$—$(Y_2)_m$ does not include O—O, or S—O groups;

each of $R_1$, $R_2$ and $R_3$, independently of the others, is hydrogen, lower alkyl, especially methyl, ethyl, n-propyl, isopropyl or tert-butyl, lower alkenyl, especially isopropenyl, hydroxy-lower alkyl, especially hydroxy-propyl, lower alkoxy, especially methoxy, halo, especially chloro or bromo, halo-lower alkyl, especially trifluoromethyl, halo-lower alkoxy, especially trifluoromethoxy or trifluoroethoxy, amino-lower alkyl, especially aminomethyl, amino-lower alkoxy, especially aminoethoxy, di-lower alkyl-amino, especially diethylamino, hydroxy-lower alkyl-amino, especially hydroxy-propylamino, bis-(lower alkoxy-lower alkylyamino, especially bis-(2-methoxy-ethyl)-amino, di-lower alkyl-amino-lower alkyl, especially dimethylaminomethyl, phenyl, morpholinyl, especially morpholin-4-yl, piperidyl, especially piperidin-1-yl, piperidyl-lower alkyl, especially piperidin-1-ylmethyl, lower alkyl-piperazinyl, especially 4-methyl-piperazin-1-yl or 4-ethyl-piperazin-1-yl, lower alkyl-piperazinyl-lower alkyl, especially 4-methyl-piperazin-1-ylmethyl or 4-ethyl-piperazin-1-ylmethyl, pyridyl, especially pyridin-2-yl, or lower alkyl-imidazolyl, especially 2- or 4-methyl-imidazol-1-yl;

if r is 1, $R_4$ is lower alkyl, especially methyl, ethyl or ispropyl, hydroxy, aminocarbonyl, lower alkyl-carbonyl, especially methylcarbonyl, cyclohexyl, halo, especially chloro or fluoro, halo-lower alkyl, especially trifluoromethyl, lower alkoxy, especially methoxy, amino, lower alkyl-amino, especially methylamino, ethylamino, isopropylamino or tert-butylamino, di-lower alkyl-amino, especially dimethylamino, lower alkenyl-amino, especially prop-2-enylamino or but-3-enylamino, lower alkyl-carbonyl-amino, especially methylcarbonylamino, cyano, azido, hydroxyphenyl-amino, especially 3- or 4-hydroxy-phenyl-amino, mono or tri-lower alkoxy-phenyl-amino, especially methoxy-phenyl-amino or trimethoxy-phenyl-amino, lower alkoxy-halo-phenyl-amino, especially methoxy-fluoro-phenyl-amino, phenyl-lower alkylamino, especially benzylamino, (mono or di-lower alkoxy)-phenyl-lower alkylamino, especially methoxy-benzylamino or dimethoxy-benzylamino, aminosulfonyl-phenyl-lower alkylamino, especially aminosulfonyl-benzylamino, amino-lower alkoxy-phenyl-amino, especially aminoethoxy-phenyl-amino, lower alkyl-amino-sulfonyl-lower alkyl-phenylamino, especially methylamino-sulfonylmethyl-phenylamino, lower alkyl-piperazinyl-lower alkylamino, especially 4-methylpiperazin-1-yl-propylamino, morpholinyl-lower alkylamino, especially morpholin-4-yl-propylamino, lower alkyl-piperidyl-amino, especially 1-methyl-piperidin-4-ylamino, tetrazolyl, especially 1H-tetrazol-5-yl, lower alkyl-tetrazolyl, especially lower alkyl-tetrazol-5-yl such as 1-methyl-1H-tetrazol-5yl or 2-methyl-2H-tetrazol-5-yl, or (di-lower alkyl)-amino-lower alkyl-tetrazolyl, especially (di-lower alkyl)-amino-lower alkyl-tetrazol-5-yl such as 2-(3-dimethylaminopropyl)-2H-tetrazol-5-yl; and $R_5$ is most preferably hydrogen, or lower alkyl, especially methyl, or halo, especially chloro.

Especially preferred is the USE of a compound of the formula I or a tautomer thereof, or pharmaceutically acceptable salts thereof, where, in the compound of the formula I A and A' are both N,n is 1, m is 0, p is 0 or 2, r is 1, X is NH if p is 0, or if p is 2, X is nitrogen which together with $(CH_2)_2$ and the bonds represented in dotted (interrupted) lines (including the atoms to which they are bound) forms a ring, $Y_1$ is O, G is not present, Z is a radical of the formula Ia, at least one of $R_1$, $R_2$ and $R_3$ is a basic organic moiety, $R_4$ is amino or lower alkylamino and $R_5$ is hydrogen.

Preferred is further also the USE of a compound of the formula I* or a tautomer thereof, or pharmaceutically acceptable salts thereof, where, in the compound of the formula I* A is CH, N or N→O and A' is N or N→O, with the proviso that not more than one of A and A' can be N→O;
n is 1;
m is 0;
p is 0, 2 or 3;
r is 0, 1 or 2;
X is NR if p is 0, wherein R is hydrogen or lower alkyl, or if p is 2 or 3, X is nitrogen which together with $(CH_2)_p$ and the bonds represented in dotted (interrupted) lines (including the atoms to which they are bound).forms a ring, or
X is $CH_2$ and p is zero, with the proviso that the bonds represented in dotted lines, if p is zero, are absent;
$Y_1$ is O or $CH_2$;
each of $R_1$, $R_2$ and $R_3$ independently of the others, is hydrogen, lower alkyl, halo, especially bromo or chloro, halolower alkyl, especially trifluoromethyl, lower alkoxy, especially methoxy, halo-lower alkoxy, especially 2,2,2-trifluoroethoxy, phenyl, piperidyl, especially piperidin-1-yl, piperazinyl, especially piperazin-1-yl, morpholinyl, especially morpholine, thiomorpholinyl, especially thiomorpholino, or any two of them together form a lower alkylene-dioxy bridge bound via the oxygen atoms, and the remaining one of these moieties is hydrogen or one of the moieties mentioned;
if r is not zero, $R_4$ is lower alkyl, especially methyl or ethyl, lower alkoxy, especially methoxy, lower alkanoylamino, especially acetylamino, hydroxyphenylamino, especially p-hydroxyphenylamino, amino-lower alkyl-oxyphenyl-amino, especially 4-[(2-aminoethyl)-oxyphenyl]-amino, sulfamoylphenylamino, especially 4-sulfamoylphenylamino, carbamo-ylphenylamino, especially 4-carbamoylphenylamino, [N-(hydroxy-lower alkyl)-carbamoyl]-phenylamino, especially [N-(2-hydroxyethyl)-carbamoyl]-phenylamino, halo, especially chloro, or hydroxyl; and
$R_5$ is hydrogen, lower alkyl or halo, especially hydrogen.

Preferred among the novel compounds of the formula I are those wherein G is either not present, lower alkylene, especially methylene or ethylene, or $C_3$-$C_5$cycloalkylene, especially cyclopropylene, and Z is a radical of the formula Ia, or G is not present and Z is a radical of the formula Ib;
A is CH or N and A' is N or N→O;
n is 1;
m is 0 or 1;
p is 0, 2 or 3;
r is 1;
X is NR if p is 0, wherein R is hydrogen or lower alkyl, or if p is 2 or 3, X is nitrogen, which together with $(CH_2)_p$ and the bonds represented in dotted (interrupted) lines (including the atoms to which they are bound) forms a ring, or
X is CHK wherein K is hydrogen and p is zero, with the proviso that the bonds represented in dotted lines, if p is zero, are absent;
$Y_1$ is O, S or $CH_2$;
$Y_2$ is O;
with the proviso that $(Y_1)_n$—$(Y_2)_m$ does not include O—O, or S—O groups;
each of $R_1$, $R_2$ and $R_3$, independently of the others, is hydrogen, lower alkyl, especially methyl, ethyl, n-propyl, isopropyl or tert-butyl, lower alkenyl, especially isopropenyl, hydroxy-lower alkyl, especially hydroxy-propyl, lower alkoxy, especially methoxy, halo, especially chloro or bromo, halo-lower alkyl, especially trifluoromethyl, halo-lower alkoxy, especially trifluoromethoxy or trifluoroethoxy, amino-lower alkyl, especially aminomethyl, amino-lower alkoxy, especially aminoethoxy, di-lower alkyl-amino, especially diethylamino, hydroxy-lower alkyl-amino, especially hydroxy-propylamino, bis-(lower alkoxy-lower alkyl)-amino, especially bis-(2-methoxyethyl)-amino, di-lower alkyl-amino-lower alkyl, especially dimethylaminomethyl, phenyl, morpholinyl, especially morpholinyl, piperidyl, especially piperidin-1-yl, piperidyl-lower alkyl, especially piperidin-1-ylmethyl, lower alkyl-piperazinyl, especially 4-methyl-piperazin-1-yl or 4-ethyl-piperazin-1-yl, lower alkyl-piperazinyl-lower alkyl, especially 4-methyl-piperazin-1-ylmethyl or 4-ethyl-piperazin-1-ylmethyl, pyridyl, especially pyridin-2-yl, or lower alkyl-imidazolyl, especially 2- or 4-methyl-imidazol-1-yl, with the proviso that if G is not present and Z is a radical of the formula Ia, $R_1$, $R_2$ and $R_3$ cannot all be hydrogen and with the further proviso that if one of $R_1$, $R_2$ and $R_3$ is halo, the other two cannot both be hydrogen;
$R_4$ is lower alkyl, especially methyl, ethyl or ispropyl, hydroxy, aminocarbonyl, lower alkyl-carbonyl, especially methylcarbonyl, cyclohexyl, halo, especially chloro or fluoro, halo-lower alkyl, especially trifluoromethyl, lower alkoxy, especially methoxy, amino, lower alkyl-amino, especially methylamino, ethylamino, isopropylamino or tert-butylamino, di-lower alkyl-amino, especially dimethylamino, lower alkenyl-amino, especially prop-2-enylamino or but-3-enylamino, lower alkyl-carbonyl-amino, especially methylcarbonylamino, cyano, azido, hydroxyphenyl-amino, especially 3- or 4-hydroxy-phenyl-amino, mono or tri-lower alkoxy-phenyl-amino, especially methoxy-phenyl-amino or trimethoxy-phenyl-amino, lower alkoxy-halo-phenyl-amino, especially methoxy-fluoro-phenyl-amino, phenyl-lower alkylamino, especially benzylamino, (mono or di-lower alkoxy)-phenyl-lower alkylamino, especially methoxy-benzylamino or dimethoxy-benzylamino, aminosulfonyl-phenyl-lower alkylamino, especially aminosulfonyl-benzylamino, amino-lower alkoxy-phenyl-amino, especially aminoethoxy-phenyl-amino, lower alkyl-amino-sulfonyl-lower alkyl-pheny-lamino, especially methylamino-sulfonylmethyl-pheny-lamino, lower alkyl-piperazinyl-lower alkylamino, especially 4-methylpiperazin-1-yl-propylamino, morpholinyl-lower alkylamino, especially morpholin-4-yl-propylamino, lower alkyl-piperidyl-amino, especially 1-methyl-piperidin-4-ylamino, tetrazolyl, especially 1H-tetrazol-5-yl, lower alkyl-tetrazolyl, especially lower alkyl-tetrazol-5-yl such as 1-methyl-1H-tetrazol-5-yl or 2-methyl-2H-tetrazol-5-yl, or (di-lower alkyl)-amino-lower alkyl-tetrazolyl, especially (di-lower alkyl)-amino-lower alkyl-tetrazol-5-yl such as 2-(3-dimethylaminopropyl)-2H-tetrazol-5-yl, with the proviso that if X is NH, $R_4$ is not aminocarbonyl or lower alkyl-carbonyl and with the further proviso that if n is 1, m is 0, p is 0, r is 1, X is NH, $Y_1$ is O, G is not present and Z is a radical of the formula Ia, $R_4$, together with the benzene ring containing A and A', does not form methylpyridinyl, 2-hydroxy-pyridinyl or 1-H-2-oxo-1,2-dihydropyridin-4-yl;

$R_5$ is most preferably hydrogen, or lower alkyl, especially methyl, or halo, especially chloro;

or a tautomer thereof;

or pharmaceutically acceptable salts thereof.

Very preferred among the novel compounds of the formula I are those wherein

A and A' are both N, n is 1, m is 0, p is 0 or 2, r is 1, X is NH if p is 0, or if p is 2, X is nitrogen which together with $(CH_2)_2$ and the bonds represented in dotted (interrupted) lines (including the atoms to which they are bound) forms a ring, $Y_1$ is O, G is not present, Z is a radical of the formula Ia, at least one of $R_1$, $R_2$ and $R_3$ is a basic organic moiety, $R_4$ is amino or lower alkylamino and $R_5$ is hydrogen, or a tautomer thereof, or pharmaceutically acceptable salts thereof.

Preferred among the novel compounds of the formula I* are those wherein

A, A', n, m, p, $Y_1$, $Y_2$, $R_1$, $R_2$, $R_3$ and $R_4$ have the meanings given under formula I* above, and r is 1 to 5, X is NR if p is 0, wherein R is hydrogen or an organic moiety, or if p is 2 or 3, X is nitrogen which together with $(CH_2)_p$ and the bonds represented in dotted (interrupted) lines (including the atoms to which they are bound) forms a ring, or X is $CH_2$ and p is zero, and, if p is zero, the bonds represented in dotted lines are absent;

with the proviso that if X is NH, each of $R_4$, independently of the others, if present, is a moiety as defined under formula I* above but not bound to the rest of formula I* via a —C(=O)—, —C(NR)— or —S(O$_2$)— bridge, and the substituents $R_1$, $R_2$ and $R_3$ are selected from the following moieties, whereby positions (o=ortho, m=meta, p=para) are indicated with regard to the position where the ring is bound to the rest of the molecule in formula I* (via the NH—C(=O)—X-moiety):

if only $R_1$ is other than hydrogen:

$R_1$=p-lower alkyl, especially p-methyl, p-ethyl, p-n-propyl;
m-halo-lower alkyl, especially m-trifluoromethyl; or
phenyl, p-piperidin-1-yl or p-piperazin-1-yl;

if both $R_1$ and $R_2$ are other than hydrogen:
$R_1$=m-halo-lower alkyl, especially m-trifluoromethyl, and $R_2$=p-halo, especially p-bromo;

$R_1$=m-halo-lower alkyl, especially m-trifluoromethyl, and $R_2$=p-halo-lower alkoxy, especially p-(2,2,2-trifluoroethoxy);

$R_1$=m-halo-lower alkyl, especially m-trifluoromethyl, and $R_2$=m-lower alkoxy, especially m-methoxy;

$R_1$=m-halo-lower alkyl, especially m-trifluoromethyl, and $R_2$=p-phenyl;

$R_1$=m-halo-lower alkyl, especially m-trifluoromethyl, and $R_2$=p-piperidin-1-yl or p-piperazin-1-yl;

$R_1$=m-halo-lower alkyl, especially m-trifluoromethyl, and $R_2$=p-N-morpholino or p-N-thiomorpholino;

$R_1$=m-lower alkoxy, especially m-methoxy, and $R_2$=p-halo, especially p-bromo (less preferred);

$R_1$=m-lower alkoxy, especially m-methoxy, and $R_2$=p-halo-lower alkoxy, especially p-2,2,2-trifluoroethoxy;

$R_1$=m-lower alkoxy, especially m-methoxy, and $R_2$=p-phenyl; or $R_1$=m-lower alkoxy, especially m-methoxy, and $R_2$=p-piperidin-1-yl or p-piperazin-1-yl;

or, if $R_1$, $R_2$ and $R_3$ are other than hydrogen:
$R_1$=m-lower alkoxy, especially m-methoxy; $R_2$=m-lower alkoxy, especially m-methoxy; and $R_3$=p-lower alkoxy, especially p-methoxy; or $R_1$=lower alkoxy, especially methoxy, and $R_2$ and $R_3$ together form a lower-alkylene-dioxy, especially —O—CH$_2$—CH$_2$—O—, bridge;

and $R_5$ is hydrogen, lower alkyl or halo, especially hydrogen; with the proviso that if n is 1, m is 0, p is 0, r is 1, X is NH and $Y_1$ is O, $R_4$, together with the benzene ring containing A and A', does not form methylpyridinyl, 2-hydroxy-pyridin-4-yl or 1-H-2-oxo-1,2-dihydropyridin-4-yl;

or a tautomer thereof;

or pharmaceutically acceptable salts thereof.

Further preferred among the novel compounds of the formula I* are those wherein

A is CH, N or NO and A' is N or NO, with the proviso that not more than one of A and A' can be N→O;

n is 1;

m is 0;

p is 0, 2 or 3;

r is 1 or 2;

X is NR if p is 0, wherein R is hydrogen or lower alkyl, or if p is 2 or 3, X is nitrogen which together with $(CH_2)_p$ and the bonds represented in dotted (interrupted) lines (including the atoms to which they are bound) forms a ring, or X is $CH_2$ and p is zero, with the proviso that the bonds represented in dotted lines, if p is zero, are absent;

$Y_1$ is O or $CH_2$;

$R_1$, $R_2$ and $R_3$ are selected from the following moieties, whereby positions (o=ortho, m=meta, p=para) are indicated with regard to the position where the ring is bound to the rest of the molecule in formula I* (via the NH—C(=O)—X-moiety):

if only $R_1$ is other than hydrogen:
$R_1$=p-lower alkyl, especially p-methyl, p-ethyl, p-n-propyl;
m-halo-lower alkyl, especially m-trifluoromethyl; or
phenyl, p-piperidin-1-yl or p-piperazin-1-yl;

if both $R_1$ and $R_2$ are other than hydrogen:
$R_1$=m-halo-lower alkyl, especially m-trifluoromethyl, and $R_2$=p-halo, especially p-bromo;

$R_1$=m-halo-lower alkyl, especially m-trifluoromethyl, and $R_2$=p-halo-lower alkoxy, especially p-(2,2,2-trifluoroethoxy);

$R_1$=m-halo-lower alkyl, especially m-trifluoromethyl, and $R_2$=m-lower alkoxy, especially m-methoxy;

$R_1$=m-halo-lower alkyl, especially m-trifluoromethyl, and $R_2$=p-phenyl;

$R_1$=m-halo-lower alkyl, especially m-trifluoromethyl, and $R_2$=p-piperidin-1-yl or p-piperazin-1-yl;

$R_1$=m-halo-lower alkyl, especially m-trifluoromethyl, and $R_2$=p-N-morpholino or p-N-thiomorpholino;

$R_1$=m-lower alkoxy, especially m-methoxy, and $R_2$=p-halo, especially p-bromo (less preferred);

$R_1$=m-lower alkoxy, especially m-methoxy, and $R_2$=p-halo-lower alkoxy, especially p-2,2,2-trifluoroethoxy;

$R_1$=m-lower alkoxy, especially m-methoxy, and $R_2$=p-phenyl; or $R_1$=m-lower alkoxy, especially m-methoxy, and $R_2$=p-piperidin-1-yl or p-piperazin-1-yl;

or, if $R_1$, $R_2$ and $R_3$ are other than hydrogen:

$R_1$=m-lower alkoxy, especially m-methoxy; $R_2$=m-lower alkoxy, especially m-methoxy; and $R_3$=p-lower alkoxy, especially p-methoxy; or $R_1$=lower alkoxy, especially methoxy, and $R_2$ and $R_3$ together form a lower-alkylene-dioxy, especially —$CH_2$—$CH_2$—O—, bridge;

and, if r is not zero, $R_4$ is lower alkoxy, especially methoxy, lower alkanoylamino, especially acetylamino, hydroxyphenylamino, especially p-hydroxyphenylamino, amino-lower alkyl-oxyphenyl-amino, especially 4-[(2-aminoethyl)-oxyphenyl]-amino, sulfamoylphenylamino, especially 4-sulfamoylphenylamino, carbamoylphenylamino, especially 4-carbamoylphenylamino, [N-(hydroxy-lower alkyl)-carbamoyl]-phenylamino, especially [N-(2-hydroxyethyl)-carbamoyl]-phenylamino, or halo, especially chloro;

and $R_5$ is halo, especially chloro, lower alkyl, especially methyl, or preferably hydrogen:

or a tautomer thereof;

or pharmaceutically acceptable salts thereof.

Very preferred is a novel compound of the formula I or I*, as well as their USE, provided in the Examples, or a pharmaceutically acceptable salt thereof. Very preferred is also the method of synthesis for these compounds analogously to the methods described in the Examples.

Pharmaceutical Compositions

The invention relates also especially to pharmaceutical compositions comprising a novel compound of the formula I or I*, to the use of a compound of the formula I or I* in the therapeutic (in a broader aspect of the invention also prophylactic) treatment or a method of treatment of a (especially tyrosin) protein kinase dependent disease, especially the preferred diseases mentioned above, to the compounds of formula I or I* for said use and to the preparation of pharmaceutical preparations, especially for said uses.

The pharmacologically acceptable compounds of the present invention may be used, for example, for the preparation of pharmaceutical compositions that comprise a pharmaceutically effective amount of a compound of the formula I or I*, or a pharmaceutically acceptable salt thereof, as active ingredient together or in admixture with a significant amount of one or more inorganic or organic, solid or liquid, pharmaceutically acceptable carriers.

The invention relates also to a pharmaceutical composition that is suitable for administration to a warm-blooded animal, especially a human (or to cells or cell lines derived from a warm-blooded animal, especially a human, e.g. lymphocytes), for the treatment or, in a broader aspect of the invention, prevention of (=prophylaxis against) a disease that responds to inhibition of tyrosin protein kinase activity, especially one of the diseases mentioned above as being preferred for USE of a compound of formula I or I*, comprising an amount of a novel compound of formula I or I*, or a pharmaceutically acceptable salt thereof, which is effective for said inhibition, together with at least one pharmaceutically acceptable carrier.

The pharmaceutical compositions according to the invention are those for enteral, such as nasal, rectal or oral, or parenteral, such as intramuscular or intravenous, administration to warm-blooded animals (especially a human), that comprise an effective dose of the pharmacologically active ingredient, alone or together with a significant amount of a pharmaceutically acceptable carrier. The dose of the active ingredient depends on the species of warm-blooded animal, the body weight, the age and the individual condition, individual pharmacokinetic data, the disease to be treated and the mode of administration.

The invention relates also to a method of treatment for a disease that responds to inhibition of an (especially tyrosine) protein kinase, especially one of the diseases mentioned above as being preferred for USE of a compound of formula I or I*; which comprises administering an (against the mentioned disease) prophylactically or especially therapeutically effective amount of a compound of formula I or I* according to the invention, especially to a warm-blooded animal, for example a human, that, on account of one of the mentioned diseases, requires such treatment.

The dose of a compound of the formula I or I*, or a pharmaceutically acceeptable salt thereof to be administered to warm-blooded animals, for example humans of approximately 70 kg body weight, is preferably from approximately 3 mg to approximately 30 g, more preferably from approximately 10 mg to approximately 1.5 g, most preferably from about 100 mg to about 1000 mg per person per day, divided preferably into 1 to 3 single doses which may, for example, be of the same size. Usually, children receive half of the adult dose.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, drageesi tablets or capsules.

The pharmaceutical compositions of the present invention are prepared in a manner known per se, for example by means of conventional dissolving, lyophilising, mixing, granulating or confectioning processes.

Solutions of the active ingredient, and also suspensions, and especially isotonic aqueous solutions or suspensions, are one preferred form used, it being possible, for example in the case of lyophilised compositions that comprise the active ingredient alone or together with a carrier, for example mannitol, for such solutions or suspensions to be produced prior to use. The pharmaceutical compositions may be sterilised and/or may comprise excipients, for example preservatives, stabilisers, wetting and/or emulsifying agents, solubilisers, salts for regulating the osmotic pressure and/or buffers, and are prepared in a manner known per se, for example by means of conventional dissolving or lyophilising processes. The said solutions or suspensions may comprise viscosity-increasing substances, such as sodium carboxymethylcellulose, carboxymethylcellulose, dextran, polyvinylpyrrolidone or gelatin.

Suspensions in oil comprise as the oil component the vegetable, synthetic or semi-synthetic oils customary for injection purposes. There may be mentioned as such especially liquid fatty acid esters that contain as the acid component a long-chained fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brasidic acid or linoleic acid, if desired with the addition of antioxidants, for example vitamin E, β-carotene or 3,5-di-tert-butyl-4-hydroxytoluene. The alcohol component of those fatty acid esters has a maximum of 6 carbon atoms and is a mono- or poly-hydroxy, for example a mono-, di- or tri-hydroxy, alcohol, for example methanol, ethanol, propanol, butanol or pentanol or the isomers thereof, but especially glycol and glycerol. The following examples of fatty acid esters are therefore to be mentioned: ethyl oleate, isopropyl myristate, isopropyl palmitate, "Labrafil M 2375" (polyoxyethylene glycerol trioleate, Gattefossé, Paris), "Miglyol 812" (tri-glyceride of saturated fatty acids with a chain length of $C_8$ to $C_{12}$, Hüls AG, Germany), but especially vegetable oils, such as cottonseed oil, almond oil, olive oil, castor oil, sesame oil, soybean oil and more especially groundnut oil.

Injection compositions are prepared in customary manner under sterile conditions; the same applies also to introducing the compositions into ampoules or vials and sealing the containers.

Pharmaceutical compositions for oral administration can be obtained by combining the active ingredient with solid carriers, if desired granulating a resulting mixture, and processing the mixture, if desired or necessary, after the addition of appropriate excipients, into tablets, dragée cores or capsules. It is also possible for them to be incorporated into plastics carriers that allow the active ingredients to diffuse or be released in measured amounts.

Suitable carriers are especially fillers, such as sugars, for example lactose, saccharose, mannitol or sorbitol, cellulose preparations and/or calcium phosphates, for example tricalcium phosphate or calcium hydrogen phosphate, and binders, such as starch pastes using for example corn, wheat, rice or potato starch, gelatin, tragacanth, methylcellulose, hydroxypropylmethylcellulose, sodium carboxymethylcellulose and/or polyvinylpyrrolidone, and/or, if desired, disintegrators, such as the above-mentioned starches, and/or carboxymethyl starch, crosslinked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Dragée cores are provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents, or, for the preparation of enteric coatings, solutions of suitable cellulose preparations, such as ethylcellulose phthalate or hydroxypropylmethylcellulose phthalate. Capsules are dry-filled capsules made of gelatin and soft sealed capsules made of gelatin and a plasticiser, such as glycerol or sorbitol. The dry-filled capsules may comprise the active ingredient in the form of granules, for example with fillers, such as lactose, binders, such as starches, and/or glidants, such as talc or magnesium stearate, and if desired with stabilisers. In soft capsules the active ingredient is preferably dissolved or suspended in suitable oily excipients, such as fatty oils, paraffin oil or liquid polyethylene glycols, it being possible also for stabilisers and/or antibacterial agents to be added. Dyes or pigments may be added to the tablets or dragèe coatings or the capsule casings, for example for identification purposes or to indicate different doses of active ingredient.

A compound of the formula I or I* may also be used to advantage in combination with other antiproliferative agents. Such antiproliferative agents include, but are not limited to aromatase inhibitors, antiestrogens, topoisomerase I inhibitors, topoisomerase II inhibitors, microtubule active agents, alkylating agents, histone deacetylase inhibitors, farnesyl transferase inhibitors, COX-2 inhibitors, MMP inhibitors, mTOR inhibitors, antineoplastic antimetabolites, platin compounds, compounds decreasing the protein kinase activity and further ant-angiogenic compounds, gonadorelin agonists, anti-androgens, bengamides, bisphosphonates, antiproliferative antibodies and temozolomide (TEMODAL®).

The term "aromatase inhibitors" as used herein relates to compounds which inhibit the estrogen production, i.e. the conversion of the substrates androstenedione and testosterone to estrone and estradiol, respectively. The term includes, but is not limited to steroids, especially exemestane and formestane and, in particular, non-steroids, especially aminoglutethimide, vorozole, fadrozole, anastrozole and, very especially, letrozole. Exemestane can be administered, e.g., in the form as it is marketed, e.g. under the trademark AROMASIN™. Formestane can be administered, e.g., in the form as it is marketed, e.g. under the trademark LENTARON™. Fadrozole can be administered, e.g., in the form as it is marketed, e.g. under the trademark AFEMA™. Anastrozole can be administered, e.g., in the form as it is marketed, e.g. under the trademark ARIMIDEX™. Letrozole can be administered, e.g., in the form as it is marketed, e.g. under the trademark FEMARA™ or FEMAR™. Aminoglutethimide can be administered, e.g., in the form as it is marketed, e.g. under the trademark ORIMETEN™.

A combination of the invention comprising an antineoplastic agent which is an aromatase inhibitor is particularly useful for the treatment of hormone receptor positive breast tumors.

The term "antiestrogens" as used herein relates to compounds which antagonize the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX™. Raloxifene hydrochloride can be administered, e.g., in the form as it is marketed, e.g. under the trademark EVISTA™. Fulvestrant can be formulated as disclosed in U.S. Pat. No. 4,659,516 or it can be administered, e.g., in the form as it is marketed, e.g. under the trademark FASLODEX™.

The term "topolsomerase I inhibitors" as used herein includes, but is not limited to topotecan, irinotecan, 9-nitrocamptothecin and the macromolecular camptothecin conjugate PNU-166148 (compound A1 in WO99/17804). Irinotecan can be administered, e.g., in the form as it is marketed, e.g. under the trademark CAMPTOSAR™. Topotecan can be administered, e.g., in the form as it is marketed, e.g. under the trademark HYCAMTIN™.

The term "topoisomerase II inhibitors" as used herein includes, but is not limited to the antracyclines doxorubicin (including liposomal formulation, e.g. CAELYX™), epirubicin, idarubicin and nemorubicin, the anthraquinones mitoxantrone and losoxantrone, and the podophillotoxines etoposide and teniposide. Etoposide can be administered, e.g., in the form as it is marketed, e.g. under the trademark ETOPOPHOS™. Teniposide can be administered, e.g., in the form as it is marketed, e.g. under the trademark VM 26-BRISTOL™.

Doxorubicin can be administered, e.g., in the form as it is marketed, e.g. under the trademark ADRIBLASTIN™. Epirubicin can be administered, e.g., in the form as it is marketed, e.g. under the trademark FARMORUBICIN™. Idarubicin can be administered, e.g., in the form as it is marketed, e.g. under the trademark ZAVEDOS™. Mitoxantrone can be administered, e.g., in the form as it is marketed, e.g. under the trademark NOVANTRON™.

The term "microtubule active agents" relates to microtubule stabilizing and microtubule destabilizing agents including, but not limited to the taxanes paclitaxel and docetaxel, the vinca alkaloids, e.g., vinblastine, especially vinblastine sulfate, vincristine especially vincristine sulfate, and vinorelbine, discodermolide and epothilones, such as epothilone B and D. Docetaxel can be administered, e.g., in the form as it is marketed, e.g. under the trademark TAXOTERE™. Vinblastine sulfate can be administered, e.g., in the form as it is marketed, e.g. under the trademark VINBLASTIN R.P.™. Vincristine sulfate can be administered, e.g., in the form as it is marketed, e.g. under the trademark FARMISTIN™. Discodermolide can be obtained, e.g., as disclosed in U.S. Pat. No. 5,010,099.

The term "alkylating agents" as used herein includes, but is not limited to cyclophosphamide, ifosfamide and melphalan. Cyclophosphamide can be administered, e.g., in the form as it is marketed, e.g. under the trademark CYCLOSTIN™. Ifosfamide can be administered, e.g., in the form as it is marketed, e.g. under the trademark HOLOXAN™.

The term "histone deacetylase inhibitors" relates to compounds which inhibit the histone deacetylase and which possess antiproliferative activity.

The term "farnesyl transferase inhibitors" relates to compounds which inhibit the farnesyl transferase and which possess antiproliferative activity.

The term "COX-2 inhibitors" relates to compounds which inhibit the cyclooxygenase type 2 enyzme (COX-2) and which possess antiproliferative activity such as celecoxib (Celebrex®), rofecoxib (Vioxx®) and lumiracoxib (COX189).

The term "MMP inhibitors" relates to compounds which inhibit the matrix metalloproteinase (MMP) and which possess antiproliferative activity.

The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "antineoplastic antimetabolites" includes, but is not limited to 5-fluorouracil, tegafur, capecitabine, cladribine, cytarabine, fludarabine phosphate, fluorouridine, gemcitabine, 6-mercaptopurine, hydroxyurea, methotrexate, edatrexate and salts of such compounds, and furthermore ZD 1694 (RALTITREXED™), LY231514 (ALIMTA™), LY264618 (LOMOTREXOL™) and OGT719.

The term "platin compounds" as used herein includes, but is not limited to carboplatin, cisplatin and oxaliplatin. Carboplatin can be administered, e.g., in the form as it is marketed, e.g. under the trademark CARBOPLAT™. Oxaliplatin can be administered, e.g., in the form as it is marketed, e.g. under the trademark ELOXATIN™.

The term "compounds decreasing the protein kinase activity and further anti-angiogenic compounds" as used herein includes, but is not limited to compounds which decrease the activity of e.g. the Vascular Endothelial Growth Factor (VEGF), the Epidermal Growth Factor (EGF), c-Src, protein kinase C, the Platelet-derived Growth Factor (PDGF), Bcr-Abl, c-Kit, Flt-3, the insulin-like Growth Factor I Receptor (IGF-IR) and the Cyclin-dependent kinases (CDKs), and anti-angiogenic compounds having another mechanism of action than decreasing the protein kinase activity.

Compounds which decrease the activity of VEGF are especially compounds which inhibit the VEGF receptor, especially the tyrosine kinase activity of the VEGF receptor, and compounds binding to VEGF, and are in particular those compounds, proteins and monoclonal antibodies generically and specifically disclosed in WO 98/35958 (describing compounds of formula I), WO 00/09495, WO 00/27820, WO 00/59509, WO 98/11223, WO 00/27819, WO 01/55114, WO 01/58899 and EP 0 769 947; those as described by M. Prewett et al in Cancer Research 59 (1999) 5209-5218, by F. Yuan et al in Proc. Natl. Acad. Sci. USA, vol. 93, pp.14765-14770, December 1996, by Z. Zhu et al in Cancer Res. 58, 1998, 3209-3214, and by J. Mordenti et al in Toxicologic Pathology, vol. 27, no. 1, pp 14-21, 1999; in WO 00/37502 and WO 94/10202; Angiostatin™, described by M. S. O'Reilly et al, Cell 79, 1994, 315-328; and Endostatin™, described by M. S. O'Reilly et al, Cell 88,1997, 277-285;

compounds which decrease the activity of EGF are especially compounds which inhibit the EGF receptor, especially the tyrosine kinase activity of the EGF receptor, and compounds binding to EGF, and are in particular those compounds generically and specifically disclosed in WO 97/02266 (describing compounds of formula IV), EP 0 564 409, WO 99/03854, EP 0520722, EP 0 566 226, EP 0 787 722, EP 0 837 063, WO 98/10767, WO 97/30034, WO 97/49688, WO 97/38983 and, especially, WO 96/33980;

compounds which decrease the activity of c-Src include, but are not limited to, compounds inhibiting the c-Src protein tyrosine kinase activity as defined below and to SH2 interaction inhibitors such as those disclosed in WO97/07131 and WO97/08193;

compounds inhibiting the c-Src protein tyrosine kinase activity include, but are not limited to, compounds belonging to the structure classes of pyrrolopyrimidines, especially pyrrolo[2,3-d]pyrimidines, purines, pyrazopyrimidines, especially pyrazo[3,4-d]pyrimidines, pyrazopyrimidines, especially pyrazo[3,4-d]pyrimidines and pyridopyrimidines, especially pyrido[2,3-d]pyrimidines. Preferably, the term relates to those compounds disclosed in WO 96/10028, WO 97/28161, W097/32879 and W097/49706;

compounds which decreases the activity of the protein kinase C are especially those staurosporine derivatives disclosed in EP 0 296 110 (pharmaceutical preparation described in WO 00/48571) which compounds are protein kinase C inhibitors;

further specific compounds that decrease protein kinase activity and which may also be used in combination with the compounds of the present invention are Imatinib (Gleevec®/Glivec®), PKC412, Iressa™ (ZD1839), PK1166, PTK787, ZD6474, GW2016, CHIR-200131, CEP-7055/CEP-5214, CP-547632, KRN-633 and SU5416;

anti-angiogenic compounds having another mechanism of action than decreasing the protein kinase activity include, but are not limited to e.g. thalidomide (THALOMID), celecoxib (Celebrex) and ZD6126.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX™. Abarelix can be formulated, e.g. as disclosed in U.S. Pat. No. 5,843,901.

The term "anti-androgens" as used herein includes, but is not limited to bicalutamide (CASODEX™), which can be formulated, e.g. as disclosed in U.S. Pat. No. 4,636,505.

The term "bengamides" relates to bengamides and derivatives thereof having aniproliferative properties.

The term "bisphosphonates" as used herein includes, but is not limited to etridonic acid, clodronic acid, tiludronic acid, pamidronic acid, alendronic acid, ibandronic acid, risedronic acid and zoledronic acid. "Etridonic acid" can be administered, e.g., in the form as it is marketed, e.g. under the trademark DIDRONEL™. "Clodronic acid" can be administered, e.g., in the form as it is marketed, e.g. under the trademark BONEFOS™. "Tiludronic acid" can be administered, e.g., in the form as it is marketed, e.g. under the trademark SKELID™. "Pamidronic acid" can be administered, e.g., in the form as it is marketed, e.g. under the trademark AREDIA™. "Alendronic acid" can be administered, e.g., in the form as it is marketed, e.g. under the trademark FOSAMAX™. "Ibandronic acid" can be administered, e.g., in the form as it is marketed, e.g. under the trademark BONDRANAT™. "Risedronic acid" can be administered, e.g., in the form as it is marketed, e.g. under the trademark ACTONEL™. "Zoledronic acid" can be administered, e.g., in the form as it is marketed, e.g. under the trademark ZOMETA™.

The term "antiproliferative antibodies" as used herein includes, but is not limited to trastuzumab (Herceptin™), Trastuzumab-DM1, erlotinib (Tarceva™), bevacizumab (Avastin™), rituximab (Rituxan®), PRO64553 (anti-CD40) and 2C4 Antibody.

For the treatment of acute myeloid leukemia (AML), compounds of formula I or I* can be used in combination with standard leukemia therapies, especially in combination with therapies used for the treatment of AML. In particular, compounds of formula I or I* can be administered in combination with e.g. farnesyltransferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The structure of the active agents identified by code nos., generic or trade names may be taken from the actual edition of the standard compendium "The Merck Index" or from databases, e.g. Patents International (e.g. IMS World Publications).

The above-mentioned compounds, which can be used in combination with a compound of the formula I or I*, can be prepared and administered as described in the art such as in the documents cited above.

EXAMPLES

The following Examples serve to illustrate the invention without limiting the scope thereof.

| Abbreviations: | |
|---|---|
| abs. | absolute |
| AcOEt | ethyl acetate |
| AcOH | acetic acid |
| Anal. | elemental analysis (for indicated atoms, difference between calculated and measured value ≦ 0.4 %) |
| brine | saturated solution of NaCl in water |
| cat. | catalyst |
| conc. | concentrated |
| d | day(s) |
| decomp. | decomposition |
| DIBAH | diisobutyl-aluminium-hydride |
| DIEA | diisopropyl-ethyl-amine |
| DMF | dimethyl formamide |
| DMPU | 1,3-dimethyl-3,4,5,6-tetrahydro-2-(1H)pyrimidinone |
| DMEU | 1,3-dimethyl-2-imidazolidinone |
| DMSO | dimethylsulfoxide |
| DMSO-d$_6$ | per-deuterated dimethylsulfoxide |
| ether | diethylether |
| EtOH | ethanol |
| equiv | equivalent(s) |
| Ex. | Example |
| h | hour(s) |
| HPLC | high pressure liquid chromatography |
| L | liter(s) |
| Me | methyl |
| min | minute(s) |
| m.p. | melting point |
| MPLC | medium pressure liquid chromatography (Combi Flash system) |
| NEt$_3$ | triethylamine |
| NMM | N-methylmorpholine |
| NMR | Nuclear Magnetic Resonance |
| R$_f$ | ratio of fronts (thin layer chromatography) |
| rt | room temperature |
| TBS | tert-butyl-dimethylsilyl |
| TBTU | O-(benzotriazol-1-yl)-N,N,N',N'-tetramethyluronium tetrafluoroborate |
| THF | tetrahydrofuran (distilled from Na/benzophenone) |
| TFA | trifluoroacetic acid |
| TLC | thin layer chromatography |
| TPTU | O-(2-oxo-1(2H)-pyridyl)-N,N,N',N'-tetramethyluronium tetrafluoroborate |
| t$_R$ | retention time (HPLC) |
| triphosgene | bis(trichloromethyl) carbonate |
| Tween 80 | polyoxyethylen(20)sorbitane monooleate (trademark of ICI, Uniquema) |

HPLC Conditions

System 1: HPLC is performed on an Agilent HP 1100 using a Nucleosil 100-3 C18 HD 125×4.0 mm column (1 ml/min; Linear gradient 20-100% CH$_3$CN (0.1% TFA) and H$_2$O (0.1% TFA) in 7 min).

System 2: Linear gradient 2-100% CH$_3$CN (0.1% TFA) and H$_2$O (0.1% TFA) in 10 min +2 min 100% CH$_3$CN (0.1% TFA); detection at 215 nm, flow rate 0.7 ml/min at 25 or 30° C. Column: Nucleosil 120-3 C18 (125×3.0 mm).

System 3: Linear gradient 20-100% CH$_3$CN (0.1% TFA) and H$_2$O (0.1% TFA) in 13 min +5 min 100% CH$_3$CN (0.1% TFA); detection at 215 nm, flow rate 1 m/min at 25 or 30° C. Column: Nucleosil 120-3 C18 (125×3.0 mm).

Example 1

N-(4-pyridin-4-yl-oxy-phenyl)-N'-(4-ethyl-phenyl)-urea

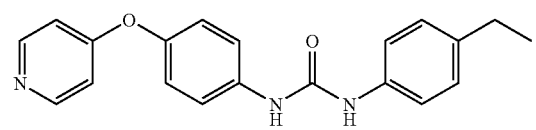

A solution of pyridine (3.46 ml, 43 mmol), 4-ethyl aniline (0.69 ml, 5.37 mmol) and phosgene (11.1 ml, 20% in toluene; 21.5 mmol) in CH$_2$Cl$_2$ (66 mL) is stirred at 0° C. overnight. After concentrating under reduced pressure, the reaction mixture is taken in THF (26 ml), filtrated, and added to a solution of 4-(pyridin-4-yl-oxy)-phenylamine (Stage 1.1; 0.5 g, 2.69 mmol) and pyridine (0.43 ml, 0.43 mmol) in THF (3.3 ml) and stirred at rt for 24 h. The reaction solution is filtered over silica gel (30 g), taken up in AcOEt (100 ml), washed with $H_2O$ (20 ml), $NaHCO_3$ (5%, 20 ml), and brine (20 ml, 2×), dried over $Na_2SO_4$, concentrated under reduced pressure, and flash chromatographed (silica gel, 2×18 cm; AcOEt/hexane=2:1→4:1) giving compound of Example 1 as a colorless solid; M+H=334, $^1$H-NMR (400 MHz, DMSO-$d_6$): 8.70 (s, 1H, NH), 8.60 (s, 1H, NH), 8.44 (d, Hz, 6.5 Hz, 2H, pyridinyl), 7.54 (d, 9.5 Hz, 2H, 4-ethyl-phenyl), 7.37 (d, 9.5 Hz, 2H, oxo-phenyl-amine), 7.11 (d/d, 9.5 Hz, 4H, oxo-phenyl-amine/4-ethyl-phenyl), 6.89 (d, 6.5 Hz, 2H, pyridinyl), 2.55 (qu, 7.5 Hz, 2H, $CH_2$), 1.16 (t, 7.5 hz, 3H, $CH_3$); $R_f$(AcOEt/hexane=2:1): 0.16; m.p.=166.5-168° C.

The starting material is prepared as follows:

Stage 1.1: (4-(pyridin-4-yl-oxy)-phenyl-amine)

A solution of 4-aminophenol (15 g, 0.135 mol), 4-chloropyridine hydrochloride (22.5 g, 0.148 mol), and KOtBu (45.8 g, 0.404 mol) in DMPU (208 ml) and DMF (52 ml) is stirred at 100° C. for 24 h, cooled to rt, poured into $H_2O$ (0.6 L), and extracted with AcOEt (150 ml, 6×). The combined organic phases are washed with $H_2O$ (100 ml, 2×), brine (100 ml, 2×), dried ($Na_2SO_4$), concentrated under reduced pressure, and flash chromatographed (silica gel, 4.5×25 cm; AcOEt/hexane=1:9→3:7) to give the title compound of Stage 1.1 as a colorless solid: M+H=187.2; $^1$H-NMR (400 MHz, DMSO-$d_6$): 8.37 (d, 6.5 Hz, 2H, pyridinyl), 6.79 (d, 9.5 Hz, 2H, phenyl), 6.78 (d, 9.5 Hz, 2H, pyridinyl) 5.12 (s, 2H, $NH_2$); $R_f$ (AcOEt/$CH_2Cl_2$=3:7): 0.23; m.p.=165.8-166.6° C.

Compounds of Examples 2-15 are synthesized analogously to the preparation of the compound of Example 1 via urea formation of the corresponding aryl isocyanates and 4-(pyridin-4-yl-oxy)phenylamine, methyl-[4-(pyridin-4-yl-oxy)-phenyl]amine, 4-(pyridin-4-ylmethyl)-phenylamine or methyl-[4-(pyridin-4-ylmethyl)-phenyl]amine, respectively. Structures and analytical data are given below (Table 1).

Starting materials: Methyl-[4-(pyridin-4-yl-oxy)-phenyl]amine for the synthesis of compounds of Examples 5-8 is prepared according to the procedure of the preparation of the compound of Stage 1.1. After flash chromatography, the product is further purified by Kugelrohr distillation (110° C., 0.3 mbar) and crystallized from AcOEt/hexane: M+H=201.1; $^1$H-NMR (400 MHz, DMSO-$d_6$): 8.37 (d, 6.5 Hz, 2H, pyridinyl), 6.78 (d, 9.5 Hz, 2H, pyridinyl), 6.56 (d, 9.5 Hz, 2H, phenyl), 5.71 (s/broad, 1H, NH), 2.65 (d, 2.5 Hz, 3H, $CH_3$—N); $R_f$ (acetone/$CH_2Cl_2$=3:7): 0.23.

TABLE 1

Structures and analytical data of compounds of Examples 2-15

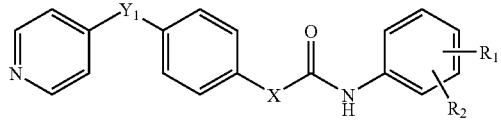

| Ex. | $Y_1$ | X | $R_1, R_2$ | Analytical data |
|---|---|---|---|---|
| 2 | O | NH | 3-$CF_3$, - | M − H = 372.1; $^1$H-NMR (400 MHz, DMSO-$d_6$): 9.07 (s, 1H, NH), 8.95 (s, 1H, NH), 8.44 (d, Hz, 6.5 Hz, 2H, pyridinyl), 8.02 (s, 1H, 3-$CF_3$-phenyl), 7.58 (d, 9.5 Hz, 2H, oxo-phenyl-amine), 7.5 (d, 8 Hz, 1H, 3-$CF_3$-phenyl), 7.53 (t, 8.0 Hz, 1H, 3-$CF_3$-phenyl), 7.30 (d, 8.0 Hz, 1H, 3-$CF_3$-phenyl), 7.14 (d, 9.5 Hz, 2H, oxo-phenyl-amine), 6.89 (d, 6.5 Hz, 2H, pyridinyl); $R_f$ (AcOEt/hexane = 2:1): 0.12; m.p. = 147-149° C.. |
| 3 | O | NH | 4-n-Propyl, - | M + H = 348.3; $^1$H-NMR (400 MHz, DMSO-$d_6$): 8.73 (s, 1H, NH), 8.56 (s, 1H, NH), 8.42 (d, Hz, 6.5 Hz, 2H, pyridinyl), 7.55 (d, 9.5 Hz, 2H, 4-propyl-phenyl), 7.37 (d, 9.5 Hz, 2H, oxo-phenyl-amine), 7.09 (d/d, 9.5 Hz, 4H, oxo-phenyl-amine/4-propyl-phenyl), 6.84 (d, 6.5 Hz, 2H, pyridinyl), 2.47 (t, 7.5 Hz, 2H, $CH_2$), 1.56 (sext, 7.5 Hz, 2H, $CH_2$, 0.88 (t, 7.5 hz, 3H, $CH_3$); $R_f$ (AcOEt/hexane = 2:1): 0.18; m.p. = 173-174.5° C.. |
| 4 | O | NH | 4-Methyl, - | M + H = 320.1; $^1$H-NMR (400 MHz, DMSO-$d_6$): 8.73 (s, 1H, NH), 8.54 (s, 1H, NH), 8.40 (d, Hz, 6.5 Hz, 2H, pyridinyl), 7.54 (d, 9.5 Hz, 2H, 4-methyl-phenyl), 7.32 (d, 9.5 Hz, 2H, oxo-phenyl-amine), 7.09 (d/d, 9.5 Hz, 4H, oxo-phenyl-amine/ 4-methyl-phenyl), 6.85 (d, 6.5 Hz, 2H, pyridinyl), 2.49 (s, 3H, $CH_3$); $R_f$ (AcOEt/hexane = 2:1): 0.15; m.p. = 190.5-192° C.. |
| 5 | O | NMe | 4-Ethyl, - | M + H = 348.1; $^1$H-NMR (400 MHz, DMSO-$d_6$): 8.49 (d, Hz, 6.5 Hz, 2H, pyridinyl), 8.10 (s, 1H, NH), 7.39 (d, 9.5 Hz, 2H, 4-ethyl-phenyl), 7.22 (d, 9.5 Hz, 2H, oxo-pheny/-amine), 7.07 (d, 9.5 Hz, 4H, oxo-phenyl-amine), 7.07 (d, 9.5 Hz, 2H, 4-ethyl-phenyl), 7.00 (d, 6.5 Hz, 2H, pyridinyl), 3.26 (s, 3H, $CH_3$—N), 2.49 (qu, 7.5 Hz, 3H, $CH_2$), 1.11 (t, 7.5 Hz, 3H, $CH_3$); $R_f$ (AcOEt/hexane = 2:1): 0.10; oil. |
| 6 | O | NMe | 3-$CF_3$, - | M + H = 388.2; $^1$H-NMR (400 MHz, DMSO-$d_6$): 8.53 (s, 1H, NH), 8.48 (d, Hz, 6.5 Hz, 2H, pyridinyl), 7.83 (s, 1H, 3-$CF_3$-phenyl), 7.74 (d/broad, 8.0 Hz, |

TABLE 1-continued

Structures and analytical data of compounds of Examples 2-15

[Structure: pyridin-4-yl–$Y_1$–phenyl–X–C(=O)–NH–phenyl(–$R_1$,–$R_2$)]

| Ex. | $Y_1$ | X | $R_1$, $R_2$ | Analytical data |
|---|---|---|---|---|
| | | | | 1H, —CF$_3$-phenyl), 7.44 (t, 8.0 Hz, 1H, 3-CF$_3$-phenyl), 7.41 (d, 9.5 Hz, 2H, oxo-phenyl-amine), 7.28 (d/broad, 8.0 Hz, 1H, —CF$_3$-phenyl), 7.19 (d, 9.5 Hz, 2H, oxo-phenyl-amine), 6.97 (d, 6.5 Hz, 2H, pyridinyl); R$_f$ (AcOEt/hexane = 2:1): 0.26; m.p. = 126-128.5° C.. |
| 7 | O | NMe | 4-n-Propyl, - | M + H = 362.1; $^1$H-NMR (400 MHz, DMSO-d$_6$): 8.46 (d, Hz, 6.5 Hz, 2H, pyridinyl), 8.09 (s, 1H, NH), 7.41 (d, 9.5 Hz, 2H, 4-propyl-phenyl), 7.35 (d, 9.5 Hz, 2H, oxo-phenyl-amine), 7.19 (d, 9.5 Hz, 4H, oxo-phenyl-amine), 7.02 (d, 9.5 Hz, 2H, 4-propyl-phenyl), 6.97 (d, 6.5 Hz, 2H, pyridinyl), 3.13 (s, 3H, CH$_3$—N), 2.49 (t, 7.5 Hz, 3H, CH$_2$), 1.53 (sext, 7.5 Hz, 2H, CH$_2$), 0.84 (t, 7.5 Hz, 3H, CH$_3$); R$_f$ (AcOEt/hexane = 2:1): 0.38; oil. |
| 8 | O | NMe | 4-Methyl, - | M + H = 334.2; $^1$H-NMR (400 MHz, DMSO-d$_6$): 8.48 (d, Hz, 6.5 Hz, 2H, pyridinyl), 8.07 (s, 1H, NH), 7.41 (d, 9.5 Hz, 2H, 4-methyl-phenyl), 7.31 (d, 9.5 Hz, 2H, oxo-phenyl-amine), 7.19 (d, 9.5 Hz, 4H, oxo-phenyl-amine), 7.03 (d, 9.5 Hz, 2H, 4-methyl-phenyl), 6.98 (d, 6.5 Hz, 2H, pyridinyl), 3.24 (s, 3H, CH$_3$—N), 2.20 (s, 3H, CH$_3$); R$_f$ (AcOEt/hexane = 2:1): 0.17; oil. |
| 9 | O | NH | 3-CF$_3$, 4-Br | M + H = 452.1/454.1; $^1$H-NMR (400 MHz, DMSO-d$_6$): 9.18 (s, 1H, NH), 8.96 (s, 1H, NH), 8.42 (d, Hz, 6.5 Hz, 2H, pyridinyl), 8.11 (s, 1H, Br/CF$_3$-phenyl), 7.75 (d, 8.0 Hz, 1H, Br/CF$_3$-phenyl), 7.56 (d, 8.0 Hz, 1H, Br/CF$_3$-phenyl), 7.54 (d, 9.5 Hz, 2H, oxo-phenyl-amine), 7.11 (d, 9.5 Hz, 2H, oxo-phenyl-amine), 6.84 (d, 6.5 Hz, 2H, pyridinyl); R$_f$ (Acetonitrile/CH$_2$Cl$_2$ = 1:3): 0.22; m.p. = 180-183° C.. |
| 10 | O | NH | 3-CF$_3$, 4-O—CH$_2$—CF$_3$ | M + H = 472.1; $^1$H-NMR (400 MHz, DMSO-d$_6$): 8.89 (s, 1H, NH), 8.85 (s, 1H, NH), 8.42 (d, Hz, 6.5 Hz, 2H, pyridinyl), 7.88 (d, 3.0 Hz, 1H, O—CH$_2$—CF$_3$/CF$_3$-phenyl), 7.75 (dd, 8.0 Hz, 3.0 Hz, 1H, O—CH$_2$—CF$_3$/CF$_3$-phenyl), 7.54 (d, 9.5 Hz, 2H, oxo-phenyl-amine), 7.31 (d, 8.0 Hz, 1H, O—CH$_2$—CF$_3$/CF$_3$-phenyl), 7.08 (d, 9.5 Hz, 2H, oxo-phenyl-amine), 6.89 (d, 6.5 Hz, 2H, pyridinyl), 4.90 (qu, 7.5 Hz, 2H, CH$_2$); R$_f$ (MeOH/CH$_2$Cl$_2$ = 5:95): 0.15; m.p. = 188.5-190.5° C.. |
| 11 | O | NH | 5-CF$_3$, 3-OMe | M + H = 404.1; $^1$H-NMR (400 MHz, DMSO-d$_6$): 9.07 (s, 1H, NH), 8.87 (s, 1H, NH), 8.40 (d, Hz, 6.5 Hz, 2H, pyridinyl), 7.55 (d, 9.5 Hz, 2H, oxo-phenyl-amine), 7.48 (s, 1H, CH$_3$—O—/CF$_3$-phenyl), 7.24 (s, 1H, O—CH$_3$/CF$_3$-phenyl ), 7.09 (d, 9.5 Hz, 2H, oxo-phenyl-amine), 6.84 (d, 6.5 Hz, 2H, pyridinyl), 6.80 (s, 1H, CH$_3$—O—/CF$_3$-phenyl), 3.79 (s, 3H, CH$_3$—O); R$_f$ (MeOH/CH$_2$Cl$_2$ = 1:3): 0.19; m.p. = 162.5-164.5° C.. |
| 12 | CH$_2$ | NH | 4-n-Propyl, - | M + H = 346.3; $^1$H-NMR (400 MHz, DMSO-d$_6$): 8.58 (s, 1H, NH), 8.50 (s, 1H, NH), 8.44 (d, Hz, 6.5 Hz, 2H, pyridinyl), 7.36 (d, 9.5 Hz, 2H, 4-propyl-phenyl), 7.33 (d, 9.5 Hz, 2H, oxo-phenyl-amine), 7.22 (d, 6.5 Hz, 2H, pyridinyl), 7.13/7.04 (d/d, 9.5 Hz, 4H, oxo-phenyl-amine/4-propyl-pheny/), 3.87 (s, 2H, aryl-CH$_2$-aryl), 2.48 (t, 7.5 Hz, 2H, CH$_2$), 1.56 (sext, 7.5 Hz, 2H, CH$_2$, 0.86 (t, 7.5 hz, 3H, CH$_3$); R$_f$ (acetone/CH$_2$Cl$_2$ = 1:3): 0.27; m.p. = 164-166° C.. |
| 13 | CH$_2$ | NH | 4-Ethyl, - | M + H = 332.1; $^1$H-NMR (400 MHz, DMSO-d$_6$): 8.54 (s, 1H, NH), 8.50 (s, 1H, NH), 8.43 (d, Hz, 6.5 Hz, 2H, pyridinyl), 7.38/7.33 (d/d, 9.5 Hz, 4H, 4-ethyl-phenyl/, oxo-phenyl-amine), 7.19 (d, 6.5 Hz, 2H, pyridinyl), 7.16/7.09 (d/d, 9.5 Hz, 4H, oxo-phenyl-amine/4-ethyl-phenyl), 3.87 (s, 2H, aryl-CH$_2$-aryl), 2.51 (qu, 7.5 Hz, 2H, CH$_2$), 1.11 (t, 7.5 hz, 3H, CH$_3$); R$_f$ (AcOEt/hexane = 2.1): 0.25; m.p. = 182.2-183.6° C.. |

TABLE 1-continued

Structures and analytical data of compounds of Examples 2-15

| Ex. | $Y_1$ | X | $R_1, R_2$ | Analytical data |
|---|---|---|---|---|
| 14 | $CH_2$ | NH | 4-Methyl, - | M= = 317; $^1$H-NMR (400 MHz, DMSO-$d_6$): 8.54 (s, 1H, NH), 8.50 (s, 1H, NH), 8.42 (d, Hz, 6.5 Hz, 2H, pyridinyl), 7.37/7.31 (d/d, 9.5 Hz, 4H, 4-methyl-phenyl, propyl-phenyl), 7.20 (d, 6.5 Hz, 2H, pyridinyl), 7.14/7.06 (d/d, 9.5 Hz, 4H, oxo-phenyl-amine/4-methyl-phenyl), 3.87 (s, 2H, aryl-$CH_2$-aryl), 2.20 (s, 3H, $CH_3$); $R_f$ (AcOEt/hexane = 2.1): 0.35; m.p. = 197-198.5° C.. |
| 15 | $CH_2$ | NH | 3-$CF_3$, - | M + H = 372.1; $^1$H-NMR (400 MHz, DMSO-$d_6$): 9.14 (s/broad, 1H, NH), 8.89 (s/broad, 1H, NH), 8.44 (d, 6.0 Hz, 2H, pyridinyl), 8.00 (s, 1H, phenyl-$CF_3$), 7.55 (d, 7.5 Hz, 1H, phenyl-$CF_3$), 7.49 (t, 7.5 Hz, 1H, phenyl-$CF_3$), 7.40 (d, 8.0 Hz, 2H, phenyl-NH), 7.30 (d, 7.5 Hz, 4H, phenyl-$CF_3$), 7.23 (d, 6.0 Hz, 2H, pyridinyl), 7.18 (d, 8.0 Hz, 2H, phenyl-NH), 3.90 (s, 2H, aryl-$CH_2$-aryl); $R_f$ (AcOEt/hexane = 2:1): 0.23; m.p. = 127-129° C.. |

Example 16

N-(4-pyridin-4-yl-oxy-phenyl)acetyl-(4-ethyl-phenyl)-amide

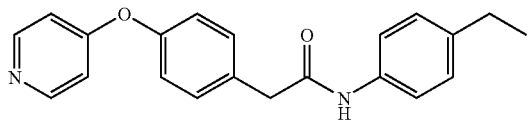

Aryl ether formation of 4-chloropyridine and N-(4-ethyl-phenyl)-2-(4-hydroxy-phenyl)-acetamide (Stage 16.1) is performed according to the procedure of the synthesis of Stage 1.1: M+H=333.1; $^1$H-NMR (400 MHz, DMSO-$d_6$): 10.10 (s, 1H, NH), 8.42 (d, Hz, 6.5 Hz, 2H, pyridinyl), 7.48/7.41 (d/d, 9.5 Hz, 4H, phenyl), 6.81 (d, 6.5 Hz, 2H, pyridinyl), 7.10 (d/d, 9.5 Hz, 4H, phenyl), 3.62 (s, 2H, aryl-$CH_2$-aryl), 2.52 (qu, 7.5 Hz, 2H, $CH_2$), 1.12 (t, 7.5 Hz, 3H, $CH_3$); $R_f$ (AcOEt/hexane=2:1): 0.35; oil.

The starting material is prepared as follows:

Stage 16.1: N-(4-Ethyl-phenyl)-2-(4-hydroxy-phenyl)-acetamide

4-Hydroxyphenyl acetic acid (1.55 g, 10.2 mmol), 4-ethyl-phenylamine (1.28 ml, 10.3 mmol), TBTU (4.82 g, 15 mmol), and NMM (8.79 ml, 80 mmol) are stirred in DMF (30 ml) at rt for 5 h. The reaction mixture is taken up in AcOEt (0.2 L), washed with $H_2O$ (40 ml, 2×) and brine (40 ml, 2×), dried ($Na_2SO_4$), concentrated under reduced pressure, and flash chromatographed (silica gel, 3.5×25 cm, AcOEt/hexane=1:2→2:3) giving the title compound of Stage 16.1 as a colorless solid (1.68 g, 6.59 mmol; 66%) M+H=256.1; $^1$H-NMR (400 MHz, DMSO-$d_6$): 10.0/9.24 (s/s, 1H, NH/OH), 7.46 (d, 8.5 Hz, 2H, phenyl), 7.09 (d, 8.5 Hz, 4H, phenyl), 6.66 (d, 8.5 Hz, 2H, phenyl), 3.47 (s, 2H, aryl-$CH_2$), 2.53 (qu, 7.5 Hz, 2H, $CH_2$), 1.13 (t, 7.5 Hz, 3H, $CH_3$); R. (AcOEt/hexane=1:1): 0.66; m.p. =146-148° C.

Compounds of Examples 17 and 18 are synthesized analogously to the preparation of the compound of Example 16 (data are enlisted on Table 2).

TABLE 2

Structures and analytical data of compounds of Examples 17-18

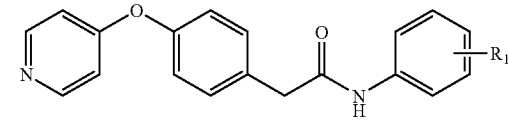

| Ex. | $R_1$ | Analytical data |
|---|---|---|
| 17 | 4-Methyl | M + H = 319.1; $^1$H-NMR (400 MHz, DMSO-$d_6$): 10.10 (s, 1H, NH), 8.44 (d, Hz, 6.5 Hz, 2H, pyridinyl), 7.48 (d, 9.5 Hz, 2H, phenyl-NH), 7.40 (d, 9.5 Hz, 2H, phenyl-O), 7.13 (d, 9.5 Hz, 2H, phenyl-NH), 7.11 (d, 9.5 Hz, 2H, phenyl-O), 6.91 (d, 6.5 Hz, 2H, pyridinyl), 3.65 |

TABLE 2-continued

Structures and analytical data of compounds of Examples 17-18

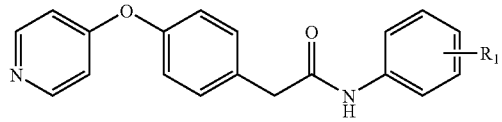

| Ex. | R₁ | Analytical data |
|---|---|---|
| | | (s, 2H, aryl-CH₂-aryl), 2.24 (s, 3H, CH₃); R$_f$(AcOEt/hexane = 2:1): 0.12; m.p. = 157.5-158° C. |
| 18 | 4-n-Propyl | M + H = 347.3; ¹H-NMR (400 MHz, DMSO-d₆): 10.12 (s, 1H, NH), 8.44 (d, Hz, 6.5 Hz, 2H, pyridinyl), 7.50 (d, 9.5 Hz, 2H, phenyl), 7.46 (d, 9.5 Hz, 2H, phenyl), 7.18 (d, 9.5 Hz, 2H, phenyl), 7.13 (d, 9.5 Hz, 2H, phenyl), 6.91 (d, 6.5 Hz, 2H, pyridinyl), 3.68 (s, 2H, aryl-CH₂-aryl), 2.49 (t, 7.5 Hz, 2H, CH₂), 1.57 (sext, 7.5 Hz, 2H, CH₂), 0.87 (t, 7.5 Hz, 3H, CH₃); R$_f$(AcOEt/hexane = 1:3): 0.25; oil. |

In Table 3, analytical data of compounds of the starting materials, Stage 17.1 and 18.1, are given.

Starting Materials:

TABLE 3

Structures and analytical data of compounds of Stages 17.1 and 18.1

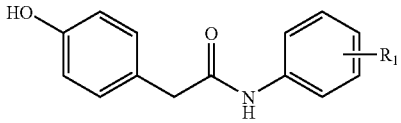

| Stage | R₁ | Analytical data |
|---|---|---|
| 17.1 | 4-Methyl | M + H = 241; ¹H-NMR (400 MHz, DMSO-d₆): 9.99/9.21 (s/s, 2H, NH/OH), 7.46 (d, 9.5 Hz, 2H, phenyl), 7.10 (d, 9.5 Hz, 2H, phenyl), 7.08 (d, 9.5 Hz, 2H, phenyl), 6.68 (d, 9.5 Hz, 2H, phenyl), 3.48 (s, 2H, aryl-CH₂-aryl), 3.40 (s, 3H, CH₃); R$_f$(AcOEt/hexane = 1:2): 0.24. |
| 18.1 | 4-Propyl | M − H = 268.2; ¹H-NMR (400 MHz, DMSO-d₆): 9.99/9.22 (s/s, 2H, NH/OH), 7.46 (d, 9.5 Hz, 2H, phenyl), 7.10 (d, 9.5 Hz, 2H, phenyl), 7.08 (d, 9.5 Hz, 2H, phenyl), 6.68 (d, 9.5 Hz, 2H, phenyl), 3.46 (s, 2H, aryl-CH₂-aryl), 2.47 (t, 7.5 Hz, 2H, CH₂), 1.53 (sext, 7.5 Hz, 2H, CH₂), 0.83 (t, 7.5 Hz, 3H, CH₃); R$_f$(AcOEt/hexane = 1:1): 0.57. |

Example 19

5(4-pyridyloxy)-N-(3-trifluoromethyl-phenyl)aminocarbonyl-2,3-dihydroindole

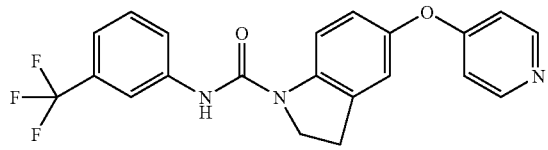

After stirring a solution of 3-(trifuoromethyl)-phenyl isocyanate (0.348 ml, 2.45 mmol), 5-(pyridin-4-yl-oxy)-2,3-dihydroindole (Stage 19.1; 0.13 g, 0.613 mmol), pyridine (0.104 ml, 1.29 mmol) in THF (4 ml) is stirred at rt for 4 d. The reaction mixture is concentrated under reduced pressure and flash chromatographed (silica gel, 2.5×18 cm, acetone/CH₂Cl₂=1:3) to give compound of Example 19 as a beige solid: M+H=400.1; ¹H-NMR (400 MHz, DMSO-d₆): 8.87 (s, 1H, NH), 8.41 (d, Hz, 6.5 Hz, 2H, pyridinyl), 8.02 (s, 1H, 3-CF₃-phenyl), 9.5 Hz, H, indoline), 7.86 (d, 8.0 Hz, H, —CF₃-phenyl), 7.53 (t, 8.0 Hz, 1H, 3-CF₃-phenyl), 7.36 (d, 8.0 Hz, H, CF₃-phenyl), 7.07 (d, 3.5 Hz, 1H, indoline), 6.94 (dd, 9.5 Hz, 3.5 Hz, 1H, indoline), 6.84 (d, 6.5 Hz, 2H, pyridinyl), 4.19 (t, 8.0 Hz, 2H, CH₂), 3.19 (t, 8.0 Hz, 2H, CH₂); R$_f$(acetone/H₂Cl₂=1:3): 0.22; m.p.=171-172.5° C.

The starting materials are prepared as follows:

Stage 19.1: 5-(pyridin-4-yl-oxy)-2,3-dihydroindole

During 5 min, NaBH₃CN (315 mg, 4.76 mmol) is added to a solution of 5-pyridin-4-yl-oxy-indoline (Stage 19.2; 0.2 g, 0.95 mmol) in AcOH (4.75 ml) at 0° C. After stirring for 4 h at rt, ice (10 g) is added and the AcOH is evaporated under reduced pressure. The resulting oil is adjusted to pH=11 by adding 1 N NaOH, extracted with ether (20 ml, 3×). The combined ether phases are washed with 1 N NaOH (10 ml), H₂O (10 ml, 2×), and brine (10 ml, 2×), dried (MgSO₄), concentrated under reduced pressure, and flash chromatographed (silica gel, 2.5×18 cm; acetone/CH₂Cl₂=1:3) to give the title compound of Stage 19.1 as a pale solid: M+H=213.1; ¹H-NMR (400 MHz, DMSO-d₆): 8.37 (d, Hz, 6.5 Hz, 2H, pyridinyl), 6.82 (d, 3.5 Hz, 1H, indoline), 6.80 (d, 6.5 Hz, 2H, pyridinyl), 6.67 (dd, 9.5 Hz, 3.5 Hz, 1H, indoline), 6.50 (d, 9.5

Hz, H, indoline), 5.54 (s/broad, 1H, NH), 3.44 (t, 8.0 Hz, 2H, CH$_2$), 2.92 (t, 8.0 Hz, 2H, CH$_2$); R$_f$ (acetone/H$_2$Cl$_2$=1:3): 0.22; m.p.=115.5-117.5° C.

Stage 19.2: 5-pyridin-4-yl-oxyindoline

The title compound of Stage 19.2 is synthesized according to the procedure of the preparation of the compound of Stage 1.1: M+H=211.0; $^1$H-NMR (400 MHz, DMSO-d$_6$): 8.37 (d, Hz, 6.5 Hz, 2H, pyridinyl), 7.47 (d, 9.5 Hz, 1H, indole-H7), 7.44 (d, 2.0 Hz, 1H, indole-H2), 7.34 (d, 2.0 Hz, 1H, indole-H5), 6.84 (d, 9.5 Hz, H, Indole-H8), 6.83 (d, Hz, 6.5 Hz, 2H, pyridinyl), 6.42 (d, 2.0 Hz, 1H, indole-H3); R$_f$ (acetone/H$_2$Cl$_2$=1:3): 0.38; m.p.=176-177.5° C.

Example 20

5-(4-pyridyl-oxy)-N-(3-trifluoromethyl-phenyl) amino-carbonyl-1,2,3,4-tetrahydroquinoline

The title compound of Example 20 is prepared analogously to the synthesis of the compound of Example 19 via urea formation with 6-(pyridin-4-yl-oxy)-1,2,3,4-tetrahydroquinoline (Stage 20.1): M+H=414.0; $^1$H-NMR (400 MHz, DMSO-d$_6$): 9.19 (s, 1H, NH), 8.42 (d, Hz, 6.5 Hz, 2H, pyridinyl), 7.94 (s, 1H, 3-CF$_3$-phenyl), 7.73 (d, 9.5 Hz, H, indoline), 7.45 (t, 8.0 Hz, 1H, 3-CF$_3$-phenyl ), 7.43 (s, 1H, 1H, dihydroquinole-H8), 7.29 (d, 8.0 Hz, H, CF$_3$-phenyl), 6.98 (d, 3.5 Hz, 1H, dihydroquinole-H5), 6.93 (dd, 9.5 Hz, 3.5 Hz, 1H, dihydroquinole-H7), 6.89 (d, 6.5 Hz, 2H, pyridinyl), 3.75 (t, 8.0 Hz, 2H, CH$_2$), 2.75 (t, 8.0 Hz, 2H, CH$_2$), 1.90 (sext, 8.0 Hz, 2H, CH$_2$); R$_f$(acetone/CH$_2$Cl$_2$=1:3): 0.33; m.p.=185.5-188° C.

The starting materials are prepared as follows:

Stage 20.1: 6-(pyridin-4-yl-oxy)-1,2,3,4-tetrahydroquinoline

The title compound is prepared via reduction of the corresponding quinoline (Stage 20.2) analogously to the synthesis of the compound of Example 19.1: M+H=227.1; $^1$H-NMR (400 MHz, DMSO-d$_6$): 8.37 (d, Hz, 6.5 Hz, 2H, pyridinyl), 6.78 (d, 6.5 Hz, 2H, pyridinyl), 6.66 (m, 2H, tetrahydroquinoline), 6.46 (d, 9.5 Hz, 3.5 Hz, 1H, tetrahydroquinoline), 5.74 (s/broad, 1H, NH), 3.17 (t, 8.0 Hz, 2H, CH$_2$), 2.65 (t, 8.0 Hz, 2H, CH$_2$) 1.74 (sext, 8.0 Hz, 2H, CH$_2$); R$_f$(acetone/H$_2$Cl$_2$=1:3): 0.26; m.p.=117-121.5° C.

Stage 20.2: 6-(pyridin-4-yl-oxy)-quinoline

The compound of Stage 20.2 is synthesized according to the procedure of the preparation of the compound of Stage 19.2: M+H=211.0; $^1$H-NMR (400 MHz, DMSO-d$_6$): 8.87 (dd, 3.5 Hz, 2.0 Hz, 1H, quinoline-H1), 8.48 (d, 6.5 Hz, 2H, pyridinyl), 8.35 (dd, 7.7 Hz, 2.0 Hz, 1H, quinoline-H3), 8.11 (d, 9.0 Hz, 1H, quinoline-H8), 7.75 (d, 3.0 Hz, 1H, quinoline-H5), 7.59 (dd, 9.0 Hz, 3.0 Hz, 1H, quinoline-H7), 7.54 (dd, 7.7 Hz, 3.5 Hz, 1H, quinoline-H2), 7.03 (d, Hz, 6.5 Hz, 2H, pyridinyl); R$_f$(acetone/H$_2$Cl$_2$=1:3): 0.26.

Example 21

N-(4-(6-Chloropyrimidin-4-yl)-oxyphenyl)-N'-(3-trifluoromethylphenyl)-urea

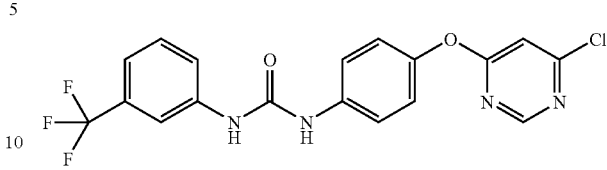

After stirring 3-trifluoromethyl-phenyl isocyanate (412 mg, 2.2 mmol), 4-(6-chloro-pyrimidin-4-yl-oxy)-aniline (Stage 21.1; 0.25 g, 1.1 mmol), and pyridine (0.18 ml), dissolved in THF (3 ml) overnight, the reaction solution is concentrated under reduced pressure and flash chromatographed (silica gel, 2.5×17 cm; acetone/CH$_2$Cl$_2$=5:95→1:9) to give compound of Example 21 as a colorless solid: M+H=408.9/410.9; $^1$H-NMR (400 MHz, DMSO-d$_6$): 9.07 (s, 1H, NH), 8.89 (s, 1H, NH), 8.63 (d, 2.0 Hz, 1H, pyridinyl), 8.01 (s, 1H, 3-CF$_3$-phenyl), 7.57 (d/broad, 8.0 Hz, 1H, CF$_3$-phenyl), 7.52 (d, 9.5 Hz, 2H, oxo-phenyl-amine), 7.50 (m, 1H, 3-CF$_3$-phenyl), 7.32 (d, 2.0 Hz, 1H, pyridinyl), 7.29 (d/broad, 8.0 Hz, 1H, —CF$_3$-phenyl), 7.15 (d, 9.5 Hz, 2H, oxo-phenyl-amine), (d, 6.5 Hz, 2H, pyridinyl); R$_f$(acetone/CH$_2$Cl$_2$=1:9): 0.54; m.p.=187.4-189.7° C.

The starting materials are prepared as follows:

Stage 21.1: 4-(6-Chloro-pyrimidin-4-yl-oxy)-aniline

4-Chloro-6(4-nitro-phenoxy)-pyrimidine (Stage 21.2; 3.6 g, 14.3 mmol) dissolved in MeOH (250 ml) is hydrogenated in the presence of Raney-Ni (3 g) at 40° C. for 3 d. The reaction solution is filtered, concentrated under reduced pressure and crystallized from AcOEt/hexane to give the title compound of Stage 21.1: M+H=222/224; $^1$H-NMR (400 MHz, DMSO-d$_6$): 8.62 (s, 1H), 7.13 (s, 1H), 6.83 (d, 9 Hz, 2H, phenyl), 6.56 (d, 9 Hz, 2H, phenyl), 5.12 (s, 2H, NH$_2$); m.p.=135.5-138.1° C.

Stage 21.2: 4-Chloro-6-(4-nitro-phenoxy)-pyrimidine

4-Nitrophenol (2.8 g, 20.1 mmol), 2,4-dichloro-pyrimidine (3 g, 20.1 mmol), NaOH (0.8 g, 20.1 mmol) dissolved in H$_2$O/acetone (80 ml; 1:1) are stirred at 60-65° C. for 1 h. The reaction solution is concentrated under reduced pressure and flash chromatographed (silica gel, 4.5×22 cm, AcOEt/hexane=1:4) to give the title compound of Stage 21.2 as a colorless solid: M+H=252/254; $^1$H-NMR (400 MHz, DMSO-d$_6$): 8.67 (s, 1H, pyrimidinyl), 8.34 (d, 9 Hz, 2H, phenyl), 7.58 (d, 9 Hz, 2H, phenyl), 7.53 (s, 1H, pyrimidinyl); R$_f$ (AcOEt/hexane=1:1): 0.16; m.p.=125.4-126.6° C.

Example 22

N-(4-(4-(4-hydroxyphenylamino)-pyrimidin-6-yl)-oxyphenyl)-N'-(3-trifluoromethylphenyl)-urea

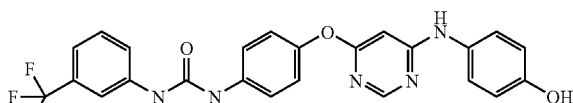

1-(4-{6-[4-(tert-Butyl-dimethyl-silyloyloxy)-phenylamino]-pyrimidin-4-yl-oxy}-phenyl)-3-(3-trifluoromethylphenyl)urea (Stage 22.1; 0.7 g, 1.17 mmol) is dissolved in HF/pyridine (70%, 1 ml) and MeCN/THF (4 ml/2 ml) at 0° C. After stirring for 3 h at rt, the reaction mixture is neutralized by adding phosphate buffer (pH=7, 10 mL) and the product is taken up in AcOEt (10 ml, 2×), dried (MgSO$_4$), flash chromatographed (silica gel, 2.5×17 cm, MeOH/CH$_2$Cl$_2$=1:9) to give the title compound of Example 22 as a colorless solid: M+H=481.9; $^1$H-NMR (400 MHz, DMSO-d$_6$): 9.23/9.21 (s/s, 2H, NH, OH), 9.10/8.91 (s/s, 2H, NH-urea,), 8.23 (s, 1H, pyrimidinyl), 8.01 (s, 1H, CF$_3$-phenyl), 7.58 (d, 8.8 Hz, 1H, CF3-phenyl), 7.51 (m, 3H, phenyl-urea/CF3-phenyl), 7.26 (m, 3H, phenyl-OH/CF3-phenyl), 7.10 (d, 8.8 Hz, 2H, phenyl-urea), 6.71 (d, 8.8 Hz, 2H, phenyl-OH), 5.90 (s, 1H, pyrimidinyl); R$_f$ (MeOH/CH$_2$Cl$_2$=1:9)=0.29 (silica gel); m.p.=142° C. (decomp.).

The starting materials are prepared as follows:

Stage 22.1: 1-(4-{6-[4-(tert-Butyl-dimethyl-silyloxy)-phenylamino]-pyrimidin-4-yl-oxy}-phenyl)-3-(3-trifluoromethyl-phenyl)urea After stirring [6-(4-amino-phenoxy)-pyrimidin-4-yl][4-(tert-butyl-dimethyl-silyloxy)-phenyl]-amine (Stage 22.2; 1 g, 2.45 mmol), 3-trifluoromethyl-phenyl-isocyanate (916 mg, 4.9 mmol), NEt$_3$ (0.682 ml, 4.9 mmol) dissolved in DMF (6 ml) for 1 h, the reaction mixture is concentrated under reduced pressure and flash chromatographed (silica gel, 2.5× 19 cm, AcOEt/hexane=1:2→2:1) to give the title compound of Stage 22.1 as a colorless solid: M+H=595.9; $^1$H-NMR (400 MHz, DMSO-d$_6$): 9.36\9.07\8.85 (s/s/s, 3H, NH-urea, NH), 8.24 (s, 1H, pyrimidinyl), 8.02 (s, 1H, CF$_3$-phenyl), 7.57 (d, 8.8 Hz, 1H, CF$_3$-phenyl), 7.50 (m, 3H, phenyl-urea/CF3-phenyl), 7.39 (m, 3H, phenyl-OTBS/CF$_3$-phenyl), 7.10 (d, 8.8 Hz, 2H, phenyl-urea), 6.78 (d, 8.8 Hz, 2H, phenyl-OTBS), 5.92 (s, 1H, pyrimidinyl), 0.90 (s, 9H, TBS), 0.18 (s, 6H, TBS).

Stage 22.2: [6-(4-Amino-phenoxy)-pyrimidin-4-yl][4-(tert-butyl-dimethyl-silyloxy)-phenyl]-amine

[4-(tert-Butyl-dimethyl-silyloxy)-phenyl]-[6-(4-nitro-phenoxy)-pyrimidin-4-yl]-amine (Stage 22.3; 1.8 g, 4.1 mmol) is reduced by means of Raney-Ni (0.4 g) in EtOH/THF (35/15 ml) during 3 h and purified by flash chromatography (silica gel, 3.0×18 cm, AcOEt/hexane=1:1→4:1) to give compound of Stage 22.2 as a colorless solid: M+H=409.1; $^1$H-NMR (400 MHz, DMSO-d$_6$): 9.22 (s, 1H, NH), 8.20 (s, 1H, pyrimidinyl), 7.37 (d, 8.8 Hz, 2H, phenyl-OTBS), 6.77 (d, 8.8 Hz, 2H, phenyl-NH$_2$), 6.70 (d, 8.8 Hz, 2H, phenyl-OTBS), 6.55 (8.8 Hz 2H, phenyl-NH$_2$), 5.79 (s, 1H, pyrimidinyl), 5.02 (s, 2H, NH$_2$), 0.90 (s, 9H, TBS), 0.12 (s, 6H, TBS); R$_f$(AcOEt/hexane=2:1): 0.22.

Stage 22.3: [4-(tert-Butyl-dimethyl-silyloxy)-phenyl]-[6-(4-nitro-phenoxy)-pyrimidin-4-yl]l-amine 4-[6-(4-Nitro-phenoxy)pyrimidin-4-ylamino]-phenol (Stage 22.4; 1.5 g, 4.63 mmol), tert-butyl-dimetylsilyl chloride (1.39 g, 9.26 mmol), NEt$_3$ (1.29 ml, 9.26 mmol) dissolved in DMF (20 ml) are stirred for 3.5 h. After concentrating the reaction mixture under reduced pressure and dissolving in phosphate buffer (50 ml, pH=7), the product is extracted by means of AcOEt (10 ml) and purified by flash chromatography (silica gel, 3.0×17 cm, AcOEt/hexane=1:1→4:1) to give the title compound compound of Stage 22.3 as a colorless solid: M+H=439.0; $^1$H-NMR (400 MHz, DMSO-d$_6$): 9.56 (s, 1H, NH), 8.28 (m, 3H, pyrimidinyl, phenyl-NO$_2$), 7.40 (m, 4H, phenyl-OTBS, phenyl-NO$_2$), 6.81 (d, 8.8 Hz, 2H, phenyl-OTBS, 6.20 (s, 1H, pyrimidinyl), 0.93 (s, 9H, TBS), 0.18 (s, 6H, TBS).

Stage 22.4: 4-[6-(4-Nitro-phenoxy)-pyrimidin-4-ylamino]-phenol

4-Chloro-6-(4nitro-phenoxy)pyrimidine (Stage 22.5; 3 g, 11.9 mmol), 4-nitrophenol (1.95 g, 17.9 mmol), and diisopropylethylamine (DIPEA) (3.04 ml, 179 mmol) dissolved in 2-propanol (50 ml) are stirred at 85° C. for 18 h. After concentrating the reaction mixture under reduced pressure, the product precipitates as a colorless fine solid: M+H=245.0; $^1$H-NMR (400 MHz, DMSO-d$_6$): 9.40/9.25 (s/s, 2H, NH/OH), 8.28 (d, 7.5 Hz, 2H, phenyl-NO$_2$), 8.26 (s, 1H, pyrimidinyl), 7.40 (d, 7.5 Hz, 2H, phenyl-NO$_2$), 7.24 (d, 8.0 Hz, 2H, phenyl-OH), 6.77 (d, 8.0 Hz, 2H, phenyl-OH), 6.15 (s, 1H, pyrimidinyl); R$_f$(AcOEt/hexane=2:1): 0.48.

Stage 22.5: 4-Chloro-6-(4-nitro-phenoxy)-pyrimidine 4,6-Dicholoropyrimidine (3 g, 20 mmol), 4-nitrophenol (2.8 g, 20 mmol), NaOH (0.8 g, 20 mmol) dissolved in H$_2$O/acetone (25/25 ml) are stirred at 45° C. for 22 h. The precipitated product is isolated by filtration: M+H=252.0/254.0; $^1$H-NMR (400 MHz, DMSO-d$_6$): 9.67 (s, 1H, pyrimidinyl), 9.32 (d, 8.2 Hz, 2H, phenyl), 7.58 (s, 1H, pyrimidinyl), 7.56 (d, 8.2 Hz, 2H, phenyl); R$_f$(AcOEt/hexane=1:1): 0.20.

In accordance with the methods described hereinbefore, the following compounds, with the substituents given in Table 4, are prepared:

TABLE 4

| Ex. | Q | R$_1$ | R$_2$ |
|---|---|---|---|
| 23 | 4-pyridinyl | 4-phenyl | 3-trifluoromethyl |

TABLE 4-continued

| Ex. | Q | R₁ | R₂ |
|---|---|---|---|
| 24 | 4-pyridyl | 4-morpholino | 3-trifluoromethyl |
| 25 | 4-pyridyl | 3-methoxy | 4,5-dimethoxy |
| 26 | 4-pyridyl | 3-methoxy | 4-phenyl |
| 27 | 4-pyridyl | 3-methoxy | 4-O—CH₂—CF₃ |
| 28 | 4-pyridyl | 3-methoxy | 4-piperidino |
| 29 | 4-pyridyl | H | 4-piperidino |
| 30 | 2-methyl-4-pyridyl | 3-trifluoromethyl | H |
| 31 | 6-(4-hydroxyphenylamino)pyrimidin-4-yl | 3-trifluoromethyl | H |
| 32 | 6-(4-hydroxyphenylamino)pyrimidin-4-yl | 3-trifluoromethyl | 4-(2,2,2-trifluoroethoxy) |
| 33 | pyridine N-oxide-4-yl | 3-trifluoromethyl | H |

TABLE 4-continued

| Ex. | Q | R₁ | R₂ |
|---|---|---|---|
| 34 | (structure: 4-(2-aminoethoxy)phenyl-NH-pyrimidin-4-yl linker) | 3-trifluoromethyl | H |

Example 23

M+H=450.0; $^1$H-NMR (400 MHz, DMSO-d$_6$): 9.15 (s, 1H, NH), 8.95 (s, 1H, NH), 8.44 (d, 6.5 Hz, 2H, pyridinyl), 8.09 (s, 1H, CF$_3$/phenyl-phenyl), 7.67 (d, 6.5 Hz, 1H, CF$_3$/phenyl-phenyl), 7.57 (d, 8.5 Hz, 2H, oxo-phenyl-amine), 7.41 (M, 3H, phenyl), 7.31 (t, 7.5 Hz, 2H, phenyl), 7.15 (d, 8.5 Hz, 2H, oxo-phenyl-amine), 6.90 (m, 4H, pyridinyl/piperidinyl-phenyl), 2.99 (t, 6.5 Hz, 4H, CH$_2$, piperidinyl), 1.60 (t/broad, 4H, CH$_2$, piperidinyl), 1.47 (m/broad, 1H, piperidinyl); R$_f$ (acetone/CH$_2$Cl$_2$=1:3): 0.22; m.p: 120° C. (decomp.).

Example 24

M+H=458.9; $^1$H-NMR (400 MHz, DMSO-d$_6$): 8.97 (s, 1H, NH), 8.85 (s, 1H, NH), 8.43 (d, Hz, 6.5 Hz, 2H, pyridinyl), 7.89 (s, 1H, 3-CF$_3$-phenyl), 7.59 (d, 9.5 Hz, 1H, 3-CF$_3$-phenyl), 7.54 (d, 8.0 Hz, 2H, oxo-phenyl), 7.49 (t, 8.0 Hz, 1H, 3-CF$_3$-phenyl), 7.11 (d, 8.0 Hz, 2H, oxo-phenyl), 6.84 (d, 6.5 Hz, 2H, pyridinyl), 3.68 (s/broad, 4H, morpholinyl), 2.78 (s/broad, 4H, morpholinyl); R$_f$(MeOH/CH$_2$Cl$_2$=1:19): 0.11; m.p.>120° C. (decomp.).

Example 25

M+H=396.0; $^1$H-NMR (400 MHz, DMSO-d$_6$): 8.73 (s, 1H, NH), 8.62 (s, 1H, NH), 8.42 (d/broad, 6.5 Hz, 2H, pyridinyl), 7.56 (d, 9.5 Hz, 2H, oxo-phenyl-amine), 7.10 (d, 9.5 Hz, 2H, oxo-phenyl-amine), 6.84 (d, 6.5 Hz, 2H, pyridinyl), 6.77 (s, 2H, trimethoxy-phenyl), 3.73 (s, 6H, CH$_3$) 3.32 (s, 3H, CH$_3$); R$_f$ (acetone/CH$_2$Cl$_2$=1:3): 0.26; m.p: 179° C. (decomp.).

Example 26

Is synthesized according to the synthesis of compound of Example 1 starting from 2-methoxy-biphenyl-4-ylamine (Stage 26.1): M+H=412.0; $^1$H-NMR (400 MHz, DMSO-d$_6$): 8.81/8.79 (s/s, 2H, NH), 8.41 (d, 6.5 Hz, 2H, pyridinyl), 7.56 (d, 9.5 Hz, 2H, oxo-phenyl-amine), 7.44 (d, 7.0 Hz, 2H, phenyl), 7.36 (t/s, 7.0 Hz, 3H, phenyl/phenyl-OMe), 7.24 (t, 7.0 Hz, 1H, phenyl), 7.18 (d, 8.5 Hz, 1H, phenyl-OMe), 7.09 (d, 9.5 Hz, 2H, oxo-phenyl-amine), 7.01 (d, 8.5 Hz, 1H, phenyl-OMe), 6.84 (d, 6.5 Hz, 2H, pyridinyl), 3.73 (s, 6H, CH$_3$) 3.73 (s, 3H, CH$_3$); R$_f$ MeOH/CH$_2$Cl$_2$=5:95): 0.31.

Stage 26.1

2-Methoxy-4-nitro-biphenyl (Stage 26.2) (867 mg, 3.78 mmol) dissolved in THF/EtOH (1:5, 20 mL) is hydrogenated in the presence of Pd/C (100 mg) at rt for 30 min. After filtering off the catalyst and washing with EtOH (5 mL), the reaction solution is evaporated under reduced pressure to give compound of Stage 26.1 as colorless oil: M+H=200.0; $^1$H-NMR (400 MHz, DMSO-d$_6$): 7.37 (d, 7.0 Hz, 2H, phenyl), 7.31 (t, 7.0 Hz, 2H, phenyl), 7.17 (t, 7.0 Hz, 1H, phenyl), 6.83 (d, 8.5 Hz, 1H, phenyl-OMe), 6.30 (s, 1H, phenyl-OMe), 5.21 (s, 2H, NH$_2$), 3.64 (s, 3H OMe); HPLC (System 1): 3.92 min.

Stage 26.2

To 1-bromo-2-methoxy-4-nitro-benzene (1.0 g, 4.3 mmol) dissolved in DMF (37 mL), under Ar-atmosphere, phenyl-boronic acid (578 mg, 4.74 mmol), (AcO)$_2$Pd (48 mg, 0.215 mmol), tri-o-tolyl-phosphane (131 mg, 0.431 mmol), and K$_2$CO$_3$ (1M, 11 mL, 10.77 mmol) are added. After stirring at 120° C. for 1 h, the reaction solution is filtered over Hyflo, concentrated under reduced pressure, partitioned between AcOEt and H$_2$O (100 mL/100 mL), and extracted with AcOEt (50 mL, 2×). The combined organic phases are washed with H$_2$O (50 mL), dried (Na$_2$SO$_4$), concentrated under reduced pressure, and flash chromatographed (silica gel, 4.5×22 cm, hexane/AcOEt=9:1) to give compound of Stage 26.2 as colorless oil: M+H=231.0; $^1$H-NMR (400 MHz, DMSO-d$_6$): 7.92 (d, 7.0 Hz, 1H), 7.88 (s, 1H), 7.57 (d, 7.0 Hz, 1H), 7.54 (d, 7.0 Hz, 1H), 7.49 (t, 7.0 Hz, 3H), 7.42 (d, 7.0 Hz, 1H), 3.92 (s, 3H OMe); HPLC (System 1): 7.06 min.

Example 27

M+H=434.0; $^1$H-NMR (400 MHz, DMSO-d$_6$): 8.74 (s, 1H, NH), 8.62 (s, 1H, NH), 8.41 (d, Hz, 6.5 Hz, 2H, pyridinyl), 7.52 (d, 8.5 Hz, 2H, oxo-phenyl-amino), 7.29 (s, 1H, MeO-phenyl), 7.09 (d, 8.0 Hz, 2H, oxo-phenyl-amino), 6.97

(d, 8.5 Hz, 1H, MeO-phenyl), 6.94 (d, 6.5 Hz, 2H, pyridinyl), 3.77 (s, 3H, MeO); R$_f$(MeOH/CH$_2$Cl$_2$=5:95): 0.27.

Example 28

Is synthesized according to the synthesis of compound of Example 1 starting from 3-methoxy-4-piperidin-1-yl-phenylamine (Stage 28.1): M+H=419.1; $^1$H-NMR (400 MHz, DMSO-d$_6$): 8.68/8.51 (s/s, 2H, NH), 8.39 (d, 6.5 Hz, 2H, pyridinyl), 7.52 (d, 9.5 Hz, 2H, oxo-phenyl-amine), 7.17 (s, 1H, phenyl-OMe), 7.09 (d, 9.5 Hz, 2H, oxo-phenyl-amine), 6.85 (d, 6.5 Hz, 2H, pyridinyl), 6.83/6.78 (d/d, 8.0 Hz, 4H, phenyl-OMe), 3.74 (s, 6H, O—CH$_3$) 2.80/1.60 (m/m, 4H/4H, CH$_2$-piperidinyl), 1.48 (m, 2H, CH$_2$-piperidinyl); R$_f$MeOH/CH$_2$Cl$_2$=1:9): 0.42.

Stage 28.1

1-(2-Methoxy-4-nitro-phenyl)-piperidine (Stage 28.2) (3.9 g, 16.5 mmol) dissolved in EtOH (20 mL) is hydrogenated in the presence of Pd/C (100 mg) at rt for 3 h. After filtering off the catalyst and washing with EtOH (5 mL), the reaction solution is evaporated under reduced pressure to give compound of Stage 28.1 as colorless oil: M+H=207.1; $^1$H-NMR (400 MHz, DMSO-d$_6$): 6.58 (d, 8.0 Hz, 1H, phenyl), 6.19 (s, 1H, phenyl), 6.03 (d, 8.0 Hz, 1H, phenyl), 4.64 (s, 2H, NH$_2$), 3.66 (s, 6H, O—CH$_3$) 2.91/1.57 (m/m, 4H/4H, CH$_2$-piperidinyl), 1.42 (m, 2H, CH$_2$-piperidinyl); HPLC (System 1): 4.36 min.

Stage 28.2

1-Bromo-2-methoxy-4-nitro-benzene (5 g, 21.5 mmol) and piperidine (8.5 mL, 86.2 mmol) are stirred under reflux for 4 h. After taking up in H$_2$O (80 mL), the reaction solution is extracted with CH$_2$Cl$_2$ (80 mL, 2×). The combined organic phases are dried (Na$_2$SO$_4$), concentrated under reduced pressure, and flash chromatographed (silica gel, 5.5×22 cm, hexane/AcOEt=9:1) to give compound of Stage 28.2 as colorless solid: M+H=237.1; $^1$H-NMR (400 MHz, DMSO-d$_6$): 7.80 (d, 8.0 Hz, 1H, phenyl), 7.63 (s, 1H, phenyl), 6.97 (d, 8.0 Hz, 1H, phenyl), 4.64 (s, 2H, NH$_2$), 3.88 (s, 6H, O—CH$_3$), 3.16/1.61 (m/m, 4H/4H, CH$_2$-piperidinyl), 1.58 (m, 2H, CH$_2$-piperidinyl); HPLC (System 1): 4.90 min.

Example 29

M+H=389.2; $^1$H-NMR (400 MHz, DMSO-d$_6$): 8.64 (s, 1H, NH), 8.21 (d, 6.5 Hz, 2H, pyridinyl), 8.38 (s, 1H, NH), 7.51 (d, 9.5 Hz, 2H, oxo-phenyl-amine), 7.23 (s, 1H, phenyl-piperidinyl), 7.07 (d, 9.5 Hz, 2H, oxo-phenyl-amine), 6.86 (m, 4H, pyridinyl/phenyl-pyridinyl), 2.99/1.60 (m/m, 4H/4H, CH$_2$piperidinyl), 1.48 (m, 2H, CH$_2$-piperidinyl); R$_f$(acetone/CH$_2$Cl$_2$=3:7): 0.14.

Example 30

M+H=387.9; $^1$H-NMR (400 MHz, DMSO-d$_6$): 9.07 (s, 1H, NH), 8.85 (s, 1H, NH), 8.29 (d, Hz, 6.5 Hz, 1H, pyridinyl), 8.01 (s, 1H, 3-CF$_3$-phenyl, 7.58 (d, 9.5 Hz, 2H, oxo-phenyl-amine), 7.50 (d, 8 Hz, 1H, oxo-phenyl), 7.53 (t, 8.0 Hz, 1H, 3-CF$_3$-phenyl), 7.30 (d, 8.0 Hz, 1H, 3-CF$_3$-phenyl), 7.04 (d, 9.5 Hz, 2H, oxo-phenyl, 6.73 (d, 3.5 Hz, 1H, pyridinyl), 6.69 (dd, 3.5 Hz, 6.5 Hz, 1H, pyridinyl), 2.18 (s, 3H, CH$_3$); R$_f$(acetone/CH$_2$Cl$_2$=1:3): 0.19; m.p=160-163° C. (decomp.).

Example 31

Is synthesized in analogy to the preparation of compound of Example 22:
M+H=482.4; $^1$H-NMR (400 MHz, DMSO-d$_6$): 10.25/9.98 (s/s, 2H, NH/OH), 9.2718.99 (s/s, 2H, NH-urea,), 8.26 (d, 6.5 Hz, 1H, pyrimidinyl), 7.96 (s, 1H, CF$_3$-phenyl), 7.70 (m, 2H, CF$_3$-phenyl), 7.53 (d, 8 Hz, 2H, oxo-phenyl-urea), 7.44 (d, 7.0 Hz, 1H, CF$_3$-phenyl), 7.30 (d, 8.0 Hz, 2H, hydroxy-phenyl-amino), 7.18 (d, 8.0 Hz, 2H, oxo-phenyl-urea), 6.58 (d, 8-0 Hz, 2H, hydroxy-phenyl-amino), 6.30 (d, 6.5 Hz, 1H, pyrimidinyl); HPLC (System 1): 6.55 min.

Example 32

Is synthesized in analogy to the preparation of compound of Example 22:
M+H=579.8; $^1$H-NMR (400 MHz, DMSO-d$_6$): 9.25/9.23 (s/s, 2H, NH, OH), 8.94/8.88 (s/s, 2H, NH-urea,), 8.23 (s, 1H, pyrimidinyl), 7.94 (d, 2 Hz, 1H, CF$_3$—CH$_2$—O—/CF$_3$-phenyl), 7.65 (dd, 8.5 Hz, 2 Hz, 1H, CF$_3$—CH$_2$—O—/CF$_3$-phenyl), 7.55 (d, 9.0 Hz, 2H, oxo-phenyl-amino), 7.36 (d, 8.5 Hz, 1H, CF$_3$—CH$_2$—O—/CF$_3$-phenyl), 7.29 (d, 9.0 Hz, 2H, oxo-phenyl-urea), 7.10 (d, 8.8 Hz, 2H, oxo-phenyl-urea), 6.75 (d, 9.0 Hz, 2H, oxo-phenyl-amino), 5.93 (s, 1H, pyrimidinyl), 4.38 (q, 8.4 Hz, 2H, CH$_2$); R$_f$ (NH$_3$/MeOH/CH$_2$Cl$_2$=0.01:1:9): 0.27.

Example 33

Compound of Example 2 (29 mg, 0.078 mmol) and m-chloro-perbenzoic acid (28.9 mg, 0.17 mmol) are stirred in CH$_2$Cl$_2$/CHCl$_3$ (1:1; 3 mL) for 3 h at 45° C. Separation is performed by preparative TLC (2 plates, 20×20 cm, MeOH/CH$_2$Cl$_2$=1:4): M+H=390.0; $^1$H-NMR (400 MHz, DMSO-d$_6$): 9.39 (s, 1H, NH), 9.21 (s, 1H, NH), 8.11 (d, 9.0 Hz, 2H, pyridinyl), 8.01 (s, 1H, CF$_3$-phenyl), 7.59 (d, 8.5 Hz, 1H CF$_3$-phenyl), 7.54 (d, 10.0 Hz, 2H, oxo-phenyl), 7.49 (t, 8.5 Hz, 1H, CF$_3$-phenyl), 7.28 (d, 8.5 Hz, 1H, CF$_3$-phenyl), 7.09 (d, 10.0 Hz, 2H, oxo-phenyl), 6.93 (d, 9.0 Hz, 1H, pyridinyl); R$_f$(MeOH/CH$_2$Cl$_2$=1:9): 0.19.

Example 34

Is preapared according to the procedure of the synthesis of compound of Example 22:
M+H=525.7; $^1$H-NMR (400 MHz, DMSO-d$_6$): 9.13/8.90 (s/s, 2H, NH-urea), 8.22 (s, 1H, pyrimidinyl), 7.98 (s, 1H, CF$_3$-phenyl), 7.56 (d, 7.5 Hz, 1H, CF$_3$-phenyl), 7.47 (t, .5 Hz, 1H, CF$_3$-phenyl), 7.42 (d, 8.3 Hz, 2H, oxo-pheny-urea), 7.29 (d, 7.5 Hz, 1H, CF$_3$-phenyl), 7.13 (d, 8.8 Hz, 2H, oxo-phenyl-amino), 6.96 (d, 8.3 Hz, 2H, oxo-phenyl-urea), 5.87 (s, 1H, pyrimidinyl), 5.42 (s, 1H, NH), 3.91/2.83 (t/t/broad, 4H, CH$_2$).

Example 35

N-[4-(pyridin-4-yl-oxy)-3-chloro-phenyl]-N'-(3-trifluoromethyl-phenyl)-urea

Triphosgene (91 mg, 0.30 mmol) dissolved in CH$_2$Cl$_2$ (9 mL) is added to a solution of 3-chloro-4-(pyridin-4-yloxy)-phenylamine (Stage 35.1) (0.2 g, 0.906 mmol) and NEt$_3$ (0.11 mL, 1.5 mmol) in CH$_2$Cl$_2$ (4.5 mL) during 4 min at 0° C. After stirring the reaction solution for 10 min at rt, a solution of 3-trifluoromethyl-phenylamine (0.114 mL, 0.906 mmol) and NEt$_3$ (0.11 mL, 1.5 mmol) in CH$_2$Cl$_2$ (4.5 mL) is added. After stirring for 4.5 h, the rection solution is poured onto concentrated NaHCO$_3$ solution, and extracted with CH$_2$Cl$_2$ (25 mL, 5×). The combined organic phases are washed with brine (20 mL), died (MgSO$_4$), concentrated under reduced pressure, and fklash chromatographed (silica gel, 3.5×35 cm; AcOEt/hexane=2:1→3:1) to give compound of Example 35 as slightly yellowish solid (301 mg, 0.74 mmol; 81%), M+H=408.0; $^1$H-NMR (400 MHz, DMSO-d$_6$): 9.20/9.11 (s/s, 2H, NH), 8.45 (d, 6.5 Hz, 2H, pyrimidinyl), 8.01 (s, 1H, CF$_3$-phenyl), 7.90 (s, 1H, Cl-phenyl), 7.60 (d, 7.5 Hz, 1H, CH$_3$-phenyl, 7.53 (t, 7.5 Hz, 1H, CF$_3$-phenyl), 7.41 (d, 8.5 Hz, 1H, Cl-phenyl), 7.33 (m, 2H, phenyl-Cl/CF$_3$-phenyl), 6.88 (s, 2H, pyrimidinyl); HPLC (System 1): 5.43 min.

Stage 35.1

Is prepared according to the synthesis of compound of Stage 1.1: M+H=221.0; $^1$H-NMR (400 MHz, DMSO-d$_6$): 8.38 (d, 6.5 Hz, 2H, pyrimidinyl), 6.98 (d, 8.5 Hz, 1H Cl-phenyl), 6.77 (d, 7.0 Hz, 2H, Cl-phenyl), 6.73 (s, 1H, Cl-phenyl), 6.53 (s, 2H, pyrimidinyl), 5.44 (s, 2H, NH$_2$); HPLC (System 1): 5.43 min.

Example 36

N-[4-(pyridin-4-yl-oxy)-3-methyl-phenyl]-N'-(3-trifluoromethyl-phenyl)-urea

The title compound is synthesized according to the preparation of compound of Example 35 starting from Stage 36.1: M+H=388.2; $^1$H-NMR (400 MHz, DMSO-d$_6$): 9.03/8.90 (s/s, 2H, NH), 8.39 (d, 6.5 Hz, 2H, pyrimidinyl), 8.01 (s, 1H, CF$_3$-phenyl), 7.53 (d, 7.5 Hz, 1H, CF$_3$-phenyl, 7.46 (m, 2H, CH$_3$-phenyl), 7.35 (d, 8.5 Hz, 1H, CF$_3$-phenyl), 7.29 (d, 7.5 Hz, 1H, CF$_3$-phenyl), 7.00 (d, 7.5 Hz, 1H, CH$_3$-phenyl), 6.76 (d, 6.5 Hz, 2H, pyrimidinyl), 3.30 (s, 3H, CH$_3$); HPLC (System 1): 5.26 min.

Stage 36.1

The compound is synthesized according to the preparation of compound of Stage 35.1: slightly brownish solid: M+H=201.1; $^1$H-NMR (400 MHz, DMSO-d$_6$): 8.36 (d, 6.5 Hz, 2H, pyrimidinyl), 6.73 (m, 3H, pyrimidiny/phenyl-CH$_3$), 6.49 (s, 1H, phenyl-CH$_3$), 6.44 (m, 2H, phenyl-CH$_3$), 5.06 (s, 2H, NH$_2$), 1.96 (s, 3H, CH$_3$); R$_f$ (hexane/AcOEt=1:2): 0.14.

Example 37

1-(3-Methoxy-5-trifluoromethyl-phenyl)-3-[4-(pyridin-4-yloxy)-phenyl]-urea

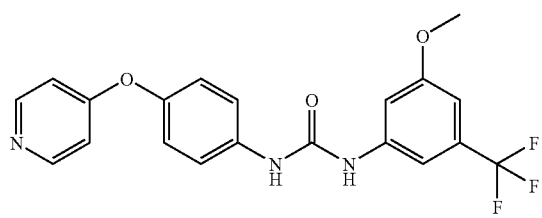

The title comound is synthesized analogously to the described procedures: M+H=404.1; $^1$H-NMR (400 MHz, DMSO-d$_6$): 9.07 (s, 1H, NH), 8.87 (s, 1H, NH), 8.40 (d, Hz, 6.5 Hz, 2H, pyridinyl), 7.55 (d, 9.5 Hz, 2H, oxo-phenyl-amine), 7.48 (s, 1H, CH$_3$—O—CF$_3$-phenyl), 7.24 (s, 1H, O—CH$_3$/CF$_3$-phenyl), 7.09 (d, 9.5 Hz, 2H, oxo-phenyl-amine), 6.84 (d, 6.5 Hz, 2H, pyridinyl), 6.80 (s, 1H, CH$_3$—O—/CF$_3$phenyl), 3.79 (s, 3H, CH$_3$—O); R$_f$ (MeOH/CH$_2$Cl$_2$=1:3): 0.19; m.p.=162.5-164.5° C.

Example 38

1-{4-[Bis-(2-methoxy-ethyl)-amino]-3-trifluoromethyl-phenyl}-3-[4-(pyridin-4-yloxy)-phenyl]-urea

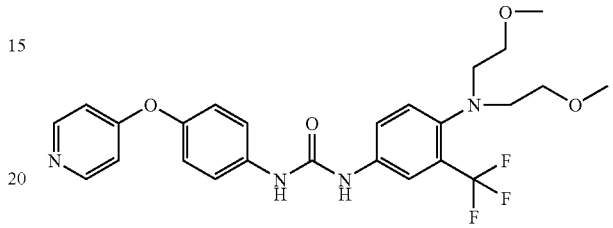

The title compound is synthesized according to the preparation of compound of Example 1 starting from N*1*,N*1*-bis-(2-methoxy-ethyl)-2-trifluoromethyl-benzene-1,4diamine (Stage 38.1): M+H=505.0; $^1$H-NMR (400 MHz, DMSO-d$_6$): 8.97 (s, 1H, NH), 8.86 (s, 1H, NH), 8.40 (d, 6.5 Hz, 2H, pyridinyl), 7.88 (s, 1H, CF$_3$—CH$_2$—O—/CF$_3$-phenyl), 7.55 (m, 4H, oxo-phenyl-amine, CF$_3$—CH$_2$—O—/CF$_3$-phenyl), 7.11 (d, 9.5 Hz, 2H, oxo-phenyl-amine), 6.84 (d, 6.5 Hz, 2H, pyridinyl), 3.27 (t, 8 Hz, 4H, CH$_2$), 3.16 (s, 6H, CH$_3$—O), 3.08 (t, 8 Hz, 4H, CH$_2$); R$_f$(acetone/CH$_2$Cl$_2$=1:3): 0.20.

Stage 38.1

The compound is synthesized by nucleophilic substitution reaction from 1-bromo-4-nitro-2-trifluoromethyl-benzene with bis-(2-methoxy-ethyl)amine (140° C., 4 h) and further hydrogenolytic reduction of the nitro-function to the amine by means of Raney Nickel: M+H=293.0; $^1$H-NMR (400 MHz, DMSO-d$_6$): 7.24 (d, 9 Hz, 1H), 6.77 (m, 2H), 5.37 (s/broad, 2H, NH$_2$), 3.26 (t, 8 Hz, 4H, CH$_2$), 3.16 (s, 6H, CH$_3$—O), 2.98 (t, 8 Hz, 4H, CH$_2$); R$_f$(acetone/CH$_2$Cl$_2$=1:3): 0.50; m.p.=64.5-65° C.

Example 39

1-(4-Diethylamino-3-trifluoromethyl-phenyl)-3-[4-yloxy)-phenyl]-urea

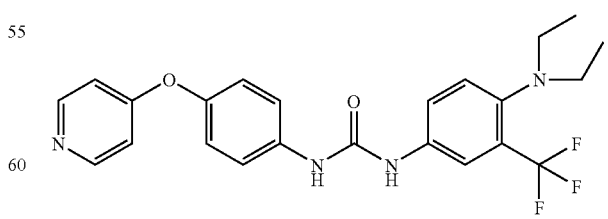

The title compound is synthesized according to the preparation of compound of Example 1 starting from N*1*,N*1*-diethyl-2-trifluoromethyl-benzene-1,4diamine (Stage 39.1): M+H=445.0; $^1$H-NMR (400 MHz, DMSO-d$_6$): 8.94 (s, 1H, NH), 8.86 (s, 1H, NH), 8.42 (d/broad, 6.5 Hz, 2H, pyridinyl), 7.89 (s, 1H, NEt$_2$-/CF$_3$-phenyl), 7.59 (d/broad, 9.5 Hz, 1H, NEt$_2$-/CF$_3$-phenyl), 7.56 (d, 9.5 Hz, 2H, oxo-phenyl-amine), 7.43 (d, 9.5 Hz, 1H, NEt$_2$-/CF$_3$-phenyl), 7.11 (d, 9.5 Hz, 2H, oxo-phenyl-amine), 6.84 (q, 6.5 Hz, 2H, pyridinyl), 2.84 (qu, 7.5 Hz, 4H, CH$_2$), 0.90 (t, 7.5 Hz, 6H, CH$_3$); R$_f$(acetone/CH$_2$Cl$_2$=1:3): 0.21; m.p.: 60° C. (decomp.).

Stage 39.1

The compound is synthesized according to the preparation of Stage 38.1: M+H=293.0; $^1$H-NMR (400 MHz, DMSO-d$_6$): 7.24 (d, 9 Hz, 1H), 6.77 (m, 2H), 5.37 (s/broad, 2H, NH$_2$), 3.26 (t, 8 Hz, 4H, CH$_2$), 3.16 (s, 6H, CH$_3$—O), 2.98 (t, 8 Hz, 4H, CH$_2$); R$_f$(acetone/CH$_2$Cl$_2$=1:3): 0.50.

Example 40

N-Methyl-C-[4-(6-{4-[3-(3-trifluoromethyl-phenyl)-ureido]-phenoxy}pyrimidin-4-ylamino)-phenyl]-methanesulfonamide

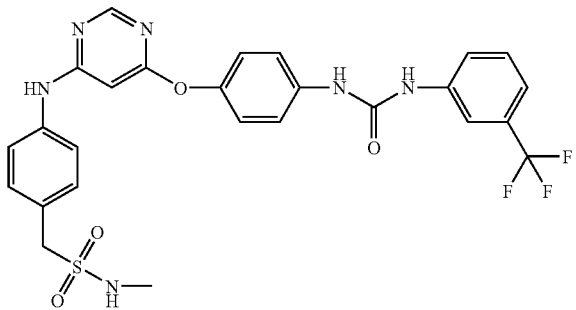

The title compound is synthesized in analogy to the preparation of compound of Example 22:
M+H=572.8; $^1$H-NMR (400 MHz, DMSO-d$_6$): 9.61 (s, 1H, NH), 9.01/8.87 (s/s, 2H, NH-urea), 8.36 (s, 1H, pyrimidinyl), 8.02 (s, 1H, CF$_3$-phenyl), 7.58 (m, 3H, amino-phenyl/CF$_3$-phenyl), 7.50 (m, 3H, oxo-phenyl-urea/CF$_3$-phenyl), 7.12 (d, 8.0 Hz, 2H, oxo-pheny-urea), 6.85 (q, 5.0 Hz, 1H, NH-SO$_2$), 6.04 (s, 1H, pyrimidinyl), 4.22 (s, 2H, CH$_2$), 2.57 (d, 5.0 Hz, 3H, CH$_3$);
HPLC (System 1): 5.80 min.

Examples 41

1-[4-(4-Methyl-piperazin-1-yl)-3-trifluoromethyl-phenyl]-3-[4-(pyridin-4-yloxy)-phenyl]-urea

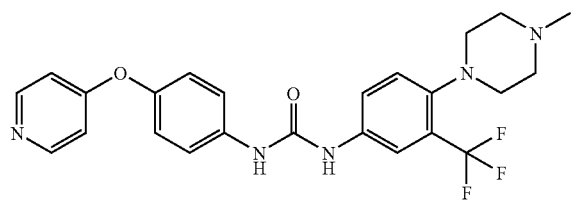

The title compound is synthesized according to the preparation of Example 1 starting from 4-(4-methyl-piperazin-1-yl)-3-trifluoromethyl-phenylamine (Stage 41.1): M+H=472.0; $^1$H-NMR (400 MHz, DMSO-d$_6$): 9.18 (s, 1H, NH), 9.08 (s, 1H, NH), 8.43 (d, Hz, 6.5 Hz, 2H, pyridinyl), 7.90 (s, 1H, 3-CF$_3$-phenyl), 7.59 (d, 9.5 Hz, 1H, 3-CF$_3$-phenyl), 7.54 (d, 8.0 Hz, 2H, oxo-phenyl), 7.49 (t, 8.0 Hz, 1H, 3-CF$_3$-phenyl), 7.13 (d, 8.0 Hz, 2H, oxo-phenyl), 6.89 (d, 6.5 Hz, 2H, pyridinyl), 2.85 (s/broad, 4H, piperidinyl), 2.56 (s/broad, 4H, piperidinyl), 2.32 (s/broad, 3H, NMe); R$_f$(MeOH/CH$_2$Cl$_2$=1:9): 0.10; m.p.>100° C. (decomp.).

Stage 41.1

The compound is synthesized according to the preparation of Stage 39.1: M+H=260.1; $^1$H-NMR (400 MHz, DMSO-d$_6$): 7.21 (d, 9 Hz, 1H), 6.74 (m, 2H), 5.35 (s/broad, 2H, NH$_2$), 2.70 (m/broad, 4H, CH$_2$), 2.36 (s/broad, 4H, CH$_2$), 2.18 (s, 3H, CH$_3$); R$_f$(MeOH/CH$_2$Cl$_2$=1:5): 0.17; m.p.=121-123° C.

Example 42

1-[4-(2-Hydroxy-proylamino)-3-trifluoromethyl-phenyl]-3-[4-(pyridin-4-yloxy)-phenyl]-urea

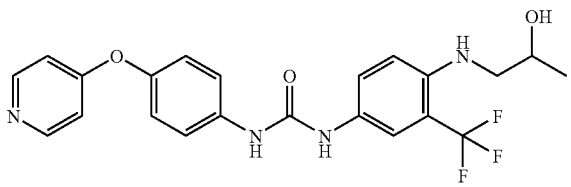

The title compound is synthesized according to the preparation of Example 22 starting from 4-(4-methyl-piperazin-1-yl)-3-trifluoromethyl-phenylamine (Stage 42.1): M+H=447.0; $^1$H-NMR (400 MHz, DMSO-d$_6$): 8.70 (s, 1H, NH), 8.48 (s, 1H, NH), 8.39 (d/broad, 6.5 Hz, 2H, pyridinyl), 7.62 (s, 1H, HO-propyl-NH-/CF$_2$phenyl), 7.53 (d, 11 Hz, 2H, oxo-phenyl-amine), 7.37 (d/broad, 9.5 Hz, 1H, HO-propyl-NH-/CF$_3$-phenyl), 7.09 (d, 11 Hz, 2H, oxo-phenyl-amine), 6.84 (d, 6.5 Hz, 2H, pyridinyl), 6.78 (d, 9.5 Hz, 1H, HO-propyl-NH—/CF$_3$-phenyl), 4.90 (t/broad, 1H, NH), 4.84 (d, 6.5 Hz, 1H, OH), 3.81 (sept/broad, 1H, CH), 3.11/2.90 (m/m, 2H, CH$_2$), 1.10 (d, 6.5 Hz, 3H, CH$_3$); R$_f$(acetone/CH$_2$Cl$_2$=1:3): 0.11; m.p.: 140 ° C. (decomp.).

Stage 42.1

The compound is synthesized according to the preparation of Stage 39.1: M+H =236.2; $^1$H-NMR (400 MHz, DMSO-d$_6$): 6.74 (s, 1H) 6.72 (d, 9 Hz, 1H), 6.60 (d, 9.0 Hz, 1H), 4.80 (s/broad, 1H, NH), 4.67 (2, 2H.NH$_2$), 4.37 (m/broad, 1H, OH), 3.80 (m/broad, 1H, CH), 3.02 (m/broad, 1H, CH$_2$), 2.79 (m/broad, 1H, CH$_2$), 1.07 (s, 3H, CH$_3$); R$_f$(hexane/AcOEt=1:1): 0.13; m.p.=91-93° C.

Example 43

1-(4-Methyl-3-trifluoromethyl-phenyl)-3-[4-(pyridin-4-yloxy)-phenyl]-urea

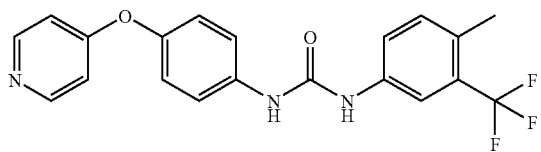

The comound is synthesized analogously to the described procedures: M+H=388.2; $^1$H-NMR (400 MHz, DMSO-d$_6$):

8.96 (s, 1H, NH), 8.84 (s, 1H, NH), 8.42 (d/broad, 6.5 Hz, 2H, pyridinyl), 7.93 (s, 1H, CF$_3$/Me-phenyl), 7.56 (d, 9.5 Hz, 2H, oxo-phenyl-amine), 7.52 (d, 9.0 Hz, 1H, CF$_3$/Me-phenyl), 7.33 (d, 9.0 Hz, 1H, CF$_3$/Me-phenyl), 7.10 (d, 9.5 Hz, 2H, oxo-phenyl-amine), 6.84 (d, 6.5 Hz, 2H, pyridinyl), 2.36 (s, 3H, CH$_3$); R$_f$(acetone/CH$_2$Cl$_2$=1:3): 0.25; m.p.: 149° C. (decomp.).

Example 44

5-(pyridin-4-yloxy)-2,3-dihydro-indole-1-carboxylic acid [4-(2,2,2,-trifluoro-ethoxy)-3-trifluoromethyl-phenyl]-amide

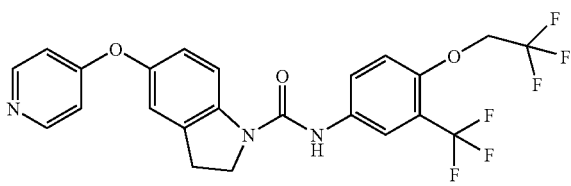

Is prepared in analogy to the synthesis of compound of Example 20: M+H=497.9; $^1$H-NMR (400 MHz, DMSO-d$_6$): 8.73 (s, 1H, NH), 8.40 (d, Hz, 6.5 Hz, 2H, pyridinyl), 7.92 (m, 2H, indolinyl/3-CF$_3$-phenyl), 7.82 (d, 8.0 Hz, H, 3-CF$_3$-phenyl), 7.36 (t, 8.0 Hz, 1H, 3-CF$_3$-phenyl), 7.04 (s, 1H, indoline), 6.95 (dd, 9.5 Hz, 3.5 Hz, 1H, indoline), 6.84 (d, 6.5 Hz, 2H, pyridinyl), 4.89 (q, 9.0 Hz, 2H, CF$_3$—CH$_2$), 4.26 (t, 7.5 Hz, 2H, CH$_2$-indolinyl), 3.17 (t, 7.5 Hz, 2H, CH$_2$-indolinyl); R$_f$(acetone/CH$_2$Cl$_2$=1:3): 0.20.

Example 45

1-{4-[6-(4-Hydroxy-phenylamino)-pyrimidin-4-yloxy]-phenyl}-3-(4-morpholin-4-yl-3-trifluoromethyl-phenyl)-urea

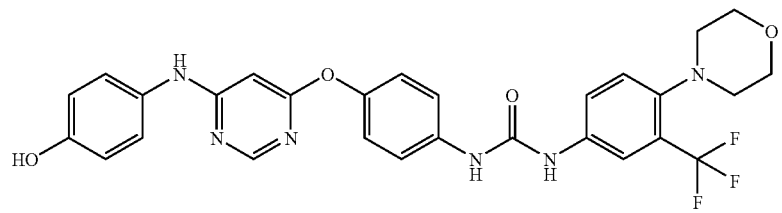

The title compound is synthesized according to the synthesis of compound of Example 22: M+H=564.8; $^1$H-NMR (400 MHz, DMSO-d$_6$): 9.23 (s, 2H, NH, OH), 8.96/8.78 (s/s, 2H, 3 NH-urea), 8.21 (s, 1H, pyrimidinyl), 7.92 (s, 1H, morpholinyl-phenyl), 7.53 (m, 3H, morpholinyl-phenyl/oxo-phenyl-amino), 7.24 (d, 8.5 Hz, 1H, morpholinyl-phenyl), 7.08 (d, 9.0 Hz, 2H, oxo-phenyl-urea), 6.69 (d, 9.0 Hz, 2H, oxo-phenyl-amino), 5.87 (s, 1H, pyrimidinyl), 3.65 (m, 4H, CH$_2$), 2.79 (m, 4H, CH$_2$); R$_f$(NH$_3$/MeOH/CH$_2$Cl$_2$=0.01:1:9): 0.33.

Example 46

C-[4-(6-{4-[3-(4-Ethyl-phenyl)-ureido]-phenoxy}-pyrimidin-4-ylamino)-phenyl]-N-methyl-methane-sulfonamide

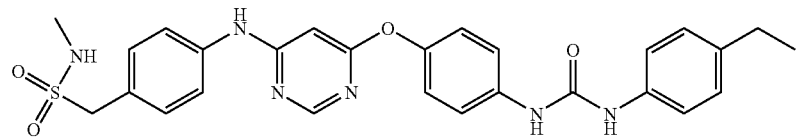

1-Ethyl-4-isocyanato-benzene (25.7 mg, 0.175 mmol) is slowly added to C-{4-[6-(4-amino-phenoxy)-pyrimidin-4-ylamino]-phenyl}-N-methyl-methanesulfonamide (45 mg, 0.117 mmol) and pyridine (18.9 mL, 0.234 mmol) dissolved in THF/DMF (2:1, 3 mL) at 0° C. After stirring at rt for 4 h, the solvent is evaporated under reduced pressure, and the product is isolated by preparative thin layer chromatography (4 plates of 20×20 cm, acetone/$CH_2Cl_2$=3:7) giving the compound of Example 46 as a white solid: M+H=532.5; $^1$H-NMR (400 MHz, DMSO-$d_6$): 8.70/8.57(s/s, 2H, NH-urea), 8.33 (s, 1H, pyrimidinyl), 7.59 (d, 9.5 Hz, 2H, phenyl-$CH_2$), 7.55 (d, 9.5 Hz, 2H, amino-phenyl), 7.36 (d, 9.5 Hz, 2H, ethyl-phenyl), 7.25 (d, 9.5 Hz, 2H, pheny-$CH_2$), 7.10 (d, 9.5 Hz, 4H, ethyl-phenyl/amino-phenyl), 6.83 (m, 2H, NH-sulfonamide), 6.05 (s, 1H, pyrimidinyl), 4.22 (s, 2H, $CH_2$), 2.57 (m, 5H, $CH_3$-ethyl/NH—$CH_3$), 1.16 (t, 7.5 Hz, 3H, $CH_3$-ethyl); $R_f$ (acetone/$CH_2Cl_2$=3:7): 0.32.

Example 47

1-{4-[6-(4-Methoxy-phenylamino)-pyrimidin-4-yloxy]-phenyl}-3-(4-morpholin-4-yl-3-trifluoromethyl-phenyl)-urea

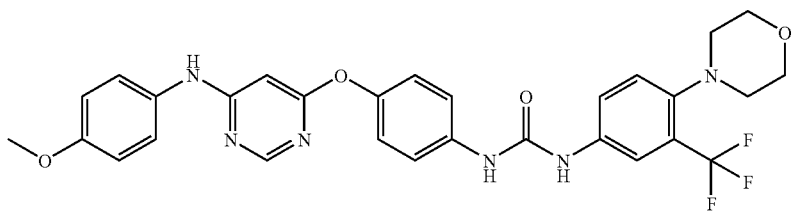

[6-(4-Amino-phenoxy)-pyrimidin-4-yl]-(4methoxy-phenyl)-amine (Stage 47.1; 200 mg, 0.648 mmol) and triethylamine (0.075 ml, 0.54 mmol) dissolved in $CH_2Cl_2$ (6 mL) is slowly added to a solution of triphosgene (64 mg, 0.213 mmol) in $CH_2Cl_2$ (10 mL) at 4° C. After stirring at rt for 15 min, a solution of 4-morpholin-4-yl-3-trifluoromethyl-phenylamine (160 mg, 0.648 mmol) and triethylamine (0.075 ml, 0.54 mmol) in $CH_2Cl_2$ (6 mL) is added and the reaction mixture is stirred for 2 h. After adding concentrated $NaHCO_3$ solution (20 mL), the product is extracted with $CH_2Cl_2$ (20 ml, 2×). The combined organic phases are washed with water (20 mL), dried ($Na_2SO_4$), and concentrated under reduced pressure. The product is purified by flash chromatography (silica gel, 2.5×20 cm, MeOH/$CH_2Cl_2$=5:95) giving a white solid:

M+H=580.9; $^1$H-NMR (400 MHz, DMSO-$d_6$): 9.32 (s, 1H, NH), 9.35/8.78 (s/s, 2H, NH-urea), 8.23 (s, 1H, pyrimidine), 7.89 (s, phenyl-$CF_3$), 7.58 (d, 8.5 Hz, 1H, phenyl-$CF_3$), 7.53 (d, 8.5 Hz, 1H, phenyl-$CF_3$), 7.49/7.40/7.08/6.86 (d/d/d/d, 9.0 Hz, 8H, phenyl-oxo/phenyl-OMe), 5.91 (s, 1H, pyrimidinyl), 3.70 (s, 3H, $CH_3$—O), 3.66/2.79 (m/m, 4H/4H, morpholinyl); $R_f$ (MeOH/$CH_2Cl_2$=5:95): 0.16; HPLC (System 1): 6.31 min.

Stage 47.1: [6-(4-Amino-phenoxy)-pyrimidin-4-yl]-(4-methoxy-phenyl)-amine (4-Methoxy-phenyl)-[6-(4-nitro-phenoxy)-pyrimidin-4-yl]-amine (Stage 47.2; 1.06 g, 3.13 mmol) dissolved in THF/EtOH (1:2; 27 mL) is hydrogenated in the presence of Raney-Ni (0.2 g) during 36 h. After filtering off the catalyst and washing with EtOH (20 mL), the solvent is evaporated under reduced pressure and flash chromatographed (silica gel, 4.5× 26 cm, MeOH/$CH_2Cl_2$=5:95) giving a white solid: M+H=309.1; $^1$H-NMR (400 MHz, DMSO-$d_6$): 9.23 (s, 1H, NH-pyrimidinyl), 8.22 (s, 1H, pyrimidine), 7.40/6.85/6.79/6.57 (d/d/d/d, 9.0 Hz, 8H, phenyl-oxo/phenyl-OMe), 5.81 (s, 1H, pyrimidinyl), 5.07 (s, 2H, $NH_2$), 3.72 (s, 3H, $CH_3$—O); $R_f$ (MeOH/$CH_2Cl_2$=1:9): 0.44; HPLC (System 1): 3.45 min.

Stage 47.2: (4-Methoxy-phenyl)-[6-(4-nitro-phenoxy)-pyrimidin-4-yl]-amine

4-Chloro-6-(4-nitro-phenoxy)-pyrimidine (1 g, 3.97 mmol), p-anisidine (514 mg, 4.178 mmol), and diisopropylethylamine (0.715 mL, 4.178 mmol) dissolved in 2-propanol (27 mL) are stirred under reflux under Ar. After 16 h, p-anisidine (245 mg, 1.99 mmol) is added and the reaction mixture is stirred for additional 20 h. After cooling the reaction mixture down to rt, compound of Stage 47.2 precipitates as white crystals: M+H=339.1; $^1$H-NMR (400 MHz, DMSO-$d_6$): 9.49 (s, 1H, NH-pyrimidinyl), 8.25 (s, 1H, pyrimidine), 8.23/7.40/6.90 (d/d/d/, 9.0 Hz, 2H/4H/2H, phenyl-oxolphenyl-OMe), 6.18 (s, 1H, pyrimidinyl), 3.72 (s, 3H, $CH_3$—O); $R_f$ (MeOH/$CH_2Cl_2$=1:9): 0.44; HPLC (System 1): 6.15 min.

Example 48

N-Methyl-C-[4-(6-{4-[3-(4-morpholin-4-yl-3-trifluoromethyl-phenyl)-ureido]-phenoxy}-pyrimidin-4-ylamino)-phenyl]-methanesulfonamide

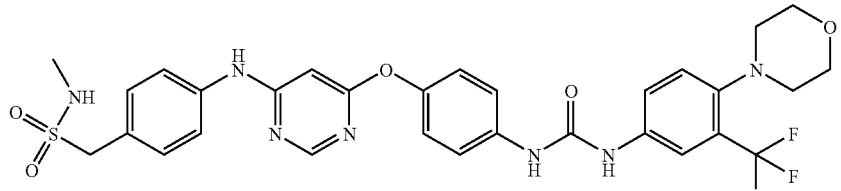

4-Morpholin-4-yl-3-trifluoromethyl-phenylamine (28.8 mg, 0.117 mmol), triethylamine (0.05 mL, 0.36 mmol), and triphosgene (35 mg, 0.117 mmol) are dissolved in CHCl$_3$ (2 mL) at 0° C. After stirring at rt for 15 min, C-{4-[6-(4-amino-phenoxy)-pyrimidin-4-ylamino]-phenyl}-N-methyl-methanesulfonamide (45 mg, 0.117 mmol) and triethylamine (0.05 mL) dissolved in DMF/DMSO (4:1; 5 mL) are added and stirring is continued for 16 h. After evaporating the solvent under reduced pressure, the product is isolated by preparative thin layer chromatography (four 20×20 cm plates, acetone/CH$_2$Cl$_2$=3.7) giving the compound of Example 48 as a white solid: M+H=658.1; $^1$H-NMR (400 MHz, DMSO-d$_6$): 9.57 (s, 1H, phenyl-NH-phenyl), 8.97/8.81(s/s, 2H, NH-urea), 8.34 (s, 1H, pyrimidinyl), 7.89 (s, 1H, phenyl-CF$_3$), 7.58 (d, 9.0 Hz, 3H, phenyl-CF$_3$/phenyl-CH$_2$), 7.50 (d, 9.0 Hz, 3H, phenyl-CF$_3$/oxo-phenyl), 7.24 (d, 9.0 Hz, 2H, phenyl-CH$_2$), (d, 9.0 Hz, 2H, oxo-phenyl), 6.83 (d, 4.0 Hz, 1H, NH-sulfonamide), 6.06 (s, 1H, pyrimidinyl), 4.23 (s, 2H, CH$_2$), 3.64/2.78 (m/m, 4H/4H, morpholinyl), 2.52 (d, 4.0 Hz, CH$_3$—N); R$_f$(acetone/CH$_2$Cl$_2$=3:7): 0.40.

Example 49

1-{4-[6-(3-Hydroxy-phenylamino)-pyrimidin-4-yloxy]-phenyl}-3-(4-morpholinyl-4-yl-3-trifluoromethyl-phenyl)-urea

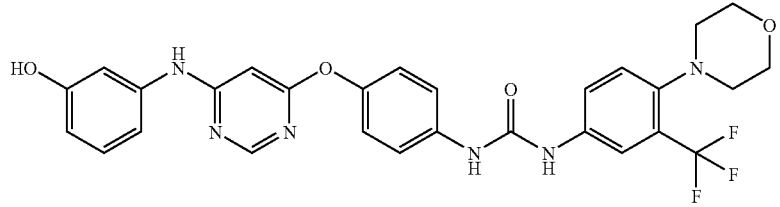

To a solution of 1-(4-{6-[3-(tert-butyl-dimethyl-silanyloxy)phenylamino]-pyrimidin-4-yloxy}-phenyl)-3-(4-morpholin-4-yl-3-trifluoromethyl-phenyl)-urea (Stage 49.1) (283 mg, 0.415 mmol) in MeCN/THF (1.9 mL/0.95 mL), HF (30% in pyridine; 0.5 mL) is added at 4° C. After stirring at rt for 2 h, phosphate buffer (pH=7, 10 mL) is added and the product is extracted with AcOEt (2×, 20 mL). The combined organic layers are washed with H$_2$O (20 mL), dried (MgSO$_4$), concentrated under reduced pressure, and flash chromatographed (silica gel, 3.0×20 cm, MeOH/CH$_2$Cl$_2$=5:95) giving a white solid: M+H=566.9; $^1$H-NMR (400 MHz, DMSO-d$_6$): 9.40/9.35 (s/s, 2H, NH-urea), 9.05/8.87 (s/s, 2H, OH/NH), 8.33 (s, 1H, pyridinyl), 7.92 (s, 1H, phenyl-CF$_3$), 7.62 (d, 8.5 Hz, 1H, phenyl-OH), 7.52 (d, 9.0 Hz, 3H, phenyl-oxo/phenyl-CF$_3$), 7.15 (s, 1H, phenyl-OH), 7.13 (d, 9.0 Hz, 2H, phenyl-oxo), 7.06 (t, 9.0 Hz, 1H, phenyl-OH), 6.97 (d, 9.0 Hz, 1H, phenyl-OH), 6.41 (d, 8.5 Hz, 1H, phenyl-CF$_3$), 6.06 (s, 1H, pyrimidinyl), 3.69/2.81 (m/m, 4H/4H, morpholinyl); R$_f$(MeOH/CH$_2$Cl$_2$=1:9): 0.31; HPLC (System 1): 5.80 min.

Stage 49.1: 1-(4-{6-[3-(tert-Butyl-dimethyl-silanyloxy)-phenylamino]-pyrimidin-4-yloxy}-phenyl)-3-(4-morpholin-4-yl-3-trifluoromethyl-phenyl)-urea

[6-(4-Amino-phenoxy)-pyrimidin-4-yl]-[3-(tert-butyl-dimethyl-silanyloxy)-phenyl]-amine (Stage 49.2; 121 mg, 0.489 mmol) and triethylamine (0.057 mL, 0.83 mmol) dissolved in CH$_2$Cl$_2$ (6 mL) are added to a solution of triphosgene (48 mg, 0.161 mmol) in CH$_2$Cl$_2$ (10 mL) at 4° C. under Ar. After stirring at rt for 15 min, 4-morpholin-4-yl-3-trifluoromethyl-phenylamine (121 mg, 0.489 mmol) and triethylamine (0.057 mL) dissolved in CH$_2$Cl$_2$ (6 mL) are added and the reaction mixture is stirred for 2 h at rt. After adding concentrated NaHCO$_3$ (20 mL), the reaction mixture is extracted with CH$_2$Cl$_2$ (20 ml, 2×). The combined organic layers are washed with H$_2$O, dried (Na$_2$SO$_4$), concentrated under reduced pressure, and flash chromatograped (silica gel, 2.5×22 cm, MeOH/CH$_2$Cl$_2$=2:098) to give the compound of Stage 49.1 as a white solid: M+H=680.9; $^1$H-NMR (400 MHz, DMSO-d$_6$): 9.49 (s, 1H, NH-pyrimidinyl), 8.94/8.80 (s/s, 2H, NH-urea), 8.33 (s, 1H, pyrimidinyl), 7.89 (s, 1H, phenyl-CF$_3$), 7.59 (d, 8.5 Hz, 1H, phenyl-CF$_3$), 7.50 (d, 9.0 Hz, 3H, phenyl-OTBS/phenyl-oxo), 7.23 (s/broad, 1H, phenyl-OTBS), 7.16 (t, 8.0 Hz, 1H, phenyl-OTBS), 7.11 (d, 9.0 Hz, 3H, phenyl-OTBS/pheny/-oxo), 6.44 (d/broad, 8.0 Hz, 1H, phenyl-CF$_3$), 6.02 (s, 1H, pyrimidinyl), 3.69/2.80 (m/m, 4H/4H, morpholinyl) 0.92 (s, 9H, tert-butyl-Si), 0.20 (s, 6H, Me-Si); R$_f$ (MeOH/CH$_2$Cl$_2$=5:95): 0.31; HPLC (System 1): 8.54 min.

Stage 49.2: [6-(4-Amino-phenoxy)-pyrimidin-4-yl]-[3-(tert-butyl-dimethyl-silanyloxy)-phenyl]-amine

[3-(tert-Butyl-dimethyl-silanyloxy)-phenyl]-[6-(4-nitro-phenoxy)-pyrimidin-4-yl]-amine (Stage 49.3, 1.01 g, 2.306 mmol) dissolved in EtOH/THF (2:1; 26 mL) are hydrogenated in the presence of Raney-Ni (0.2 g) for 22 h. After filtering off the catalyst and washing with EtOH (20 mL), the reaction solution is evaporated and the crude product is flash chromatographed (silica gel, 4.5×28 cm, MeOH/CH$_2$Cl$_2$=2:98) to give compound of Stage 49.2 as a white solid: M+H=409.1; $^1$H-NMR (400 MHz, DMSO-d$_6$): 9.39 (s, 1H, NH-pyrimidinyl), 8.35 (s, 1H, pyrimidinyl), 7.23 (s, 1H, phenyl-OTBS), 7.17 (d, 8.5 Hz, 1H, phenyl-OTBS), 7.11 (t, 8.5 Hz, 1H, phenyl-OTBS), 7.16 (t, 8.0 Hz, 1H, phenyl-OTBS), 7.11 (d, 9.0 Hz, 1H, phenyl-OTBS), 6.82/6.58 (d/d, 8.5 Hz/8.5 Hz, 4H, phenyl-oxo), 6.44 (d, 8.5 Hz, 1H, phenyl-OTBS), 5.92 (s, 1H, pyrimidinyl), 5.09 (s, 2H, NH$_2$), 0.96 (s, 9H, tert- butyl-Si), 0.19 (s, 6H, Me-Si); R$_f$ (MeOH/CH$_2$Cl$_2$=5:95): 0.32; HPLC (System 1): 6.31 min.

Stage 49.3: [3-(tert-Butyl-dimethyl-silanyloxy)-phenyl]-[6-(4-nitro-phenoxy)-pyrimidin-4-yl]-amine 3-[6-(4-Nitro-phenoxy)-pyrimidin-4-ylamino]-phenol (Stage 49.4; 830 mg, 2.56 mmol), tert-butyl-dichlorosilane (579 mg, 3.84 mmol), and triethylamine (0.536 mL, 3.84 mmol) dissolved in DMF (11 mL) are stirred under Ar for 3 at rt. After adding H$_2$O (20 mL), the reaction mixture is extracted with CH$_2$Cl$_2$ (20 mL, 2×). The combined organic phases are washed with H$_2$O (10 mL), dried (Na$_2$SO$_4$), concentrated under reduced pressure, and flash chromatographed (silica gel, 5.5×30 cm, MeOH/CH$_2$Cl$_2$=5:95) to give the compound of Stage 49.3 as a white solid: M+H=439.0; $^1$H-NMR (400 MHz, DMSO-d$_6$): 9.65 (s, 1H, NH-pyrimidinyl), 8.35 (s, 1H, pyrimidinyl), 7.23 (s, 1H, phenyl-OTBS), 7.17 (m, 2H, phenyl-OTBS), 6.50 (d, 8.0 Hz, 1H, phenyl-OTBS), 8.29/7.43 (d/d, 8.5 Hz/8.5 Hz, 4H, phenyl-oxo), 6.28 (s, 1H, pyrimidinyl), 0.96 (s, 9H, tert-butyl-Si), 0.19 (s, 6H, Me-Si); R$_f$ (MeOH/CH$_2$Cl$_2$=5:95): 0.34; HPLC (System 1): 8.87 min.

Stage 49.4:
3-[6-(4-Nitro-phenoxy)-pyrimidin-4-ylamino]-phenol

4-Chloro-6-(4-nitro-phenoxy)-pyrimidine (1 g, 3.97 mmol), 3-amino-phenol (456 mg, 4.175 mmol), diisopropylethylamine (0.715 mL, 4.175 mmol) dissolved in 2-propanol (17 mL) are stirred under reflux. After 16 and 22 h, the same amount of 3-amino-phenol and diisopropylethylamine is added to the reaction mixture. After 42 h, the solvent is evaporated under reduced pressure, and the reaction mixture is flash chromatographed (silica gel, 4.5×26 cm, MeOH/CH$_2$Cl$_2$=5:95) to give the compound of Stage 49.4 as a white solid: M+H=325.1; $^1$H-NMR (400 MHz, DMSO-d$_6$): 9.59/9.37 (s/s, 2H, NH-pyrimidinyl/OH), 8.35 (s, 1H, pyrimidinyl), 8.27/7.43 (d/d, 9.5 Hz/9.5 Hz, 2H/2H, phenyl-NO$_2$), 7.12 (s, 1H, phenyl-OH), 7.06 (t, 8.5 Hz, 1H, phenyl-OH), 6.94/6.44 (d/d, 8.5 Hz/8.5 Hz, 2H, phenyl-OH), 6.31 (s, 1H, pyrimidinyl); R$_f$(MeOH/CH$_2$Cl$_2$=1:9): 0.58; HPLC (System 1): 5.43 min.

The following compounds are synthesized according to the procedure of the synthesis of compound of Example 1 (Table 5).

TABLE 5

| Ex. | Structure | Analytical data |
| --- | --- | --- |
| 50 | [structure] | M + H = 417.0; R$_f$ (AcOEt/hexane = 2:1): 0.21; Anal.: C: 57.11 (57.70)%, H: 3.61 (3.63)%, N: 13.43 (13.46)%. |
| 51 | [structure] | M + H = 464.0; R$_f$ (AcOEt/hexane = 2:1): 0.13; Anal.: C: 66.50 (67.38)%, H: 4.59 (4.35)%, N: 8.64 (9.07)%. |
| 52 | [structure] | M + H = 472.0; R$_f$ (CH$_2$Cl$_2$/MeOH = 4:1): 0.41. |
| 53 | [structure] | M + H = 479.0; R$_f$ (CH$_2$Cl$_2$/MeOH = 95:5): 0.12; HPLC (System 1): 5.01 min. |

TABLE 5-continued

| Ex. | Structure | Analytical data |
|---|---|---|
| 54 | ![structure] | M + H = 388.0; $R_f$ ($CH_2Cl_2$/acetone = 3:1): 0.24; HPLC (System 1): 4.97 min; Anal.: C: 60.58 (62.01)%, H: 4.32 (4.16)%, N: 10.14 (10.85)%. |

The starting material 4-(pyridin-4-ylmethoxy)-phenylamine (Stage 51.1) for the synthesis of the compounds of Example 51 and 54 is generated from 4-(4-nitro-phenoxymethyl)-pyridine by hydrogenation in the presence of Raney-Ni in EtOH at 40° C. during 3 h: M+H=201.0; $R_f$ ($CH_2Cl_2$/acetone=85:15): 0.17.

4-(4-Nitro-phenoxymethyl)pyridine 4-hydroxymethyl-pyridine (2.23 g, 20 mmol) is added to a suspension of KOH (1.32 g, 20 mmol) and Aliquat 336 (0.937 mL). After stirring for 5 min at rt, 1-chloro-4-nitro-benzene (2.68 g, 16.7 mmol) is added. The resulting reaction mixture is further stirred at rt for 5 min and then at 80° C. for 2 h. The reaction mixture is filtered over silica gel (15 g), concentrated under reduced pressure, and flash chronatographed (silica gel, 3×50 cm, acetone/$CH_2Cl_2$=5:95→15:85) to give the title compound as a yellow solid: M+H=231.0; $^1$H-NMR (400 MHz, DMSO-$d_6$): 8.58 (d, 6.5 Hz, 2H, pyrimidinyl), 8.22 (d, 8.5 Hz, 2H, phenyl-$NO_2$), 7.44 (d, 6.5 Hz, pyrimidinyl), 7.21 (d, 8.5 Hz, 2H, phenyl-$NO_2$), 5.34 (s, 2H, $CH_2$); $R_f$(acetone/$CH_2Cl_2$=15:85): 0.32; HPLC (System 1): 3.40 min.

The substituted 3-trifluoromethyl-anilines for the synthesis of compounds of Examples 52 and 53 are prepared from the 1-bromo-3-nitro-5-trifluoromethyl-benzene by nucleophilic substitution of the bromine by the corresponding amine and subsequent hydrogenation of the nitro function to the amine by means of Raney-Ni.

Example 55

1-(4-Aminomethyl-phenyl)-3-[4-(pyridin-4-yloxy)-phenyl]-urea

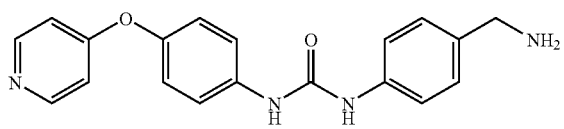

4-{3-[4-(Pyridin-4-yloxy)-phenyl]-ureido}-benzyl)-carbamic acid benzyl ester (Stage 55.1) (0.1 g, 0.213 mmol) dissolved in EtOH/THF (2:1, 6 mL) is hydrogenated in the presence of Pd/C (Engelhard 4505, 100 mg) for 5 h. After filtering of the catalyst, the reaction solution is concentrated under reduced pressure and flash chromatographed (silica gel, 2.5×46 cm, $CH_2Cl_2$/MeOH/conc. $NH_3$=9:1:0.01→85:15:0.1) to give the compound of Example 55 as a white solid: M+H=335.0; $R_f$ ($CH_2Cl_2$/MeOH/conc. $NH_3$=85:15:0.1): 0.15; HPLC (System 1): 5.74 min.

Stage 55.1: 4-{3-[4-(Pyridin-4-yloxy)-phenyl]-ureido}-benzyl)-carbamic acid benzyl ester The compound is synthesized in analogy to the preparation of compound of Example 1 starting from (4-amino-benzyl)-carbamic acid benzyl ester (Stage 55.2): M+H=469.1; $R_f$ ($CH_2Cl_2$/MeOH=85:15): 0.26; HPLC (System 1): 4.85 min.

Stage 55.2: (4-amino-benzyl)-carbamic acid benzyl ester

After stirring [4-(benzyloxycarbonylamino-methyl)phenyl]-carbamic acid tert-butyl ester (Stage 55.3) (1.06 g, 2.97 mmol) in TFA/$H_2O$ (95:5, 10 mL), the solvent is evaporated in vacuo. The residue is taken up in $NaHCO_3$ (20 mL) and extracted with AcOEt (20 mL). The organic phase is dried ($MgSO_4$), concentrated under reduced pressure, and flash chromatographed (silica gel, 4.5×52 cm, MeOH/$CH_2Cl_2$=5:95) to give the compound of Stage 55.2 as a colorless solid: M+H=257.1; $R_f$ ($CH_2Cl_2$/MeOH=95:5): 0.67; HPLC (System 1): 3.62 min.

Stage 55.3: [4-(benzyloxycarbonylamino-methyl)-phenyl]-carbamic acid tert-butyl ester To a solution of 4-(aminomethyl)-1-N-Boc-aniline (1 g, 4.5 mmol) dissolved in $CH_2Cl_2$ (10 mL), triethylamine (0.626 mL, 4.5 mmol) and chloro-formic acid benzyl ester (0.698 mL, 4.95 mmol) are added, the reaction solution is stirred at rt for 2 h, taken up in $CH_2Cl_2$ (10 mL) and washed with concentrated $NaHCO_3$ solution (20 mL) and $H_2O$ (20 mL). The aqueous phase is washed with $CH_2Cl_2$ (20 mL). The combined organic phases are dried ($Na_2SO_4$), concentrated under reduced pressure and flash chromatographed (silica gel, 3.5×60 cm, AcOt/hexane=1:4) to give the compound of Stage 55.3 as a white solid: M+H=355.1; $R_f$ (AcOEt/hexane=1:4): 0.15; HPLC (System 1): 6.53 min.

Example 56

1-[4-(6-Chloro-pyrimidin-4-yloxy)-phenyl]-3-(3-trifluoromethyl-phenyl)-urea

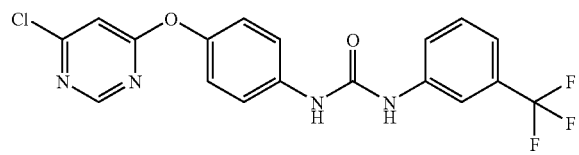

After stirring 3-trifluoromethyl-phenyl isocyanate (412 mg, 2.2 mmol), 4-(6-chloro-pyrimidin-4-yloxy)anillne (Stage 56.1; 0.25 g, 1.1 mmol), and pyridine (0.18 mL) over night, the reaction solution is concentrated under reduced pressure and flash chromatographed (silica gel, 2.5×17 cm; acetone/CH$_2$Cl$_2$=5:95→1:9) to give the compound of Example 56 as a white solid material: M+H=408.9/410.9; $^1$H-NMR (400 MHz, DMSO-d$_6$): 9.07 (s, 1H, NH), 8.89 (s, 1H, NH), 8.63 (d, 2.0 Hz, 1H, pyridinyl), 8.01 (s, 1H, 3-CF$_3$-phenyl), 7.57 (d/broad, 8.0 Hz, 1H, CF$_3$-pheny), 7.52 (d, 9.5 Hz, 2H, oxo-phenyl-amine), 7.50 (m, 1H, 3-CF$_3$-phenyl), 7.32 (d, 2.0 Hz, 1H, pyridinyl), 7.29 (d/broad, 8.0 Hz, 1H, —CF$_3$-phenyl), 7.15 (d, 9.5 Hz, 2H, oxo-phenyl-amine), (d, 6.5 Hz, 2H, pyridinyl); R$_f$ (acetone/CH$_2$Cl$_2$=1:9): 0.54; m.p.=187.4-189.7° C.

Stage 56.1: 4-(6-chloro-pyrimidin-4-yloxy)-aniline

4-Chloro-6-(4-nitro-phenoxy)-pyrimidine (Stage 56.2; 3.6 g, 14.3 mmol) dissolved in MeOH (250 mL) is hydrogenated in the presence of Raney-Ni (3 g) at 40° C. for 3 d. The reaction solution is filtred, concentrated under reduced pressure and crystalized from AcOEt/hexane to give the compound of Stage 56.1: M+H=222/224; $^1$H-NMR (400 MHz, DMSO-d$_6$): 8.62 (s, 1H, piperidinyl), 7.13 (s, 1H, piperidinyl), 6.83 (d, 9 Hz, 2H, phenyl), 6.56 (d, 9 Hz, 2H, phenyl), 5.12 (s, 2H, NH$_2$); m.p.=135.5-138.1° C.

Stage 56.2: 4-Chloro-6-(4-nitro-phenoxy)-pyrimidine

4-Nitrophenol (2.8 g, 20.1 mmol), 2,4-dichloro-pyrimidine (3 g, 20.1 mmol), NaOH (0.8 g, 20.1 mmol) dissolved in H$_2$O/acetone (80 mL; 1:1) are stirred at 60-65° C. for 1 h. The reaction solution is concentrated under reduced pressure and flash chromatographed (silica gel, 4.5×22 cm, AcOEt/hexane=1:4) to give the compound of Stage 56.2 as a white solid material: M+H=252/254; $^1$H-NMR (400 MHz, DMSO-d$_6$): 8.67 (s, 1H, piperidinyl), 8.34 (d, 9 Hz, 2H, phenyl), 7.58 (d, 9 Hz, 2H, phenyl), 7.53 (s, 1H, piperidinyl); R$_f$ (AcOEt/hexane=1:1): 0.16; m.p.=125.4-126.6° C.

Example 57

1-[4-(6-Methylamino-pyrimidin-4-yloxy)-phenyl]-3-(3-trifluoromethyl-phenyl)-urea

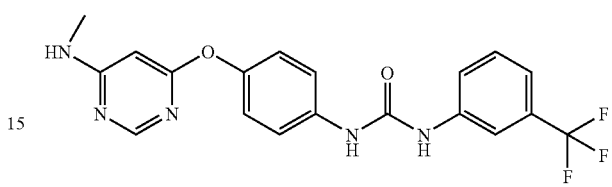

1-[4-(6-Chloro-pyrimidin-4-yloxy)-phenyl]-3-(3-trifluoromethyl-phenyl)-urea (Example 56) (42.7 mg, 0.1 mmol) is dissolved in methylamine (30% in EtOH, 1 mL) in a sealable tube and heated under Ar for 10 min at 50° C. After evaporating the solvent, the product is purified by preparative TLC (2 20×20 cm plates, acetone/CH$_2$Cl$_2$=3:7) to give the title compound as a white solid: M+H=404.1; $^1$H-NMR (400 MHz, CDCl$_3$): 8.22 (s, 1H, pyridinyl), 7.84 (s/broad, 1H, NH), 7.62 (s, 1H, 3-CF$_3$-phenyl), 7.52 (d, 8.0 Hz, 1H, CF$_3$-phenyl), 7.35 (t, 8.0 Hz, 1H, 3-CF$_3$-phenyl), 7.28 (m, 3H, CF$_3$-phenyl/oxo-phenyl-amine), 6.97 (d, 9.5 Hz, 2H, oxo-phenyl-amine), 5.62 (d/broad, 2H, pyridinyl), 5.44 (s/broad, 1H, NH), 2.89 (s/broad, CH$_3$—N); R$_f$(acetone/CH$_2$Cl$_2$=3:7): 0.36.

The following compounds are synthesized in analogy to the preparation of compound of Example 56 by stirring the corresponding chloride and the amine at a temperature range between 20 and 80° C. for a time period between 10 min up to several hours. Structures and analytical data of the compounds are given in Table 6.

TABLE 6

| Ex. | Structure | Analytical data |
|---|---|---|
| 58 | 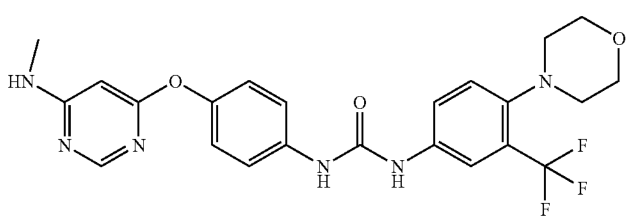 | M + H = 489.1; R$_f$ CH$_2$Cl$_2$/acetone = 7:3): 0.12; $^1$H-NMR (400 MHz, CDCl$_3$): 8.21 (s, 1h, pyrimidinyl), 7.71 (s/broad, 1H, urea), 7.53 (d, 8.0 Hz, 1H, aryl), 7.51 (s, 1H, aryl), 7.42 (s/broad, 1H, urea), 7.25 (m, 3H, aryl), 6.98 (d, 9.0 Hz, 2H, amino-phenyl-oxy), 5.67 (s, 1H, pyrimidinyl), 5.36 (m/broad, 1H, NH—Me), 3.78 (m, 4H, morpholinyl), 2.91 (d/broad, 3H, NH-Me), 2.84 (m, 4h, morpholinyl). |
| 59 | 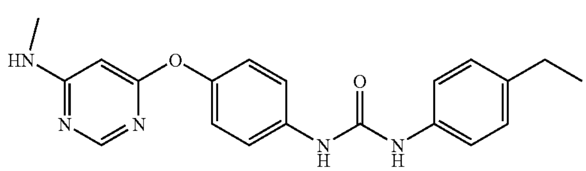 | M + H = 364.0; R$_f$ (CH$_2$Cl$_2$/MeOH = 95:5): 0.16; HPLC (System 1): 5.06 min. |

TABLE 6-continued

| Ex. | Structure | Analytical data |
|---|---|---|
| 60 | 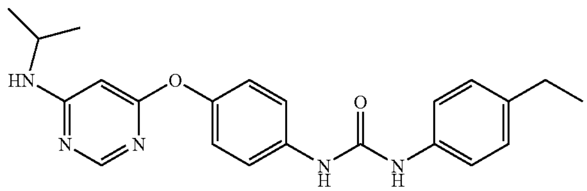 | M + H = 392.0; $R_f$ (CH$_2$Cl$_2$/MeOH = 95:5): 0.21; HPLC (System 1): 5.52 min. |
| 61 | 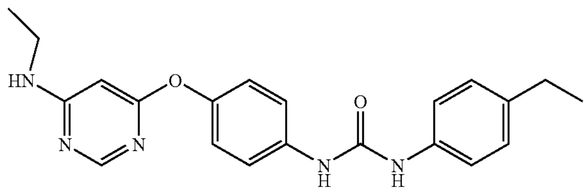 | M + H = 378.0; $R_f$ (CH$_2$Cl$_2$/MeOH = 95:5): 0.16; HPLC (System 1): 5.26 min; $^1$H-NMR (400 MHz, DMSO-d$_6$): 8.69/8.34 (s/s, 2H, urea), 8.10 (s/broad, 1H, pyrimidinyl), 7.44/7.33,/7.09/7.03 (d/d/d/d, 8.5 Hz, 8 H, aryl), 7.00 (s/broad, 1H, NH), 5.65 (s/broad, 1H, pyrimidinyl), 3.25 (s/broad, 2H, CH$_2$), 2.54 (qu, 8.0 Hz, 2H, CH$_2$), 1.16/1.09 (t/t, 8.0 Hz, CH$_3$). |
| 62 | 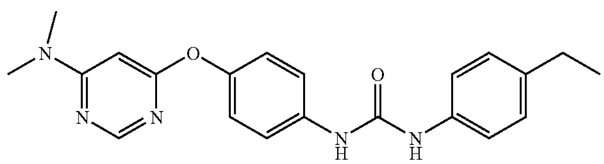 | M + H = 378.0; $R_f$ (CH$_2$Cl$_2$/MeOH = 95:5): 0.29; HPLC (System 1): 5.33 min. |
| 63 | 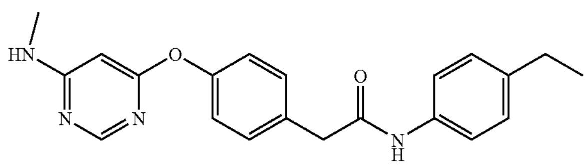 | M + H = 378.0; $R_f$ (hexane/AcOEt = 2:3): 0.40; HPLC (System 1): 4.94 min. |
| 64 | 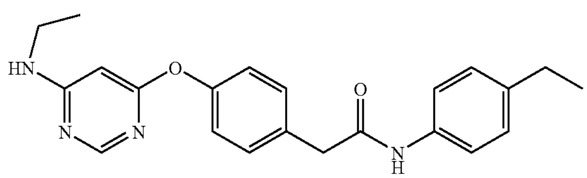 | M + H = 377.1; $R_f$ (hexane/AcOEt = 1:4): 0.14; HPLC (System 1): 5.17 min. |
| 65 | 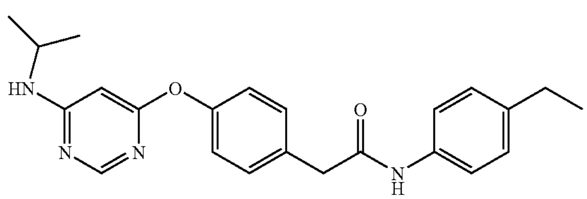 | M + H = 391.1; $R_f$ (hexane/AcOEt = 2:3): 0.17; HPLC (System 1): 5.49 min. |
| 66 | 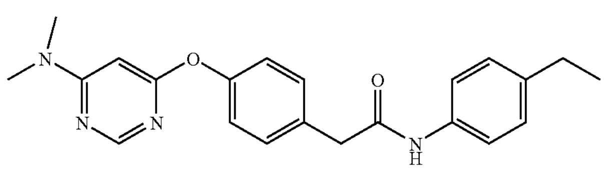 | M + H = 377.1; $R_f$ (hexane/AcOEt = 2:3): 0.20; HPLC (System 1): 5.22 min. |
| 67 | 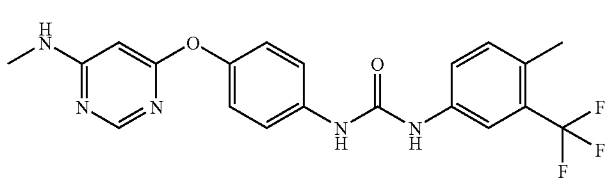 | $R_f$(CH$_2$Cl$_2$/acetone = 7:3): 0.19; m.p. = 202-203° C. (decomp.). |

TABLE 6-continued

| Ex. | Structure | Analytical data |
|---|---|---|
| 68 | 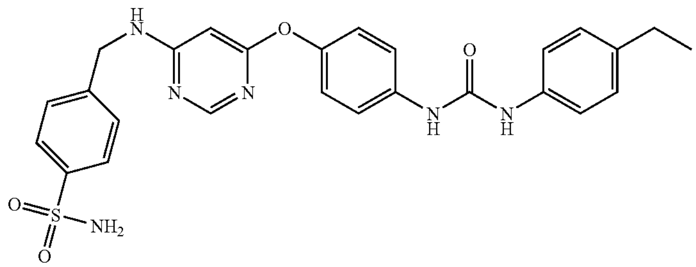 | M + H = 518.9; $R_f$ (CH$_2$Cl$_2$/MeOH/NH$_3$ conc. = 9:1:0.01): 0.31; HPLC (System 1): 5.32 min. |
| 69 | 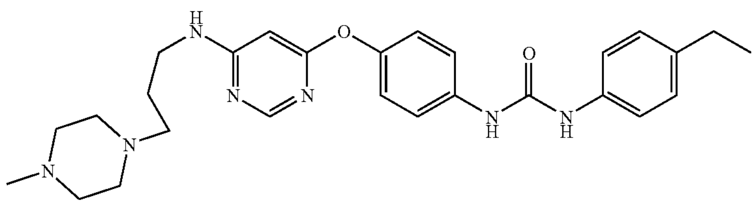 | M + H = 490.1; $R_f$ (CH$_2$Cl$_2$/MeOH/NH$_3$ conc. = 9:1:0.01): 0.17; HPLC (System 1): 4.24 min. |
| 70 | 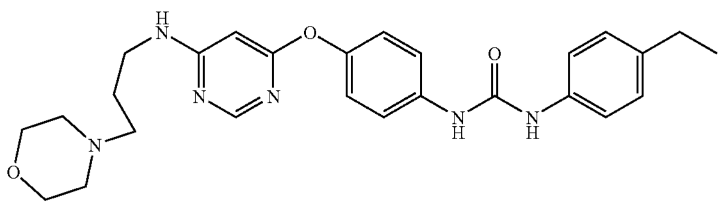 | M + H = 477.0; $R_f$ (CH$_2$Cl$_2$/MeOH/NH$_3$ conc. = 9:1:0.01): 0.46; HPLC (System 1): 4.69 min. |
| 71 | 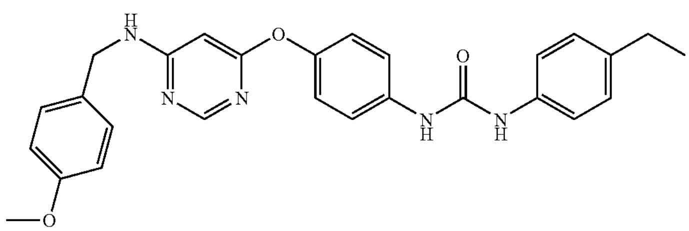 | M + H = 470.0; $R_f$ (CH$_2$Cl$_2$/MeOH/NH$_3$ conc. = 95:5:0.1): 0.38; HPLC (System 1): 6.04 min. |
| 72 | 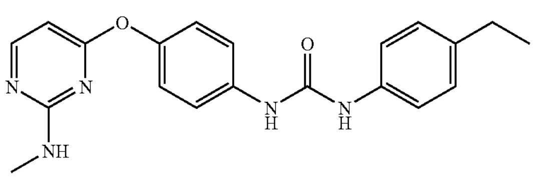 | M + H = 364.1; $R_f$ (hexane/AcOEt = 1:1): 0.12; HPLC (System 1): 5.18 min; $^1$H-NMR (400 MHz, DMSO-d$_6$): 8.66/8.54 (s/s, 2H, urea), 8.12 (s/broad, 1H, pyrimidinyl), 7.47/7.33,/7.09/7.09 (d/d/d/d, 8.5 Hz, 8 H, aryl), 7.03 (s/broad, 1H, NH), 6.08 (s/broad, 1H, pyrimidinyl), 2.70 (s/broad, 3H, Me-NH), 2.55 (qu, 8.0 Hz, 2H CH$_2$), 1.13 (t, 8.0 Hz, CH$_3$). |
| 73 | 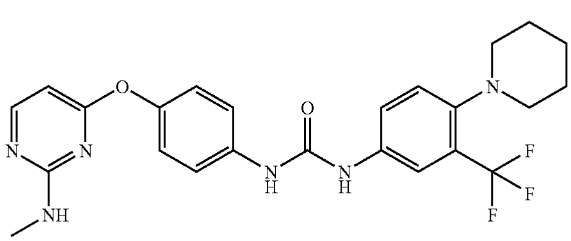 | M + H = 487.0; $R_f$ (AcOEt/hexane = 2:1): 0.45; HPLC (System 1): 6.44 min |

4-Piperidin-1-yl-3-trifluoromethyl-phenylamine (Stage 73.1) for the synthesis of compound of Example 74 is synthesized according to the preparation of compound of Stage 38.1: M+H=245.1; $R_f$ (AcOEt/hexane=1:5): 0.11.

Example 74

1-{4-[2-(4-Hydroxy-phenylamino)-pyrimidin-4-yloxy]-phenyl}-3-(4-morpholin-4yl-3-trifluoromethyl-phenyl)-urea

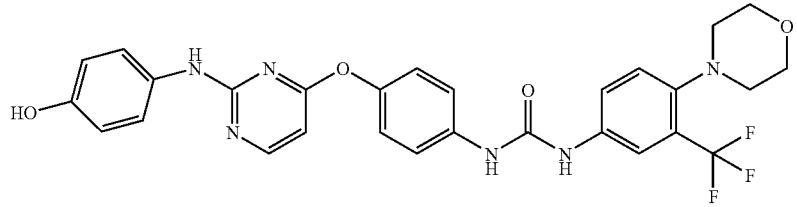

The compound is synthesized in analogy to the preparation of compound of Example 22: M+H=566.8; $R_f$ (CH$_2$Cl$_2$/MeOH): 0.21, HPLC (System 1): 5.59 min.

Example 75

1-{4-[2-(4-Methoxy-phenylamino)-pyrimidin-4-yloxy]-phenyl}-3-(4-piperidin-1yl-3-trifluoromethyl-phenyl)-urea

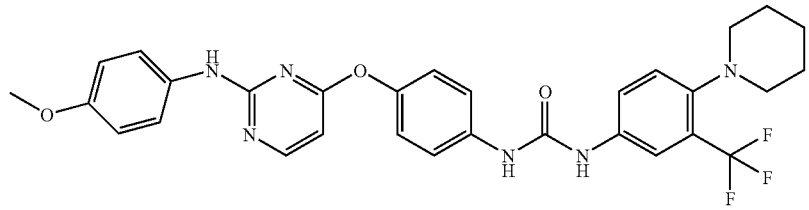

The compound is synthesized in analogy to the preparation of compound of Example 22: M+H=578.9; $R_f$ (Hexane/AcOEt=1:1): 0.26; HPLC: 6.44 min (System 1).

Example 76

1-[4-(6-Chloro-pyrimidin-4-yloxy)-phenyl]-3-(4-methyl-3-trifluoromethyl-phenyl)-urea

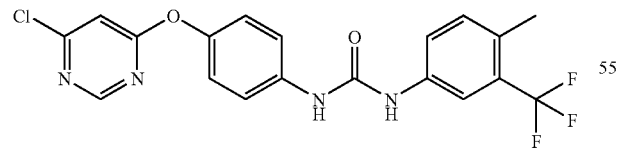

The title compound is synthesized in analogy to the preparation of compound of Example 48 starting from compound of Stage 56.1: M+H=423.1/M+18=440.1; $R_f$ (CH$_2$Cl$_2$/acetone=9:1): 0.42; $^1$H-NMR (400 MHz, DMSO-d$_6$): 8.93/8.80 (s/s, 2H, urea), 7.91 (d, 2 Hz, 1H, pyrimidinyl), 7.51 (d, 9.5 Hz, 2H, phenyl), 7.47 (d, 8.0 Hz, 1H, phenyl-CF$_3$), 7.29 (d, 8 Hz, 1H, phenyl-CF$_3$), 7.27 (s, 1H, phenyl-CF$_3$), 7.13 (d, 9.5 Hz, 2H, phenyl), 4.08 (m, 1H, pyrimidinyl), 2.63 (s/broad, 3H, CH$_3$); m.p.=183.0-184.5° C.

Example 77

1-[4-(6-Amino-pyrimidin-4-yloxy)-phenyl]-3-(3-trifluoromethyl-phenyl)-urea

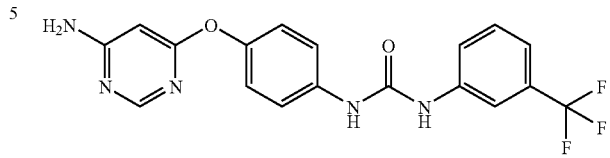

Compound of Example 56 (50 mg, 0.122 mmol) is dissolved in 2 mL EtOH and 2 mL NH$_3$ (25% aqueous) and stirred at 80° C. in a sealed tube for 13 h. After evaporating the solvent under reduced pressure, the product is isolated by TLC (two 20×20 cm plates, 10% MeOH in CH$_2$Cl$_2$): M+H=390.0; $R_f$ (CH$_2$Cl$_2$/MeOH=9:1): 0.15; $^1$H-NMR (400 MHz, DMSO-d$_6$): 9.07/8.87 (s/s, 2H, urea), 7.98 (s/broad, 1H, pyrimidinyl), 7.56 (d, 8.0 Hz, H, phenyl-CF$_3$), 7.47 (d, 8.0 Hz, 1H, phenyl-CF$_3$), 7.49 (d, 8.5 Hz, 2H, phenyl), 7.46 (s, 1H, phenyl-CF$_3$), 7.27 (d, 8.0 Hz, 1H, phenyl-CF$_3$), 7.04 (d, 8.5 Hz, 2H, phenyl), 6.77 (s/broad, 2H, NH$_2$), 5.64 (s/broad, 1H, pyrimidinyl).

Example 78

1-[4-(2-Chloro-pyrimidin-4-yloxy)-phenyl]-3-(4-ethyl-phenyl)-urea

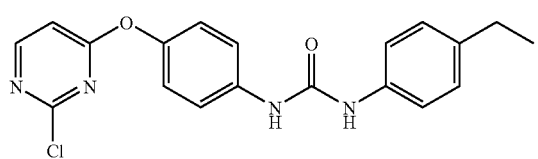

The title compound is synthesized in analogy to the preparation of compound of Example 56: M+H=369.0/371.0; $R_f$ (Hexane/AcOEt=1:1): 0.31; Anal.: C, 62.20%; (61.88%); H, 4.85%; (4.65%); N, 14.73%; (15.19%).

Example 79

1-[4-(2-Chloro-pyrimidin-4-yloxy)-phenyl]-3-(4-piperidin-1-yl-3-trifluoromethyl-phenyl)-urea

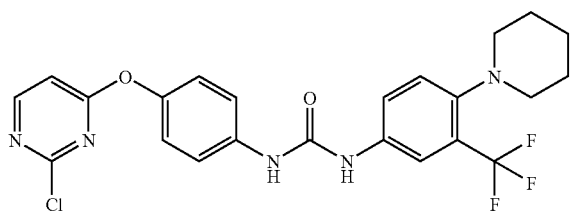

The title compound is synthesized in analogy to the preparation of compound of Example 56: M+H=491.9/493.9; $R_f$ (Hexane/AcOEt=1:1): 0.38; Anal.: C, 55.67%; (56.16%); H, 4.32%; (4.30%); N, 13.62%; (14.24%).

Example 80

N-(4-(6-Chloropyrimidin-4yl-oxy)-phenyl)-N'-(4-tert-butylphenyl)-urea

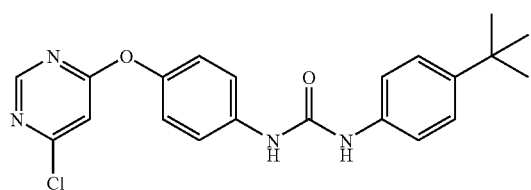

To a solution of 4-(6-chloro-pyrimidin-4-yl-oxy)-aniline (Stage 21.1; 3.77 g, 15 mmol) in THF (55 ml) under $N_2$-atmosphere, 4-tertbutylphenyl isocyanate (5.26 g, 30 mmol) dissolved in THF (5 ml) is added. During stirring for 1 h at rt a suspension is formed. The mixture is then re-dissolved in AcOEt and a solution of NaHCO$_3$ in water, the aqueous layer separated off and extracted twice with AcOEt. The organic phases are washed with water and brine, dried (Na$_2$SO$_4$) and concentrated in vacuo. Stirring of the resulting solid in Et$_2$O finally yields the title compound: m.p.: 111-112° C.; $^1$H-NMR (DMSO-d$_6$): 8.75 (s, HN), 8.65 (s, 1H), 8.62 (s, HN), 7.51 (d, 2H), 7.36 (d, 2H), 7.33 (s, 1H), 7.31 (d, 2H), 7.17 (d, 2H), 1.27 (Me$_3$C).

Example 81

N-(4-(6-Chloropyrimidin-4yl-oxy)phenyl)-N'-(4-chloro-3-trifluoromethyl-phenyl)-urea

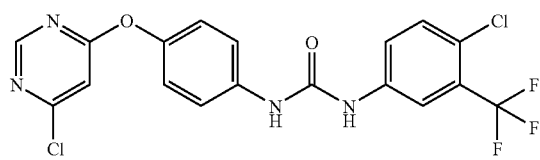

To a solution of 4-(6-chloro-pyrimidin-4-yl-oxy)-aniline (Stage 21.1; 3.77 g, 15 mmol) in THF (40 ml) under $N_2$-atmosphere, 4-chloro-3-trifluoromethylphenyl isocyanate (4.98 g, 22.5 mmol) dissolved in THF (20 ml) is added. After 1 h at rt the solution is diluted with AcOEt and NaHCO$_3$ in water, the aqueous layer separated off and extracted twice with AcOEt. The organic phases are washed with water and brine, dried (Na$_2$SO$_4$) and concentrated in vacuo. Stirring of the resulting solid in Et$_2$O finally yields the title compound: m.p.: 180-181° C.; $^1$H-NMR (DMSO-d$_6$): 9.22 (s, HN), 8.97 (s, HN), 8.65 (s, 1H), 8.11 (s, 1H), 7.65 (m, 1H), 7.63 (m, 1H), 7.53 (d, 2H), 7.34 (s, 1H), 7.19 (d, 2H); Anal.: CHNClFO.

Example 82

N-(4-(4-Methylaminopyrimidin-6-yl-oxy)-phenyl)-N'-(4-tert-butylphenyl)-urea

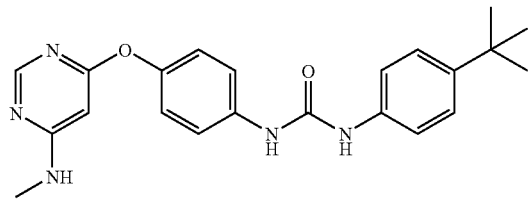

Under $N_2$-atmosphere, a solution of N-(4-(4-chloropyrimidin-6-yl-oxy)-phenyl)-N'-(4-tert-butylphenyl)-urea (319 mg, 0.80 mmol) in methylamine/ethanol (8.03 M; 5 ml) is stirred for 50 min at 40° C. Then the reaction mixture is concentrated in vacuo, the residue re-dissolved in water and AcOEt, the aqueous layer separated off and extracted twice with AcOEt. The organic phases are washed with water and brine, dried (Na$_2$SO$_4$) and concentrated in vacuo after adding 2 g of SiO$_2$. The resulting powder is put on top of a SiO$_2$-column and eluted with AcOEt/hexane 9:1, yielding the title compound: m.p.: 245-246° C.; $^1$H-NMR (DMSO-d$_6$): 8.7 (s, HN), 8.6 (s, HN), 8.13 (s, 1H), 7.45 (d, 2H), 7.35 (d, 2H), 7.31 (d, 2H), 7.05 (d, 2H), 6.78 (s, HN), 5.79 (s, 1H), 2.83 (MeN), 1.30 (Me$_3$C).

Example 83

N-(4-(4-Benzylaminopyrimidin-6-yl-oxy)-phenyl)-N'-(4-tert-butylphenyl)-urea

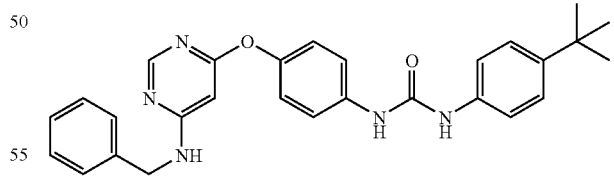

Under $N_2$-atmosphere, a suspension of N-(4-(4-chloropyrimidin-6-yl-oxy)-phenyl)-N'-(4-tert-butylphenyl)-urea (397 mg, 1.00 mmol) and benzylamine (327 μM) in isopropanol (3 ml) is stirred for 21 h at 70° C. Then the reaction mixture is concentrated in vacuo, the residue re-dissolved in saturated NaHCO$_3$ solution and AcOEt, the aqueous layer separated off and extracted twice with AcOEt. The organic phases are washed with water and brine, dried (Na$_2$SO$_4$) and concentrated. The crude product is dissolved in CH$_2$Cl$_2$ and after addition of SiO$_2$ again concentrated. The resulting powder is put on top of a SiO₂-column and eluted with AcOEt/hexane 3:1, yielding the title compound: m.p.: 118-120° C.; ¹H-NMR (DMSO-d₆): 8.73 (s, HN), 8.62 (s, HN), 8.13 (s, 1H), 7.84 (s, HN), 7.46 (d, 2H), 7.35 (d, 2H), 7.30 (m, 4H), 7.28 (m, 2H), 7.24 (m, 1H), 7.03 (d, 2H), 5.78 (s, 1H), 4.49 (s, 2H), 1.26 (Me₃C).

Example 84

N-(4-(4-Aminopyrimidin-6-yl-oxy)phenyl)N'-(4chloro-3-trifluoromethyl-phenyl)-urea

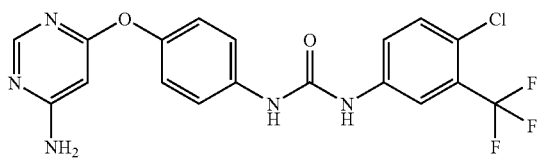

In a sealed tube under N₂-atmosphere, N-(4-(4-chloropyrimidin-6-yl-oxy)-phenyl)-N'-(4-chloro-3-trifluoromethyl-phenyl)-urea (443 mg, 1.00 mmol) and 25% aqueous NH₃ (2 ml) in ethanol (2 ml) is stirred for 22 h at 80° C. Then the reaction mixture is diluted with water and AcOEt, the aqueous layer separated off and extracted 3 times with AcOEt. The organic phases are washed with 3 portions of water and brine, dried (Na₂SO₄) and concentrated. Column chromatography (SiO₂; CH₂Cl₂/MeOH 9:1) yields the title compound: m.p.: 197-198° C.; ¹H-NMR (DMSO₆): 9.20 (s, HN), 8.93 (s, HN), 8.12 (m, 1H), 8.08 (s, 1H), 7.63 (m, 2H), 7.51 (d, 2H), 7.08 (d, 2H), 6.82 (s, H₂N), 5.67 (s, 1H).

Example 85

N-(4-(4-Chloropyrimidin-6-yl-oxy)-phenyl)-N'-(3-methoxy-4-piperidin-1-yl-phenyl)-urea

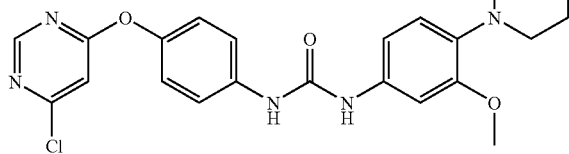

A solution of triphosgene (1.4 g, 4.7 mmol) in CH₂Cl₂ (95 ml) under N₂-atmosphere is cooled by an ice bath. 3-Methoxypiperidin-1-yl-phenylamine (Stage 85.1; 2.95 g, 14.3 mmol) and NEt₃ (2.0 ml; 14.3 mmol) in CH₂Cl₂ (48 ml) is then added dropwise and the resulting suspension stirred for 20 min at rt. Then a solution of 4-(6-chloro-pyrimidin-4-yl-oxy)-aniline (Stage 21.1; 3.17 g, 14.3 mmol) and NEt₃ (2.0 ml; 14.3 mmol) in CH₂Cl₂ (48 ml) is added dropwise, whereby a brown solution is formed, which is stirred for 4.5 h at rt. The reaction mixture is added to saturated NaHCO₃ solution (0.3 L) and extracted with CH₂Cl₂. The organic phase is washed with water and brine, dried (Na₂SO₄) and concentrated. The crude product is dissolved in AcOEt/methanol, SiO₂ is then added and the solvent evaporate off in vacuo. The resulting powder is put on top of a chromatography column (SiO₂; AcOEt/hexane 4:1) and the title compound eluted with AcOEt/hexane 4:1: m.p.: 175° C.; ¹H-NMR (DMSO-d₆): 8.68 (s, 1H), 8.62 (s, 1H), 8.50 (s, 1H), 7.50 (d, 2H), 7.30 (s, 1H), 7.13 (m, 3H), 6.85 (d, 1H), 6.77 (d, 1H), 3.75 (s, 3H), 2.82 (m, 4H), 1.60 (m, 4H), 1.49 (m, 2H).

The starting materials are prepared as follows:

Stage 85.1:
3-Methoxy-4-piperidin-1-yl-phenylamine 1-(2-Methoxy-4-nitro-phenyl)-piperidine (Stage 85.2; 4.0 g, 17 mmol) in ethanol/THF 5:1 (90 ml) is hydrogenated in the presence of Pd/C 10 % ("Engelhard 4505"; 0.4 g). Then the catalyst is filtered off and the filtrate is concentrated yielding the title compound: ¹H-NMR (DMSO-d₆): 6.58 (d, 1H), 6.19 (d, 1H), 6.04 (dd, 1H), 4.66 (s, H₂N), 3.65 (s, H₃CO), 2.70 (m, 4H), 1.56 (m, 4H), 1.43 (m, 2H).

Stage 85.2: 1-(2-Methoxy-4-nitro-phenyl)-piperidine

2-Bromo-5-nitroanisole (5.0 g, 21.5 mmol) and piperidine (8.5 ml) is stirred for 5 h at 105° C. under N₂-atmosphere. Water (80 ml) is added and the mixture is extracted twice with CH₂Cl₂ (2×80 ml). The organic phases are washed with water and brine, dried (Na₂SO₄) and concentrated. The crude product is dissolved in AcOEt, SiO₂ is then added and the solvent evaporate off In vacuo. The resulting powder is put on top of a chromatography column (SiO₂; AcOEt/hexane 9:1) and the title compound eluted with hexane/AcOEt 9:1→4:1: MS: [M+1]⁺=237; R_f=0.2 (AcOEt/hexane 9:1).

Example 86

N-(4-(6-Chloropyrimidin-4-yl-oxy)phenyl)-N'-(4-(4-ethyl-piperazin-1-yl)-3-methoxy-phenyl)-urea

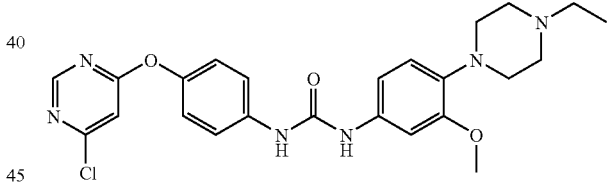

The title compound is prepared from 4-(4-ethyl-piperazin-1-yl)-3-methoxy-phenylamine (Stage 86.1; 3.99 g, 16.5 mmol) and 4-(6-chloro-pyrimidin-4-yl-oxy)-aniline (Stage 21.1; 3.67 g, 16.5 mmol) analogously to Example 85: m.p.: 170-171° C.; ¹H-NMR (DMSO-d₆): 8.67 (s, 1H), 8.61 (s, 1H), 8.52 (s, 1H), 7.48 (d, 2H), 7.28 (s, 1H), 7.15 (d, 1H), 7.12 (d, 2H), 6.84 (d, 1H), 6.77 (d, 1H), 3.74 (s, 3H), 2.86 (m, 4H), 2.44 (m, 4H), 2.33 (q, 2H), 0.98 (t, H₃C); Anal.: CHNCl.

The starting materials are prepared as follows:

Stage 86.1:
4-(4-Ethyl-piperazin-1-yl-3-methoxy-phenylamine

1-Ethyl-4-(2-methoxy-4-nitro-phenyl)-piperazine (Stage 86.2; 2.89 g, 11 mmol) in ethanol/THF 5:1 (70 ml) is hydrogenated in the presence of Pd/C 10% ("Engelhard 4505"; 0.3 g). Then the catalyst is filtered off and the filtrate is concentrated yielding the title compound: ¹H-NMR (CD₃OD): 6.79 (d, 1H), 6.44 (d, 1H), 6.29 (dd, 1H), 3.80 (s, H₃CO), 2.97 (m, 4H), 2.65 (m, 4H), 2.52 (q, 2H), 1.14 (t, H₃C).

Stage 86.2:
1-Ethyl-4-(2-methoxy-4-nitro-phenyl)-piperazine

2-Bromo-5-nitroanisole (4.7 g, 20 mmol) and N-ethyl-piperazin (10.3 ml) is stirred for 13 h at 110° C. under $N_2$-atmosphere. Water (80 ml) is added and the mixture extracted twice with $CH_2Cl_2$ (2×80 ml). The organic phases are washed with water and brine, dried ($Na_2SO_4$) and concentrated. Column chromatography ($SiO_2$; $CH_2Cl_2$/MeOH 19:1→9:1) gives the title compound: m.p.: 84-85° C.

Example 87

N-(4-(4-Chloropyrimidin-6-yl-oxy)-phenyl)-N'-(3-methoxy-4-(piperidin-1-ylmethyl)-phenyl)-urea

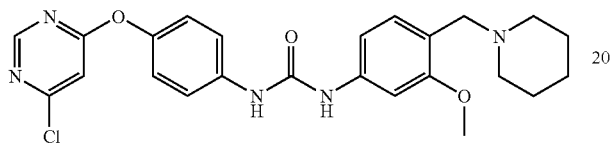

The title compound is prepared from 3-methoxy(piperidin-1-ylmethyl)phenylamine (Stage 87.1) and 4-(6-chloro-pyrimidin-4-yl-oxy)-aniline (Stage 21.1) analogously to Example 85: MS: $[M+1]^+$=468.

The starting materials are prepared as follows:

Stage 87.1:
3-Methoxy-4-(piperidin-1-ylmethyl)-phenylamine

Hydrogenation of 1-(2-methoxy-4-nitro-benzyl)-piperidine (Stage 87.2) in THF with Raney Nickel as catalyst affords the title compound: MS: $[M+1]^+$=221.

Stage 87.2: 1-(2-Methoxy-4-nitro-benzyl)-piperidine (2-Methoxy-4-nitro-phenyl)-piperidin-1-yl-methanone (Stage 87.3; 200 mg, 0.76 mmol) is dissolved in THF (8 ml) at −20° C. DIBAH (1 M in THF: 2.3 ml) then is added. After 90 min at −20° C., another portion of DIBAH (0.8 ml) is added and stirring continued for 2 h. Then the reaction mixture is hydrolysed by water (30 ml) and a saturated solution of sodium potassium tartrate (25 ml) and extracted 3 times with AcOEt. The organic phases are washed with brine, dried ($Na_2SO_4$) and concentrated. The crude product is dissolved in AcOEt, $SiO_2$ is then added and the solvent evaporate off in vacuo. The resulting powder is put on top of a chromatography column ($SiO_2$; AcOEt) and the title compound eluated with AcOEt: $^1$H-NMR (DMSO-$d_6$): 7.83 (dd, 1H), 7.73 (d, 1H), 7.60 (d, 1H), 3.91 (s, $H_3$CO), 3.49 (s, 2H), 2.36 (m, 4H), 1.52 (m, 4H), 1.39 (m, 2H).

Stage 87.3: (2-Methoxy-4-nitro-phenyl)-piperidin-1-yl-methanone

To an ice-cooled suspension of 2-methoxy-4-nitro-benzoic acid (5.915 g, 30 mmol) in acetonitrile (50 ml) and $CH_2Cl_2$ (40 ml) under $N_2$-atmosphere, TPTU (8.912 g, 30 mmol) and $NEt_3$ (8.36 ml, 60 mmol) is added. After stirring for 40 min, piperidine (3.26 ml, 33 mmol) is added and the reaction mixture is slowly warmed up to rt. After 16 h, AcOEt (0.5 L), water (0.4 L) and saturated $NaHCO_3$ solution (0.2 L) is added, the aqueous phase separated off and extracted 3× with AcOEt. The organic layers are washed with 10% citric acid solution, water and brine, dried ($Na_2SO_4$) and concentrated. Crystallization from AcOEt/hexane yields the title compound: m.p.: 104° C.; $^1$H-NMR (DMSO-$d_6$): 7.88 (dd, 1H), 7.84 (d, 1H), 7.47 (d, 1H), 3.93 (s, $H_3$C), 3.7-3.5 (m, 2H), 3.07 (m, 2H), 1.64-1.5 (m, 4H), 1.42 (m, 2H).

Example 88

The following compounds can be prepared analogously to the described procedures (Table 7):

TABLE 7

| | | Reaction-conditions | m.p. [° C.] | MS $[M + 1]^+$ | Anal. |
|---|---|---|---|---|---|
| a) 4-tert-butylaniline | ethylamine | EtOH 20 h, rt | 153-156 | 406 | |

TABLE 7-continued
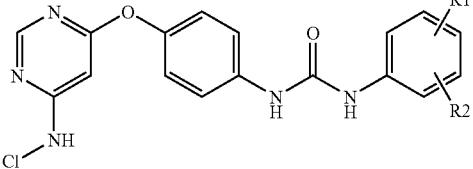
| | 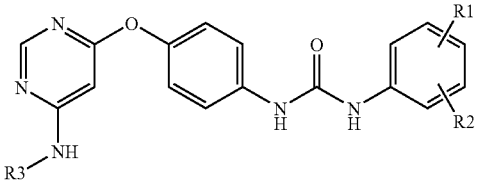 | 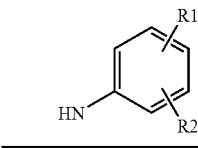 | Reaction-conditions | m.p. [° C.] | MS [M + 1]+ | Anal. |
|---|---|---|---|---|---|---|
| b) | | 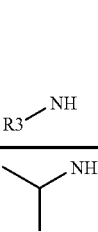 | neat<br>20 h, rt | 184-185 | 420 | |
| c) | |  | NH₃ 25% in<br>H₂O; dioxane;<br>12 h, 80° C. | 117-118 | 378 | |
| d) | |  | neat<br>2 h, 40° C. | 107-108 | 498 | |
| e) | |  | isopropanol<br>12 h, 60° C. | 96-97 | 518 | |
| f) | |  | isopropanol<br>24 h, 80° C. | 129-130 | 475 | |
| g) | |  | isopropanol<br>29 h, 85° C. | 215-216 | 502 | |
| h) | |  | | | | |
| i) |  | 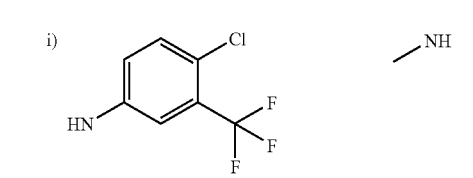 | EtOH<br>8 h, 40° C. | 208-209 | 438 | |
| j) | |  | EtOH<br>20 h, rt | 154-156 | 452 | |
| k) | |  | neat<br>20 h, rt | 220-221 | 466 | |
| l) | |  | isopropanol<br>17 h, 60° C. | 178-179 | 544 | |
| m) | |  | isopropanol<br>4 h, 60° C. | 92-93 | 564 | |

TABLE 7-continued
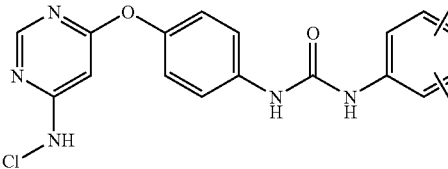
| | R3-NH | Reaction-conditions | m.p. [° C.] | MS [M + 1]+ | Anal. |
|---|---|---|---|---|---|
| n) | 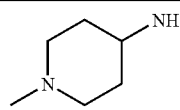 | isopropanol 24 h, 80° C. | 126-128 | 521 | |
| o) | 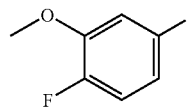 | isopropanol 26 h, 85° C. | 152-154 | 548 | |
| p) | 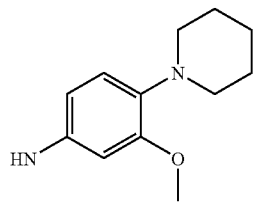 | EtOH 90 min, 50° C. | 191–192 | 449 | CHN |
| q) | 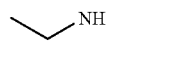 | EtOH 20 h, rt | 189-191 | 463 | CHN |
| r) | 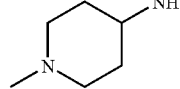 | THF/isopropanol NaI 60 h, 60° C. | | 532 | |
| s) | 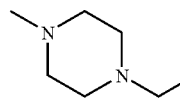 | isopropanol 8 h, 60° C. | | 575 | |
| t) | 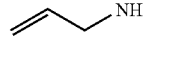 | 5 h rt | 191-192 | 475 | CHN |
| u) |  | | | | |
| v) | 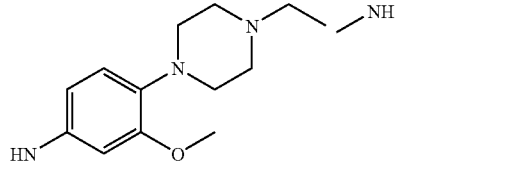 | EtOH 1 h, rt | 178-180 | 478 | |
| w) | 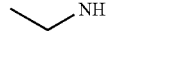 | EtOH 11 h, rt | | 492 | |
| x) | 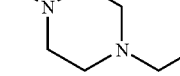 | isopropanol 19 h, 50° C. | | 604 | |

TABLE 7-continued

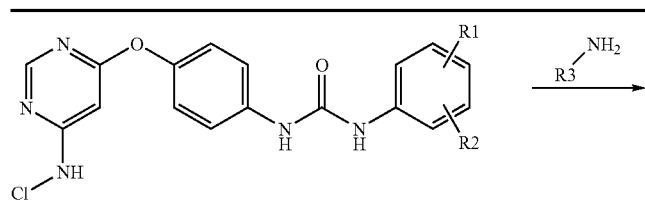

| | R3—NH | Reaction-conditions | m.p. [° C.] | MS [M + 1]⁺ | Anal. |
|---|---|---|---|---|---|
| y) | 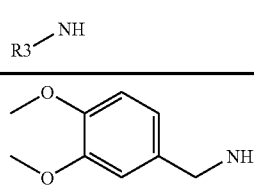 | isopropanol 15 h, 70° C. | 189-190 | 614 | CHN |
| z) |  | | | | |
| aa) | 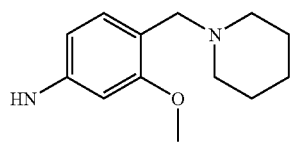 | | | | |
| ab) |  | EtOH, NaI 100 min, 40° C. | | 477 | |
| ac) | 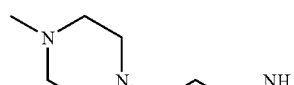 | Isopropanol/ THF NaI cat., 50° C. | | 589 | |

Example 89

(±)-trans-N-(4-(4-Ethylaminopyrimidin-6-yl-oxy)-phenyl)-N'-(2-phenyl-cyclopropyl)-urea (Method A)

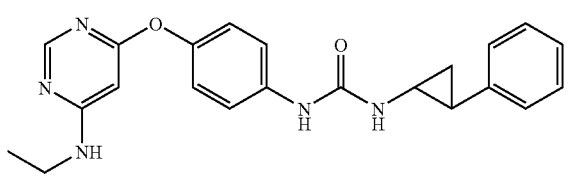

To a solution of 4-(4-ethylaminopyrimidin-6-yl-oxy)-aniline (Stage 89.1; 271 mg, 1.177 mmol) In THF (5 ml) under N₂-atmosphere, trans-2-phenyl-cyclopropyl-isocyanate (188 mg, 1.18 mmol; Aldrich) Is added. Then the solution is stirred for 8 h, whereas a precipitate is formed. Filtration and washing with THF and ether yields the title compound: m.p.: 205-206° C.; ¹H-NMR (DMSO-d₆): 8.50 (s, HN), 8.11 (s, 1H), 7.42 (d, 2H), 7.27 (m, 3H), 7.15 (m, 3H), 7.01 (d, 2H), 6.67 (s, HN), 5.67 (s, 1H), 3.25 (m, 2H), 2.74 (m, 1H), 1.98 (m, 1H), 1.17 (m, 2H), 1.09 (t, 3H); Anal.: CHN.

The starting materials are prepared as follows:

Stage 89.1:
4-(4-Ethylaminopyrimidin-6-yl-oxy)aniline

A suspension of 4-(6-chloro-pyrimidin-4-yl-oxy)-aniline (Stage 21.1; 5.0 g, 22.6 mmol) in ethylamine dissolved in ethanol (≈35%; 5 ml) under N₂-atmosphere is stirred for 16 h at rt. Then the resulting brown solution is diluted with water and AcOEt, the aqueous layer separated off and extracted twice with AcOEt. The organic phases are washed with 3 portions of water and brine, dried (Na₂SO₄) and concentrated. Re-crystallisaton from boiling AcOEt gives the title compound: m.p.: 143-145° C.; ¹H-NMR (CDCl₃): 8.24 (s, 1H), 7.24 (s, HN), 6.91 (d, 2H), 6.69 (d, 2H), 5.63 (s, 1H), 4.97 (s, H₂N), 3.25 (m, 2H), 1.25 (t, 3H). More product can be isolated from the filtrate of the re-crystallization by column chromatography (SiO₂; AcOEt→AcOEt/EtOH 19:1).

Example 90

N-(4-(4-Ethylaminopyrimidin-6-yl-oxy)-phenyl)-N'-[(R)-5-bromo-indan-2-yl]-urea (Method B)

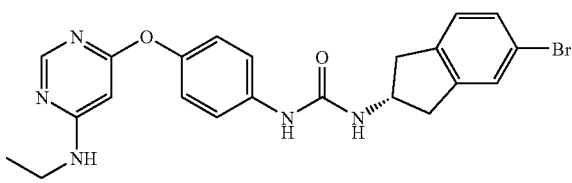

A solution of triphosgene (117 mg, 0.393 mmol) in $CH_2Cl_2$ (12 ml) under $N_2$-atmosphere is cooled by an ice bath. A solution of [(R)-5-bromo-indan-2-yl-amine (250 mg, 1.178 mmol; preparation see *Adv. Synth. Catal.* 2001, 343, 461) and $NEt_3$ (164 µl; 1.177 mmol) in $CH_2Cl_2$ (10 ml) is added dropwise, the dropping funnel rinsed with $CH_2Cl_2$ (2 ml) and the resulting suspension stirred for 60 min at rt. Then a solution of 4-(4-ethylaminopyrimidin-6-yl-oxy)-aniline (258 mg, 1.12 mmol) and $NEt_3$ (164 µl; 1.177 mmol) in $CH_2Cl_2$ (10 ml) is added dropwise and the dropping funnel rinsed with $CH_2Cl_2$ (2 ml). A brown solution is formed, which is stirred for 16 h at rt. $SiO_2$ is then added to the resulting mixture. After concentration in vacuo, the powder is put on top of a MPLC column ($SiO_2$). Eluation with $SiO_2$/AcOEt 4:1→AcOEt, partial concentration and filtration of the crystallized material yields the title compound: m.p.: 247° C.; $^1$H-NMR (DMSO-$d_6$): 8.33 (s, 1H), 8.06 (s, 1H), 7.43 (s, 1H), 7.36 (d, 2H), 7.30 (m, 1H), 7.26 (t, 1H), 7.19 (d, 1H), 6.96 (d, 2H), 6.43 (d, 1H), 5.63 (s, 1H), 4.40 (m, 1H), 3.2 (m, 4H), 2.75 (AB×d, 2H), 1.07 (t, 3H); Anal.: CHNBr.

Example 91

The following compounds can be prepared analogously to the described procedures (Table 8):

TABLE 8

| | HN-R | Reaction-conditions | m.p. [° C.] | MS [M + 1]$^+$ | Anal. |
|---|---|---|---|---|---|
| a) | HN-CH$_2$-(4-methylphenyl) | A: THF; 16 h, rt | 230-232 | 378 | CHN |
| b) | HN-CH$_2$CH$_2$-phenyl | A: THF; 16 h, rt | 222 | 378 | CHN |
| c) | HN-CH$_2$-(3-methylphenyl) | A: THF; 6 h, rt | 226-227 | 378 | CHN |
| d) | HN-phenyl | A: THF; 16 h, rt | 209-210 | 350 | CHN |
| e) | HN-CH$_2$-(3-methoxyphenyl) | A: THF; 8 h, rt | 224 | 394 | |

TABLE 8-continued

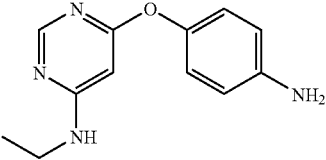

| HN^R | Reaction-conditions | m.p. [° C.] | MS [M + 1]⁺ | Anal. |
|---|---|---|---|---|
| f) 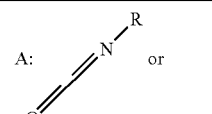 | B: CH₂Cl₂, Et₃N | 241 | 390 | CHN |
| g) 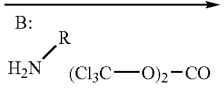 | B: CH₂Cl₂, Et₃N | 243-244 | 468/470 | |
| h) 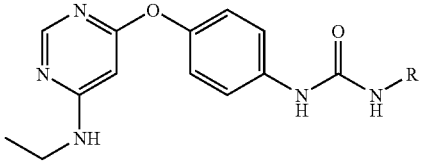 | B: CH₂Cl₂, Et₃N | 208-210 | 450 | |

Example 92

N-(4-(2-Methoxypyridin-4-yl-oxy)-phenyl)-N'-(4-ethyl-phenyl)-urea

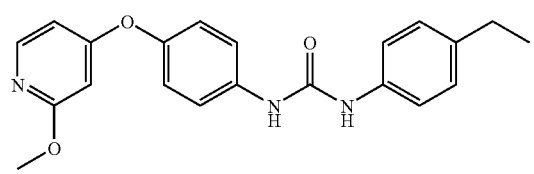

The title compound is prepared from 4-(4-amino-phenoxy)-2-methoxy-pyridine (Stage 92.1; 91 mg, 0.42 mmol) and 4-ethyl-phenyl-isocyanate (124 µl, 0.84 mmol) analogously to Example 89: m.p.: 196° C.; Anal.: CHN.

The starting materials are prepared as follows:

Stage 92.1:
4-(4-Amino-phenoxy)-2-methoxy-pyridine

Hydrogenation of 2-methoxy-4-(4-nitro-phenoxy)pyridine (Stage 92.2; 0.12 g, 0.5 mmol) in AcOEt (10 ml) in the presence of Raney Nickel (20 mg) affords after filtration and concentration of the filtrate the title compound: ¹H-NMR (CDCl₃): 7.97 (d, 1H), 6.86 (d, 2H), 6.67 (d, 2H), 6.48 (d, 1H), 6.13 (s, 1H), 3.89 (s, H₃CO), 3.70 (s, H₂N).

Stage 92.2: 2-Methoxy-4-(4-nitro-phenoxy)-pyridine (A) and 1-methyl-4-(4-nitro-phenoxy)-1H-pyridin-2-one (B)

In a sealed tube under N₂-atmosphere, 4-(4-nitro-phenoxy)-1H-pyridin-2-one (Stage 92.3; 800 mg, 3.45 mmol), Ag₂CO₃ (552 mg, 2.0 mmol), methyl-iodide (474 µl, 7.6 mmol) and acetonitrile (70 ml) are stirred for 16 h at 60° C. The reaction mixture is filtered through Celite, the filtrate concentrated and chromatographed (SiO2; AcOEt) yielding (A) followed by (B): ¹H-NMR (DMSO-d₆) (A): 8.32 (d, 2H), 8.18 (d, 1H), 7.37 (d, 2H), 6.78 (d, 1H), 6.49 (s, 1H), 3.86 (s, H₃CO); (B): 8.30 (d, 2H), 7.80 (d, 1H), 7.40 (d, 2H), 6.15 (d, 1H), 5.80 (s, 1H), 3.40 (s, H₃CO).

Stage 92.3: 4-(4-Nitro-phenoxy)-1H-pyridin-2-one

A suspension of 2,4-dihydroxy-pyridine (2.33 g, 21 mmol), 4-fluoro-nitrobenzene (2.22 ml, 21 mmol) and Cs₂CO₃ (10.2 g, 31.3 mmol) in N-methyl-pyrrolidine (30 ml) is stirred for 3 h at 100° C. under N₂-atmosphere. The reaction mixture is poured into water and the precipitate filtered off and washed with water. The solid is dissolved in CH₂Cl₂/MeOH. Then SiO₂ (≈20 g) is added and the mixture Is concentrated in vacuo. The resulting powder is put on top of a SiO₂-column and eluted with toluene/AcOEt 3:1→AcOEt→AcOEt/EtOH 9:1, yielding the title compound: m.p.: 227-228° C.; ¹H-NMR (DMSO-d₆): 11.60 (s, HN), 8.31 (d, 2H), 7.47 (d, 1H), 7.39 (d, 2H), 6.07 (dd, 1H), 5.67 (d, 1H).

Example 93

N-(4-(1-H-6-oxo-1,6-dihydro-pyridin-3-yl-oxy)-phenyl)-N'-(4-tert-butyl-phenyl)-urea

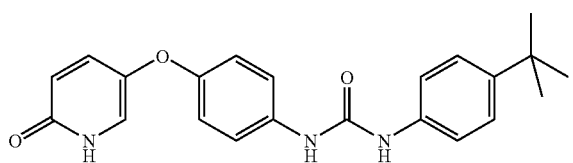

The title compound Is prepared from 3-(4-amino-phenoxy)-1H-pyridin-6-one (Stage 93.1; 1.00 mmol) and 4-tert-butyl-phenyl-isocyanate (346 µl, 2.0 mmol) In THF (10 ml) analogously to Example 89: m.p.: 234° C.; Anal.: CHN.

The starting materials are prepared as follows:

Stage 93.1: 3-(4-amino-phenoxy)-1H-pyridin-6-one

Hydrogenation of 3-(4-nitro-phenoxy)-1H-pyridin-6-one (Stage 93.2; 464 mg, 2.0 mmol) in DMEU (10 ml) in the presence of Raney Nickel (100 mg) affords after filtration and concentration of the filtrate the title compound: ¹H-NMR (DMSO-d₆): 11.2 (s, HN), 7.25 (dd, 1H), 7.11 (d, 1H), 6.68 (d, 2H), 6.51 (d, 2H), 6.35 (d, 1H), 4.87 (s, H₂N).

Stage 93.2: 3-(4-Nitro-phenoxy)-1H-pyridin-6-one

A suspension of 2,5-dihydroxy-pyridine (4.65 g, 41.9 mmol), 4-fluoro-nitrobenzene (2.22 ml, 21 mmol) and Cs₂CO₃ (13.7 g, 41.9 mmol) in N-methyl-pyrrolidine (60 ml) is stirred for 18 h at 90° C. under N₂-atmosphere. The reaction mixture is diluted with water and AcOEt, the aqueous layer separated off and extracted twice with AcOEt. The organic phases are washed with a NaHCO₃ solution and brine, dried (Na₂SO₄) and partially concentrated. Thereby the title compound crystallizes and can be filtered off and washed with AcOEt: m.p.: 214-217° C.; ¹H-NMR (DMSO-d₆): 11.6 (s, HN), 8.22 (d, 2H), 7.57 (d, 1H), 7.43 (dd, 1H), 6.14 (d, 2H), 6.46 (d, 1H).

Example 94

The following compounds can be prepared analogously to the described procedures (Table 9):

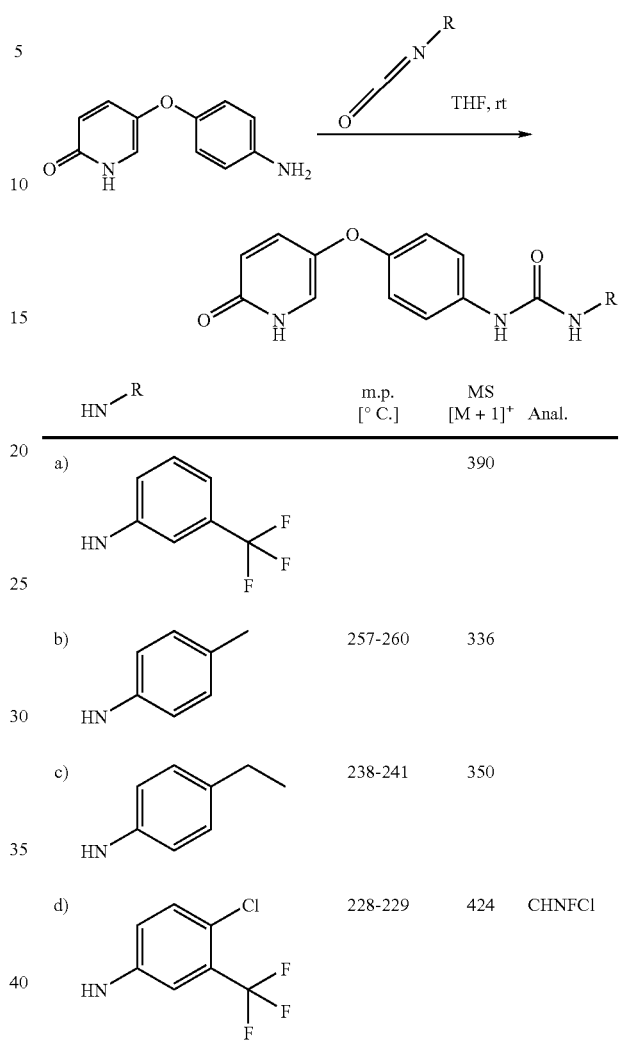

Example 95

N-(4-(6-Methoxy-pyridin-3-ylmethyl)-phenyl)-N'-(4-methyl-phenyl)-urea

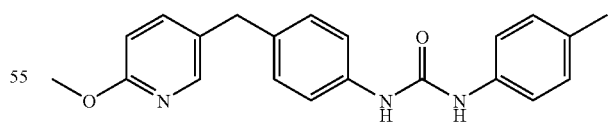

The title compound is prepared from 4-(6-methoxy-pyridin-3-ylmethyl)-phenylamine (Stage 95.1; 300 mg, 1.40 mmol) and 4-methyl-phenyl-isocyanate (0.35 ml, 2.8 mmol) in THF (11 ml) analogously to Example 89: ¹H-NMR (DMSO-d₆): 8.68 (s, 2 HN), 8.02 (d, 1H), 7.49 (dd, 1H), 7.33 (d, 2H), 7.29 (d, 2H), 7.09 (d, 2H), 7.03 (d, 2H), 6.70 (d, 1H), 3.79 (2s, 5H), 2.21 (s, 3H).

The starting materials are prepared as follows:

Stage 95.1: 4-(6-methoxy-pyridin-3-ylmethyl)-phenylamine

Rac-(6-methoxy-pyridin-3-yl)-(4-nitro-phenylmethanol (Stage 95.2; 5.4 g, 21 mmol) in methanol (0.3 L) is hydrogenated with Pd/C 10% ("Engelhard 4505"; ≈5 g) as catalyst for 3 days under 1 atmosphere $H_2$-pressure. Then the catalyst is filtered off, the filtrate concentrated and chromatographed ($SiO_2$; hexane/AcOEt 3:2→1:1) yielding the title compound: $^1$H-NMR (CDCl$_3$): 7.99 (d, 1H), 7.34 (dd, 1H), 6.95 (d, 2H), 6.65 (d, 1H), 6.62 (d, 2H), 3.93 (s, H$_3$CO), 3.78 (s, 2H), 3.6 (sb, H$_2$N).

Stage 95.2: Rac-(6-methoxy-pyridin-3-yl)-(4-nitro-phenyl)methanol

A solution of n-butyl-lithium (1.6 m in hexane; 28 ml, 44.8 mmol) in ether (40 ml) is cooled down to −50° C. in a dried vessel under an atmosphere of $N_2$. Then a solution of 5-bromo-2-methoxy-pyridine (5.7 ml, 44 mmol) in ether (48 ml) is added dropwise, whereby a yellowish suspension is formed, and the reaction mixture stirred for 1 h at −50° C. In a second vessel, 4-nitro-benzaldehyde (6.04 g, 40 mmol) in THF (60 ml) is prepared at −60° C. Then the yellowish suspension of 5-lithio-2-methoxy-pyridine Is transferred via canula into the second vessel. After 30 min stirring at −40° C., a mixture of water (20 ml) and saturated NH$_4$Cl-solution (10 ml) is added. The resulting mixture is poured into water and AcOEt, the aqueous layer separated off and extracted twice with AcOEt. The organic phases are washed with water and brine, dried (Na$_2$SO$_4$) and concentrated. Column chromatography (SiO$_2$; hexane/AcOEt 3:1→2:1) yields the title compound: m.p.: 142° C.; $^1$H-NMR (CDCl$_3$): 8.20 (d, 2H), 8.15 (dd, 1H), 7.57 (d, 2H), 7.47 (dd, 1H), 6.73 (d, 1H), 5.91 (d, 1H), 3.93 (s, H$_3$CO), 2.50 (s, HO).

Example 96

N-(4-(6-Oxo-1,6-dihydro-pyridin-3-ylmethyl)-phenyl)-N'-(4-methyl-phenyl)-urea

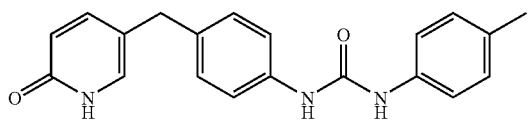

A suspension of N-(4-(6-methoxy-pyridin-3-ylmethyl)-phenyl)-N'-(4-methyl-phenyl)-urea (Example 95; 0.28 g, 0.81 mmol) and trimethylsilyl-jodide (0.6 ml) in chloroform (10 ml) is stirred for 16 h at 60° C. Then CH$_2$Cl$_2$ (4 ml), water (10 ml) and saturated NaHCO$_3$ solution (5 ml) is added and the suspension stirred vigorously. Filtration, washing with CH$_2$Cl$_2$ and water followed by column chromatography (SiO$_2$; AcOEt/MeOH 9:1→4:1 MeOH) yields the title compound: $^1$H-NMR (DMSO-d$_6$): 11.4 (s, HN), 8.52 (s, HN), 8.47 (s, HN), 7.33 (d, 2H), 7.29 (d, 2H), 7.25 (dd, 1H), 7.16 (s, 1H), 7.07 (d, 2H), 7.04 (d, 2H), 6.24 (d, 1H), 3.58 (s, 2H), 2.22 (s, 3H).

Example 97

1-[4-(6-Chloro-pyrimidin-4-yloxy)-phenyl]-3-p-tolyl-urea

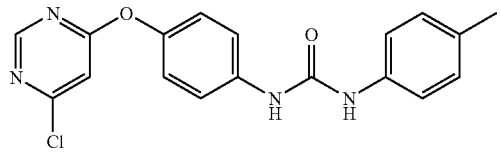

4-(6-Chloro-pyrimidin-4-yloxy)-phenylamine (331 mg, 1.50 mmol) is dissolved in DMF (3 mL) under an argon atmosphere at rt. Pyridine (133.2 µL, 1.65 mmol) is added dropwise followed by dropwise addition of p-tolylisocyanate (221 µL, 1.80 mmol). The reaction Is stirred for 30 min at rt. The solvent is removed in vacuo and the residual crude product is titurated with ethyl acetate/hexanes 9:1 to give the title compound as a white powder: m.p.=217-219° C.; C$_{18}$H$_{15}$N$_4$O$_2$Cl: M+=355.1; $^1$H-NMR (DMSO-d$_6$): 8.78 (s, 1H), 8.61 (s, 1H), 8.59 (s, 1H, HN), 7.52 (d, 2H), 7.37 (d, 2H), 7.17 (d, 2H), 7.05 (d, 2H), 2.21 (s, 3H).

Example 98

1-[4-(6-Chloro-pyrimidin-4-yloxy)-phenyl]-3-(3-trifluoromethyl-phenyl)-urea

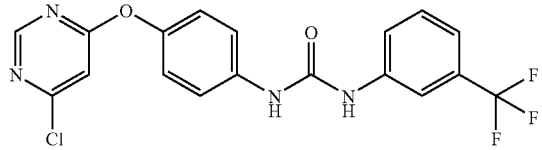

The title compound is prepared in analogy to Example 97 and purified by flash chromatography (SiO2, gradient hexanes/ethyl acetate 7:3 to 4:6) to yield a white powder m.p.=180-183° C; $^1$H-NMR (DMSO-d$_6$): 9.15 (s, 1H, HN), 8.90 (s, 1H, HN), 8.81 (s, 1H), 8.00 (s, 1H), 7.59-7.40 (m, 3H), 7.37-7.29 (m, 2H), 7.16 (d, 2H).

Example 99

1-[4-(6-Ethyl-pyrimidin-4-yloxy)phenyl]-3-p-tolyl-urea

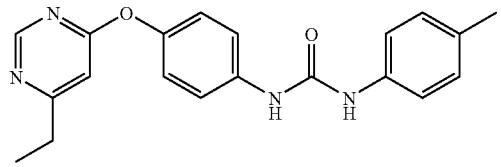

1-[4-(6-Chloro-pyrimidin-4-yloxy)-phenyl]-3-p-tolyl-urea (Example 97; 106 mg, 0.3 mmol) is dissolved in THF (10 mL) under an argon atmosphere and CuCN (215 mg, 2.4 mmol) is added. The mixture is then cooled to −78° C. and EtMgBr (1.8 ml of a 3 M solution in THF) is added via a canula. The reaction mixture is allowed to stir for 30 min at −78° C. and then warmed to rt resulting in a brown suspension. It Is stirred for additional 30 min at rt and then the solvent is removed in vacuo. The residual crude product is re-dissloved in CH$_2$Cl$_2$/MeOH 1:1 and purified by flash chromatography (SiO$_2$, gradient hexanes/ethyl acetate 1:1 to 3:7) to give the title compound which is further purified by preparative TLC (SiO$_2$, hexanes/AcOEt 3:7): m.p.=160-162° C.; C$_{20}$H$_{20}$N$_4$O$_2$: M$^+$=349.1; $^1$H-NMR (DMSO-d$_6$): 9.55 (s, 1H, HN), 9.45 (s, 1H, HN), 8.64 (s, 1H), 7.55 (d, 2H); 7.40 (d, 2H), 7.10-7.06 (m, 4H), 6.92 (s, 1H), 2.70 (q, 2H), 2.24 (s, 3H), 1.22 (t, 3H).

The following Examples 100 a)-g) of Table 10 are prepared in analogy to the procedure of Example 99:

TABLE 10

| Ex. | R1 | R2 | $^1$H-NMR (DMSO-d$_6$): | m.p. [° C.] | MS [M + 1]$^+$ |
|---|---|---|---|---|---|
| a) | iso-propyl | 4-Me | 8.99 (s, 1H, HN); 8.70 (s, 1H, HN), 8.65 (s, 1H), 7.50 (d, 2H), 7.34 (d, 2H), 7.19-6.99 (m, 4H), 6.95 (s, 1H), 3.12-2.95 (m, 1H), 2.24 (s, 3H), 1.22 (d, 6H). | 160-162 | 363.2 |
| b) | Et | 3-CF$_3$ | 9.26 (8, 1H, HN), 9.10 (s, 1H, HN), 8.63 (s, 1H), 8.02 (s, 1H), 7.58 (d, 1H), 7.55-7.50 (m, 3H), 7.31 (d, 1H), 7.13 (d, 2H), 6.95 (s, 1H), 2.72 (q, 2H), 1.21 (t, 3H). | 140-142 | 402.9 |
| c) | cyclo-hexyl | 4-Me | 8.75 (s, 1H, HN), 8.53 (s, 1H), 8.59 (s, 1H, HN), 7.48 (d, 2H), 7.33 (d, 2H), 7.19-7.00 (m, 4H), 6.91 (s, 1H), 2.69-2.63 (m, 1H), 1.93-1.75 (m, 2H), 1.75-1.70 (m, 1H), 1.52-1.45 (m, 2H), 1.36-1.32 (m, 1H). | 179-181 | 403.1 |
| d) | Me | 4-Me | 8.77 (s, 1H, HN), 8.63 (s, 1H, HN), 8.61 (s, 1H), 7.49 (d, 2H), 7.33 (d, 2H), 7.19-7.01 (m, 4H), 6.92 (s, 1H), 2.42 (s, 3H), 2.24 (s, 3H). | 180-182 | 335.1 |
| e) | cyclo-hexyl | 3-CF$_3$ | 9.24 (s, 1H, HN), 9.00 (s, 1H, HN), 8.64 (s, 1H), 8.02 (s, 1H), 7.61 (d, 1H), 7.55-7.41 (m, 3H), 7.30 (d, 1H), 6.92 (s, 1H), 2.65-6.61 (m, 1H), 1.85-1.81 (m, 2H), 1.49-1.44 (m, 2H), 1.36-1.32 (m, 1H). | 149-151 | 457.2 |
| f) | iso-propyl | 3-CF$_3$ | 9.24 (s, 1H, HN), 8.90 (s, 1H, HN), 8.65 (s, 1H), 8.02 (, s1H), 7.58 (d, 1H), 7.53-7.49 (m, 3H), 7.32 (d, 1H), 7.14 (d, 2H), 6.97 (s, 1H), 3.09-2.90 (m, 1H), 1.22 (d, 6H). | 166-168 | 417.0 |
| g) | Me | 3-CF$_3$ | 9.20 (s, 1H, HN), 8.61 (s, 1H), 8.02 (s, 1H), 7.58 (d, 1H), 7.53-7.49 (m, 3H), 7.32 (d, 1H), 7.13 (d, 2H), 6.94 (s, 1H), 2.43 (s, 3H). | 149-151 | 389.1 |

Example 101

1-[4-(6-Acetyl-pyrimidin-4-yloxy)-phenyl]3-3(-trifluoromethylphenyl)-urea

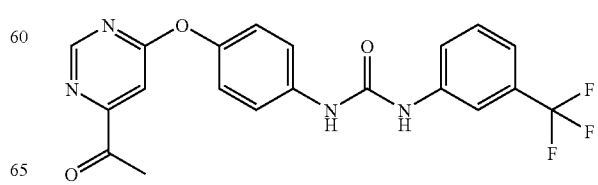

Stage 101.1: (4-Chloro-pyridin-2-yl)-pyrrolidin-1-yl-methanone

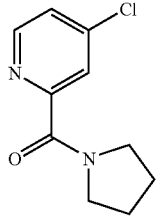

4-Chloro-pyridine-2-carboxylic acid methylester (200 mg, 1.17 mmol) and $MgCl_2$ (555 mg, 0.58 mmol) are suspended in THF (5 mL) at rt. The mixture is stirred for 5 min and then pyrrolidine (193 µL, 2.33 mmol) is added and the mixture stirred for an additional 15 min. It is worked up by addition of aqueous HCl solution (1M, 1.2 mL) and extraction with ethyl acetate. The combined organic extracts are washed with brine dried over $MgSO_4$. The volatiles are removed under reduced pressure to give the title compound as a yellow oil: $C_{10}H_{11}ClN_2O$: $M^+$=211.3; $^1$H-NMR (DMSO-$d_6$): 8.55 (d, 1H), 7.82 (s, 1H), 7.59 (d, 1H), 3.62-3.42 (m, 4H), 1.93-1.75 (m, 4H).

Stage 101.2: [4-(4-Amino-phenoxy)-pyridin-2-yl]pyrrolidin-1-yl-methanone

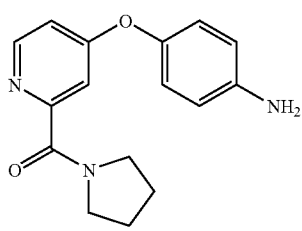

4-Aminophenol (122 mg, 1.12 mmol) is dissolved in DMF (3 ml) and treated with potassium-tert-butylate (131 mg, 1.16 mmol) at rt. The reaction mixture is stirred for 2 h to give a brown suspension. (4-Chloro-pyridin-2-yl)-pyrrolidin-1-yl-methanone (Stage 101.1; 236 mg, 1.12 mmol) and $K_2CO_3$ (82 mg, 0.59 mmol) are added. The reaction mixture is then stirred for 12 h at 80° C. It Is allowed to cool to rt again and the solvent is removed in vacuo. The residual brown oil is taken up in ethyl acetate and washed with brine. The organic layer is dried over $MgSO_4$, concentrated and the residual crude product is purified by flash chromatography ($SiO_2$; gradient $CH_2Cl_2$/MeOH 99:1 to 92:8) to give the title compound as a slightly brown solid: $C_{16}H_{17}N_3O_2$: $M^+$=284.2.

Stage 102.3: 1-{4-[2-Pyrrolidine-1-carbonyl)-pyridin-4-yloxy]-phenyl}-3-p-tolyl-urea

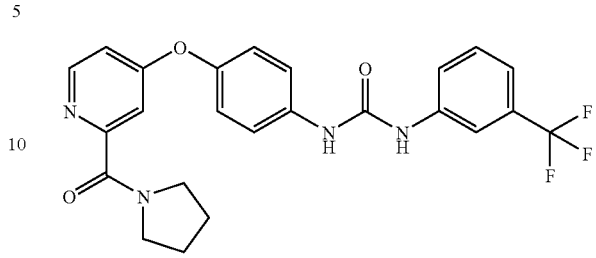

[4-(4-Amino-phenoxy)-pyridin-2-yl]pyrrolidin-1-yl-methanone (Stage 101.2; 118 mg, 0.42 mmol) is dissolved in DMF (3 mL) and cooled in an ice bath. Pyridine (37 µL, 0.46 mmol) and 3-(trifluoromethyl)phenyl-isocyanate (70 µL, 0.50 mmol) are added and the reaction mixture allowed to reach rt. After 30 min it is worked up by removal of all volatiles under reduced pressure and purification of the residual crude product by flash chromatography ($SiO_2$; gradient $CH_2Cl_2$/MeOH 99:1 to 95:5) to give the title compound as a slightly brown solid: $C_{24}H_{21}F_3N_4O_3$: $M^+$=471.5; $^1$H-NMR (DMSO-$d_6$): 9.09 (s, 1H, HN), 8.92 (s, 1H, HN), 8.42 (d, 1H), 7.99 (s, 1H), 7.61-7.42 (m, 4H), 7.29 (d, 1H), 7.17 (d, 2H), 7.03 (d, 1H), 7.01 (dd, 1H), 3.62-3.58 (m, 2H), 3.49-3.39 (m, 2H), 1.87-1.72 (m, 4H).

Stage 101.4: 1-[4-(6-Acetyl-pyrimidin-4-yloxy)-phenyl]-3-(-trifluoromethyl-phenyl)urea

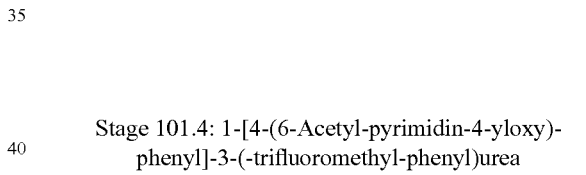

1-{4-[2-Pyrrolidine-1-carbonyl)-pyridin-4-yloxy]-phenyl}-3-p-tolyl-urea (Stage 101.3; 23 mg, 0.05 mmol) is dissolved in THF (200 µL) and cooled to −78° C. Methyllithium (98 µL, 0.10 mmol, of a 1.6 M solution in diethyl ether) is added dropwise. The reaction mixture is stirred for 30 min at −78° C. and then allowed to reach rt and stirred for additional 2 h. It is worked up by removal of all volatiles in vacuo, the residue is taken up in ethyl acetate and washed with brine and afterwards purified by preparative TLC ($SiO_2$, hexanes/ethyl acetate 7:3) to give the title compound as a white solid: m.p.=149-151° C.; $C_{21}H_{16}F_3N_3O_3$: $M^+$=416.1; $^1$H-NMR (DMSO-$d_6$): 9.36 (s, 1H), 8.99 (s, 1H), 8.60 (d, 1H), 8.02 (s, 1H), 7.58 (d, 3H), 7.54-7.51 (m, 1H), 7.35-7.30 (m, 1H), 7.28-7.25 (m, 1H), 7.15 (d, 2H), 2.16 (s, 3H).

Example 102

1-[4-(2-Cyano-pyridin-4-yloxy)-phenyl]-3-D-tolyl-urea

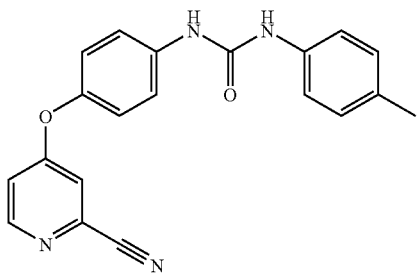

p-Tolylisocyanate (66.4 µL, 0.521 mmol, 1.1 equiv) is added to a solution of 4-(4-amino-phenoxy)-pyridine-2-carbonitrile (100 mg, 0.473 mmol) in THF abs. (1.45 mL), under an argon atmosphere. The resulting mixture is stirred at rt for 2 h, diluted with 3 mL of a hexane/CH$_2$Cl$_2$ (2/1) solution and filtered through a glass sintered funnel. The residue is washed with the above-mentioned solvents mixture and dried in vacuo to afford the title compound as a beige solid: ES-MS: 345.0 [M+H]$^+$; single peak at t$_R$=9.04 min (System 2); R$_f$=0.19 (CH$_2$Cl$_2$/Et$_2$O, 90/10).

4-(4-Amino-phenoxy)-pyridine-2-carbonitrile:

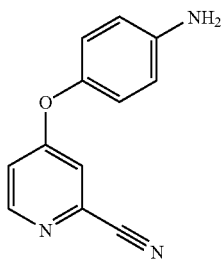

4-Amino-phenol (2.54 g, 22.8 mmol, 1.1 equiv) is added in one portion to a suspension of NaH (60% free-flowing powder moistened with oil, 1.25 g, 31.2 mmol, 1.5 equiv) in dioxane abs. (30 mL), under an argon atmosphere. When hydrogen evolution subsides, 4-nitro-pyridine N-oxide (3 g, 20.8 mmol) is added in one portion. The resulting dark mixture is heated to 100° C. (oil bath temperature) for 22 h and then allowed to cool to rt. Me$_3$SiCN (3.5 mL, 27.0 mmol, 1.3 equiv) is added. After 5 min, the reaction mixture is cooled with a 10° C. water bath and N,N-dimethylcarbamoyl chloride (2.5 mL, 27.0 mmol, 1.3 equiv) Is added dropwise. The reaction mixture is allowed to warm to rt. When the reaction becomes exothermic, the water bath (10° C.) is applied for a few minutes. The reaction mixture is allowed to warm to rt, stirred for 1 h, quenched by addition of MeOH (30 mL), and concentrated in vacuo. After addition of CH$_2$Cl$_2$ to the residue, the resulting suspension is filtered through a glass sintered funnel (washing with copious amount of the same solvent). The filtrate is concentrated in vacuo and the residue is purified by silica gel (200 g) column chromatography (CH$_2$Cl$_2$/Et$_2$O, 90/10) to afford the title compound as a brownish solid: ES-MS: 211.9 [M+H]$^+$; single peak at t$_R$=4.86 min (System 2); R$_f$=0.44 (CH$_2$Cl$_2$/Et$_2$O, 80/20).

Example 103

1-[4-(2-Cyano-pyridin-4-yloxy)-phenyl]-3-(4-ethyl-pheny)-urea

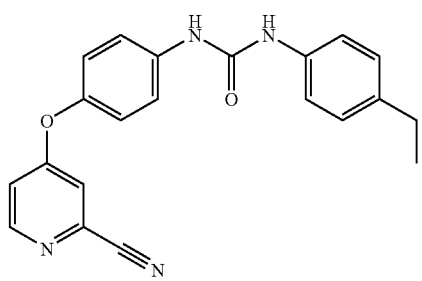

The title compound is prepared as described in Example 102 but using 4ethyl-phenyl-isocyanate. After a 2.5 h stirring, the reaction mixture is concentrated in vacuo and the residue is purified by silica gel (18 g) column chromatography (CH$_2$Cl$_2$/Et$_2$O, 90/10) to afford the title compound as a beige solid: ES-MS: 359.0 [M+H]$^+$; single peak at t$_R$=9.41 min (System 2); R$_f$=0.22 (CH$_2$Cl$_2$/Et$_2$O, 90/10).

Example 104

1-[4-(2-Cyano-pyridin-4-yloxy)-phenyl]-3-(3-trifluoromethyl-pheny)urea

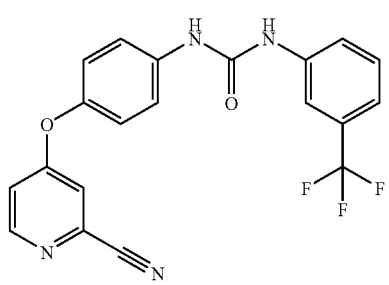

The title compound is prepared as described in Example 102 but using α,α,α-trifluoro-m-tolyl-isocyanate. After a 3 h stirring, the reaction mixture is concentrated in vacuo and the residue is purified by silica gel (18.5 g) column chromatography (CH$_2$Cl$_2$, then CH$_2$Cl$_2$/MeOH, 99/1) to afford the title compound as a light yellow solid: ES-MS: 398.9 [M+H]$^+$; single peak at t$_R$=9.54 min (System 2); R$_f$=0.067 (CH$_2$Cl$_2$/MeOH, 99/1).

Example 105

1-[4-(2-Chloro-pyridin-4-yloxy)-phenyl]-3-p-tolyl-urea

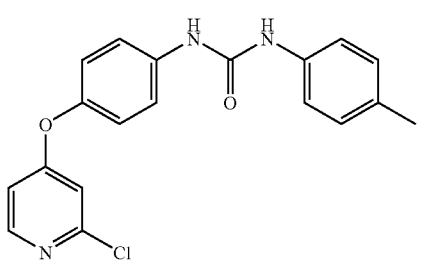

The title compound is prepared as described in Example 102 but using 4-(2-chloro-pyridin-4-yloxy)-phenylamine and stirring the reaction mixture for 3 h. The title compound is obtained as a white solid: ES-MS: 354.0 [M+H]$^+$; single peak at $t_R$=9.53 min (System 2); $R_f$=0.19 (CH$_2$Cl$_2$/Et$_2$O, 90/10).

4-(2-Chloro-pyridin-4-yloxy)-phenylamine

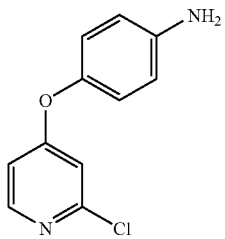

4-Amino-phenol (1.05g, 9.40 mmol, 1.1 equiv) is added in one portion to a suspension of NaH (60% free-flowing powder moistened with oil, 0.513 g, 12.8 mmol, 1.5 equiv) in dioxane abs. (6.5 mL), under an argon atmosphere. When hydrogen evolution subsides, a solution of 2-chloro-4-nitropyridine (1.35 g, 8.54 mmol) in dioxane (6 mL) is added. The resulting dark mixture is heated to 100° C. (oil bath temperature) for 70.5 h, allowed to cool to rt, quenched by addition of MeOH and partially concentrated in vacuo. The oily residue is dissolved in CH$_2$Cl$_2$/MeOH (80/20) and filtered through a glass sintered funnel containing silica gel (18 g), eluting with CH$_2$Cl$_2$/MeOH (90/10). The filtrate is partially concentrated in vacuo, diluted with CH$_2$Cl$_2$/MeOH (90/10) and purified by silica gel (70 g) column chromatography (CH$_2$Cl$_2$/Et$_2$O, 90/10, then 85/15). A second column chromatography purification affords the title compound as a yellow solid: ES-MS: 221.1 [M+H]$^+$; single peak at $t_R$=6.56 min (System 2); $R_f$=0.27 (CH$_2$Cl$_2$/Et$_2$O, 80/20).

2-Chloro-4-nitropyridine is prepared according to a literature procedure [M. A. Walters, J. J. Shay, Tetrahedron Letters, 36 (42), 7575-7578 (1995)] and used as a crude material.

Example 106

1-[4-(2-Chloro-pyridin-4-yloxy)-phenyl]-3-(4-ethyl-phenyl)-urea

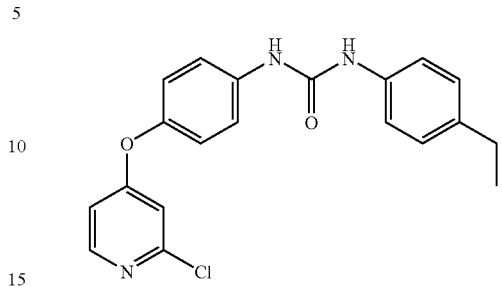

The title compound is prepared as described in Example 102 but using 4-(2-chloro-pyridin-4-yloxy)-phenylamine (Example 105) and 4-ethyl-phenyl-isocyanate. The reaction mixture is stirred for 4 h. The title compound is obtained as a beige solid: ES-MS: 368.0 [M+H]$^+$; single peak at $t_R$=9.85 min (System 2); $R_f$=0.36 (CH$_2$Cl$_2$/Et$_2$O, 90/10).

Example 107

1-[4-(2-Chloro-pyridin-4-yloxy)-phenyl]-3-(3-trifluoromethyl-pheny)-urea

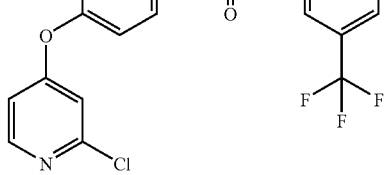

The title compound is prepared as described in Example 102 but using 4-(2-chloro-pyridin-4-yloxy)-phenylamine (Example 105) and α,α,α-trifluoro-m-tolyl-isocyanate. The reaction mixture is stirred for 4 h. The title compound is obtained as a beige solid: ES-MS: 407.9 [M+H]$^+$; single peak at $t_R$=9.99 min (System 2); $R_f$=0.30 (CH$_2$Cl$_2$/Et$_2$O, 90/10).

Example 108

1-p-Tolyl-3-[4-(2-trifluoromethyl-pyridin-4-yloxy)-phenyl]-urea

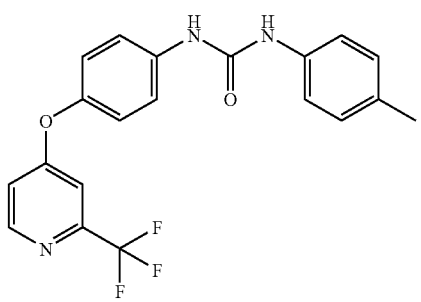

The title compound is prepared as described in Example 102 but using 4-(2-trifluoromethyl-pyridin-4-yloxy)-phenylamine and stirring the reaction mixture for 4 h. The title compound is obtained as a white solid: ES-MS: 388.0 [M+H]+; single peak at $t_R$=9.00 min (System 2); $R_f$=0.28 (CH$_2$Cl$_2$/Et$_2$O, 90/10).

4-(2-Trifluoromethyl-pyridin-4-yloxy)-phenylamine

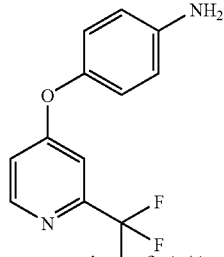

A suspension of 4-(4-nitro-phenoxy)-2-trifluoromethyl-pyridine (1.16 g, 4.08 mmol) and Raney Nickel (0.4 9, in EtOH) in MeOH (70 mL) is stirred at rt and under a hydrogen atmosphere for 7 h. Additional Raney Nickel (tip of spatula) is then added and the reaction mixture is stirred for 17 h. The mixture is filtered through a pad of celite and the filter cake is washed with copious amount of MeOH. After removal of the solvents in vacuo, the residue is purified by silica gel (50 g) column chromatography (CH$_2$Cl$_2$/Et$_2$O, 95/5) to afford the title compound as a white solid: ES-MS: 255.0 [M+H]+; single peak at $t_R$=5.97 min (System 2); $R_f$=0.40 (CH$_2$Cl$_2$/Et$_2$O, 90/10).

4-(4-Nitro-phenoxy)-2-trifluoromethyl-pyridine

A mixture of 2-trifluoromethyl-pyridin-4-ol (0.675 g, 4.14 mmol), 1-fluoro-4-nitro-benzene (0.54 mL, 4.97 mmol, 1.2 equiv), and NaOH (0.203 g,4.97 mmol, 1.2 equiv) in DMF abs. is heated to 100° C. (oil bath temperature) for 21.5 h, under an argon atmosphere. The reaction mixture is allowed to cool to rt, filtered through a glass sintered funnel and concentrated in vacuo. The residual yellow solid is purified by silica gel (100 g) column chromatography (CH$_2$Cl$_2$/hexane, 70/30) to afford the title compound as a white solid: ES-MS: 285.0 [M+H]+; single peak at $t_R$=8.71 min (System 2); $R_f$=0.25 (CH$_2$Cl$_2$/hexane, 70/30).

2-Trifluoromethyl-pyridin-4-ol is prepared according to a reported three-step procedure [V. I. Tyvorskii, D. N. Bobrov; Chemistry of Heterocyclic Compounds, 33 (8), 995-996 (1997)].

Example 109

1-(4-Ethyl-phenyl)-3-[4-(2-trifluoromethyl-pyridin-4-yloxy)-phenyl]-urea

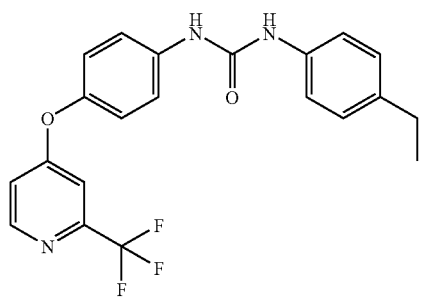

The title compound is prepared as described in Example 102 but using 4-(2-trifluoromethyl-pyridin-4-yloxy)-phenylamine (Example 108) and 4-ethyl-phenyl-isocyanate. The reaction mixture is stirred for 4.5 h. The title compound is obtained as a white solid: ES-MS: 401.9 [M+H]+; single peak at $t_R$=9.33 min (System 2); $R_f$=0.37 (CH$_2$Cl$_2$/Et$_2$O, 90/10).

Example 110

1-(3-Trifluoromethyl-phenyl)-3-[4-(2-trifluoromethyl-pyridin-4-yloxy)-phenyl]-urea

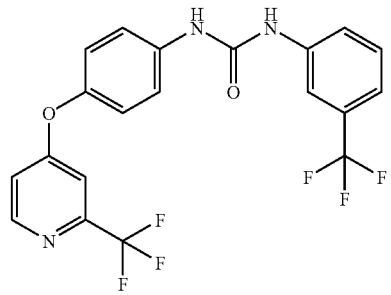

The title compound is prepared as described in Example 102 but using 4-(2-trifluoromethyl-pyridin-4-yloxy)-phenylamine (Example 108) and α,α,α-trifluoro-m-tolyl-isocyanate. The reaction mixture is stirred for 4 h. The title compound is obtained as a white solid: ES-MS: 441.8 [M+H]+; single peak at $t_R$=9.44 min (System 2); $R_f$=0.38 (CH$_2$Cl$_2$/Et$_2$O, 90/10).

Example 111

1-[4-(6-Fluoro-pyrimidin-4-yloxy)-phenyl]-3-p-tolyl-urea

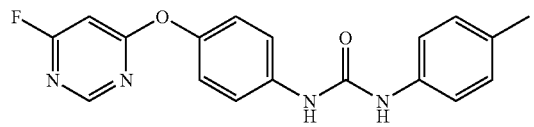

The title compound is prepared as described in Example 102 but using 4-(6-fluoro-pyrimidin-4-yloxy)-phenylamine and stirring the reaction mixture for 4 h. The title compound is obtained as a white solid: ES-MS: 339.0 [M+H]+; single peak at $t_R$=8.20 min (System 2); $R_f$=0.18 (CH$_2$Cl$_2$/Et$_2$O, 90/10).

4-(6-Fluoro-pyrimidin-4-yloxy)-phenylamine

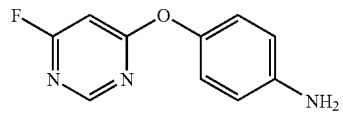

4-Amino-phenol (0.135 g, 1.21 mmol) is added in one portion to a suspension of NaH (60% free-flowing powder moistened with oil, 58.2 mg, 1.45 mmol, 1.2 equiv) in dioxane abs. (1.4 mL), under an argon atmosphere. When hydrogen evolution subsides, a solution of 4,6-difluoro-pyrimidine (0.141 g, 1.21 mmol) in dioxane (0.4 mL) Is added. The resulting dark mixture is stirred for 1.5 h at rt, quenched by addition of MeOH (2 mL) and concentrated in vacuo. After addition of CH₂Cl₂, the resulting suspension is filtered and concentrated in vacuo. The residue is purified by silica gel column chromatography (CH₂Cl₂/Et₂O, 90/10, then 85/15) to afford the title compound as a white solid: ES-MS: 204.0 [M+H]⁺; single peak at $t_R$=4.96 min (System 2); $R_f$=0.30 (CH₂Cl₂/Et₂O, 85/15).

4,6-Difluoro-pyrimidine

A mixture of 4,6-dichloro-pyrimidine (5 g, 33.6 mmol), potassium fluoride (6.3 g, 107 mmol, 3.2 equiv), and tetrabutylammonium bromide (0.134 g, 0.403 mmol, 0.012 equiv) in sulfolane (22.4 mL) is heated to 180-190° C. (oil bath temperature) for 3.5 h. Distillation of the reaction mixture provides the title compound as a colorless liquid: ¹H-NMR (300 MHz, CDCl₃): 8.62 (s, 1H), 6.65-6.55 (m, 1H); single peak at $t_R$=3.5 min (System 2).

Example 112

1-(4-Ethyl-phenyl)-3-[4-(6-Fluoro-pyrimidin-4-yloxy)-phenyl]-urea

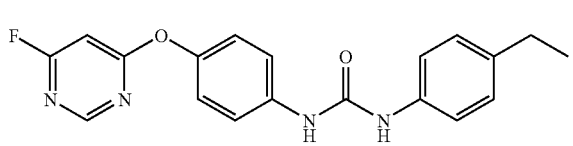

The title compound is prepared as described in Example 102 but using 4-(6-fluoro-pyrimidin-4-yloxy)-phenylamine (Example 111) and 4-ethyl-phenyl-isocyanate. The reaction mixture is stirred for 4 h. The title compound is obtained as a white solid: ES-MS: 353.0 [M+H]⁺; single peak at $t_R$=8.61 min (System 2); $R_f$=0.14 (CH₂Cl₂/Et₂O, 90/10).

Example 113

1-[4-(6-Fluoro-pyrimidin-4-yloxy)-phenyl]-3-(3-trifluoromethyl-phenyl)-urea

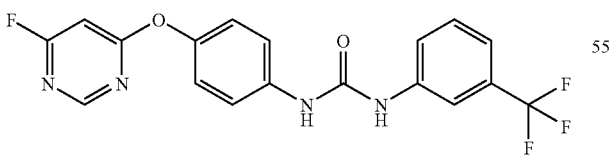

The title compound is prepared as described in Example 102 but using 4-(6-fluoro-pyrimidin-4-yloxy)-phenylamine (Example 111) and α,α,α-trifluoro-m-tolyl-isocyanate. The reaction mixture is stirred for 4 h. The title compound is obtained as a white solid: ESMS: 392.9 [M+H]⁺; single peak at $t_R$=8.90 min (System 2); $R_f$=0.14 (CH₂Cl₂/Et₂O, 90/10).

Example 114

1-p-Tolyl-3-[4-(6-trifluoromethyl-pyrimidin-4-yloxy)-phenyl]-urea

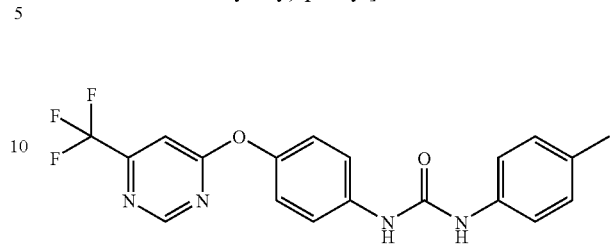

The title compound is prepared as described In Example 102 but using 4(6-trifluoromethyl-pyrimidin-4-yloxy)phenylamine and stirring the reaction mixture for 4 h. The product is recovered by vacuum filtration through a glass sintered funnel, washed with THF and dried In vacuo to afford the title compound as a white solid: ES-MS: 389.0 [M+H]⁺; single peak at $t_R$=9.38 min (System 2).

4-(6-Trifluoromethyl-pyrimidin-4-yloxy)-phenylamine

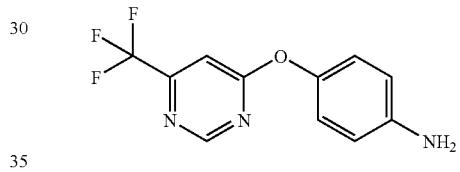

4-Amino-phenol (1.2 g, 10.9 mmol) is added in one portion to a suspension of NaH (60% free-flowing powder moistened with oil, 0.48 g, 12.0 mmol, 1.1 equiv) in dioxane abs. (18 mL), under an argon atmosphere. When hydrogen evolution subsides, a solution of 4-chloro-6-trifluoromethyl-pyrimidine (2.0 g, 10.9 mmol) in dioxane (2.0 mL) is added. The resulting dark mixture is heated to 60-65° C. (oil bath temperature) for 40 min, allowed to cool to rt, quenched by addition of MeOH and concentrated in vacuo. The residue is purified twice by silica gel (200 g) column chromatography (CH₂Cl₂/MeOH, 99/1, then 98/2) to afford the title compound as a white solid: ES-MS: 256.0 [M+H]⁺; single peak at $t_R$=6.35 min (System 2); $R_f$=0.33 (CH₂Cl₂/MeOH, 98/2).

4-Chloro-6-trifluoromethyl-pyrimidine is prepared according to a literature procedure (Kanne, David B.; Prisbylla, Michael P.: U.S. Pat. No. 5,714,438 A, 1998).

Example 115

1-(4-Ethyl-phenyl)-3-[4-(6-trifluoromethyl-pyrimidin-4-yloxy)-phenyl]-urea

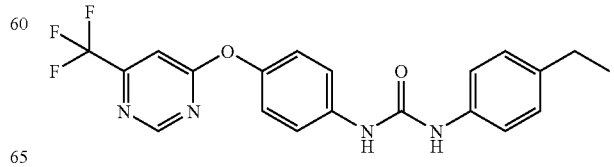

The title compound is prepared as described in Example 102 but using 4-(6-trifluoromethyl-pyrimidin-4-yloxy)-phenylamine (Example 114) and 4-ethyl-phenyl-isocyanate. The reaction mixture is stirred for 2.5 h. The title compound is obtained as a white solid: ES-MS: 403.0 [M+H]$^+$; single peak at $t_R$=9.72 min (System 2).

Example 116

1-(3-Trifluoromethyl-phenyl)-3-[4-(6-trifluoromethyl-pyrimidin-4-yloxy)-phenyl]-urea

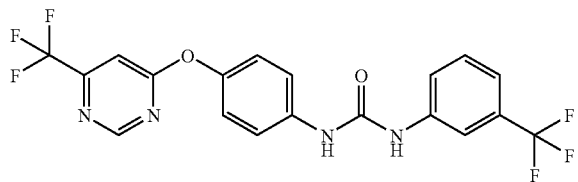

The title compound is prepared as described in Example 102 but using 4-(6-trifluoromethyl-pyrimidin-4-yloxy)-phenylamine (Example 114) and α,α,α-trifluoro-m-tolyl-isocyanate. The reaction mixture is stirred for 2.5 h. The title compound is obtained as a white solid: ES-MS: 442.9 [M+H]$^+$; single peak at $t_R$=9.83 min (System 2).

Example 117

1-[4-(6-Chloro-pyrimidin-4-ylmethyl)-phenyl]-3-(4-ethyl-phenyl)-urea

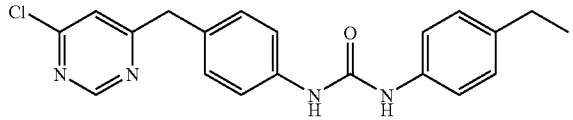

A 4 N solution of HCl in dioxane (1.2 mL, 4.96 mmol, 30 equiv) is added to a solution of [4-(6-chloro-pyrimidin-4-ylmethyl)-phenyl]-carbamic acid tert-butyl ester (50 mg, 0.156 mmol) in CH$_2$Cl$_2$ (0.67 mL), under an argon atmosphere. The resulting white suspension is stirred at rt for 4 h and concentrated in vacuo to afford 50.9 mg of crude 4-(6-chloro-pyrimidin-4-ylmethyl)-phenylamine as a white solid. DIEA (80 µL, 0.454 mmol, 2 equiv) is added to a suspension of crude 4-(6-chloro-pyrimidin-4-ylmethyl)-phenylamine (50 mg, 0.227 mmol) in THF (0.4 mL), under an argon atmosphere. 4-Ethyl-phenyl-isocyanate (40 µL, 0.250 mmol, 1.1 equiv) is then added. The resulting yellow solution is stirred at rt for 2 h and concentrated in vacuo. The residue is purified by silica gel (20 g) column chromatography (CH$_2$Cl$_2$/MeOH, 98/2). A second purification affords the title compound as a white solid: ES-MS: 367.0 [M+H]$^+$; single peak at $t_R$=8.94 min (System 2); R$_f$=0.32 (CH$_2$Cl$_2$/MeOH, 95/5).

[4-(6Chloro-pyrimidin-4-ylmethyl)-phenyl]-carbamic acid tert-butyl ester

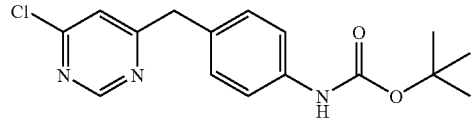

Triethylamine hydrochloride (0.93 g 6.60 mmol), N,N-dimethylaniline (0.8 mL, 6.60 mmol), and POCl$_3$ (3.7 mL, 39.6 mmol, 6 equiv) are added sequentially to a solution of [4-(6-hydroxy-pyrimidin-4-ylmethyl)-phenyl]-carbamic acid tert-butyl ester (2.0 g, 6.60 mmol) in CH$_3$CN (16.5 mL), at rt and under an argon atmosphere. The resulting yellow solution is stirred at rt for 1 h and then added to a stirred mixture of H$_2$O/ice (1/1, v/v; 80 mL, total volume). The product is extracted in CH$_2$Cl$_2$ (2×200 mL). The organic phase is washed with an aqueous saturated solution of Na$_2$CO$_3$ (70 mL), dried (Na$_2$SO$_4$), filtered and concentrated in vacuo. The residue is purified by silica gel (170 g) column chromatography (CH$_2$Cl$_2$/Et$_2$O, 95/5, then 90/10) to afford the title compound: ES-MS: 320.1 [M+H]$^+$; single peak at $t_R$=8.76 min (System 2); R$_f$=0.13 (CH$_2$Cl$_2$/Et$_2$O, 95/5).

[4-(6-Hydroxy-pyrimidin-4-ylmethyl)-phenyl]-carbamic acid tert-butyl ester

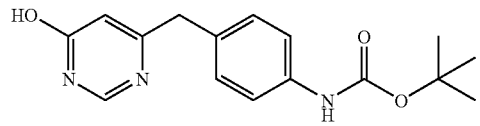

Raney Nickel (6.0 g, in EtOH) is added to a suspension of [4-(6-hydroxy-2-mercapto-pyrimidin-4-ylmethyl)-phenyl]-carbamic acid tert-butyl ester (2.0 g, 5.99 mmol) in MeOH (58 mL), under an argon atmosphere. The resulting mixture is heated to reflux for 2 h (oil bath is pre-heated to 90-95° C.), allowed to cool to rt, filtered through a pad of celite and concentrated in vacuo. The residue is purified by silica gel (160 g) column chromatography (CH$_2$Cl$_2$/MeOH, 95/5, then 90/10) to provide the title compound as a white solid: ES-MS: 302.1 [M+H]$^+$; single peak at $t_R$=6.54 min (System 2); R$_f$=0.34 (CH$_2$Cl$_2$/MeOH, 90/10).

[4-(6-Hydroxy-2-mercapto-pyrimidin-4-ylmethyl)-phenyl]-carbamic acid tert-butyl ester

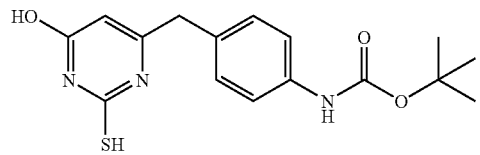

A mixture of 4-(4-tert-butoxycarbonylamino-phenyl)-3-oxo-butyric acid ethyl ester (10.5 g, 32.7 mmol), thiourea (2.5 g, 32.7 mmol) and potassium tert-butoxide (8.3 g, 71.9 mmol, 2.2 equiv) in butan-1-ol (30 mL) is heated to 50° C. (oil bath temperature) for 23 h, under an argon atmosphere. The resulting yellow suspension is diluted with butan-1-ol (30 mL), neutralized by addition on 1N HCl (65 mL), diluted with H$_2$O (20 mL) and extracted with CHCl$_3$ (2×100 mL). The organic phase is dried (Na$_2$SO$_4$), filtered (washing the filter cake with copious amount of CHCl$_3$) and concentrated in vacuo. After silica gel (300 g) column chromatography purification (CHCl$_3$/MeOH, 90/10), the product is treated with CH$_2$Cl$_2$ (200 mL). The resulting suspension is allowed to stir at rt for 20 min, then diluted with hexane (200 mL) and filtered through a glass sintered funnel. The white residue is washed with a mixture (120 mL) of CH$_2$Cl$_2$/hexane (11, v/v) and dried in vacuo to afford the title compound: ES-MS: 334.0 [M+H]$^+$; single peak at t$_R$=7.04 min (System 2); R$_f$=0.34 (CHCl$_3$/MeOH, 90/10).

4-(4-tert-Butoxycarbonylamino-phenyl)-3-oxo-butyric acid ethyl ester

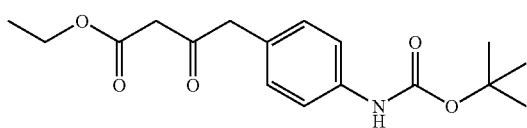

A suspension of 4-(4-nitro-phenyl)-3-oxo-butyric acid ethyl ester (8.3 g, 33.0 mmol), di-tert-butyl dicarbonate (14.4 g, 66.0 mmol, 2 equiv), and palladium (10%) on carbon (0.825 g) in EtOH (200 mL) and THF (50 mL) is stirred for 1 h at rt, under a hydrogen atmosphere. The reaction mixture is filtered through a pad of celite and the filtrate is concentrated in vacuo. The residue is purified by silica gel (300 g) column chromatography (CH$_2$Cl$_2$/AcOEt, 90/10) to provide the title compound as a white solid: ES-MS: 320.1 [M+H]$^+$; single peak at t$_R$=8.76 min (System 2); R$_f$=0.54 (CH$_2$Cl$_2$/AcOEt, 90/10).

4-(4-Nitro-phenyl)-3-oxo-butyric acid ethyl ester can be prepared according to reported protocols [M. Ohkubo, A Kuno, H. Sakai, Y. Sugiyama, H. Takasugi; Chem. Pharm. Bull. 42 (6), 1279-1285 (1994)].

Example 118

1-[4-(6-Chloro-pyrimidin-4-ylmethyl)-phenyl]-3-(3-trifluoromethyl-phenyl)-urea

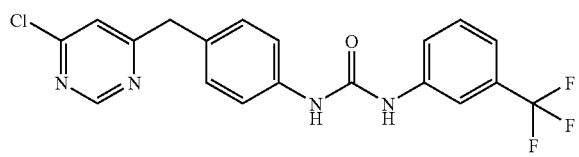

The title compound is prepared as described in Example 117 but using α,α,α-trifluoro-m-tolyl-isocyanate and stirring the reaction mixture for 3.5 h. After chromatography purification the product is repeatedly washed with small portions of CH$_2$Cl$_2$ and dried in vacuo to afford the title compound as a white solid: ES-MS: 406.9 [M+H]$^+$; single peak at t$_R$=8.84 min (System 2); R$_f$=0.29 (CH$_2$Cl$_2$/MeOH, 95/5).

Example 119

1-[4-(6-Methylamino-pyrimidin-4-ylmethyl)-phenyl]-3-p-tolyl-urea

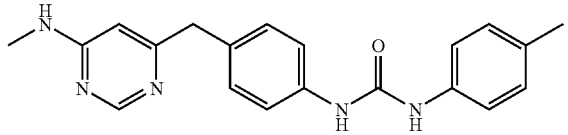

The title compound is prepared as described in Example 102 but using [6-(4-amino-benzyl)-pyrimidin-4-yl]-methyl-amine and stirring the reaction mixture for 6 h. The title compound is obtained as a white solid: ES-MS: 348.0 [M+H]$^+$; single peak at t$_R$=6.67 min (System 2).

[6-(4-Amino-benzyl)-pyrimidin-4-yl]-methyl-amine

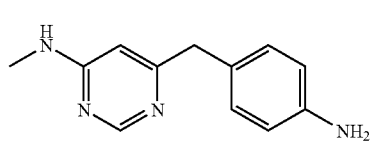

A 4 N solution of HCl in dioxane (11.7 mL, 46.9 mmol, 30 equiv) is added to a solution of [4-(6-chloro-pyrimidin-4-ylmethyl)-phenyl]-carbamic acid tert-butyl ester (Example 117) (0.50 g, 1.56 mmol) in CH$_2$Cl$_2$ (6.7 mL), under an argon atmosphere. The resulting white suspension is stirred at rt for 6.5 h. Additional 4 N HCl solution (1.1 mL, 4.6 mmol, 3.0 equiv) is added. The reaction mixture is allowed to stir for 0.5 h and concentrated in vacuo to afford 0.467 g of crude 4-(6-chloro-pyrimidin-4-ylmethyl)-phenylamine as a white solid. An 8 M solution of methylamine in EtOH (5.1 mL, 40.0 mmol, 30 equiv) Is added to a solution of crude 4-(6-chloro-pyrimidin-4-ylmethyl)phenylamine (0.300 g, 1.37 mmol) in EtOH (2.7 mL), under an argon atmosphere. The mixture Is heated to 50° C. (oil bath temperature) for 5 h, allowed to cool to rt and concentrated in vacuo. The residue is purified by silica gel (48 g) column chromatography (CH$_2$Cl$_2$/MeOH, 85/15) to afford the title compound as a light yellow oil: ES-MS: 215.0 [M+H]$^+$; single peak at t$_R$=3.03 min (System 2); R$_f$=0.49 (CH$_2$Cl$_2$/MeOH, 85/15).

Example 120

1-(4-Ethyl-phenyl)-3-[4-(6-methylamino-pyrimidin-4-ylmethyl)-phenyl]-urea

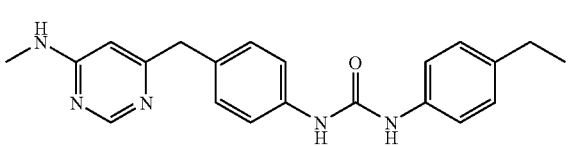

The title compound Is prepared as described in Example 102 but using [6-(4-amino-benzyl)-pyrimidin-4-yl]-methylamine (Example 119) and 4-ethyl-phenyl-isocyanate. The reaction mixture is stirred for 6 h. The title compound is obtained as a white solid: ES-MS: 362.0 [M+H]+; single peak at $t_R$=7.14 min (System 2).

Example 121

1-[4-(6-methylamino-pyrimidin-4-ylmethyl)-phenyl]-3-(3-trifluoromethyl-phenyl)-urea

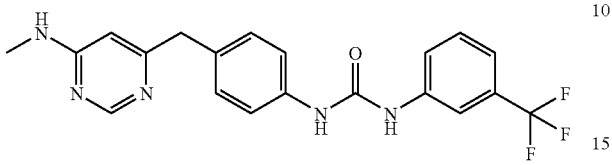

The title compound is prepared as described in Example 102 but using [6-(4-amino-benzyl)-pyrimidin-4-yl]-methylamine (Example 119) and α,α,α-trifluoro-m-tolyl-isocyanate. The reaction mixture is stirred for 3 h. The title compound is obtained as a white solid: ES-MS: 402.0 [M+H]+; single peak at $t_R$=7.34 min (System 2); $R_f$=0.32 (CH$_2$Cl$_2$/MeOH, 90/10).

Example 122

1-{4-[2-(1H-Tetrazol-5-yl)-pyridin-4-yloxy]-phenyl}-3-(3-trifluoromethyl-phenyl)-urea

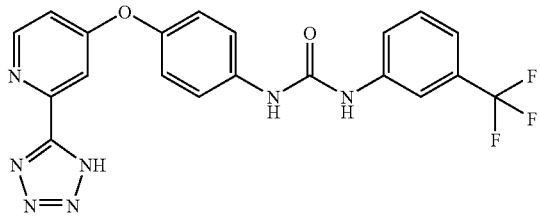

The title compound is prepared as described in Example 102 but using 4-[2-(1H-tetrazol-5-yl)-pyridin-4-yloxy]-phenylamine and α,α,α-trifluoro-m-tolyl-isocyanate. The reaction mixture is stirred for 4 h. The crude product Is washed with a solution of CH$_2$Cl$_2$/MeOH (95/5) and dried In vacuo to afford the title compound as a beige solid: ES-MS: 441.9 [M+H]+; single peak at $t_R$=7.93 min (System 2); $R_f$=0.36 (CH$_2$Cl$_2$/MeOH, 80/20).

4-[2-(1H-tetrazol-5-yl)-pyridin-4-yloxy]-phenylamine

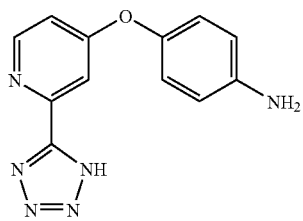

A mixture of 4-(4-amino-phenoxy)-pyridine-2-carbonitrile (Example 102) (2.6 g, 12.3 mmol), sodium azide (6.6 g, 102 mmol, 8.3 equiv), and ammonium chloride in DMF abs. (180 mL) is heated to 70° C. for 7.5 h, under an argon atmosphere. The reaction mixture is allowed to cool to rt, filtered through a glass sintered funnel and concentrated in vacuo. The residue is purified by silica gel (390 g) column chromatography (CH$_2$Cl$_2$/MeOH, 80/20) to afford the title compound as a beige solid: ES-MS: 255.0 [M+H]+; single peak at $t_R$=3.98 min (System 2); $R_f$=0.20 (CH$_2$Cl$_2$/MeOH, 75/25).

Example 123

1-(4-Ethyl-phenyl)-3-{4-[2-(1H-tetrazol-5-yl)-pyridin-4-yloxy]-phenyl}-urea

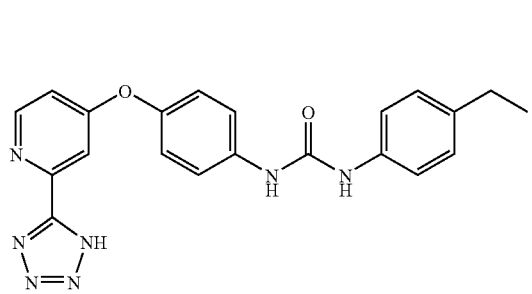

The title compound is prepared as described In Example 102 but using 4-[2-(1H-tetrazol-5-yl)-pyridin-4-yloxy]-phenylamine (Example 122) and 4-ethyl-phenyl-isocyanate. The reaction mixture is stirred for 4 h. The crude product is washed with a solution of CH$_2$Cl$_2$/MeOH (95/5) and dried in vacuo to afford the title compound as a beige solid: ES-MS: 402.0 [M+H]+; single peak at $t_R$=7.73 min (System 2); $R_f$=0.20 (CH$_2$Cl$_2$/MeOH, 80/20).

Example 124

1-{4-[2-(1-Methyl-1H-tetrazol-5-yl)-pyridin-4-yloxy]-phenyl}-3-(3-trifluoromethyl-phenyl)-urea

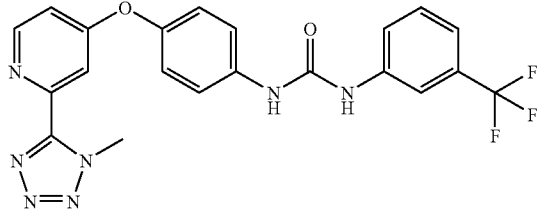

Iodomethane (0.21 mL, 3.40 mmol, 1.5 equiv) is added to a cold (0° C.) mixture of 1-{4-[2-(1H-tetrazol-5yl)-pyridin-4-yloxy]-phenyl}-3-(3-trifluoromethyl-phenyl)-urea (Example 122) (1.0 g, 2.27 mmol) and potassium carbonate (0.94 g, 6.80 mmol, 3.0 equiv) in DMF abs. (5.8 mL), under an argon atmosphere. The reaction mixture is stirred at 0° C. for 2 h, allowed to warm to rt and stirred for additional 20 h. The resulting brown suspension is filtered and concentrated in vacuo. MeOH (10 mL) and DMF (0.5 mL) are added to the residue and the resulting suspension is filtered. The white solid is washed with MeOH and dried in vacuo to afford the title compound as a white solid. The filtrate is concentrated in vacuo and the residue is purified by MPLC (CH$_3$CN/H$_2$O/TFA) to afford additional title compound as a beige solid: ES-MS: 455.9 [M+H]+; single peak at $t_R$=9.15 min (System 2).

Example 125

1-{4-[2-(2-Methyl-2H-tetrazol-5-yl)-pyridin-4-yloxy]-phenyl}-3-(3-trifluoromethyl-phenyl)-urea

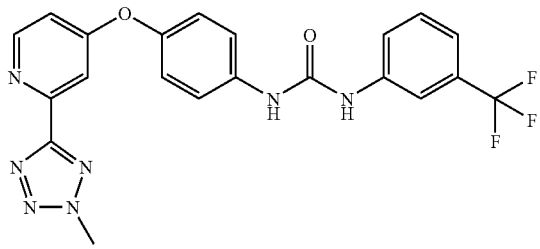

The MPLC purification of the residue obtained from the concentrated filtrate of Example 124 affords the title compound as a beige solid: ES-MS: 455.9 [M+H]$^+$; single peak at $t_R$=8.24 min (System 2).

Example 126

1-(4-Ethyl-phenyl)-3-{4-[2-(1-methyl-1H-tetrazol-5-yl)-pyridin-4-yloxy]-phenyl}-urea

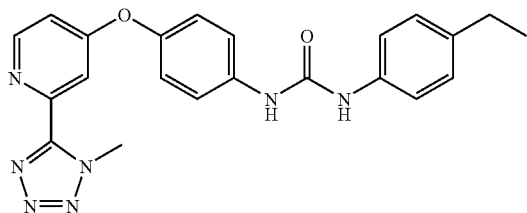

The title compound is prepared as described in Example 124 but using 1-(4-ethyl-phenyl)-3-{4-[2-(1H-tetrazol-5-yl)-pyridin-4-yloxy]-phenyl}-urea (Example 123). The crude product is purified by MPLC (CH$_3$CN/H$_2$O/TFA) to afford the title compound as a white solid: ES-MS: 416.0 [M+H]$^+$; single peak at $t_R$=8.97 min (System 2).

Example 127

1-(4-Ethyl-phenyl)-3-{4-[2-(2-methyl-2H-tetrazol-5-yl)-pyridin-4-yloxy]-phenyl}-urea

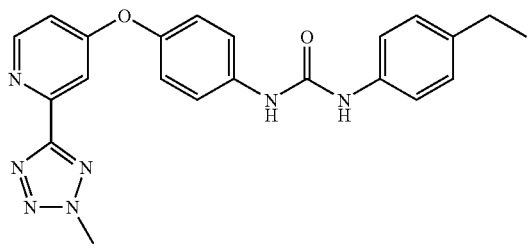

The MPLC purification of the crude product of Example 126 affords the title compound as a white solid: ES-MS: 416.0 [M+H]$^+$; single peak at $t_R$=8.06 min (System 2).

Example 128

N-(4-(4-Chloropyrimidin-6-yl-oxy)-phenyl)-N'-(3-trifluoromethyl-4-(piperidin-1-ylmethyl)-phenyl)-urea

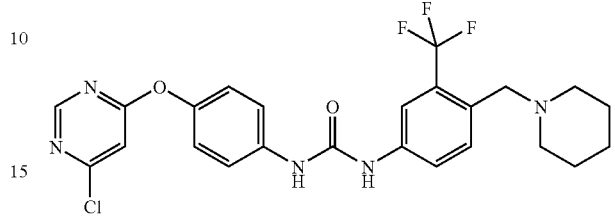

The title compound is prepared from 3-trifluormethyl-4-(piperidin-1-ylmethyl)-phenylamine (Stage 128.1) and 4-(6-chloro-pyrimidin-4-yl-oxy)-aniline (Stage 21.1) analogously to Example 85: MS: [M+1]$^+$=505; $^1$H-NMR (DMSO-d$_6$): 8.99 (s, 1H), 8.84 (s, 1H), 8.62 (s, 1H), 7.93 (s, 1H), 7.62 (d, 1H), 7.55 (m, 1H), 7.51 (d, 2H), 7.32 (s, 1H), 7.14 (d, 2H), 3.47 (s, 2H), 2.31 (sb, 4H), 1.49 (m, 4H), 1.39 (m, 2H).

The starting materials are prepared as follows:

Stage 128.1: 3-Trifluormethyl-4-(piperidin-1-ylmethyl)-phenylamine

To a solution of 2,2,2-trifluoro-N-(4-piperidin-1-ylmethyl-3-trifluoromethyl-phenyl)-acetamide (Stage 128.2; 1.427 g, 4.03 mmol) in boiling methanol (42 ml), 20 ml of a 1 N solution of K$_2$CO$_3$ in water are added dropwise. After 2 h stirring, the reaction mixture is cooled to rt, concentrated in vacuo and the residue re-dissolved in AcOEt and water. The aqueous layer is separated off and extracted twice with AcOEt. The organic phases are washed with water and brine, dried (Na$_2$SO$_4$) and concentrated to yield the title compound: MS: [M+1]$^+$=259; $^1$H-NMR (DMSO-d$_6$): 7.28 (d, 1H), 6.82 (d, 1H), 7.73 (dd, 1H), 5.40 (s, H$_2$N), 3.32 (s, 2H), 2.27 (sb, 4H), 1.46 (m, 4H), 1.39 (m, 2H).

Stage 128.2: 2,2,2-Trifluoro-N-(4-piperidin-1-ylmethyl-3-trifluoromethyl-phenyl)-acetamide To a solution of N-(4-bromomethyl-3-trifluoromethyl-phenyl)-2,2,2-trifluoro-acetamide (Stage 128.3; 1.465 g, 4.19 mmol) in acetonitril (35 ml) under N$_2$-atmosphere, piperidine (1.25 ml, 12.7 mmol) is added. After 30 min at rt the reaction mixture is diluted with water and partially concentrated in vacuo. The aqueous residue Is acidified to pH 5 by addition of 0.1 N HCl and extracted 3× with AcOEt. The organic layers are washed with water and brine, dried (Na$_2$SO$_4$) and concentrated. Column chromatography (SiO$_2$; hexane/AcOEt 3:2) gives the title compound: MS: [M+1]$^+$=355; $^1$H-NMR (DMSO-d$_6$): 11.48 (s, HN), 8.02 (s, 1H), 7.91 (dd, 1H), 7.77 (d, 1H), 3.52 (s, 2H), 2.32 (sb, 4H), 1.50 (m, 4H), 1.40 (m, 2H).

Stage 128.3: 2 N-(4-Bromomethyl-3-trifluoromethyl-phenyl)-2,2,2-trifluoro-acetamide Under N$_2$-atmosphere, a suspension of N-(4-methyl-3-trifluoromethyl-phenyl)2,2,2-trifluoro-acetamide (Stage 128.4; 5.21 g, 19.2 mmol), N-bromosuccinimide (15 g, 84 mmol) and azo-iso-butyronitrile (740 mg, 4.5 mmol) in 430 ml of CCl₄ is heated to 85° C. for 15 h. The hot mixture is filtered, the solid washed with CCl₄ and discarded. The filtrate is concentrated, the residue re-dissolved in CH₂Cl₂ (0.7 L) and washed twice with 0.5 M solution of Na₂S₂O₃ and brine. The inorganic phases are extracted with 2 portions of CH₂Cl₂, the organic phases dried (Na₂SO₄) and concentrated. Column chromatography (SiO₂; hexane/CH₂Cl₂ 1:1) yields the title compound: ¹H-NMR (DMSO-d₆): 11.59 (s, HN), 8.06 (d, 1H), 7.97 (dd, 1H), 7.76 (d, 1H), 4.77 (s, 2H).

Stage 128.4: N-(4-Methyl-3-trifluoromethyl-phenyl)-2.2.2-trifluoro-acetamide

To an ice-cooled solution of 5-amino-2-methylbenzotrifluoride (3.77 g, 21.5 mmol) and pyridine (17.3 ml, 215 mmol) in 50 ml of CH₂Cl₂ under N₂-atmosphere, trifluoroacetic acid anhydride (3.3 ml, 23 mmol) is added dropwise. After warming up to rt, the mixture is diluted with CH₂Cl₂ and washed 3× with a 10% solution of citric acid in water. The aqueous layers are extracted twice with CH₂Cl₂, the organic phases dried (Na₂SO₄) and concentrated. Sublimation in a Kugelrohr oven (0.1 mbar; oven at 150° C.) yields the title compound: m.p.: 72-74° C.

Example 129

N-(4-(4-Chloropyrimidin-6-yl-oxy)-phenyl)-N'-(3-methoxy-4-(4-methyl-piperazin-1-ylmethyl)-phenyl)-urea

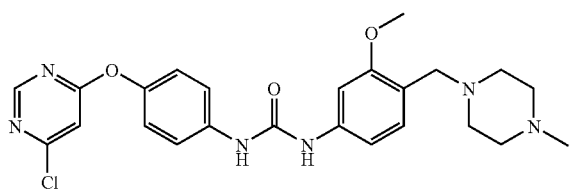

A solution of triphosgene (580 mg, 1.96 mmol) in CH₂Cl₂ (60 ml) under N₂-atmosphere is cooled by an ice bath. 4-(6-Chloro-pyrimidin-4-yl-oxy)-aniline (Stage 21.1; 1.30 g, 5.86 mmol) and NEt₃ (0.82 ml, 5.86 mmol) in CH₂Cl₂ (30 ml) is added dropwise and the suspension stirred for 15 min. Then a solution of 3-methoxy-4-(4-methyl-piperazin-1-ylmethyl)-phenylamine (Stage 129.1; 1.15 g, 4.89 mmol) and NEt₃ (0.68 ml, 4.89 mmol) in CH₂Cl₂ (30 ml) is added dropwise and the mixture stirred for 30 min in the ice bath, whereby a solution is formed. After stirring for 4.5 h at rt, the reaction mixture is added to a saturated NaHCO₃ solution and extracted 3× with CH₂Cl₂. The organic phases are washed with water and brine, dried (Na₂SO₄) and concentrated. Medium pressure reverse phase liquid chromatography (Nucleosil C18; water-acetonitrile gradient+TFA) yields after neutralization the title compound: MS: [M+1]⁺=483; ¹H-NMR (DMSO-d₆): 8.74 & 8.69 (2s, 2HN), 8.63 (s, 1H), 7.50 (d, 2H), 7.31 (s, 1H), 7.24 (s, 1H), 7.13 (m, 3H), 6.88 (d, 1H), 3.75 (s, H₃C), 3.37 (s, 2H), 2.5-2.2 (m, 8H), 2.15 (s, H₃C).

The starting materials are prepared as described in Example 87:

Stage 129.1: 3-Methoxy-4-(4-methyl-piperazin-1-ylmethyl)-phenylamine

Hydrogenation of 3-methoxy-4(4-methyl-piperazin-1-ylmethyl)-nitrobenzene (Raney Nickel, THF) yields the title compound: MS: [M+1]⁺=236; ¹H-NMR (DMSO-d₆): 6.80 (d, 1H), 6.15 (s, 1H), 6.06 (d, 1H), 4.95 (s, 2H), 3.63 (s, H₃C), 3.22 (s, 2H), 2.27 (sb, 8H), 2.10 )s, (H₃C).

Stage 129.2: 3-Methoxy-4(4-methyl-piperazin-1-ylmethyl)-nitrobenzene

Reduction of (4-methyl-piperazin-1-yl)-(4-nitro-2-methoxy-phenyl)methanone (DIBAH, THF, −75° C.→40° C.) yields the title compound: MS: [M+1]⁺=266; Anal.: CHN.

Stage 129.3: (4-Methyl-piperazin-1-yl)-(4-nitro-2-methoxy-phenyl)methanone

Prepared from 2-methoxy-4-nitrobenzoic acid and 1-methyl-piperazine (TPTU, CH₂Cl₂/CH₃CN, Et₃N): MS: [M+1]⁺=280; Anal.: CHN.

Example 130

N-(4-(4-Azidopyrimidin-6-yl-oxy)-phenyl)-N'-(3-trifluoromethyl-4-(piperidin-1-ylmethyl)-phenyl)-urea

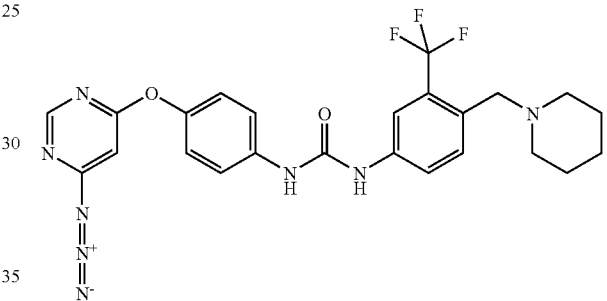

A mixture of N-(4-(4-chloropyrimidin-6-yl-oxy)-phenyl)-N'-(3-trifluoromethyl-4-(piperidin-1-ylmethyl)-phenyl)-urea (Example 128; 350 mg, 0.69 mmol) and NaN₃ (91 mg, 1.4 mmol) in 7 ml of DMF is stirred for 2 h at 70° C. The resulting mixture is concentrated in vacuo, the residue diluted with AcOEt and water, the aqueous layer separated off and extracted twice with AcOEt. The organic phases are washed with water and brine, dried (Na₂SO₄) and concentrated to yield the title compound: MS: [M+1]⁺=513.

Example 131

N-(4-(4-Aminopyrimidin-6-yl-oxy)-phenyl)-N'-(3-trifluoromethyl-4-(piperidin-1-ylmethyl)-phenyl)-urea

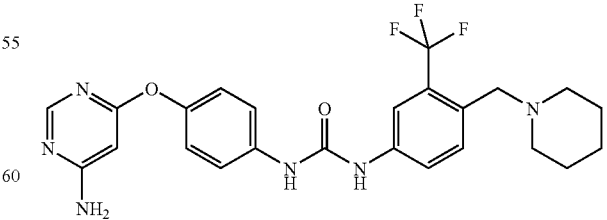

Hydrogenation of N-(4-(4-azidopyrimidin-6-yl-oxy)-phenyl)-N'-(3-trifluoromethyl-4-(piperidin-1-ylmethyl)-phenyl)-urea (Example 130; 213 mg, 0.41 mmol) in the presence of 10% Pd/C (40 mg) in 10 ml of THF during 2 h at rt, filtration and concentration of the filtrate affords the title compound: MS: [M+1]$^+$=487; $^1$H-NMR (DMSO-d$_6$): 9.09 & 8.92 (2s, 2HN), 8.03 & 7.93 (2s, 2H), 7.69 & 7.65 (2m, 2H), 7.47 & 7.03 (2d, 2×2H), 6.79 (s, 2H), 5.6 (s, 1H), 3.46 (s, 2H), 2.31 (m, 4H), 1.49 (m, 4H), 1.40 (m, 2H).

Example 132

N-(4-(4-Chloropyrimidin-6-yl-oxy)-phenyl)-N'-(3-trifluoromethyl-5-piperidin-1-ylmethyl)-phenyl)-urea

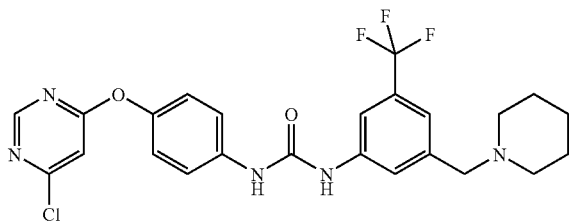

The title compound is prepared analogously to Example 129: MS: [M+1]$^+$=506; $^1$H-NMR (CD$_3$OD): 8.53 (s, 1H), 7.83 (s, 1H), 7.58 (s, 1H), 7.54 (d, 2H), 7.30 (s, 1H), 7.14 (d, 2H), 7.09 (s, 1H), 3.57 (s, 2H), 2.48 (m, 4H), 1.64 (m, 4H), 1.50 (m, 2H).

The starting materials are prepared as described in Example 87:

Stage 132.1: 3-Trifluoromethyl-5-(piperidin-1-ylmethyl)-phenylamine

Hydrogenation of 3-trifluoromethyl-5-(piperidin-1-ylmethyl)-nitrobenzene [Raney Nickel/Mo (BK 113W Degussa), THF] yields the title compound: MS: [M+1]$^+$=259; $^1$H-NMR (DMSO-d$_6$): 6.70, 6.64 & 6.62 (3d, 3H), 5.59 (s, H$_2$N), 3.26 (s, 2H), 2.25 (m, 4H), 1.44 (m, 4H), 1.33 (m, 2H).

Stage 132.2: 3-Trifluoromethyl-5-(piperidin-1-ylmethyl)-nitrobenzene

Reduction of (piperidin-1-yl)-(3-nitro-5-trifluormethyl-phenyl)-methanone (DIBAH, THF, −25° C.) yields the title compound: MS: [M]$^-$=288.

Stage 132.3: (Piperidin-1-yl)-(3-nitro-5-trifluormethyl-phenyl)-methanone

Prepared from 3-nitro-5-trifluormethyl-benzoic acid and piperidine (TPTU, CH$_2$Cl$_2$/CH$_3$CN, Et$_3$N): MS: [M+1]$^+$=303; TLC R$_f$=0.27 (hexane/AcOEt 7:3).

Example 133

N-(4-(4-Chloropyrimidin-6-yl-oxy)-phenyl)-N'-(3-trifluoromethyl-4-(4-ethyl-piperazin-1-ylmethyl)-phenyl)-urea

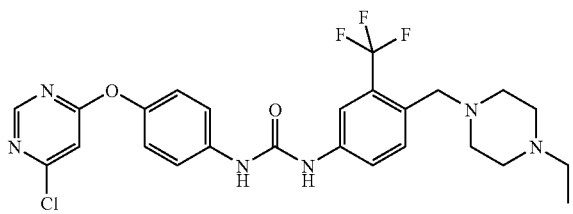

The title compound is prepared analogously to Example 128: MS: [M+1]$^+$=535; $^1$H-NMR (DMSO-d$_6$): 9.00 & 8.84 (2s, 2HN), 8.69 (s, 1H), 7.92 (s, 1H), 7.56 (m, 2H), 7.48 (d, 2H), 7.29 (s, 1H), 7.12 (d, 2H), 3.48 (s, 2H), 2.35 (m, 10H), 0.94 (t, H$_3$C).

The starting materials are prepared as described in Example 128:

Stage 133.1: 3-Trifluormethyl-4-(4-ethylpiperazin-1-ylmethyl)-phenylamine

Hydrolysis of 2,2,2-trifluoro-N-[4-(4-ethylpiperazin-1-ylmethyl)-3-trifluoromethyl-phenyl]-acetamide gives the title compound: MS: [M+1]$^+$=288; $^1$H-NMR (DMSO-d$_6$): 7.22 (d, 1H), 6.79 (d, 1H), 7.69 (dd, 1H), 5.38 (s, H$_2$N), 3.32 (s, 2H), 2.29 (sb, 8H), 2.25 (q, 2H), 0.92 (t, H$_3$C).

Stage 133.2: 2,2,2-Trifluoro-N-(4-(4-ethylpiperazin-1-ylmethyl)-3-trifluoromethyl-phenyl)-acetamide Reaction of N-(4-bromomethyl-3-trifluoromethyl-phenyl)-2,2,2-trifluoro-acetamide (Stage 128.3) with N-ethylpiperazine gives the title compound: MS: [M+1]$^+$=384; $^1$H-NMR (CDCl$_3$): 8.0 (sb, HN), 7.8 (m, 3H), 3.63 (s, 2H), 2.51 (sb, 8H), 2.43 (q, 2H), 1.09 (t, H$_3$C).

Example 134

N-(4-(6-Chloropyrimidin-4-yl-oxy)-phenyl)-N'-{5-trifluoromethyl-3-[(4-ethylpiperazin-1-ylmethyl)]-phenyl}-urea

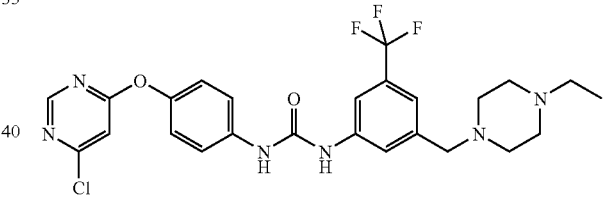

To an ice-cold solution of 4-(6-chloro-pyrimidin-4-yl-oxy)-aniline (Stage 21.1; 0.926 g, 4.18 mmol) and NEt$_3$ (0.64 ml, 4.6 mmol) in CH$_2$Cl$_2$ (30 ml) under N$_2$-atmosphere, phosgene (2.32 ml of a 20% solution in toluene, 4.39 mmol) in CH$_2$Cl$_2$ (10 ml) is added dropwise. The resulting suspension is stirred for 1 h, then filtered under exclusion of moisture and the filtrate concentrated in vacuo. THF (20 ml) and NEt$_3$ (0.64 ml, 4.6 mmol) is then added to the residue. After cooling in an ice bath, 3-(4-ethyl-piperazin-1-ylmethyl)-5-trifluoromethyl-phenylamine (1.00 g, 3.48 mmol) dissolved in THF (20 ml) is added dropwise and the reaction mixture stirred for 30 min at 0° C. and 2 h at rt. Then it is diluted with water and AcOEt, the aqueous layer separated off and extracted twice with AcOEt. The organic phases are washed with water and brine, dried (Na$_2$SO$_4$) and concentrated. Column chromatography (SiO$_2$; AcOEt/EtOH/Et$_3$N 90:10:2→80:20:2) and crystallization from ether affords the title compound: m.p.: 168-169° C.; MS: [M+1]$^+$=535; $^1$H-NMR (CD$_3$OD): 8.54 (s, 1H), 7.82 (s, 1H), 7.60 (s, 1H), 7.54 (d, 2H), 7.30 (s, 1H), 7.14 (d, 2H), 7.09 (s, 1H), 3.60 (s, 2H), 2.57 (m, 8H), 2.47 (q, 2H), 1.12 (t, 3H).

The starting materials are prepared as follows:

Stage 134.1: 3-(4-Ethyl-piperazin-1-ylmethyl)-5-trifluoromethyl-phenylamine

To a solution of (3-amino-5-trifluoromethyl-phenyl)-(4-ethyl-piperazin-1-yl)-methanone (14.6 g, 48.5 mmol) in THF (120 ml) under $N_2$-atmosphere, a 1 M solution of $BH_3$.THF (145.5 ml) is added dropwise (exothermic). The mixture is stirred for 14 h at rt and then 5 h at 65° C. After cooling to rt, HCl conc./$H_2O$ 1:1 (250 ml) Is added and the mixture stirred for 15 h. The suspension is filtered, the filtrate extracted 3 times with AcOEt. The organic phases are washed twice with 1 N HCl and then discarded. The combined acidic phases are made basic by addition of saturated $Na_2CO_3$ solution and extracted 3 times with AcOEt. The organic layers are washed twice with water and brine, dried ($Na_2SO_4$) and concentrated. Column chromatography ($SiO_2$; AcOEt/EtOH/$NH_3$ 95:5:1→90:10:1) followed by extraction between 3 portions of AcOEt, 3 portions of water and finally brine, drying ($Na_2SO_4$) and concentration yields the title compound as an oil: MS: $[M+1]^+$=288; $^1$H-NMR ($CDCl_3$): 6.94 (s, 1H), 6.82 (s, 1H), 6.78 (s, 1H), 3.82 (sb, $H_2N$), 3.46 (s, 2H), 2.51 (m, 8H), 2.44 (q, 2H), 1.10 (t, 3H).

Stage 134.2: (3-Amino-5-trifluoromethyl-phenyl)-(4-ethyl-piperazin-1-yl)-methanone Hydrogenation of (3-nitro-5-trifluoromethyl-phenyl)-(4-ethyl-piperazin-1-yl)-methanone (16.5 g, 50 mmol) in ethanol (300 ml) In the presence of Raney-Nickel (3 g), filtration through celite, concentration of the filtrate and crystallization from hexane gives the title compound: m.p.: 104° C.; MS: $[M+1]^+$=302; $^1$H-NMR ($CDCl_3$): 6.96 (s, 1H), 6.91 (s, 1H), 6.83 (s, 1H), 3.99 (sb, $H_2N$), 3.80 (m, 2H), 3.44 (m, 2H), 2.53 (m, 2H), 2.46 (q, 2H), 2.40 (m, 2H), 1.12 (t, 3H).

Stage 134.3: (3-Nitro-5-trifluoromethyl-phenyl)-(4-ethyl-piperazin-1-yl)-methanone In an ice bath under $N_2$-atmosphere, 3-nitro-5-trifluoromethyl-benzoic acid (Lancaster; 11.8 g, 50 mmol), $CH_2Cl_2$ (150 ml), a few drops of DMF and oxalylchloride (7.0 ml, 81 mmol) are mixed and then stirred for 3 h at rt. The resulting solution is concentrated in vacuo. The residue is dissolved in $CH_2Cl_2$ (170 ml) and added dropwise to an ice cooled solution of N-ethyl-piperazine (12.7 ml, 0.10 mol) in $CH_2Cl_2$ (100 ml). After stirring for 1 h at rt, the mixture is washed with a diluted solution of $Na_2CO_3$, 2 portions of water and finally brine. The aqueous layers are re-extracted twice with AcOEt, the combined organic phases dried ($Na_2SO_4$) and concentrated giving the title compound as an oil: MS: $[M+1]^+$=332; $^1$H-NMR ($CDCl_3$): 8.53 (s, 1H), 8.44 (s, 1H), 8.00 (s, 1H), 3.84 (m, 2H), 3.43 (m, 2H), 2.57 (m, 2H), 2.48 (q, 2H), 2.44 (m, 2H), 1.12 (t, 3H).

Example 135

N-(4-(6-Chloropyrimidin-4-yl-oxy)-phenyl)-N'-[5-trifluoromethyl-3-(dimethylamino-methyl)-phenyl]-urea

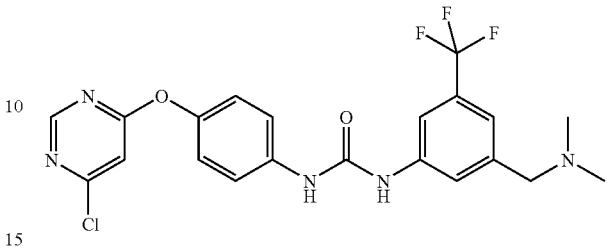

A solution of 4-chloro-6-(4-isocyanato-phenoxy)-pyrimidine (Stage 135.1; 594 mg; 2.40 mmol) in THF (2 ml) is mixed under a $N_2$-atmosphere with a solution of 3-dimethylaminomethyl-5-trifluoromethyl-phenylamine (Stage 135.2; 524 mg; 2.40 mmol) in ether (10 ml). Stirring at rt affords the title compound: MS: $[M+1]^+$=466.

The starting materials are prepared as follows:

Stage 135.1: 4-Chloro-6-(4-isocyanato-phenoxy)-pyrimidine

Apparatus: 2 litre 3-neck-roundbottle flask, dropping funnel, short Vigreux column and condenser. A phosgene solution (20% in toluene, 118 ml; 223 mmol) diluted with toluene (800 ml) under $N_2$-atmosphere is cooled to approximately −20° C. Then a solution of 4-(6-chloro-pyrimidin-4-yl-oxy)-aniline (Stage 21.1; 18.52 g, 83.6 mmol) in $CH_2Cl_2$ (400 ml) is added dropwise. The resulting suspension is heated to distil off approximately 400 ml of solvent. Distillation Is continued (boiling point: 110° C.), while a mixture of phosgene solution (20% in toluene, 59 ml) and toluene (500 ml) is added dropwise, followed by toluene (250 ml). The resulting clear solution (a 250 ml) in the reaction vessel is cooled to rt, filtered and the filtrate concentrated in vacuo. Distillation of the resulting waxy crude product on the Kugelrohr apparatus (0.2 mbar, 200° C.) gives the title compound as a solid: m.p.: 103° C.; MS: $[M+1]^+$=302; $^1$H-NMR ($CDCl_3$): 8.57 (s, 1H), 7.17 (d, 2H), 7.10 (d, 2H), 6.95 (s, 1H).

Stage 135.2: 3-Dimethylaminomethyl-5-trifluoromethyl-phenylamine

3-Amino-N,N-dimethyl-5-trifluoromethyl-benzamide (2.0 g; 8.6 mmol) dissolved in THF (20 ml) is reduced with a 1 M solution of $BH_3$.THF (26 ml) as described in Stage 134.1, yielding the title compound: MS: $[M+1]^+$=219.

Stage 135.3: 3-Amino-N,N-dimethyl-5-trifluoromethyl-benzamide

Hydrogenation of (3-nitro-N,N-dimethyl-5-trifluoromethyl-benzamide (12.6 g, 48 mmol) in THF (250 ml) in the presence of Raney-Nickel (3 g), filtration through celite, concentration of the filtrate and crystallization from hexane gives the title compound: m.p.: 154° C.; MS: $[M+1]^+$=233; $^1$H-NMR ($CD_3OD$): 6.97 (s, 1H), 6.84 (s, 2H), 3.09 (s, 3H), 2.99 (s, 3H).

Stage 135.4: (3-Nitro-N,N-dimethyl-5-trifluoromethyl-benzamide

In an ice bath under $N_2$-atmosphere, 3-nitro-5-trifluoromethyl-benzoic acid (Lancaster; 11.8 g, 50 mmol), $CH_2Cl_2$ (150 ml), 3 drops of DMF and oxalylchloride ( 7.0 ml, 81 mmol) are mixed and then stirred for 2.5 h at rt. The resulting solution is concentrated in vacuo. The residue is dissolved in CH$_2$Cl$_2$ (170 ml) and added dropwise to an ice cooled solution of dimethylamine hydrochloride (4.5 g, 55 mmol) and NEt$_3$ (21 ml; 0.15 mol) in CH$_2$Cl$_2$ (100 ml). After stirring for 15 h at rt, the mixture is worked up as described in Stage 134.3, giving the title compound as an oil: MS: [M+1]$^+$=263;

$^1$H-NMR (CDCl$_3$): 8.53 (s, 1H), 8.47 (s, 1H), 8.03 (s, 1H), 3.18 (s, 3H), 3.04 (s, 3H).

Example 136

The following compounds of Table 11 can be prepared analogously to the described procedures:

TABLE 11

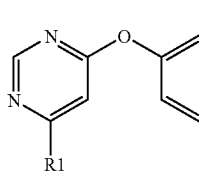

| | | R1 | HPLC t$_R$ [min] System 3 | m.p. [° C.] | MS [M + 1]$^+$ | Anal. |
|---|---|---|---|---|---|---|
| a) | | N=N$^+$=N$^-$ | | | 490 | CHN H$_2$O |
| b) | | NH$_2$ | | | 464 | CHN |
| c) | | N=N$^+$=N$^-$ | 11.3 | | 461 | |
| d) | | NH$_2$ | 7.6 | | 435 | |
| e) | | N=N$^+$=N$^-$ | 11.4 | | 542 | |
| f) | | NH$_2$ | 8.0 | | 516 | |
| g) | | NH—CH$_3$ | 8.4 | | 530 | |
| h) | | N=N$^+$=N$^-$ | | | 475 | |
| i) | | NH$_2$ | 8.1 | | 449 | |
| j) | | N=N$^+$=N$^-$ | 9.4 | | 490 | |
| k) | | NH$_2$ | 6.4 | | 464 | |
| l) | | NH—CH$_3$ | 6.8 | | 478 | |

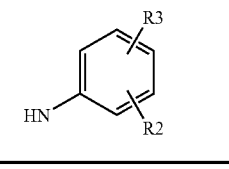

TABLE 11-continued

| | R3/R2 aryl | R1 | HPLC $t_R$ [min] System 3 | m.p. [° C.] | MS $[M + 1]^+$ | Anal. |
|---|---|---|---|---|---|---|
| m) | 3-CF₃-5-(piperidin-1-ylmethyl)phenyl | N=N⁺=N⁻ | 12.7 | | 513 | |
| n) | 3-CF₃-5-(piperidin-1-ylmethyl)phenyl | NH₂ | 9.2 | | 487 | CHNF H₂O |
| o) | 3-CF₃-5-(piperidin-1-ylmethyl)phenyl | NH—CH₃ | 9.6 | | 501 | |
| p) | 3-CF₃-5-((4-ethylpiperazin-1-yl)methyl)phenyl | N=N⁺=N⁻ | 10.9 | | 542 | |
| q) | 3-CF₃-5-((4-ethylpiperazin-1-yl)methyl)phenyl | NH₂ | 8.4 | | 516 | |
| r) | 3-CF₃-5-((4-ethylpiperazin-1-yl)methyl)phenyl | NH—CH₃ | 8.6 | | 530 | |
| s) | 3-CF₃-4-(piperidin-1-ylmethyl)phenyl | NH—CH₃ | 9.0 | | 501 | |
| t) | 4-tert-butylphenyl | N=N⁺=N⁻ | | 187-188 | | |
| u) | 3-CF₃-5-((4-methylpiperazin-1-yl)methyl)phenyl | NH—CH₃ | | | | |
| v) | 3-CF₃-5-((4-methylpiperazin-1-yl)methyl)phenyl | NH₂ | | | | |

TABLE 11-continued

| | | R1 | HPLC $t_R$ [min] System 3 | m.p. [° C.] | MS [M + 1]$^+$ | Anal. |
|---|---|---|---|---|---|---|
| w) | F, F (3,5-difluoro) | NH—CH$_3$ | | | 461 | |
| x) | F, F | NH$_2$ | | | 447 | |
| y) | F,F,F-trifluoromethyl with dimethylaminomethyl | NH—CH$_3$ | | | | |
| z) | (same with N-methylpiperazinylmethyl) | NH$_2$ | | | | |

Example 137

(±)trans-N-(4-(4-Aminopyrimidin-6-yl-oxy)-phenyl)-N'-(2-phenyl-cyclopropyl)-urea

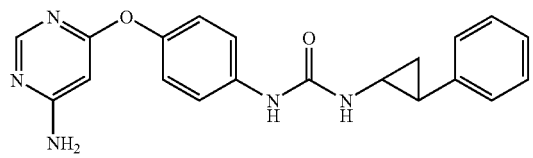

The title compound is prepared analogously to Examples described above: MS: [M+1]$^+$=362; $^1$H-NMR (DMSO-d$_6$): 8.52 & 8.03 (2s, 2H), 7.39 (d, 2H), 7.24 (m, 2H), 7.12 (m, 3H), 6.98 (d, 2H), 6.75 (s, H$_2$N), 6.68 (s, 1H), 5.61 (s, 1H), 2.73 (m, 1H), 1.95 (m, 1H), 1.15 (m, 2H).

Example 138

N-Methyl-C-[4-(4-{4-[3-(4-piperidin-1-yl-3-trifluoromethyl-phenyl)ureido]-phenoxy}-pyrimidin-2-ylamino)-phenyl]-methanesulfonamide

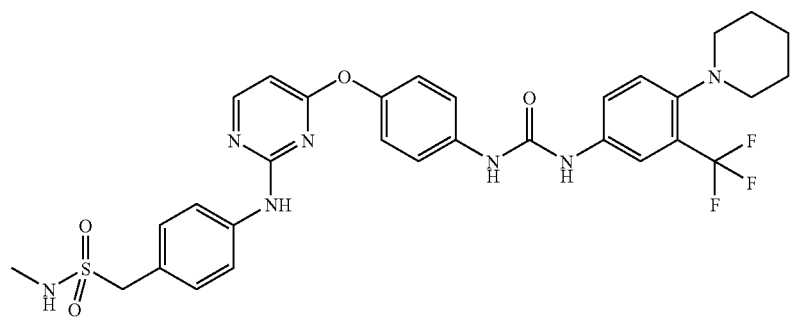

A suspension of 1-[4-(2-chloro-pyrimidin-4-yloxy)-phenyl]-3-(4-piperidin-1-yl-3-trifluoromethyl-phenyl)-urea (compound of Example 79; 140 mol, 0.285 mmol) and of C-(4-amino-phenyl)-N-methyl-methanesulfonamide (855 mg, 4.27 mmol) in ethanol (5 mL) is stirred in a sealed tube at 60° C. for 27 h. After evaporating the solvent, the reaction mixture is flash chromatographed (silica gel, 2.5×45 cm, hexane/AcOEt=1:1→1:2) to give compound of Example 138 as a beige solid: M+H=655.8; $R_f$ (Hexane/AcOEt=1:1): 0.319; HPLC: 6.65 min (System 1).

Compounds of Examples 139 and 140 are synthesized in analogy to the preparation of compound of Example 35 by urea formation between the corresponding chloro-pyrimidinyloxy-phenylamines and the substituted 3-trifuoromethyl-phenyl amines by means of triphosgene. Sturctures and analytical data are given in Table 12.

TABLE 12

| Ex. | Structure | Analytical data |
|---|---|---|
| 139 | 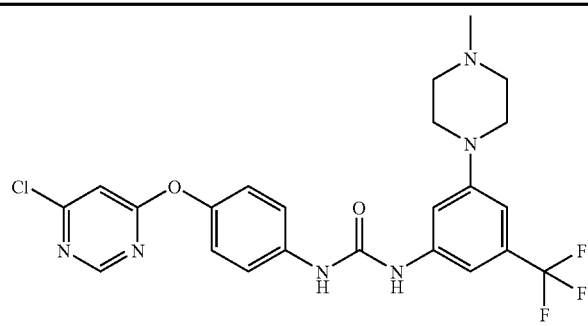<br>1-[4-(6-Chloro-pyrimidin-4-yloxy)-phenyl]-3-[3-(4-methyl-piperazin-1-yl)-5-trifluoromethyl-phenyl]-urea | M + H = 506.9/508.9; $R_f$ CH$_2$Cl$_2$/MeOH = 9:1): 0.21; HPLC: 5.31 min (System 1). |
| 140 | 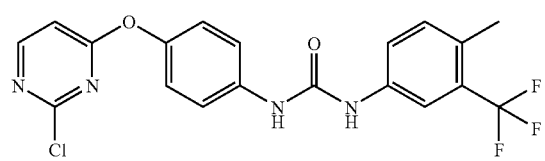<br>1-[4-(2-Chloro-pyrimidin-4-yloxy)-phenyl]-3-(4-methyl-3-trifluoromethyl-phenyl)-urea | M + H = 420.9/422.9; $R_f$ hexane/AcOEt = 1:1): 0.22; HPLC: 7.31 min (System 1). |

Compounds of Examples 141-143 are synthesized analogously to the preparation of compound of Example 138. Structures and analytical data are given in Table 13.

TABLE 13

| Ex. | Structure | Analytical data |
|---|---|---|
| 141 | 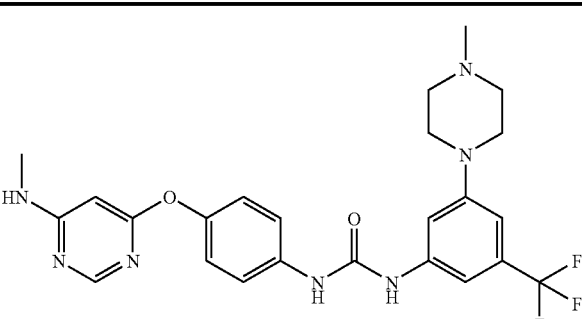<br>1-[4-(6-Methylamino-pyrimidin-4-yloxy)phenyl]-3-[3-(4-methyl-piperazin-1-yl)-5-trifluoromethyl-phenyl]-urea | M + H = 502.0; $R_f$ CH$_2$Cl$_2$/MeOH = 9:1): 0.09; HPLC: 3.98 min (System 1). |

TABLE 13-continued

| Ex. | Structure | Analytical data |
|---|---|---|
| 142 | 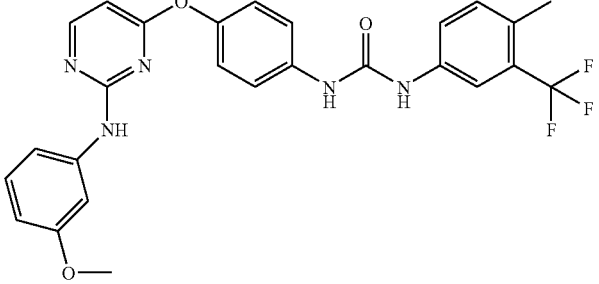<br>1-{4-[2-(3-Methoxy-phenylamino)-pyrimidin-4-yloxy]-phenyl}-3-(4-methyl-3-trifluoromethyl-phenyl)-urea | M + H = 509.9; $R_f$ hexane/AcOEt = 1:1): 0.17; HPLC: 6.37 min (System 1). |
| 143 | 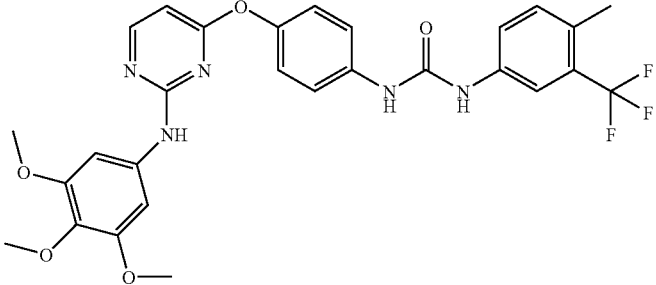<br>1-(4-Methyl-3-trifluoromethyl-phenyl)-3-{4-[2-(3,4,5-trimethoxy-phenylamino)-pyrimidin-4-yloxy]-phenyl}-urea | M + H = 569.8; $R_f$ hexane/AcOEt = 1:2): 0.16; HPLC: 6.86 min (System 1). |

Compounds of Examples 144-151 are formed by urea formation between the corresponding anilines and 4-(4-amino-phenoxy)-pyrimidin-2-ylamine (Examples 144-146) and [6-(4-amino-phenoxy)-pyrimidin-4-yl]-methyl-amine (Examples 147-151), respectively, analogously to the preparation of compound of Example 35. Structures and analytical data are given in Table 14.

TABLE 14

| Ex. | Structure | Analytical data |
|---|---|---|
| 144 | 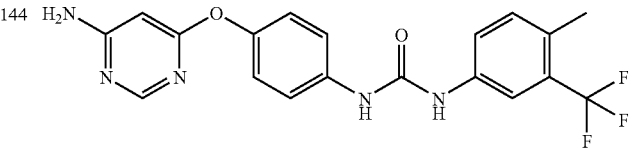<br>1-[4-(6-Amino-pyrimidin-4-yloxy)-phenyl]-3-(4-methyl-3-trifluoromethyl-phenyl)-urea | M + H = 471.8; $R_f$ (AcOEt/hexane = 2:1): 0.24; HPLC: 5.60 min (System 1). |

TABLE 14-continued

| Ex. | Structure | Analytical data |
|---|---|---|
| 145 | 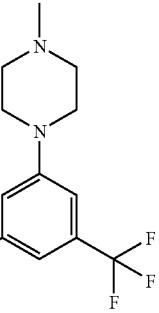<br>1-[4-(6-Amino-pyrimidin-4-yloxy)-phenyl]-3-[3-(4-methyl-piperazin-1-yl)-5-trifluoromethyl-phenyl]-urea | M + H = 487.9; $R_f$ (CH$_2$Cl$_2$/MeOH/NH$_3$ = 8:2:0.1): 0.20; HPLC: 3.78 min (System 1). |
| 146 | 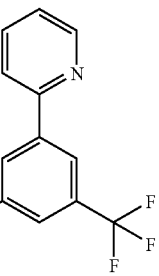<br>1-[4-(6-Amino-pyrimidin-4-yloxy)-phenyl]-3-(3-pyridin-2-yl-5-trifluoromethyl-phenyl) urea | M + H = 466.9 |
| 147 | 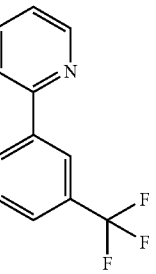<br>1-[4-(6-Methylamino-pyrimidin-4-yloxy)-phenyl]-3-(3-pyridin-2-yl-5-trifluoromethyl-phenyl)-urea | |
| 148 | 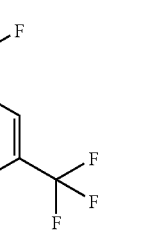<br>1-(3,5-Bis-trifluoromethyl-phenyl)-3-[4-(2-methylamino-pyrimidin-4-yloxy)-phenyl]-urea | M + H = 471.8; $R_f$ (hexane/AcOEt = 2:1): 0.24; HPLC: 6.00 min (System 1). |

TABLE 14-continued

| Ex. | Structure | Analytical data |
|---|---|---|
| 149 | 1-[4-(2-Methylamino-pyrimidin-4-yloxy)-phenyl]-3-(4-methyl-3-trifluoromethyl-phenyl)-urea | M + H = 415.9; $R_f$ (hexane/AcOEt = 1:4): 0.23; HPLC: 5.51 min (System 1); Anal.: C: 57.65% (57.55%), H: 4.21% (4.35%), N: 16.52% (16.78%). |
| 150 | 1-(4-Methoxy-3-trifluoromethyl-phenyl)-3-[4-(2-methylamino-pyrimidin-4-yloxy)-phenyl]-urea | M + H = 431.9; $R_f$ (hexane/AcOEt = 1:4): 0.21; HPLC: 5.07 min (System 1); Anal.: C: 55.73% (55.43%), H: 4.32% (4.19%), N: 15.90% (16.16%). |
| 151 | 1-[4-(2-Methylamino-pyrimidin-4-yloxy)-phenyl]-3-(3-methyl-5-trifluoromethyl-phenyl)-urea | M + H = 417.9; $R_f$ (hexane/AcOEt = 1:4): 0.24; HPLC: 5.53 min (System 1); Anal.: C: 57.56% (57.55%), H: 4.43% (4.35%), N: 16.47% (16.78%). |

6-(4-Amino-phenoxy)-pyrimidin-4-ylamine (Compound of Stage 144.1)

Compound of Stage 56.1 (2.0 g, 9.725 mmol) dissolved in acqueous $NH_3$ (25%, 80 mL) and EtOH (60 mL) is stirred in a sealed tube at 80° C. for 23 h. After evaporating the solvent under reduced pressure on a water bath at 40° C., the residue is flash chromatographed (silica gel, 5.5×65 cm; $CH_2Cl_2$/MeOH=9:1) to give compound of Stage 144.1 as a white solid: M+H=203.0; $^1$H-NMR (400 MHz, DMSO-$d_6$): 8.01 (s, 1H, pyrimidinyl), 6.74 (d, 9 Hz, 2H, phenyl), 6.70 (s, 2H, $NH_2$), 6.57 (d, 9 Hz, 2H, phenyl), 5.51 (s, 1H, pyrimidinyl), 5.03 (s, 2H, $NH_2$); $R_f$ ($CH_2Cl_2$/MeOH=9:1): 0.37; HPLC: 3.75 min (System 1).

3-Pyridin-2-yl-5-trifluoromethyl-phenylamine (Compound of Stage 146.1)

The title compound Is synthesized via Stille coupling analogously to the procedure of Zhang et al., Synthetic Commun. 31 (8), 1129-1139 (2001) 3-amino-5-bromo-benzotrifluoride (600 mg, 2.44 mmol), 2-tributylstannyl-pyridine (1.0 g, 2.69 mmol), and tetrakistriphenylphosphin palladium (282 mg, 0.245 mmol) dissolved in THF (10 mL) is stirred under Ar at 90° C. for 7 d. After concentrating under reduced pressure, the reaction mixture is flash chromatographed (silica gel, 2.6×46 cm, AcOEt/hexane: 1:2→2:3) to give compound of Stage 146.1 as a yellow oil: M+H=239.1; $^1$H-NMR (400 MHz, DMSO-$d_6$): 8.64 (d, 5.0 Hz, 1H), 7.82 (m, 2H), 7.54/7.45 (s/s, 1H/1H), 7.36 (m, 1H9, 6.90 (s, 1H), 5.73 (s/broad, 2H); HPLC: 3.49 min (System 1); $R_f$ (hexane/AcOEt=2:1): 1.5.

[6-(4-Amino-phenoxy)-pyrimidin-4yl]-methyl-amine (Compound of Stage 148.1)

Compound of Stage 148.2 (1.28 g, 5.2 mmol) dissolved in MeOH/THF (45 mL/15 mL) is hydrogenated (1 atm) in the presence of Raney-Ni during 8 h. After evaporating the solvent under reduced pressure, the residue is flash chromatographed (silica gel, 5.5×60 cm; AcOEt/hexane=1:1) to give compound of Stage 148.1 as a beige solid: M+H=217.0; $^1$H-NMR (400 MHz, DMSO-$d_6$): 8.04 (s, 1H, NH), 6.93 (s/broad, 1H, pyriminidyl), 6.75 (d, 9.0 Hz, 2H, phenyl), 6.53 (d, 9.0 Hz, 2H, phenyl), 5.85 (m/broad, 1H, pyrimidinyl), 5.03 (s, 2H, $NH_2$), 2.66 (s/broad, 3H, Me); $R_f$ (AcOEt/hexane=1:1): 0.12; HPLC: 3.60 min (System 1).

Methyl-[4-(4-nitro-phenoxy)-pyrimidin-2-yl]-amine (Compound of Stage 148.2):

Compound of Stage 148.3 (2 g, 7.95 mmol) is stirred in $MeNH_2$ (30% in EtOH, 40 mL) at rt for 50 min. After evaporating the solvent under reduced pressure, the residue is flash chromatographed (silica gel, 5.5×60 cm; AcOEt/hexane=1:1)

to give compound of Stage 148.2 as a white solid: M+H=247.1; $R_f$(AcOEt/hexane=1:1): 0.23; HPLC: 3.60 min (System 1).

2-Chloro4-(4-nitro-phenoxy)-pyrimidine (Compound of Stage 148.3)

The title compound is synthesized analogously to the preparation compound of Stage 22.5: M+H=252.0/253.8; HPLC: 5.97 min (System 1); $^1$H-NMR (400 MHz, DMSO-$d_6$): 8.67 (d, 5.5 Hz, 1H, pyriminidyl), 8.35 (d, 9.0 Hz, 2H, phenyl), 7.55 (d, 9.0 Hz, 2H, phenyl), 76.32 d, 5.5 Hz, 1H, pyrimidinyl).

4-Methoxy-3-trifluoromethyl-phenylamine (Compound of Stage 149.1)

The title compound is prepared from 1-methoxy-4-nitro-2-trifluoromethyl-benzene (1 g, 4.43 mmol) by hydrogenation (5→1.4 bar) in the presence of Raney-Ni (0.3 g) in MeOH (20 mL) during 15 h. The product is isolated by filtration of the reaction suspension over Hyflo and evaporation of the solvent under reduced pressure to give compound of Stage 149.1 as a beige solid: M+H=191.9; $R_f$ (AcOEt/hexane=1:1): 0.33.

Example 152

1-{4-[6-(4-Methoxy-phenylamino)-pyrimidin-4-yloxy]-phenyl}-3-[4-(2-methyl-imidazol-1-yl)-3-trifluoromethyl-phenyl-urea

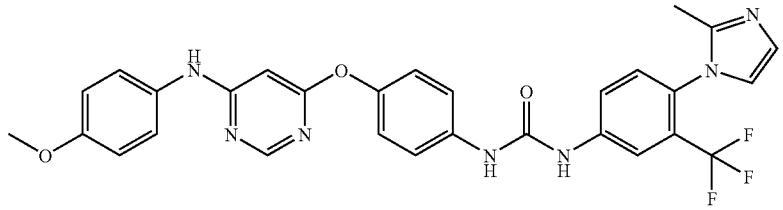

The title compound is synthesized analogously to the preparation of compound of Example 47 by urea formation with [6-(4-amino-phenoxy)-pyrimidin-4-yl]-(4-methoxy-phenyl)-amine (Stage 47.1) and 4-(2-methyl-imidazol-1-yl)-3-trifluoromethyl-phenylamine (Stage 152.1): M+H=575.8; HPLC: 4.73 min (System 1); $R_f$ (AcOEt/hexane=1:1): 0.33; $^1$H-NMR (400 MHz, DMSO-$d_6$): 9.33 (s, 1H), 9.29 (s, 1H), 8.94 (s, 1H), 8.24 (s, 1H), 8.14 (s, 1H), 7.71 (d, 9.0 Hz, 1H, phenyl-CF$_3$), 7.52 (d, 8.5 Hz, 2H), 7.44 (d, 9.0 Hz, 1H, phenyl-CF$_3$), 7.39 (d, 8.5 Hz, 2H), 7.13 (s, 1H), 7.11 (d, 8.5 Hz, 2H), 6.86 (d, 8.5 Hz, 2H), 5.94 (s, 1H, pyrmidinyl), 3.71 (s, 3H, CH$_3$—O), 2.04 (s, 3H, CH$_3$-imidazolyl).

4-(2-Methyl-imidazol-1-yl)-3-trifluoromethyl-phenylamine (Compound of Stage 152.1)

The title compound is generated from 2-methyl-1-(4-nitro-2-trifluoromethyl-phenyl)-1H-imidazole (Stage 152.2) by hydrogenation in the presence of Raney-Ni in MeOH during 14 h at rt: $R_f$ (MeOH/CH$_2$Cl$_2$=1:5): 0.42; M+H=242.0; m.p.=217-219° C.

2-Methyl-1-(4-nitro-2-trifluoromethyl-phenyl)-1H-imidazole (Compound of Stage 152.2):

The title compound is prepared by hearing 1-bromo-4-nitro-2-trifluoromethyl-benzene and 2-methyl-imidazole between 100-150° C. during 15 h: M+H=272.0; $R_f$(MeOH/CH$_2$Cl$_2$=1:5): 0.60.

In accordance with the methods described hereinbefore, the following compounds [Examples 153a)-153x)], with the substituents given in Table 15, are prepared:

TABLE 15
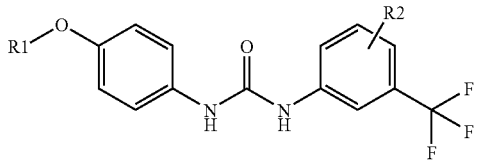
| Example 153 | R1 | R2 |
|---|---|---|
| a) | 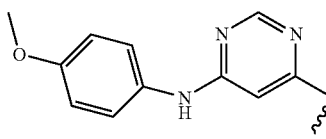 | 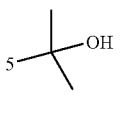 |
| b) | 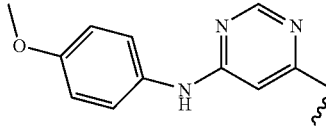 | 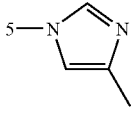 |
| c) | 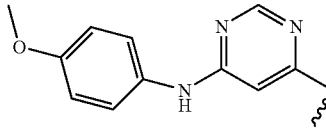 | 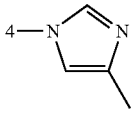 |
| d) | 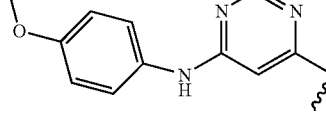 | 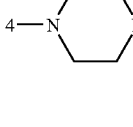 |
| e) | 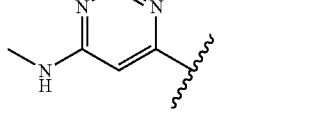 | 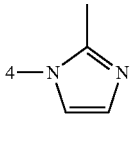 |
| f) | 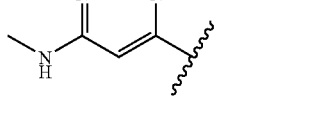 | 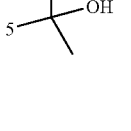 |
| g) | 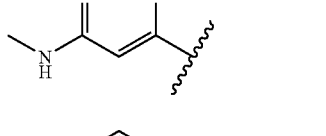 | 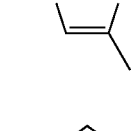 |
| h) | 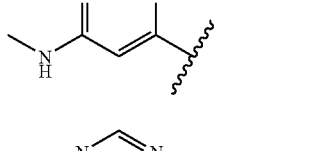 | 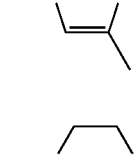 |
| i) | 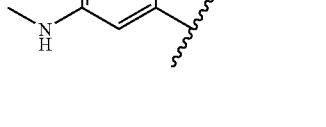 | 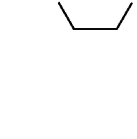 |

TABLE 15-continued
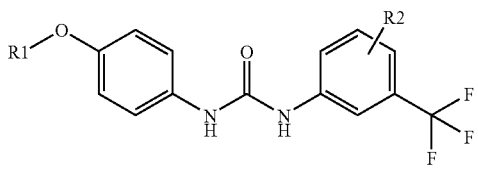
| Example 153 | R1 | R2 |
|---|---|---|
| j) | 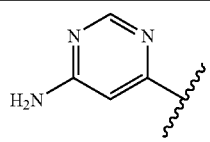 | 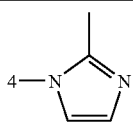 |
| k) | 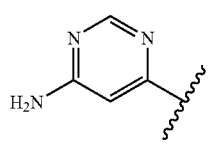 | 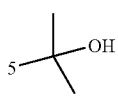 |
| l) | 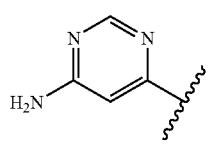 | 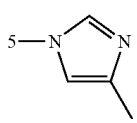 |
| m) | 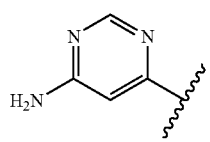 | 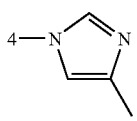 |
| n) | 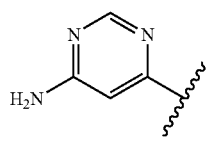 | 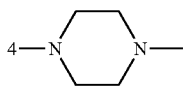 |
| o) | 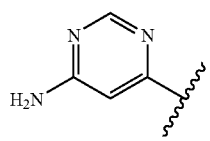 | 4-Ethyl |
| p) | 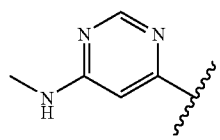 | 4-Ethyl |
| q) | 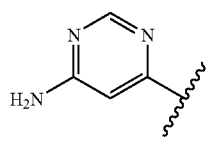 | 4-(Isopropyl) |

TABLE 15-continued
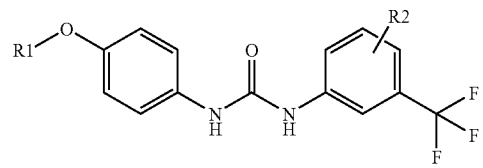
| Example 153 | R1 | R2 |
|---|---|---|
| r) | 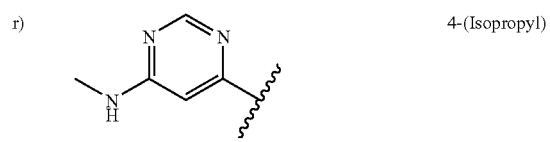 | 4-(Isopropyl) |
| s) | 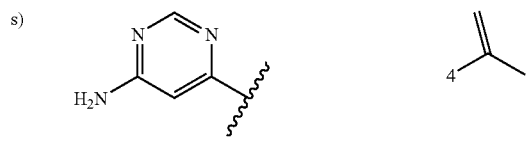 |  |
| t) | 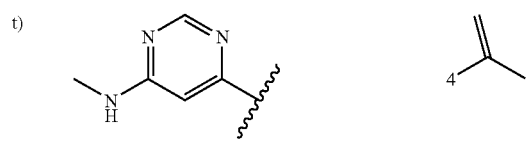 |  |
| u) | 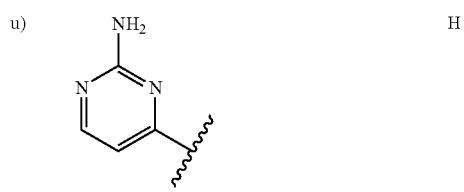 | H |
| v) | 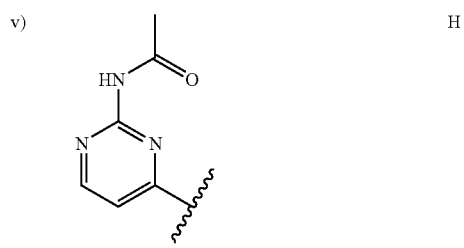 | H |
| w) |  | |
| x) | 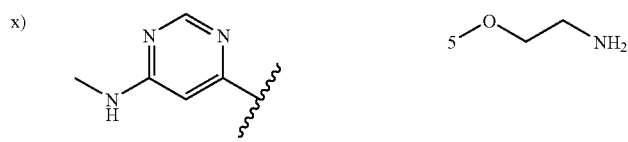 | |

In accordance with the methods described hereinbefore, the following compounds [Examples 154a)-154e)], with the substituents given in Table 16, are prepared:

TABLE 16

| Example 154 | Structure |
|---|---|
| a) | 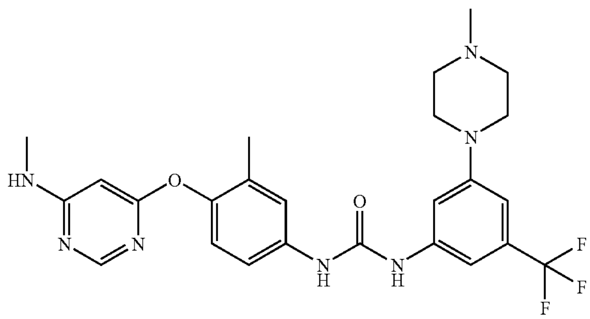 |
| b) | 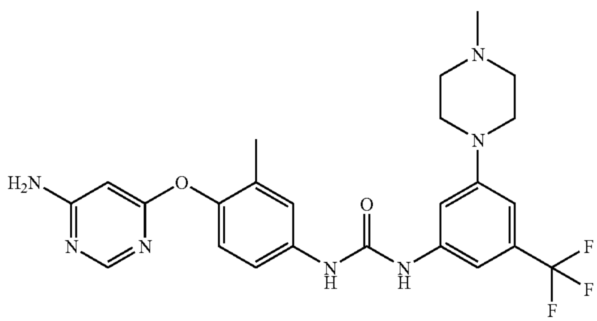 |
| c) | 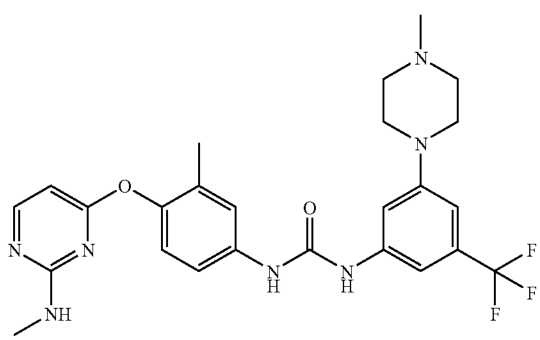 |
| d) | 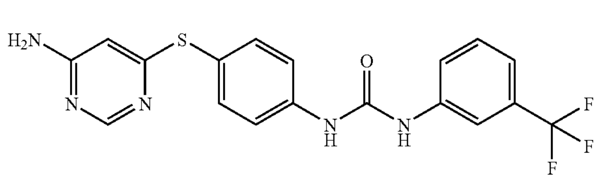 |
| e) | 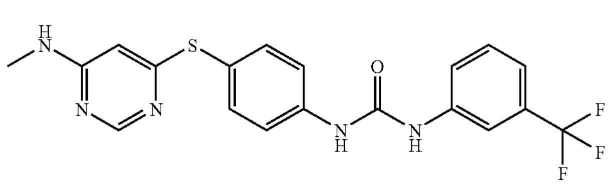 |

Example 155

N-(6-{4-[3-(3-Trifluoromethyl-phenyl)-ureido]-phenoxy}-pyrimidin-4-yl)-acetamide

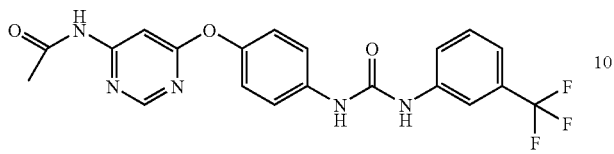

1-[4-(6-Chloro-pyrimidin-4-yloxy)-phenyl]-3-(3-trifluoromethyl-phenyl)-urea (compound of Example 56) (100 mg, 0.245 mmol)₁ acetamide (40 mg₁ 0.678 mmol), 4,5-bis(diphenylphosphino)-9,9-dimethyl-xanthrene (9 mg), and tris(dibenzylideneacetone)dipalladium (6 mg) dissolved in dioxane (3 mL) are stirred at 55° C. under Ar for 8 h. After evaporating the solvent under reduced pressure, the residue is partitioned between H₂O (60 mL) and AcOEt (200 mL). The organic phase is separated, dried (MgSO₄) and concentrated under reduced pressure. The product is purified by preparative thin layer chromatography (four 20×20 cm silica gel plates, acetone/CH₂Cl₂=3:7): M+H=431.9; R$_f$ (acetone/CH₂Cl₂=3:7): 0.29; ¹H-NMR (400 MHz, DMSO-d₆): 10.85 (s, 1H, pyrimidinyl), 9.03/8.84 (s/s, 1H/1H, urea), 8.45 (s, 1H, NH), 7.98 (s, 1H, pyrimidinyl), 7.56 (d, 8.5 Hz, 1H, phenyl-CF₃), 7.50 (d/s, 9.0 Hz, 2H/1H, phenyl/phenyl-CF₃), 7.49 (t, 1H, phenyl-CF₃), 7.29 (d, 8.5 Hz, 1H, phenyl-CF₃), 7.06 (d, 9.0 Hz, 2H, phenyl), 7.39 (d, 8.5 Hz, 2H), 7.13 (s, 1H), 7.11 (d, 8.5 Hz, 2H), 6.86 (d, 8.5 Hz, 2H), 5.94 (s, 1H, pyrimidinyl), 2.09 (s, 3H, CH₃).

Example 156

1-[3-Methyl-4-(6-methylamino-pyrimidin-4-yloxy)-phenyl]-3-(3-trifluoromethyl-phenyl)-urea

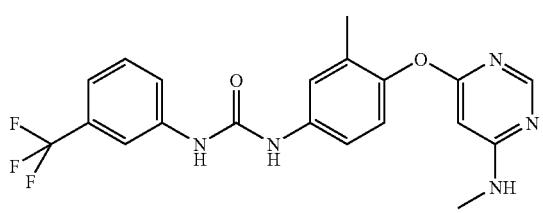

[6-(4-Amino-2-methyl-phenoxy)-pyrimidin-4-yl]-methyl-amine (73 mg, 0.31 mmol), 3-trifluoromethyl-phenyl-isocyanate (118 mg, 0.63 mmol), NEt₃ (63.5 mg, 0.63 mmol) dissolved in CH₂Cl₂ (7 mL) are stirred at rt for 1.5 h. The precipitating product is filtered off and dried in vacuo: M+H=431.9; R$_f$ (hexane/AcOEt=1:1): 0.43; HPLC (System 1): 5.26 min; ¹H-NMR (400 MHz, DMSO-d₆): 10.85 (s, 1H, pyrimidinyl), 9.23/8.92 (s/s, 1H/1H, urea), 8.07 (s/broad, 1H, NH), 7.98 (s, 1H, pyrimidinyl), 7.56 (d, 8.5 Hz, 1H, phenyl-CF₃), 7.50 (d, 9.0 Hz, 1H, phenyl-CF₃), 7.49 (t, 9.0 Hz, 1H, phenyl-CF₃), 7.39 (s, 1H), 7.36 (m, 3H), 6.95 (d, 9.0 Hz, 1H, phenyl-CF₃), 7.13 (s, 1H), 5.66 (s/broad, 1H, pyrimidinyl), 2.74 (s/broad, 3H, CH₃NH), 2.04 (s, 3H, CH₃).

[6-(4-Amino-2-methyl-phenoxy)-pyrimidin-4-yl]-methyl-amine (Compound of Stage 156.1)

The title compound is prepared from [3-methyl-4-(6-methylamino-pyrimidin-4-yloxy)-phenyl]-carbamic acid benzyl ester by hydrogenation in the presence of Pd/C in MeOH/THF: M+H=230.9; R$_f$ (acetone/CH₂Cl₂=1:1): 0.20.

[3-Methyl-4-(6-methylamino-pyrimidin-4-yloxy)-phenyl]-carbamic acid benzyl ester (Compound of Stage 156.2)

The title compound is prepared from [4-(6-chloro-pyrimidin-4-yloxy)-3-methyl-phenyl]-carbamic acid benzyl ester by aminomethylation (30% CH₃NH₂ in EtOH, 60 min, rt): M+H=363.9; R$_f$ (acetone/CH₂Cl₂=3:7): 0.26.

[4-(6-Chloro-pyrimidin-4-yloxy)-3-methyl-phenyl]-carbamic acid benzyl ester (Compound of Stage 156.3)

(4-Hydroxy-3-methyl-phenyl)-carbamic acid benzyl ester (278 mg, 1.08 mmol) and NaH (29 mg, 1.2 mmol) dissolved in DMF (5 mL) are stirred at rt for 15 min. 4,6-Dichloro-pyrimidine (177 mg, 1.19 mmol) dissolved in DMF (5 mL) is added and the reaction solution is stirred for 1 h, concentrated under reduced pressure and flash chromatographed (silica gel, 2.5×60 cm, AcOEt/hexane=1:6): M+H=370.8; R$_f$ (AcOEt/hexane=1:6): 0.31.

(4-Hydroxy-3-methyl-phenyl)-carbamic acid benzyl ester (Compound of Stage 156.4)

4-Amino-2-methyl-phenol (717 mg, 5.8 mmol) and benzyloxycarbonyl chloride (1.09 g, 6.4 mmol) are stirred in a suspension of AcOEt/concentrated Na₂CO₃ solution (50 mL/50 mL) for 7 h. The organic phase is concentrated under reduced pressure and flash chromatographed (silica gel, 3.8×66 cm, AcOEt/hexane=1:3): M+H=257.9; HPLC (System 1): 5.43 min.

Example 157

1-[4-(6-Amino-pyrimidin-4-ylmethyl)-phenyl]-3-(4-ethyl-phenyl)-urea

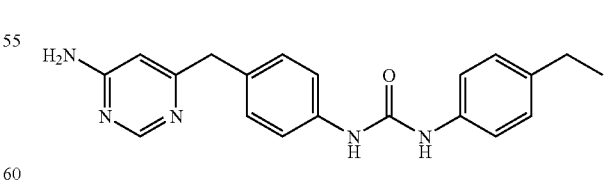

The title compound is prepared as described in Example 102 but using 6-(4-aminobenzyl)-pyrimidin-4-ylamine, 4-ethyl-phenyl-isocyanate, and DMF as the solvent. The reaction mixture is stirred for 2 h. The title compound is obtained as a white solid: ES-MS: 348.0 [M+H]⁺; single peak at t$_R$=6.94 min (System 2).

6-(4-Aminobenzyl)-pyrimidin-4-ylamine

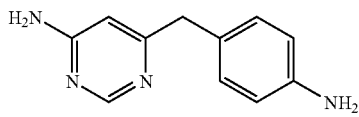

A 4 N solution of HCl in dioxane (19.2 mL, 76.4 mmol, 30 equiv) is added to a solution of [4-(6-amino-pyrimidin-4-ylmethyl)-phenyl]-carbamic acid tert-butyl ester (770 mg, 2.56 mmol) in CH$_2$Cl$_2$ (23 mL), under an argon atmosphere. The resulting white suspension is stirred at rt for 1.5 h and concentrated in vacuo. To the residue is added a 2 M methanolic solution of ammonia (3.8 mL, 7.68 mmol, 3 equiv) and the resulting yellow solution is concentrated in vacuo. The crude product is purified by silica gel (90 g) column chromatography CH$_2$Cl$_2$/MeOH, 90/10, then 80/20). The title compound is obtained as a white solid: ES-MS: 201.0 [M+H]$^+$; single peak at t$_R$=2.00 min (System 2); R$_f$=0.20 (CH$_2$Cl$_2$/MeOH, 90/10).

[4-(6-Amino-pyrimidin-4-ylmethyl)-phenyl]-carbamic acid tert-butyl ester

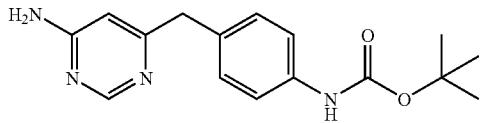

A suspension of [4-(6-azido-pyrimidin-4-ylmethyl)-phenyl]-carbamic acid tert-butyl ester (870 mg, 2.66 mmol) and 10% Pd/C (174 mg) in MeOH (35 mL) is stirred for 1.5 h at rt and a hydrogen atmosphere. The reaction mixture is filtered through a plug of celite (washing the filter cake with copious amounts of MeOH). The filtrate is concentrated in vacuo to afford the title compound as a beige solid: ES-MS: 301.1 [M+H]$^+$; single peak at t$_R$=6.25 min (System 2).

[4-(6-Azido-pyrimidin-4-ylmethyl)-phenyl]-carbamic acid tert-butyl ester

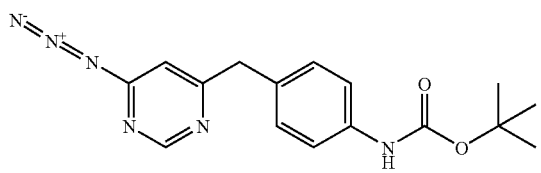

A suspension of [4-(6-chloro-pyrimidin-4-ylmethyl)-phenyl]-carbamic acid tert-butyl ester (see Example 117) (1.1 g, 3.44 mmol) and sodium azide (0.31 g, 4.81 mmol, 1.4 equiv) in DMF (13 mL) is heated to 80° C. for 2.5 h. The reaction mixture is allowed to cool to rt and concentrated in vacuo. The residue is diluted with EtOAc (25 mL) and H$_2$O (66 mL). The layers are separated and the aqueous layer is extracted with EtOAc (2×40 mL and 2×50 mL). The organic phase is dried (Na$_2$SO$_4$), filtered and concentrated. The residue is purified by silica gel (80 g) column chromatography CH$_2$Cl$_2$/Et$_2$O, 90/10). The title compound is obtained as a white solid: ES-MS: 327.0 [M+H]$^+$; single peak at t$_R$=7.42 min (System 2); R$_f$=0.26 (CH$_2$Cl$_2$/Et$_2$O, 90/10).

Example 158

1-[4-(6-Amino-pyrimidin-4-ylmethyl)-phenyl]-3-p-tolyl-urea

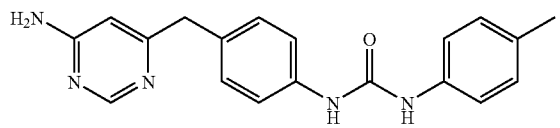

The title compound is prepared as described in Example 102 but using 6-(4-aminobenzyl)-pyrimidin-4-ylamine (see Example 157), and DMF as the solvent. The reaction mixture is stirred for 3 h. The title compound is obtained as a white solid: ES-MS: 348.0 [M+H]$^+$; single peak at t$_R$=6.94 min (System 2).

Example 159

1-[4-(6-Amino-pyrimidin-4-ylmethyl)-phenyl]-3-(3-trifluoromethyl-phenyl)-urea

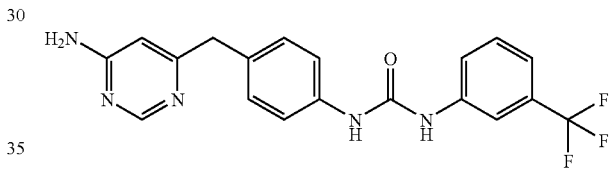

The title compound is prepared as described in Example 102 but using 6-(4-aminobenzyl)-pyrimidin-4-ylamine (see Example 157), α,α,α-trifluoro-m-tolyl-isocyanate, and DMF as the solvent. The reaction mixture is stirred for 4 h. The crude product is washed with a CH$_2$Cl$_2$/MeOH (99/1) solution. The title compound is obtained as a white solid: ES-MS: 387.9 [M+H]$^+$; single peak at t$_R$=7.12 min (System 2); R$_f$=0.23 (CH$_2$Cl$_2$/MeOH, 90/10).

Example 160

1-[4-(6-Amino-pyrimidin-4-ylmethyl)-phenyl]-3-(4-chloro-3-trifluoromethyl-phenyl)-urea

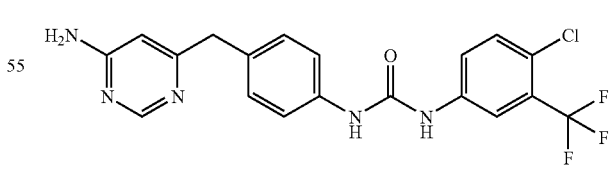

The title compound is prepared as described in Example 102 but using 6-(4-aminobenzyl)-pyrimidin-4-ylamine (see Example 157), 4-chloro-3-(trifluoromethyl)-phenyl isocyanate, and DMF as the solvent. The reaction mixture is stirred for 2 h. The title compound is obtained as a white solid: ES-MS: 422.8 [M+H]$^+$; single peak at t$_R$=7.58 min (System 2).

Example 161

1-[4-(6-Amino-pyrimidin-4-ylmethyl)-phenyl]-3-(4-tert-butyl-phenyl)-urea

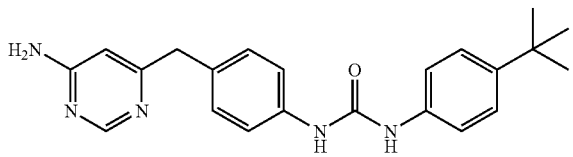

The title compound is prepared as described in Example 102 but using 6-(4-aminobenzyl)-pyrimidin-4-ylamine (see Example 157), 4-tert-butyl-phenyl-isocyanate, and DMF as the solvent. The reaction mixture is stirred for 3 h. The title compound is obtained as a white solid: ES-MS: 348.0 [M+H]$^+$; single peak at $t_R$=6.94 min (System 2).

Example 162

1-(4-{2-[2-(3-Dimethylamino-propyl)-2H-tetrazol-5-yl]-pyridin-4-yloxy}-phenyl]-3-(3-trifluoromethyl-phenyl)-urea

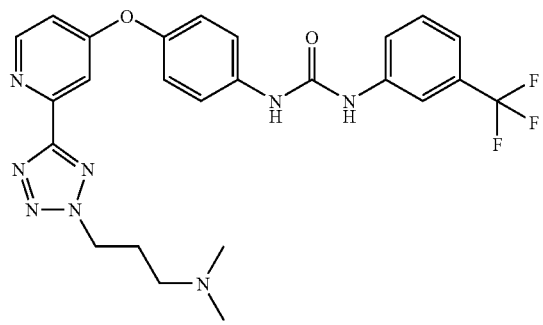

The title compound is prepared according to a procedure similar to that described in Example 125.

Example 163

5-(6-Chloro-pyrimidin-4-yloxy)-2,3-dihydro-indole-1-carboxylic acid (3-trifluoromethyl-phenyl)-amide

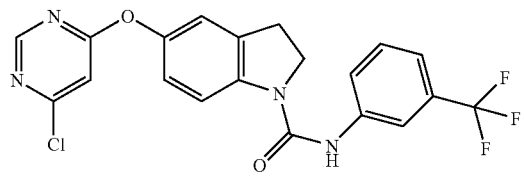

To a solution of 5-(6-chloro-pyrimidinyloxy)-1H-indole (Stage 163.1; 14.5 mmol) in acidic acid (80 ml), NaBH$_3$CN (90%; 5.06 g, 72.5 mmol) is added portionwise. After 45 min, ice (20 g) Is added and the mixture partially concentrated on the rotation evaporator. Then a 1 N solution of NaOH is added to the residue (pH=11), which then is diluted with water and AcOEt. The aqueous layer is separated off and extracted twice with AcOEt. The organic phases are washed with 2 portions of water and brine, dried (Na$_2$SO$_4$) and concentrated to give crude 5-(6-chloro-pyrimidin-4-yloxy)2,3-dihydro-1H-indole: MS: [M+1]$^+$=248. This crude 2,3-dihydro-1H-indole is then dissolved in THF (70 ml) and 3-trifluoromethyl-isocyanate (93%; 3.0 g, 14.9 mmol) is added. After 16 h at rt, the mixture is diluted with AcOEt and washed twice with water. The aqueous layer is extracted twice with AcOEt, the organic phases washed with brine, dried (Na$_2$SO$_4$) and concentrated. Column chromatography (SiO$_2$; hexane/AcOEt 3:1→2:1→1:1) gives the title compound: m.p.: 181° C.; MS: [M+1]$^+$=435; $^1$H-NMR (DMSO-d$_6$): 8.85 (s, HN), 8.62 (s, 1H), 8.00 (s, 1H), 7.88 (d, 1H), 7.84 (d, 1H), 7.50 (t, 1H), 7.33 (d, 1H), 7.29 (s, 1H), 7.09 (s, 1H), 6.98 (d, 1H), 4.19 (t, 2H), 3.20 (t, 2H).

The starting materials are prepared as follows:

Stage 163.1:
5-(6-Chloro-pyrimidin-4-yloxy)-1H-indole

To a mixture of NaOH (720 mg, 18 mmol) and acetone/water 1:1 (72 ml), 4,6-dichloropyrimidine (2.4 g, 18 mmol) and 5-hydroxy-indole (2.68 g, 18 mmol) are added. After stirring for 70 min at 65° C., the brownish solution is cooled to rt and diluted with AcOEt and water. The aqueous layer is separated off and extracted twice with AcOEt. The organic layers are washed with water, saturated Na$_2$CO$_3$ solution, water and brine, dried (Na$_2$SO$_4$) and concentrated. The crude product can be used without further purification: m.p.: 137-138° C.; MS: [M+1]$^+$=246.

Examples 164a)-c)

Starting from 5-(6-chloro-pyrimidin-4-yloxy)-2,3-dihydro-indole-1-carboxylic acid (3-trifluoromethyl-phenyl) amide (Example 163), the following derivatives are made analogously:

a): 5-(6-azido-pyrimidin-4-yloxy)-2,3-dihydro-indole-1-carboxylic acid (3-trifluoromethyl-phenyl)-amide;
b): 5-(6-amino-pyrimidin-4-yloxy)-2,3-dihydro-indole-1-carboxylic acid (3-trifluoromethyl-phenyl)amide; and
c): 5-(6-methylamino-pyrimidin-4-yloxy)-2,3-dihydro-indole-1-carboxylic acid (3-trifluoromethyl-phenyl) amide.

Example 165

Pharmacokinetic Data

The compound of formula I or I* to be tested is formulated for administration to female MAG mice from BRL, Fuellinsdorf, Switzerland, by dissolving In DMSO/Tween 80 (90:10 v/v). The solution is diluted 1:20 with distilled water and briefly sonicated to give a macroscopically homogenous suspension in 5% v/v DMSO/0.5% v/v Tween 80. Final concentrations of compound are 10, 3 and 1 mg/ml for dosed of 50 mg/kg, respectively. Each formulation is examined under a phase contrast microscope and particle form described and size are estimated.

The formulated compound is administered by gavage to provide dosages of 50 mg/kg. At the alloted time points mice (4 at each time) are anesthesized with 3% isoflurane in oxygen and heart blood is removed into heparinized tubes (ca. 30

IU/ml). The animals are subsequently killed without recovering from the anesthetic. Plasma Is prepared from the blood by centrifugation (10,000 g, 5 min) and either analysed immediately or stored frozen at −70° C. The plasma samples are mixed with an equal volume of acetonitrile and allowed to stand at rt for 20-30 min. The protein precipitate is removed by centrifugation (10,000×g) and a sample of the supernatant is analysed by reversed-phase HPLC on Merck-Hitachi LaChrom® equipment. The sample (100 μl) is injected onto a Nucleosil® 100-5 C18 column (Macherey & Nagel, Düren, F. R. G.) (125×4 mm) with a guard column (8×4 mm) of the same material. The column is equilibrated e.g. with a 5% v/v acetonitrile in water containing 0.05% trifluoroacetic acid (TFA). The sample is eluted e.g. with a gradient of 5% v/v acetonitrile to 95% v/v acetonitrile (in water with 0.05% v/v TFA) over a period of 10 min. The column is then prepared for the next sample by holding the gradient at the final conditions for 5 min, then returning to the starting conditions and reequilibrating for 5 min. The compound is detected by absorbance, e.g. at 320 nm. The identity of the peak can be confirmed by retention time and UV absorption spectrum (diode array detector 205-400 nm) compared to controls. The amount of compound is quantified by the external standard method. A calibration curve is constructed with known amounts of compound in plasma which is processed as described above.

Compounds of the formula I or I* according to the invention here show plasma concentrations in the area of e.g. 1 to 50 μM.

Example 166

In vitro Inhibition Data

Enzymatic (c-Abl, KDR, Flt3) data are given on Table 17 (% inhibition at 10 μM). (Measurements are made as described above in the general description).

TABLE 17

Enzymatic data

| Example | c-Abl (% at 10 μM) | KDR trans (% at 10 μM) | Flt3 (% at 10 μM) |
|---|---|---|---|
| 1 | 62 | 100 | — |
| 2 | 84 | 99 | — |
| 3 | 58 | 25 | — |
| 4 | 59 | 99 | 98 |
| 5 | 46 | 99 | 64 |
| 6 | 75 | 100 | 87 |
| 7 | 47 | 97 | 67 |
| 8 | 48 | 78 | 57 |
| 9 | 100 | 92 | 90 |
| 10 | 98 | 100 | 100 |
| 11 | 95 | 100 | 100 |
| 12 | 33 | 97 | 92 |
| 13 | 36 | 98 | 95 |
| 14 | 26 | 97 | 89 |
| 15 | 71 | 99 | 96 |
| 16 | 66 | 99 | 94 |
| 17 | 18 | 96 | 92 |
| 18 | 61 | 99 | 88 |
| 19 | 92 | 86 | 63 |
| 20 | 84 | 93 | 69 |
| 21 | 70 | 100 | 94 |
| 30 | 100 | 98 | 100 |
| 32 | 98 | 96 | 100 |

Example 167

Tablets Comprising Compounds of the Formula I or I*

Tables, comprising, as active ingredient, 100 mg of any one of the compounds of formula I or I* of Examples 1 to 164c) are prepared with the following composition, following standard procedures:

Composition

| | |
|---|---|
| Active Ingredient | 100 mg |
| crystalline lactose | 240 mg |
| Avicel | 80 mg |
| PVPPXL | 20 mg |
| Aerosil | 2 mg |
| magnesium stearate | 5 mg |
| | 447 mg |

Manufacture: The active ingredient is mixed with the carrier materials and compressed by means of a tabletting machine (Korsch EKO, Stempeldurchmesser 10 mm).

Avicel is microcrystalline cellulose (FMC, Philadelphia, USA).

PVPPXL is polyvinylpolypyrrolidone, cross-linked (BASF, Germany).

Aerosil is silcium dioxide (Degussa, Germany).

Example 168

Capsules

Capsules, comprising, as active ingredient, 100 mg of any one of the compounds of formula I or I* given in Examples 1 to 164c), of the following composition are prepared accoding to standard procedures:

Composition

| | |
|---|---|
| Active Ingredient | 100 mg |
| Avicel | 200 mg |
| PVPPXL | 15 mg |
| Aerosil | 2 mg |
| magnesium stearate | 1.5 mg |
| | 318.5 mg |

Manufacturing is done by mixing the components and filling them into hard gelatine capsules, size 1.

What is claimed is:

1. A compound of the formula I*

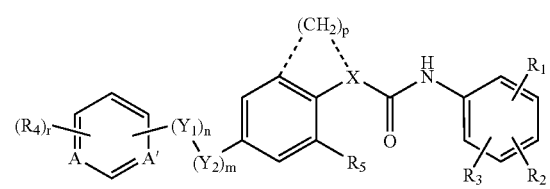

wherein
A is N or N→O and A' is N or N→O, with the proviso that not more than one of A and A' can be N→O;

n is 1;
m is 0;
p is 0, 2 or 3;
r is 0 to 5;
X is NR if p is 0, wherein R is hydrogen or lower alkyl, or if p is 2 or 3, X is nitrogen which together with $(CH_2)_p$ and the bonds represented in dotted (interrupted) lines (including the atoms to which they are bound) forms a ring, with the proviso that the bonds represented in dotted lines, if p is zero, are absent;

$Y_1$ is O;

each of $R_1$, $R_2$, $R_3$ independently of the others, is hydrogen, lower alkyl, hydroxy-lower alkyl, lower alkoxy, halo, halo-lower alkyl, halo-lower alkoxy, amino-lower alkyl, amino-lower alkoxy, di-lower alkyl-amino, hydroxy-lower alkyl-amino, bis-(lower alkoxy-lower alkyl)-amino, di-lower alkyl-amino-lower alkyl, phenyl, morpholinyl, piperidyl, piperidyl-lower alkyl, lower alkyl-piperazinyl, lower alkyl-piperazinyl-lower alkyl, pyridyl, or lower alkyl-imidazolyl; or any two of them together form a lower alkylene-dioxy bridge bound via the oxygen atoms, and the remaining one of these moieties is hydrogen, lower alkyl, hydroxy-lower alkyl, lower alkoxy, halo, halo-lower alkyl, halo-lower alkoxy, amino-lower alkyl, amino-lower alkoxy, di-lower alkyl-amino, hydroxy-lower alkyl-amino, bis-(lower alkoxy-lower alkyl)-amino, di-lower alkyl-amino-lower alkyl, phenyl, morpholinyl, piperidyl, piperidyl-lower alkyl, lower alkyl-piperazinyl, lower alkyl-piperazinyl-lower alkyl, pyridyl, or lower alkyl-imidazolyl;

$R_5$ is hydrogen, lower alkyl, or halo;

and $R_4$ (if present, that is, if r is not zero) is lower alkyl, hydroxy, aminocarbonyl, lower alkyl-carbonyl, cyclohexyl, halo, halo-lower alkyl, lower alkoxy, amino, lower alkyl-amino, di-lower alkyl-amino, lower alkenyl-amino, lower alkyl-carbonyl-amino, cyano, azido, hydroxyl-phenyl-amino mono or tri-lower alkoxy-phenyl-amino, lower alkoxy-halo-phenyl-amino, phenyl-lower alkylamino, (mono or di-lower alkoxy)-phenyl-lower alkylamino, aminosolfonyl-phenyl-lower alkylamino, amino-lower alkoxy-phenyl-amino, lower alkyl-amino-sulfonyl-lower alkyl-phenylamino, lower alkyl-piperazinyl-lower alkylamino, morpholinyl-lower alkylamino, lower alkyl-piperidyl-amino, tetrazolyl, lower alkyl-tetrazolyl, or (di-lower alkyl)-amino-lower alkyl-tetrazolyl, or a tautomer thereof; or a pharmaceutically acceptable salt thereof.

2. A compound of the formula I* according to claim 1 or a tautomer thereof, or a pharmaceutically acceptable salt thereof, where, in the compound of the formula I, A is N or N→O and A' is N or N→O, with the proviso that not more than one of A and A' can be N→O;

n is 1;
m is 0;
p is 0, 2or 3;
r is 1 to 5;
X is NR if p is 0, wherein R is hydrogen or lower alkyl, or if p is 2 or 3, X is nitrogen which together with $(CH_2)_p$ and the bonds represented in dotted (interrupted) lines (including the atoms to which they are bound) forms a ring, with the proviso that if X is NH, each of $R_4$, independently of the others if r>1, is a moiety as defined in claim 1 but not bound to the rest of formula I via a —C(=O)—, —C(NR)— or —S(O$_2$)— bridge, with the proviso that the bonds represented in dotted lines, if p is zero, are absent;

$Y_1$ is O;

each of $R_1$, $R_2$, $R_3$ independently of the others, is hydrogen, lower alkyl, hydroxy-lower alkyl, lower alkoxy, halo, halo-lower alkyl, halo-lower alkoxy, amino-lower alkyl, amino-lower alkoxy, di-lower alkyl-amino, hydroxy-lower alkyl-amino, bis-(lower alkoxy-lower alkyl)-amino, di-lower alkyl-amino-lower alkyl, phenyl, morpholinyl, piperidyl, piperidyl-lower alkyl, lower alkyl-piperazinyl, lower alkyl-piperazinyl-lower alkyl, pyridyl, or lower alkyl-imidazolyl; or any two of $R_1$, $R_2$ and $R_3$ together form a lower alkylene-dioxy bridge bound via the oxygen atoms, and the remaining one of these moieties is hydrogen, lower alkyl, hydroxy-lower alkyl, lower alkoxy, halo, halo-lower alkyl, halo-lower alkoxy, amino-lower alkyl, amino-lower alkoxy, di-lower alkyl-amino, hydroxy-lower alkyl-amino, bis-(lower alkoxy-lower alkyl)-amino, di-lower alkyl-amino-lower alkyl, phenyl, morpholinyl, piperidyl, piperidyl-lower alkyl, lower alkyl-piperazinyl, lower alkyl-piperazinyl-lower alkyl, pyridyl, or lower alkyl-imidazolyl, with the proviso that $R_1$, $R_2$ and $R_3$ cannot all be hydrogen and with the further proviso that if one of $R_1$, $R_2$ and $R_3$ is halo or lower alkyl-sulfonyl, the other two cannot both be hydrogen;

$R_5$ is hydrogen, lower alkyl, or halo;

$R_4$ is lower alkyl, hydroxyl, aminocarbonyl, lower alkyl-carbonyl, cyclohexyl, halo, halo-lower alkyl, lower alkoxy, amino, lower alkyl-amino, di-lower alkyl-amino, lower alkenyl-amino, lower alkyl-carbonyl-amino, cyano, azido, hydroxy-phenyl-amino mono or tri-lower alkoxy-phenyl-amino, lower alkoxy-halo-phenyl-amino, phenyl-lower alkylamino, (mono or di-lower alkoxy)-phenyl-lower alkylamino, aminosolfonyl-phenyl-lower alkylamino, amino-lower alkoxy-phenyl-amino, lower alkyl-amino-sulfonyl-lower alkyl-phenylamino, lower alkyl-piperazinyl-lower alkylamino, morpholinyl-lower alkylamino, lower alkyl-piperidyl-amino, tetrazolyl, lower alkyl-tetrazolyl, or (di-lower alkyl)-amino-lower alkyl-tetrazolyl, with the proviso that if p is 0, r is 1, X is NH, $R_4$, together with the benzene ring containing A and A', does not form methylpyridinyl, 2-hydroxy-pyridin-4-yl or 1-H-2-oxo-1,2-dihydropyridin-4-yl.

3. A compound of the formula I* according to claim 2 wherein

A is N and A' is N or N→O;
n is 1;
m is 0;
p is 0, 2 or 3;
r is 1;
X is NR if p is 0, wherein R is hydrogen or lower alkyl, or if p is 2 or 3, X is nitrogen, which together with $(CH_2)_p$ and the bonds represented in dotted (interrupted) lines (including the atoms to which they are bound) forms a ring, or $Y_1$ is O;

each of $R_1$, $R_2$ and $R_3$, independently of the others, is hydrogen, methyl, ethyl, n-propyl, isopropyl, tert-butyl, isopropenyl, hydroxy-propyl, methoxy, chloro, bromo, trifluoromethyl, trifluoromethoxy, trifluoroethoxy, aminomethyl, aminoethyl, diethylamino, hydroxy-propylamino, bis-(2-methoxy-ethyl)-amino dimethylaminomethyl, phenyl, morpholin-4-yl, piperidin-1-yl, piperidin-1-ylmethyl, 4-methyl-piperazin-1-yl, 4-ethyl-piperazin-1-yl, 4-methyl-piperazin-1-ylmethyl, 4-ethylpiperazin-1-ylmethyl, pyridin-2-yl, 2- or 4-methyl-imidazol-1-yl, with the proviso that $R_1$, $R_2$ and $R_3$ cannot all be hydrogen and with the further proviso that if one of $R_1$, $R_2$ and $R_3$ is halo, the other two cannot both be hydrogen;

$R_4$ is methyl, ethyl, ispropyl, hydroxy, aminocarbonyl, methylcarbonyl, cyclohexyl, chloro, fluoro, trifluoromethyl, methoxy, amino, methylamino, ethylamino, isopropylamino, tert-butylamino, dimethylamino, prop-2-enylamino, but-3-enylamino, methylcarbonylamino, cyano, azido, 3- or 4-hydroxy-phenyl-amino, methoxy-phenyl-amino, trimethoxy-phenyl-amino, methoxy-fluoro-phenyl-amino, benzylamino, methoxy-benzylamino, dimethoxy-benzylamino aminosulfonyl-benzylamino, aminoethoxy-phenyl-amino, methylamino-sulfonylmethyl-phenylamino, 4-methylpiperazin-1-yl-propylamino, morpholin-4-yl-propylamino, 1-methyl-piperidin-4-ylamino, 1H-tetrazol-5-yl, 1-methyl-1H-tetrazol-5-yl, 2-methyl-2H-tetrazol-5-yl, or (di-lower alkyl)-amino-lower alkyl-tetrazol-5-yl, or 2-(3-dimethylaminopropyl)-2H-tetrazol-5-yl, with the proviso that if X is NH, $R_4$ is not aminocarbonyl or lower alkyl-carbonyl and with the further proviso that if, p is 0, X is NH, $R_4$, together with the benzene ring containing A and A', does not form methylpyridinyl, 2-hydroxy-pyridin-4-yl or 1-H-2-oxo-1,2-dihydropyridin-4-yl;

$R_5$ is hydrogen, methyl, or chloro;

or a tautomer thereof;

or a pharmaceutically acceptable salt thereof.

4. A compound of the formula I* according to claim 2 wherein A and A' are both N, n is 1, m is 0, p is 0 or 2, r is 1, X is NH if p is 0, or if p is 2, X is nitrogen which together with $(CH_2)_2$ and the bonds represented in dotted (interrupted) lines (including the atoms to which they are bound) forms a ring, $Y_1$ is O, at least one of $R_1$, $R_2$ and $R_3$ is not H, $R_4$ is amino or lower alkylamino and $R_5$ is hydrogen, or a tautomer thereof, or a pharmaceutically acceptable salt thereof.

5. A compound of the formula I* according to claim 1 or a tautomer thereof, or a pharmaceutically acceptable salt thereof, where, in the compound of the formula I*, A is N or N→O and A' is N or N→O, with the proviso that not more than one of A and A' can be N→O;

n is 1;

m is 0;

p is 0, 2 or 3;

r is 1;

X is NR if p is 0, wherein R is hydrogen or lower alkyl, or if p is 2 or 3, X is nitrogen which together with $(CH_2)_p$ and the bonds represented in dotted (interrupted) lines (including the atoms to which they are bound) forms a ring, or with the proviso that the bonds represented in dotted lines, if p is zero, are absent;

$Y_1$ is O;

each of $R_1$, $R_2$ and $R_3$ independently of the others, is hydrogen, lower alkyl, halo, halo-lower alkyl, lower alkoxy, halo-lower alkoxy, phenyl, piperidyl, piperazinyl, morpholinyl, thiomorpholinyl, or any two of $R_1$, $R_2$ and $R_3$ together form a lower alkylene-dioxy bridge bound via the oxygen atoms, and the remaining one of these moieties is hydrogen or one of the moieties mentioned, with the proviso that $R_1$, $R_2$ and $R_3$ cannot all be hydrogen and with the further proviso that if one of $R_1$, $R_2$ and $R_3$ is halo, the other two cannot both be hydrogen;

$R_4$ is lower alkoxy lower alkanoylamino, hydroxyphenylamino, amino-lower alkyl-oxyphenyl-amino, sulfamoylphenylamino, carbamoylphenylamino, [N-(hydroxy-lower alkyl)-carbamoyl]-phenylamino or halo, and $R_5$ is hydrogen, lower alkyl or halo.

6. A compound of the formula I* according to claim 1 selected from the group consisting of
N-(4-pyridin-4-yl-oxy-phenyl)-N'-(4-ethyl-phenyl)-urea,
N-(4-pyridin-4-yl-oxy-phenyl)-N'-(3-trifluoromethyl-phenyl)-urea,
N-(4-pyridin-4-yl-oxy-phenyl)-N'-(4-(2,2,2-trifluoroethoxy)-3-trifluoromethyl-phenyl)-urea;
N-(4-(4-(4-hydroxyphenylamino)-pyrimidin-6-yl)-oxyphenyl)-N'-(3-trifluoromethylphenyl)-urea;
and N-(4-(2-methyl-pyridin-4-yl)-oxyphenyl)-N'-(3-trifluoromethyl-phenyl)-urea;
1-[4-(4-Ethyl-piperazin-1-ylmethyl)-3-trifluoromethyl-phenyl]-3-[4-(6-methylamino-pyrimidin-4-yloxy)-phenyl]-urea;

or a pharmaceutically acceptable salt thereof.

7. A compound of the formula I* according to claim 1 selected from the group consisting of
N-(4-pyridin-4-yl-oxy-phenyl)-N'-(4-n-propyl-phenyl)-urea,
N-(4-pyridin-4-yl-oxy-phenyl)-N'-(4-methyl-phenyl)-urea,
N-methyl-N-(4-pyridin-4-yl-oxy-phenyl)-N'-(4-ethyl-phenyl)-urea,
N-methyl-N-(4-pyridin-4-yl-oxy-phenyl)-N'-(3-trifluoromethyl-phenyl)-urea,
N-methyl-N-(4-pyridin-4-yl-oxy-phenyl)-N'-(4-n-propyl-phenyl)-urea,
N-methyl-N-(4-pyridin-4-yl-oxy-phenyl)-N'-(4-methyl-phenyl)-urea,
N-(4-pyridin-4-yl-oxy-phenyl)-N'-(4-bromo-3-trifluoromethyl-phenyl)-urea,
N-(4-pyridin-4-yl-oxy-phenyl)-N'-(3-methoxy-5-trifluoromethyl-phenyl)-urea,
N-(4-pyridin-4-ylmethyl-phenyl)-N'-(4-n-propyl-phenyl)-urea,
N-(4-pyridin-4-ylmethyl-phenyl)-N'-(4-ethyl-phenyl)-urea,
N-(4-pyridin-4-ylmethyl-phenyl)-N'-(4-methyl-phenyl)-urea,
N-(4-pyridin-4-ylmethyl-phenyl)-N'-(3-trifluoromethyl-phenyl)-urea,
N-(4-pyridin-4-yl-oxy-phenyl)acetyl-(4-ethyl-phenyl)-amide,
N-(4-pyridin-4-yl-oxy-phenyl)acetyl-(4-methyl-phenyl)-amide,
N-(4-pyridin-4-yl-oxy-phenyl)acetyl-(4-n-propyl-phenyl)-amide,
5-(4-pyridyl-oxy)-N-(3-trifluoromethyl-phenyl)aminocarbonyl-2,3-dihydroindole,
5-(4-pyridyl-oxy)-N-(3-trifluoromethyl-phenyl)aminocarbonyl-1,2,3,4-tetrahydroquinoline,
N-(4-(4-Chloropyrimidin-6-yl)-oxyphenyl)-N'-(3-trifluoromethylphenyl)-urea,
N-(4-pyridin-4-yl-oxyphenyl)-N'-(4-phenyl-3-trifluoromethyl-phenyl)-urea,
N-(4-pyridin-4-yl-oxyphenyl)-N'-(4-(piperidin-1-yl)-3-trifluoromethyl-phenyl)-urea,
N-(4-pyridin-4-yl-oxyphenyl)-N'-(4-(morpholino)-3-trifluoromethyl-phenyl)-urea,
N-(4-pyridin-4-yl-oxyphenyl)-N'-(3,4,5-trimethoxy-phenyl)-urea, N-(4-pyridin-4-yl-oxyphenyl)-N'-(3-methoxy-4-phenyl-phenyl)-urea,
N-(4-pyridin-4-yl-oxyphenyl)-N'-(3-methoxy-4,5-(ethylen-1,2-dioxy)-phenyl)-urea,
N-(4-pyridin-4-yl-oxyphenyl)-N'-(3-methoxy-4-(2,2,2-trifluoroethoxy)-phenyl)-urea,
N-(4-pyridin-4-yl-oxyphenyl)-N'-(3-methoxy-4-piperidin-1-yl-phenyl)-urea,
N-(4-pyridin-4-yl-oxyphenyl)-N'-(4-piperidin-1-yl-phenyl)-urea,
N-(4-[2-(4-hydroxyphenyl)-amino-pyrimidin-4-yl]-oxyphenyl-N'-(3-trifluoromethyl-phenyl)-urea,
N-(4-[4-(4-sulfamoylphenyl)-amino-pyrimidin-6-yl]-oxyphenyl-N'-(3-trifluoromethyl-phenyl)-urea,
N-(4-[4-(4-carbamoylphenyl)-amino-pyrimidin-6-yl]-oxyphenyl-N'-(3-trifluoromethyl-phenyl)-urea,
N-(4-[4-(4-(N-2-hydroxyethylcarbamoyl)7Phenyl)-amino-pyrimidin-6-yl]-oxyphenyl-N'-(3-trifluoromethyl-phenyl)-urea,
N-(4-[4-(4-hydroxyphehyl)-amino-pyrimidin-6-yl]-oxyphenyl-N'-(3-trifluoromethyl-4-(2,2,2-trifluoroethoxy)-phenyl)-urea,
N-(4-(N-oxido-pyridin-4-yl)-oxyphenyl)-N'-(3-trifluoromthyl-phenyl)-urea,
N-(4-(2-methoxypyridin-5-yl)-oxyphenyl)-N'-(3-trifluoromethyl-phenyl)-urea,
N-(4-(2-pyridon-5-yl)-oxyphenyl)-N'-(3-trifluoromethyl-phenyl)-urea,
N-[4-{(2-acetylamino)-pyridin-4-yl}-oxy]-phenyl-N'-(3-trifluoromethyl-phenyl)-urea,
N-[4-(pyridin-4-yl-oxy)-2-chloro-phenyl]-N'-(3-trifluoromethyl-phenyl)-urea,
N-[4-(pyridin-4-yl-oxy)-2-methyl-phenyl]-N'-(3-trifluoromethyl-phenyl)-urea, and
N-(4-[4-(2-aminoethoxyphenyl)-amino-pyrimidin-6-yl]-oxyphenyl-N'-(3-trifluoromethyl-phenyl)-urea,
or a pharmaceutically acceptable salt thereof.

8. A pharmaceutical preparation comprising a compound of the formula I or I* according to claim 1, or a tautomer thereof, or a pharmaceutically acceptable salt thereof, and a pharmaceutically acceptable carrier material.

9. A process for the preparation of a compound of the formula I according to claim 2, or a tautomer thereof, or a pharmaceutically acceptable salt thereof, characterized in that (a) for the synthesis of a compound of the formula I wherein X NR if p is 0, or if p is 2 or 3, X is nitrogen which together with $(CH_2)_p$ and the bonds represented in dotted (interrupted) lines (including the atoms to which they are bound) forms a ring, and G, Z, A, A', $Y_1$, $Y_2$, R, $R_1$, $R_2$, $R_3$, $R_4$, $R_5$, m, n, p and r have the meanings as defined for a compound of formula I according to claim 2, an amino compound of the formula II

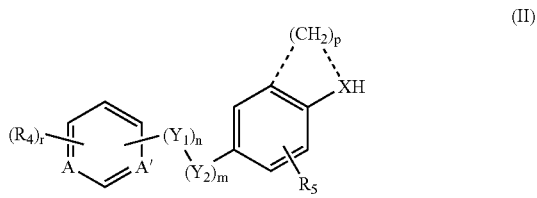

(II)

wherein X is as just defined and $R_4$, $R_5$, A, A', $Y_1$, $Y_2$, m, n, p, r and the bonds represented in dotted (interrupted) lines have the meanings as defined for a compound of formula I according to claim 2, is reacted with an isocyanate of the formula III

O=C=N-G-Z (III)

wherein G, Z, $R_1$, $R_2$ and $R_3$ have the meanings as defined for a compound of formula I according to claim 2, or (b) for the synthesis of a compound of the formula I wherein m is O (and thus $Y_2$ is missing), n is 1, $Y_1$ is O and G, Z, X, $R_1$, $R_2$, $R_3$, R4, $R_5$, A, A', p and r have the meanings as defined for a compound of formula I according to claim 2, a hydroxy compound of the formula IV

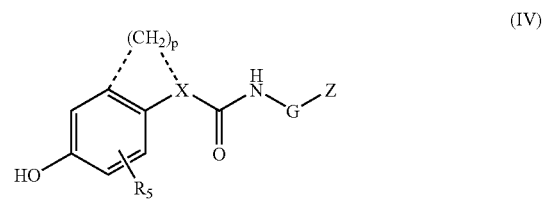

(IV)

wherein G, Z, X, $R_1$, $R_2$, $R_3$, $R_5$, p and the bonds represented in dotted (interrupted) lines have the meanings as defined for a compound of formula I according to claim 2, is etherified with a halo compound of the formula V

(V)

wherein $R_4$ and r have the meanings as defined for a compound of formula I according to claim 2 and Hal is halo, especially chloro, or (c) for the synthesis of a compound of the formula I wherein p is zero, X is CHK, especially $CH_2$, and G, Z, K, $Y_1$, $Y_2$, $R_1$, $R_2$, $R_3$, $R_4$, $R_5$, A, A', m, n and r have the meanings as defined for a compound of formula I according to claim 2, a carboxyl compound of the formula VI

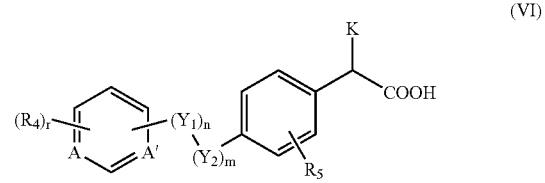

(VI)

wherein K is lower alkyl or preferably hydrogen and A, A', $Y_1$, $Y_2$, $R_4$, $R_5$, m, n and r have the meanings as defined for a compound of formula I according to claim 2, or a reactive derivative thereof, is condensed with an amino compound of the formula VII

$H_2N$-G-Z (VII)

wherein G, Z, $R_1$, $R_2$ and $R_3$ have the meanings as defined for a compound of formula I according to claim 2, or (d) for the synthesis of a compound of the formula I wherein X is NH, p is zero and G, Z, A, A', $Y_1$, $Y_2$, $R_1$, $R_2$, $R_3$, $R_4$, $R_5$, m, n and r have the meanings as defined for a compound of formula I according to claim 2, an isocyanate of the formula VIII

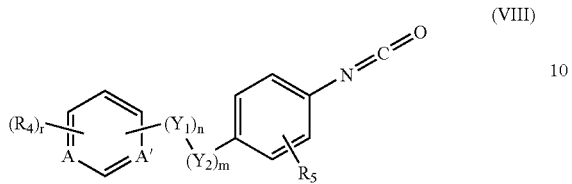

wherein $R_4$, A, A', $Y_1$, $Y_2$, m, n, r and $R_5$ have the meanings as defined for a compound of formula I according to claim 2, is reacted with an amino compound of the formula IX $H_2N-G-Z$ (IX)

wherein G, Z, $R_1$, $R_2$ and $R_3$ have the meanings as defined for a compound of formula I according to claim 2, and, if desired, after reaction (a), (b), (c) or (d) an obtainable compound of formula I is transformed into a different compound of formula I, a salt of an obtainable compound of formula I is transformed into the free compound or a different salt, or an obtainable free compound of formula I is transformed into a salt; and/or an obtainable mixture of isomers of compounds of formula I is separated into the individual isomers;

where for all reactions mentioned functional groups in the starting materials that shall not take part in the reaction are, if required, present in protected form by readily removable protecting groups, and any protecting groups are subsequently removed.

\* \* \* \* \*

UNITED STATES PATENT AND TRADEMARK OFFICE
CERTIFICATE OF CORRECTION

PATENT NO. : 7,652,022 B2  Page 1 of 1
APPLICATION NO. : 10/515113
DATED : January 26, 2010
INVENTOR(S) : Floersheimer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 902 days.

Signed and Sealed this

Twenty-third Day of November, 2010

David J. Kappos
*Director of the United States Patent and Trademark Office*